(12) United States Patent
Chan et al.

(10) Patent No.: US 7,655,229 B2
(45) Date of Patent: Feb. 2, 2010

(54) ANTI-FC-GAMMA RIIB RECEPTOR ANTIBODY AND USES THEREFOR

(76) Inventors: Andrew C. Chan, 1201 Cloud Ave., Menlo Park, CA (US) 94025; Robert L. Shields, 11 Ridgecrest Ter., San Mateo, CA (US) 94402; Lawren Wu, 1051 Pensacola St., Foster City, CA (US) 94404

(*) Notice: Subject to any disclaimer, the term of this patent is extended or adjusted under 35 U.S.C. 154(b) by 0 days.

(21) Appl. No.: 11/787,713

(22) Filed: Apr. 16, 2007

(65) Prior Publication Data

US 2007/0253948 A1 Nov. 1, 2007

Related U.S. Application Data

(63) Continuation-in-part of application No. 11/624,523, filed on Jan. 18, 2007, and a continuation-in-part of application No. 11/217,995, filed on Sep. 1, 2005, now abandoned.

(60) Provisional application No. 60/606,851, filed on Sep. 2, 2004.

(51) Int. Cl.
*A61K 39/395* (2006.01)
(52) U.S. Cl. .................................. 424/136.1
(58) Field of Classification Search ............... None
See application file for complete search history.

(56) References Cited

U.S. PATENT DOCUMENTS

| | | | |
|---|---|---|---|
| 4,515,893 A | 5/1985 | Kung et al. | |
| 4,816,567 A | 3/1989 | Cabilly et al. | |
| 5,091,313 A | 2/1992 | Chang | |
| 5,500,362 A | 3/1996 | Robinson et al. | |
| 5,622,700 A | 4/1997 | Jardieu et al. | |
| 5,672,347 A | 9/1997 | Aggarwal et al. | |
| 5,693,762 A | 12/1997 | Queen et al. | |
| 5,714,338 A | 2/1998 | Wai Fei et al. | |
| 5,721,108 A | 2/1998 | Robinson et al. | |
| 5,725,856 A | 3/1998 | Hudziak et al. | |
| 5,731,168 A | 3/1998 | Carter et al. | |
| 5,736,137 A | 4/1998 | Anderson et al. | |
| 5,807,706 A | 9/1998 | Carter et al. | |
| 5,821,333 A | 10/1998 | Carter et al. | |
| 5,821,337 A | 10/1998 | Carter et al. | |
| 5,840,523 A | 11/1998 | Simmons et al. | |
| 7,138,494 B2 | 11/2006 | Endou et al. | |
| 7,276,585 B2 * | 10/2007 | Lazar et al. | 530/387.1 |
| 2003/0077282 A1 * | 4/2003 | Bigler et al. | 424/144.1 |
| 2006/0193857 A1 | 8/2006 | Boruchov et al. | |

FOREIGN PATENT DOCUMENTS

| | | |
|---|---|---|
| EP | 0 420 937 B1 | 11/1994 |
| WO | 93/04173 | 3/1993 |
| WO | 95/19181 | 7/1995 |
| WO | 95/23865 | 9/1995 |
| WO | 96/30046 | 10/1996 |
| WO | 96/40210 | 12/1996 |
| WO | 97/26912 | 7/1997 |
| WO | 98/06248 | 2/1998 |
| WO | 98/23761 | 6/1998 |
| WO | 98/45331 | 10/1998 |
| WO | 98/51793 | 11/1998 |
| WO | 99/01556 | 1/1999 |
| WO | 00/29431 | 5/2000 |
| WO | 00/75348 A1 | 12/2000 |
| WO | 01/40309 A2 | 6/2001 |
| WO | 01/79299 A1 | 10/2001 |
| WO | 02/088317 A2 | 11/2002 |
| WO | 02/102320 A2 | 12/2002 |
| WO | 03/066095 A2 | 8/2003 |
| WO | 2004/016750 A2 | 2/2004 |
| WO | 2005/018669 A1 | 3/2005 |
| WO | 2005/110474 A2 | 11/2005 |
| WO | 2005/115452 A2 | 12/2005 |
| WO | 2006/066078 A2 | 6/2006 |

OTHER PUBLICATIONS

Heaney et al., Lancet, 2005, 365: 974-976.*
Atwell et al., J. Mol. Biol., 1997, 270: 26-35.*
Kepley et al., J. Biol. Chem., 2004, 279: 35139-35149.*
Asano et al., "L-Type Amino Acid Transporter-1 Expressed in Human Astrocytomas, U343MGa" *Biol. Pharm. Bull.* 30 (3) :415-422 (Mar. 2007).
Bae et al., "Y+ amd y+L Arginine Transporters in Neuronal Cells Expressing Tyrosine Hydroxylase" *Biochimica et Biophysica Acta* 1745:65-73 (2005).

(Continued)

*Primary Examiner*—Ilia Ouspenski
(74) *Attorney, Agent, or Firm*—Craig G. Svoboda

(57) ABSTRACT

The present application describes antibodies that selectively bind human FcγRIIB, with little or no binding to other human FcγRs, e.g., human FcγRIIA. The invention also provides isolated bispecific antibodies comprising an antibody that selectively binds FcγRIIB, and a second antibody that specifically binds an activating receptor. Various uses, including therapeutic uses, for those antibodies are also described, including administration with anti-tumor antibodies and methods of inhibiting immune responses and suppressing histamine release.

40 Claims, 50 Drawing Sheets
(4 of 50 Drawing Sheet(s) Filed in Color)

OTHER PUBLICATIONS

Berg et al., "Bispecfic Antibodies that Mediate Killing of Cells Infected with Human Immunodeficiency Virus of Any Strain" *Proc. Natl. Acad. Sci. USA* 88:4723-4727 (Jun. 1991).

Bik-Multanowski et al., "LAT1 Gene Variants—Potential Factors Influencing the Clinical Course of Phenylketonuria" *J. Inherit. Metab. Dis.* 29:684 (2006).

Bleehan et al., "A Randomised Trial of Three or Six Courses of Etoposide Cyclophosphamide Methotrexate and Vincristine or Six Courses of Etoposide and Ifosfamide in Small Cell Lung Cancer (SCLC) II: Quality of Life" *MRC Lung Cancer Workirg Party* pp. 1157-1166.

Boado et al., "Human LAT1 Single Nucleotide Polymorphism N230K Does Not Alter Phenylalanine Transport" *Molecular Genetics and Metabolism 83* pp. 306-311 (2004).

Boado et al., "Site-Directed Mutagenesis of Cysteine Residues of Large Neutral Amino Acid Transporter LAT1" *Biochimica et Biophysica Acta* 1715:104-110 (2005).

Boado et al., "Site-Directed Mutagenesis of Rabbit LAT1 at Amino Acids 219 and 234" *Journal of Neurochemistry* 84:1322-1331 (2003).

Bobrova et al., "An Immunoglobulin-like Antigen in Human Cell Lines and Sera of Cancer Patients" *Neoplasma* 39 (2) :101-105 (1992).

Brust et al., "The Influx of Neutral Amino Acids into the Porcine Brain During Development: a Positron Emission Tomography Study" *Developmental and Brain Research* 152: 241-253 (2004).

Bubnoff, D. et al., "The central role of FceRI in allergy" *Clinical & Experimental Dermatology* 28(2) :184-187 (2003).

Carter et al., "Humanization of an Anti-p185$^{HER2}$ Antibody for Human Cancer Therapy" *Proc. Natl. Acad. Sci. USA* 89(10) :4285-4289 (May 1992)

Ceriani et al., "Biological activity of two humanized antibodies against two different breast cancer antigens and comparison to their original murine forms" *Cancer Research* 55(23) :5852s-5856s (1995).

Chamow et al., "A Humanized, Bispecific Immunoadhesin-Antibody That Retargets CD3+ Effectors to Kill HIV-1-Infected Cells" *Journal of Immunology* 153(9) :4268-4280 (Nov. 1, 1994).

Choy et al., "Percentage of anti-cd4 monoclonal antibody-coated lymphocytes in the rheumatoid joint is associated with cilnical improvement" *Arthritis Rheum.* 39:52-56 (1996).

Clynes et al., "Fc Receptors Are Required in Passive and Active Immunity to Melanoma" *Proc. Natl. Acad. Sci. USA* 95(2) :652-656 (Jan. 1998).

Clynes et al., "Modulation of immune complex-induced inflammation in vivo by the coordinate expression of activation and inhibitory Fc receptors" *Journal of Experimental Medicine* 189(1):179-185 (Jan. 4, 1999).

Daeron, M. et al., "Regulation of high-affinity IgE receptor-mediated mast cell activation by murine low-affinity IgG receptors" *J. Clin. Invest.* 95:577-585 (1995).

Daeron, M. et al., "The same tyrosine-based inhibition motif, in the intracytoplasmic domain of FcγRIIB, regulates negatively Bcr-, Tcr-, and FcR-dependent cell activation" *Immunity* 3:635-646 (1995).

Dhainaut et al., "CDP571, a humanized antibody to human tumor necrosis factor-alpha: Safety, pharmacokinetics, immune response, and influence of the antibody on cytokine concentrations in patients with septic shock" *Crit. Care Med.* 23(9):1461-1469 (1995).

Ellis et al., "Engineered anti-CD38 monoclonal antibodies for immunotherapy of multiple myeloma" *European Journal of Immunology* 155:925-937 (1995).

Fraga et al., "Expression of LAT1 and LAT2 Amino Acid Transporters in Human and Rat Intestinal Epithelial Cells" *Amino Acids* 29:229-233 (Jul. 20, 2005).

Gao et al., "Expression of Cdk5, p35, and Cdk5-Associated Kinase Activity in the Developing Rat Lens" *Developmental Genetics* 20:267-275 (1997).

Gaugitsch et al., "A novel transiently expressed, integral membrane protein linked to cell activation. Molecular cloning via the rapid degradation signal AUUUA" *J Biol Chem.* 267(16) :11267-11273 (Jun. 5, 1992).

Graziano et al., "Construction and characterization of a humanized anti-γ-Ig receptor Type I (FcγRI) monoclonal antibody" *J. Immunol.* 155(10) :4996-5002 (1995).

Greenman et al., "Characterization of a new monoclonal anti-FcγRII antibody, AT10, and its incorporation into a biscpecific f(ab')$_2$ derivative for recruitment of cytotoxic effectors" *Molecular Immunology* 28:1243-1254 (1991).

Guazzi et al., "HMGB1, an Architectural Chromatin Protein and Extracellular Signalling Factor, Has a Spatially and Temporally Restricted Expression Pattern in Mouse Brain" *Gene Expression Patterns* 3:29-33 (2003).

Guberan et al., "Disability, Mortality, and Incidence of Cancer Among Geneva Painters and Electricians: A Historical Prospective Study" *British Journal of Industrial Medicine* 46:16-23 (1989).

Hourmant et al., "Administration of an Anti-CD11a Monoclonal Antibody in Recipients of Kidney Transplantation" *Transplantation* 58(3) :377-380 (Aug. 1994).

Ierino et al., "Mapping epitopes of human FcγRII (CDw32) with monoclonal antibodies and recombinant receptors" *J. Immunol.* 150:1794-1803 (1993).

Jurcic et al., "Radiolabeled anti-CD33 monoclonal antibody M195 for myeloid leukemias" *Cancer Research* 55:5908s-5910s (1995).

Juweid et al., "Treatment of non-Hodgkin's lymphoma with radiolabeled murine, chimeric, or humanized LL2, and anti-CD22 monoclonal antibody" *Cancer Research* 55 (23 Suppl) :5899s-5907s (1995).

Kajiwara et al., "Promotion of Neurite Outgrowth From Fetal Hippocampal Cells by TNF-α Receptor 1-Derived Peptide" *Cell Transplantation* 14:665-672 (2005).

Kanai et al., "Expression Cloning and Characterization of a Transporter for Large Neutral Amino Acids Activated by the Heavy Chain of 4F2 Antigen (CD98)" *The Journal of Biological Chemistry* 273(37) :23629-23632 (Sep. 11, 1998).

Kepley et al., "Co-aggregation of FcγRII with FcεRI on Human Mast Cells Inhibits Antigen-induced Secretion and Involves SHIP-Grb2-Dok Complexes" *The Journal of Biological Chemistry* 279(34) :35139-35149 (Aug. 2004).

Kersemans et al., "In Vivo Characterization of 123/125 I-2-Iodo-L-Phenylalanine R1M Rhabdomyosarcoma Athymic Mouse Model as a Potential Tumor Tracer for SPECT" *The Journal of Nuclear Medicine* 46 (3) (Mar. 2005).

Killian et al., "Targeting the Cerebrovascular Large Neutral Amino Acid Transporter (LAT1) Isoform Using a Novel Disulfide-Based Brain Drug Delivery System" *Drug Delivery* 14:25-31 (2007).

Kim et al., "Characterization of the System L Amino Acid Transporter in T24 Human Bladder Carcinoma Cells" *Biochimica et Biophysica Acta* 1565:112-122 (2002).

Kim et al., "The Vascular Endothelial Growth Factor Proteins: Identification of Biologically Relevant Regions by Neutralizing Monoclonal Antibodies" *Growth Factors* 7(1):53-64 (1992).

Litton et al., "Antibody-targeted superantigen therapy induces tumor-infiltrating lymphocytes, excessive cytokine production, and apoptosis in human colon carcinoma" *European Journal of Immunology* 26:1-9 (1996).

Looney, J. R. et al., "Human monocytes and U937 cells bear two distinct Fc receptors for IgG$^1$" *J. Immunol.* 136:1641-1647 (1986).

Lorenz, H. et al., "In vivo blockade of Tnf-α by intravenous infusion of a chimeric monoclonal TNF-α antibody in patients with rheumatoid arthritis" *J. Immunol.* 156:1646-1653 (1996).

Lyden, T.W. et al., "The Fc receptor for IgG expressed in the villus endothelium of human placenta is FcγRIIb2$_1$" *J. Immunol.* 166:3882-3889 (2001).

Malbec, O. et al., "Fcε receptor I-associated lyn-dependent phosphorylation of Fcγ receptor IIB during negative regulation of mast cell activation" *J. Immunol.* 160:1647-1658 (1998).

Mannion, B., et al., "The Light Chain of CD98 Is Identified as E16/TA1 Protein" *The J. of Biological Chemistry* 273(50):33127-29 (Dec. 11, 1998).

Mantzioris, B.X. et al., "Expression of the Fc receptor for IgG (FcγRII/Cd332) by human circulating T and B lymphocytes" *J. Immunol.* 150:5175-5184 (1993).

Merchant et al., "An efficient route to human bispecific IgG" *Nature Biotechnology* 16(7):677-681 (1998).

Moller et al., "Inter-Individual Variation in Brain Phenylalanine Concentration in Patients with PKU is not Caused by Genetic Variation in the 4F2hc/LAT1 Complex" *Molecular Genetics and Metabolism* 86: S119-S123 (2005).

Morgenstern, J.P. et al., "Advanced mammalian gene transfer: high titre retroviral vectors with multiple drug selection markers and a complementary helper-free packaging cell line" *Nucleic Acid Research* 18:3587-3596 (1990).

Morrison et al., "Chimeric Human Antibody Molecules: Mouse Antigen-Binding Domains with Human Constant Region Domains" *Proc. Natl. Acad. Sci. USA* 81(21):6851-6855 (Nov. 1984).

Nawashiro et al., "L-Type Amino Acid Transporter 1 as a Potential Molecular Target in Human Astrocytic Tumors" *Int. J. Cancer* 119:484-492 (2006).

Nawashiro et al., "The Role of CD98 in Astrocytic Neoplasms" *Human Cell* 15(1):25-31 (2002).

Nybakken et al., "Structural Basis of West Nile Virus Neutralization by a Therapeutic Antibody" *Nature* 437(29):764-768 (Sep. 29, 2005).

Ohkame et al., "Expression of L-Type Amino Acid Transporter 1 (LAT1) and 4F2 Heavy Chain (4F2hc) in Liver Tumor Lesions of Rat Models" *Journal of Surgical Oncology* 78:265-272 (2001).

Okano et al., "A Hierarchy of Hu RNA Binding Proteins in Developing and Adult Neurons" *The Journal of Neuroscience* 17(9):3024-3037 (May 1, 1997).

Ono et al., "Role of the inositol phosphatase SHIP in negative regulation of the immune system by the receptor FcγRIIB" *Nature* 383(6597):263-266 (Sep. 19, 1996).

Ozbun et al., "Differentially Expressed Nucleolar TGF-β1 Target (DENTT) in Mouse Development" *Developmental Dynamics* 226:491-511 (2003).

Presta et al., "Humanization of an Antibody Directed Against IgE" *J. Immunol.* 151(5):2623-2632 (Sep. 1, 1993).

Pulford et al., "A new monoclonal antibody (KB861) recognizing a novel antigen which is selectively expressed on a subpopulation of human B lymphocytes" *Immunology* 57:71-76 (1986).

Radner et al., "Tumor Induction by ras and myc Oncogenes in Fetal and Neonatal Brain: Modulating Effects of Developmental Stage and Retroviral Dose" *Acta Neuropathol.* 86:456-165 (1993).

Ratcliffe et al., "Netrin/DCC-Mediated Attraction of Vagal Sensory Axons to the Fetal Mouse Gut" *The Journal of Comparative Neurology* 498:567-580 (2006).

Ravetch and Bolland, "IgG Fc Receptors" *Ann. Rev. Immunol.* 19:275-290 (2001).

Ravetch et al., "Immune inhibitory receptors" *Science* 290:84-89 (2000).

Ravetch, et al., "Fc Receptors" *Annual Review Immunol.* 9:457-492 (1991).

Reichmann, L. et al., "Reshaping human antibodies for therapy" *Nature* 332:323-337 (1988).

Richman et al., "Radioimmunotherapy for breast cancer using escalating fractionated doses of [131] labeled chimeric L6 antibody with peripheral blood progenitor cell transfusions" *Cancer Research* 55((23 Suppl)):5916s-5920s (1995).

Riske et al., "High affinity human IgE receptor (FcεRI)" *Journal of Biological Chemistry* 266:11245-11251 (1991).

Rose et al., "Expression of M-Cadherin Protein in Myogenic Cells During Prenatal Mouse Development and Differentiation of Embryonic Stem Cells in Culture" *Developmental Dynamics* 201:245-259 (1994).

Sang et al., "TA1, a Highly Conserved Oncofetal Complementary DNA from Rat Hepatoma, Encodes an Integral Membrane Protein Associated with Liver Development, Carcinogenesis, and Cell Activation" *Cancer Research* 55:1152-1159 (Mar. 1, 1995).

Sathish et al., "Constitutive association of SHP-1 with leukocyte-associated Ig-like receptor-1 in human T cells" *J. Immunol.* 166:1763-1770 (2001).

Sharkey et al., "Evaluation of a complementarity-determining region-grafted (humanized) anti-carcinoembryonic antigen monoclonal antibody in preclinical studies" *Cancer Research* 55(23 Suppl):5935s-5945s (1995).

Shaw et al., "Isolation and Characterization of an Immortalized Mouse Urogenital Sinus Mesenchyme Cell Line" *The Prostate* 66:1347-1358 (2006).

Shennan et al., "Functional and Molecular Characteristics of System L in Human Breast Cancer Cells" *Biochimica et Biophysica Acta* 1611:81-90 (Jan. 2003).

Shennan et al., "L-Leucine Transport in Human Breast Cancer Cells (MCF-7 and MDA-MB-231): Kinetics, Regulation by Estrogen and Molecular Identity of the Transporter" *Biochimica et Biophysica Acta* 1664:206-216 (2004).

Shields, et al., "High resolution mapping of the binding site on human IgG1 for Fc gamma RI, Fc gamma RII, Fc gamma RIII, and FcRn and design of IgG1 variants with improved binding to the Fc gamma R" *Journal of Biological Chemistry* 276(9):6591-6604 (Mar. 2, 2001).

Simmons, L. et al., "Expression of full-length immunoglobins in *Escherichia coli*: Rapid and efficient production of aglycosylated antibodies" *Journal of Immunological Methods* 263:133-147 (2002).

Simmons-Willis et al., "Transport of a Neurotoxicant by Molecular Mimicry: the Methylmercury-L-Cysteine Complex is a Substrate for Human L-type large Neutral Amino Acid Transporter (LAT)1 and LAT2" *Biochemical Journal* 367:239-246 (2002).

Sonderman, P. et al., "Characterization and crystallization of soluble human fcγ receptor II (CD32) isoforms produced in insect cells" *Biochemistry* 38:8469-8477 (1999).

Soulez et al., "Identification of Novel Oestrogen Receptor Target Genes in Human ZR75-1 Breast Cancer Cells by Expression Profiling" *Journal of Molecular Endocrinology* 27:259-274 (2001).

St. John, R. C. et al., "Immunologic Therapy for ARDS, Septic Shock, and Multiple-Organ Failure" *Chest* 103:932-943 (1993).

Stoppa, A.M. et al., "Anti-LFA1 monoclonal antibody (25.3) for treatment of steroid-resistant grade III-IV acute graft-versus-host disease" *Transplant Intl* (4)3-7 (1991).

Tam, S.W. et al., "A bispecific antibody against human IgE and human FcγRII that inhibits antigen-induced histamine release by human mast cells and basophils" *Allergy* 59:772-780 (2004).

Tamada et al., "cDNA Cloning and Characterization of Drb1, a New Member of RRM-type Neural RNA-Binding Protein" *Biochemical and Biophysical Research Communications* 297:96-104 (2002).

Tamai et al., "Expression of L-Type Amino Acid Transporter 1 in a Rat Model of Liver Metastasis: Positive Correlation with Tumor Size" *Cancer Detection and Prevention* 25(5):439-445 (2001).

Travers et al., "Indoleamine 2,3-dioxygenase Activity and L-Tryptophan Transport in Human Breast Cancer Cells" *Biochimica et Biophysica Acta* 1661:106-112 (2004).

Umeki et al., "mRNA Expression and Amino Acid Transport Characteristics of Cultured Human Brain Microvascular Endothelial Cells (hBME)" *Drug Metabol. Pharmacokin.* 17(4):367-373 (2002).

Weinrich et al., "Epitope mapping of new monoclonal antibodies recognizing distinct human FcRII (CD32) isoforms" *Hybridoma* 15:109-116 (1996).

Wolf et al., "Expression of a Highly Conserved Oncofetal Gene, TA1/E16, in Human Colon Carcinoma and Other Primary Cancers: Homology to Schistosoma Mansoni Amino Acid Permease and Caenorhabditis Elegans Gene Products" *Cancer Research* 56:5012-5022 (Nov. 1, 1996).

Yanagida et al., "Human L-Type Amino Acid Transporter 1 (LAT1): Characterization of Function and Expression in Tumor Cell Lines" *Biochimica et Biophysica Acta* 1514:291-302 (2001).

Zhu et al., "A novel human immunoglobulin Fcγ-Fcε bifunctional fusion protein inhibits FcεRI-mediated degranulation" *Nature Medicine* 8(5):518-521 (May 2002).

Zhuang et al., "Suppression of IL-4- and CD40-induced B-lymphocyte activation by intravenous immunoglobulin is not mediated through the inhibitory IgG receptor FcγRIIb" *The Journal of Allergy and Clinical Immunology* 110(3):480-483 (Sep. 2002).

Zipf et al., "A monoclonal antibody detecting a 39,000 M.W. molecule that is present on B lymphocytes and chronic lymphocytic leukemia cells but is rare on acute lymphocytic leukemia blasts" *J. Immunol.* 131:3064-3072 (1983).

Zola, H. et al., "CD32 (FcγRII)" *J. Biol. Regul. Homeost. Agents* 14:311-316 (2000).

\* cited by examiner

| | | |
|---|---|---|
| FcgR2A | 1 | ------MAMETQMSQNVCPRNLWLLQPLTVLLLASADSQAAAPPKA 41 |
| FcgR2B 2 | 1 | MGILSFLPVLATESDWADCKSPQPWGHMLLWTAVLFLAPVAGTPAAPPKA 50 |
| FcgR2A | 42 | VLKLEPPWINVLQEDSVTLTCQGARSPESDSIQWFHNGNLIPTHTQPSYR 91 |
| FcgR2B 2 | 51 | VLKLEPQWINVLQEDSVTLTCRGTHSPESDSIQWFHNGNLIPTHTQPSYR 100 |
| FcgR2A | 92 | FKANNNDSGEYTCQTGQTSLSDPVHLTVLSEMLVLQTPHLEFQEGETIML 141 |
| FcgR2B 2 | 101 | FKANNNDSGEYTCQTGQTSLSDPVHLTVLSEMLVLQTPHLEFQEGETIVL 150 |
| FcgR2A | 142 | RCHSWKDKPLVKVTFFQNGKSQKFSRLDPTFSIPQANHSHSGDYHCTGNI 191 |
| FcgR2B 2 | 151 | RCHSWKDKPLVKVTFFQNGKSKKFSRSDPNFSIPQANHSHSGDYHCTGNI 200 |
| FcgR2A | 192 | GYTLFSSKPVTITVQVPSMGSSSPMGIIVAVVIATAVAAIVAAVVALIYC 241 |
| FcgR2B 2 | 201 | GYTLYSSKPVTITVQAP--SSSPMGIIVAVVTGIAVAAIVAAVVALIYC 247 |
| FcgR2A | 242 | RKKRISANSTDPVKAAQFEPPGRQMIAIRKRQLEETNNDYETADGGYMTL 291 |
| FcgR2B 2 | 248 | RKKRISANPTNPDEADKV----G-------AENTITYS----LLM 277 |
| | | ITIM Motif |
| FcgR2A | 292 | NPRAPTDDDKNIYLTLPPNDHVNSNN 317 SEQ ID NO: 9 |
| FcgR2B 2 | 278 | HPDALEEPDDQNRI------ 291 SEQ ID NO: 10 |

FIG. 2A

FcgR2B1 Amino Acid Sequence:

```
  1 mgilsflpvl atesdwadck spqpwghmll wtavlflapv agtpaappka vlklepqwin
 61 vlqedsvtlt crgthspesd siqwfhngnl ipthtqpsyr fkannndsge ytcqtgqtsl
121 sdpvhltvls ewlvlqtphl efqegetivl rchswkdkpl vkvtffqngk skkfsrsdpn
181 fsipqanhsh sgdyhctgni gytlysskpv titvqapsss pmgiivavvt giavaaivaa
241 vvaliycrkk risalpgype cremgetlpe kpanptnpde adkvgaenti tysllmhpda
301 leepddqnri (SEQ ID NO: 11)
```

FIG. 2B

```
               230        240        250        260        270
    humIgG1    PAPELLGGPSVFLFPPKPKDTLMISRTPEVTCVVVDVSHEDPEVKFNWYV
    humIgG2    PAP-PVAGPSVFLFPPKPKDTLMISRTPEVTCVVVDVSHEDPEVQFNWYV
    humIgG3    PAPELLGGPSVFLFPPKPKDTLMISRTPEVTCVVVDVSHEDPEVQFKWYV
    humIgG4    PAPEFLGGPSVFLFPPKPKDTLMISRTPEVTCVVVDVSQEDPEVQFNWYV
                   ****                            *      *  *

280        290        300        310        320
    humIgG1    DGVEVHNAKTKPREEQYNSTYRVVSVLTVLHQDWLNGKEYKCKVSNKALP
    humIgG2    DGVEVHNAKTKPREEQFNSTFRVVSVLTVVHQDWLNGKEYKCKVSNKGLP
    humIgG3    DGVEVHNAKTKPREEQFNSTFRVVSVLTVLHQDWLNGKEYKCKVSNKALP
    humIgG4    DGVEVHNAKTKPREEQFNSTYRVVSVLTVLHQDWLNGKEYKCKVSNKGLP
                              *    *                          *

330        340        350        360        370
    humIgG1    APIEKTISKAKGQPREPQVYTLPPSREEMTKNQVSLTCLVKGFYPSDIAV
                         D L
    humIgG2    APIEKTISKTKGQPREPQVYTLPPSREEMTKNQVSLTCLVKGFYPSDIAV
    humIgG3    APIEKTISKTKGQPREPQVYTLPPSREEMTKNQVSLTCLVKGFYPSDIAV
    humIgG4    SSIEKTISKAKGQPREPQVYTLPPSQEEMTKNQVSLTCLVKGFYPSDIAV
              **         *               *

380        390        400        410        420
    humIgG1    EWESNGQPENNYKTTPPVLDSDGSFFLYSKLTVDKSRWQQGNVFSCSVMH
    humIgG2    EWESNGQPENNYKTTPPMLDSDGSFFLYSKLTVDKSRWQQGNVFSCSVMH
    humIgG3    EWESSGQPENNYNTTPPMLDSDGSFFLYSKLTVDKSRWQQGNIFSCSVMH
    humIgG4    EWESNGQPENNYKTTPPVLDSDGSFFLYSRLTVDKSRWQEGNVFSCSVMH
                  *         *    *              *      * *

430        440
    humIgG1    EALHNHYTQKSLSLSPGK  SEQ ID NO.: 31
    humIgG2    EALHNHYTQKSLSLSPGK  SEQ ID NO.: 32
    humIgG3    EALHNRFTQKSLSLSPGK  SEQ ID NO.: 33
    humIgG4    EALHNHYTQKSLSLSLGK  SEQ ID NO.: 34
                   **         *
```

FIG. 3

Amino Acid Sequence of Murine 5A6.2.1 mIgG1 (Anti-Human FcgRIIB)

Heavy Chain

EVKLEESGGGLVQPGGSMKLSCVASGFTFSDAWMDWVRQSPERGLEWVAEIRSKPNNHATYYAESVKGRFTISRDDS
^HC FR1                        ^CDR1 ^HC FR2         ^HC CDR2                ^HC FR2

KSSVYLQMTSLRPEDTGIYYCTHFDYWGQGTTLTVSSAKTTGPSVFPLAPSSKSTSGGTAALGCLVKDYFPEPVTVSWN
                       CDR3^ ^HC FR4

SGALTSGVHTFPAVLQSSGLYSLSSVVTVPSSSLGTQTYICNVNHKPSNTKVDKKVEPKSCDKTHT    SEQ ID NO: 7

Light Chain

DIQMTQSPSSLSASLGERVSLTCRASQEISGYLSWFQQKPDGTIKRLIYAASALDSGVPKRFSGSWSGSDYSLTISS
^LC FR1                ^LC CDR1     ^LC FR2         ^LC CDR2 ^LC FR3

LESEDFADYYCLQYVSYPLTFGAGTKLELKRTVAAPSVFIFPPSDEQLKSGTASVVCLLNNFYPREAKVQWKVD
           ^LC CDR3  ^LC FR4

NALQSGNSQESVTEQDSKDSTYSLSSTLTLSKADYEKHKVYACEVTHQGLSSPVTKSFNRGEC    SEQ ID NO: 8

FIG. 10

```
GAATTCAACTTCTCCATACTTTGGATAAGGAAATACAGACATGAAAAATCTCATTGCTGA
GTTGTTATTTAAGCTTGCCCAAAAAGAAGAAGAGTCGAATGAACTGTGTGCGCAGGTAGA
AGCTTTGGAGATTATCGTCACTGCAATGCTTCGCAATATGGCGCAAAATGACCAACAGCG
GTTGATTGATCAGGTAGAGGGGGCGCTGTACGAGGTAAAGCCCGATGCCAGCATTCCTGA
CGACGATACGGAGCTGCTGCGCGATTACGTAAAGAAGTTATTGAAGCATCCTCGTCAGTA
AAAAGTTAATCTTTTCAACAGCTGTCATAAAGTTGTCACGGCCGAGACTTATAGTCGCTT
TGTTTTTATTTTTTAATGTATTTGTAACTAGTACGCAAGTTCACGTAAAAAGGGTATCTA
GAATTATGAAGAAGAATATCGCATTTCTTCTTGCATCTATGTTCGTTTTTTCTATTGCTA
CAAATGCATACGCTGACATCCAGATGACCCAGTCTCCATCTTCCTTATCTGCCTCTCTGG
GAGAAAGAGTCAGTCTCACTTGTCGGGCAAGTCAGGAAATTAGTGGTTACTTAAGCTGGT
TTCAGCAGAAACCAGATGGAACTATTAAACGCCTGATCTATGCCGCATCCGCTTTAGATT
CTGGTGTCCCAAAAAGGTTCAGTGGCAGTTGGTCTGGGTCAGATTATTCTCTCACCATCA
GCAGCCTTGAGTCTGAAGATTTTGCAGACTATTACTGTCTACAATATGTTAGTTATCCGC
TCACGTTCGGTGCTGGGACCAAACTGGAGCTGAAACGGACCGTGGCTGCACCATCTGTCT
TCATCTTCCCGCCATCTGATGAGCAGTTGAAATCTGGAACTGCCTCTGTTGTGTGCCTGC
TGAATAACTTCTATCCCAGAGAGGCCAAAGTACAGTGGAAGGTGGATAACGCCCTCCAAT
CGGGTAACTCCCAGGAGAGTGTCACAGAGCAGGACAGCAAGGACAGCACCTACAGCCTCA
GCAGCACCCTGACGCTGAGCAAAGCAGACTACGAGAAACACAAAGTCTACGCCTGCGAAG
TCACCCATCAGGGCCTGAGCTCGCCCGTCACAAAGAGCTTCAACAGGGGAGAGTGTTAAT
T   SEQ ID NO: 35
```

FIG. 25

```
GAATTCAACTTCTCCATACTTTGGATAAGGAAATACAGACATGAAAAATCTCATTGCTGA
GTTGTTATTTAAGCTTGCCCAAAAAGAAGAAGAGTCGAATGAACTGTGTGCGCAGGTAGA
AGCTTTGGAGATTATCGTCACTGCAATGCTTCGCAATATGGCGCAAAATGACCAACAGCG
GTTGATTGATCAGGTAGAGGGGGCGCTGTACGAGGTAAAGCCCGATGCCAGCATTCCTGA
CGACGATACGGAGCTGCTGCGCGATTACGTAAAGAAGTTATTGAAGCATCCTCGTCAGTA
AAAAGTTAATCTTTTCAACAGCTGTCATAAAGTTGTCACGGCCGAGACTTATAGTCGCTT
TGTTTTTATTTTTTAATGTATTTGTAACTAGTACGCAAGTTCACGTAAAAAGGGTATCTA
GAATTATGAAGAAGAATATCGCATTTCTTCTTGCATCTATGTTCGTTTTTTCTATTGCTA
CAAATGCATACGCTGATATCATGATGACTCAGTCTCCTTCTTCCATGTATGCATCTCTAG
GAGAGAGAGTCACTATCACTTGTAAGGCGAGTCAGGACATTAATAGCTATTTAAGCTGGT
TCCAGCAGAAACCAGGGAAATCTCCTAAGACCCTGATCTCTCGTGCAAACAGATTGGTAG
ATGGTGTCCCATCAAGATTCAGTGGCAGTGGATCTGGGCAAGATTATTCTCTCACCATCA
GCAGCCTGGAGTATGAAGATATGGGAATTTATTATTGTCTACAGTATGATGACTTTCCGT
TCACGTTCGGAGGGGGGACCAAGCTGGAAATAAAACGGACCGTGGCTGCACCATCTGTCT
TCATCTTCCCGCCATCTGATGAGCAGTTGAAATCTGGAACTGCCTCTGTTGTGTGCCTGC
TGAATAACTTCTATCCCAGAGAGGCCAAAGTACAGTGGAAGGTGGATAACGCCCTCCAAT
CGGGTAACTCCCAGGAGAGTGTCACAGAGCAGGACAGCAAGGACAGCACCTACAGCCTCA
GCAGCACCCTGACGCTGAGCAAAGCAGACTACGAGAAACACAAAGTCTACGCCTGCGAAG
TCACCCATCAGGGCCTGAGCTCGCCCGTCACAAAGAGCTTCAACAGGGGAGAGTGTTAAT
T   SEQ ID NO: 36
```

FIG. 26

ACGCGTACGCTGAAGTGAAGCTGGAGGAGTCTGGAGGAGGCTTGGTGCAACCTGGAGGAT
CCATGAAACTCTCTTGTGTTGCCTCTGGATTCACTTTTAGTGACGCCTGGATGGACTGGG
TCCGCCAGTCTCCAGAGAGGGGGCTTGAGTGGGTTGCTGAAATTAGAAGCAAACCTAATA
ATCATGCAACATACTATGCTGAGTCTGTGAAGGGAGGTTCACCATCTCAAGAGATGATT
CCAAAAGTAGTGTCTACCTGCAAATGACCAGCTTAAGACCTGAAGACACTGGCATTTATT
ACTGTACCCACTTTGACTACTGGGGCCAAGGCACCACTCTCACAGTCTCCTCAGCCAAAA
CGACGGGCCC  SEQ ID NO: 37

FIG. 27

ACGCGTACGCTGAAGTGAAGCTGGTGGAGTCTGGGGGAGGCTTAGTGAAGCCTGGAGGGT
CCCTGAAACTCTCCTGTGCAGCCTCTGGATTCACTTTCAGTAGCTATGGCATGTCTTGGG
TTCGCCAGACTCCGGAGAAGAGGCTGGAGTGGGTCGCAACCATTAGTGGTGGTAATAATT
ACACCTTCTATCCAGACAATTTGAAGGGCGCTTCACCATCTCCAGAGACAATGCCAAGA
ACATCCTGTACCTGCAAATCAGCAGTCTGAGGTCTGTCGACACGGCCTTGTATTACTGTG
CAAGCCTGTGGTACCGCGCCTCGTTTGCTTACTGGGGCCAAGGGACTCTGGTCACCGTCT
CCTCAGCAAAAACGACGGGCCC  SEQ ID NO: 38

FIG. 28

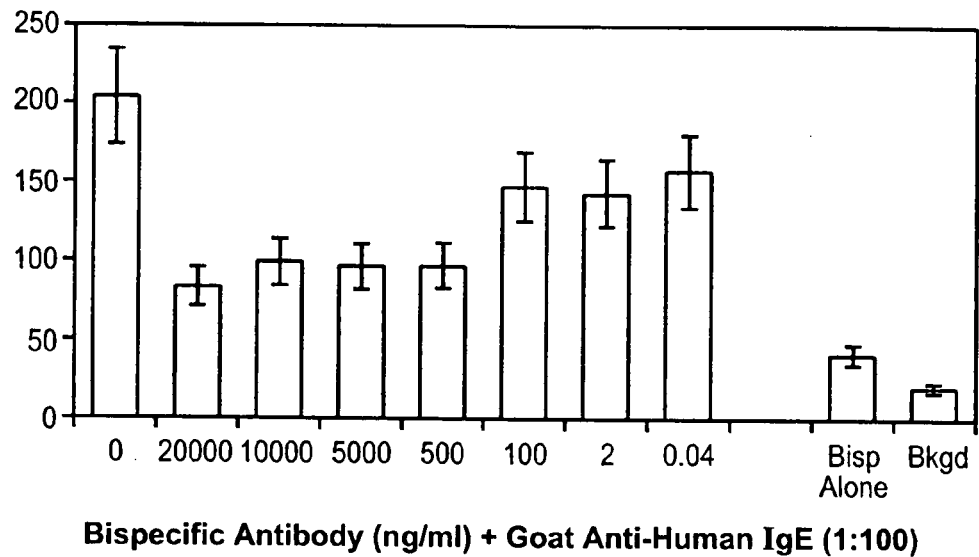
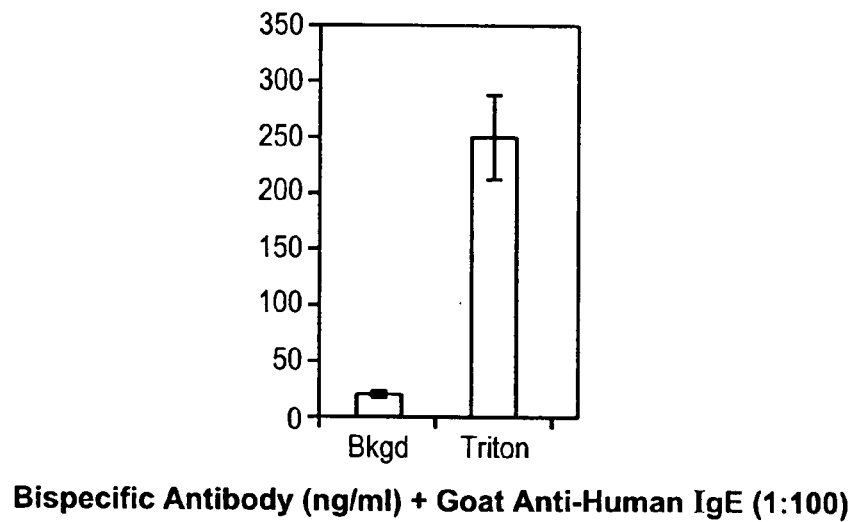
FIG. 62

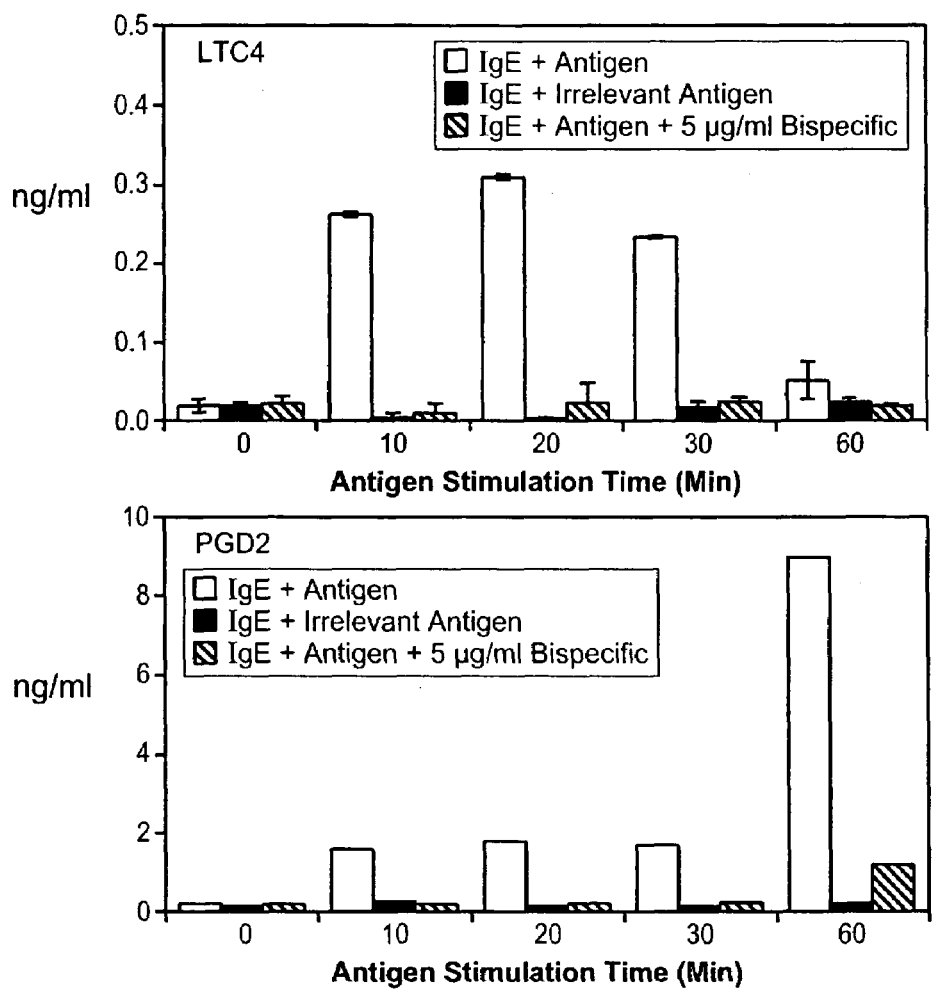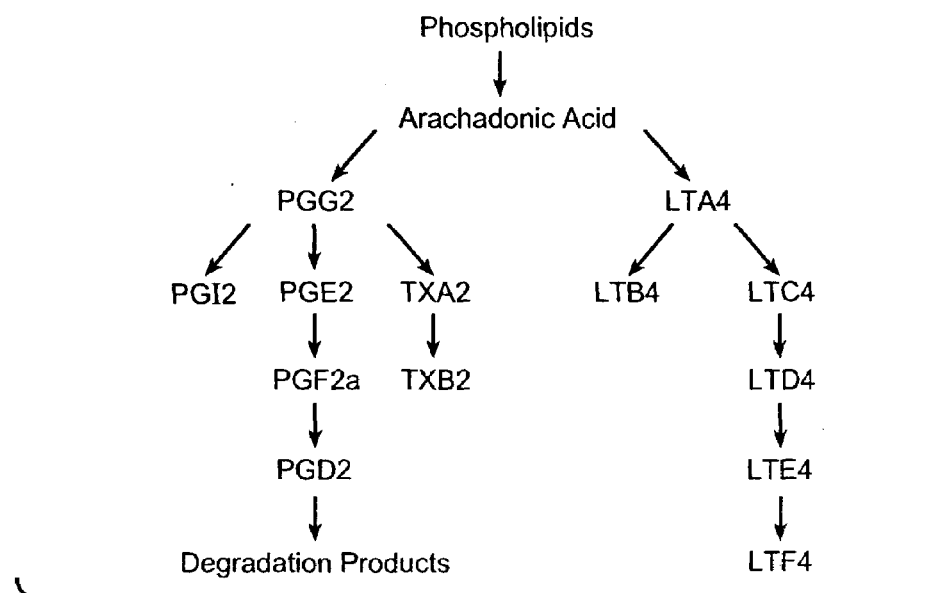
FIG. 65

Fig. 68A
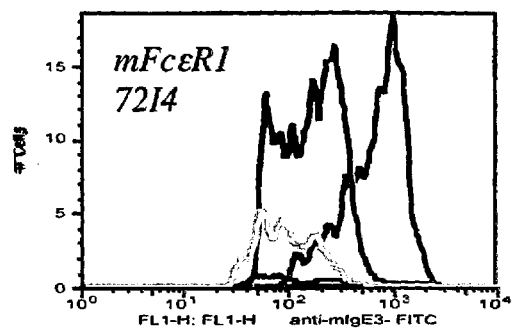
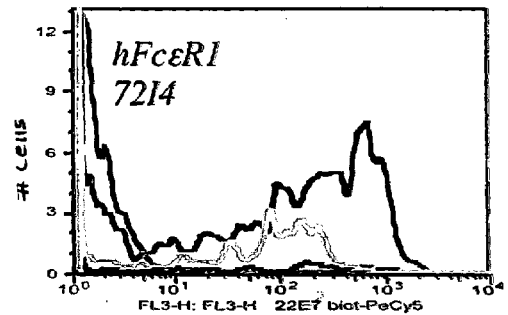
Fig. 68B
red WT    blue 72-I-4.79.258
green 72-I-4.106.274    72-I-4.157.292
Fig. 68C
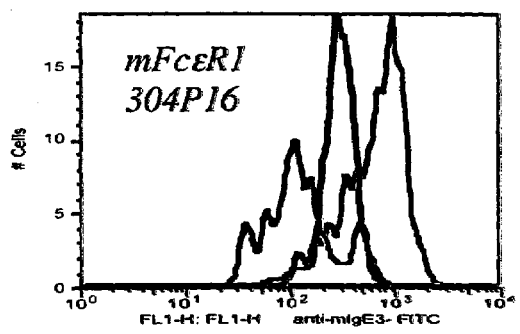
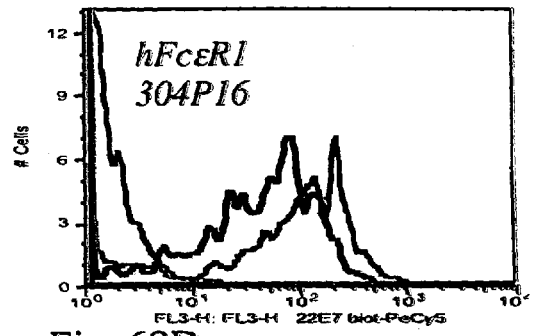
Fig. 68D
red WT    blue 304-P-16.129.231
green 304-P-16.181.223

ANTI-FC-GAMMA RIIB RECEPTOR ANTIBODY AND USES THEREFOR

This application is a continuation-in-part of (1) U.S. Ser. No. 11/624,523, filed Jan. 18, 2007 and a continuation-in-part of (2) U.S. Ser. No. 11/217,995, filed Sep. 1, 2005, now abandoned which claims priority under 35 U.S.C. §119(e) to U.S. Ser. No. 60/606,851, filed Sep. 2, 2004, the entire contents of which applications are hereby incorporated by reference.

FIELD OF THE INVENTION

The present invention pertains to antibodies that preferentially bind human FcγRIIB over human FcγRIIA, as well as uses for those antibodies.

BACKGROUND OF THE INVENTION

An antibody binds to an antigen and neutralizes it by preventing it from binding to its endogenous target (e.g. receptor or ligand) or by inducing effector responses that lead to antigen removal. To efficiently remove and/or destroy antigens foreign to the body, an antibody should exhibit both high affinity for its antigen and efficient effector functions. Antibodies having multispecificities (such as, for example, bispecific antibodies) are useful for mediating complementary or synergistic responses of multiple antigens.

Antibody effector functions are mediated by an antibody Fc region. Effector functions are divided into two categories: (1) effector functions that operate after the binding of antibody to an antigen (these functions involve the participation of the complement cascade or Fc receptor (FcR)-bearing cells); and (2) effector functions that operate independently of antigen binding (these functions confer persistence of antibody in the circulation and its ability to be transferred across cellular barriers by transcytosis). See, for example, Ward and Ghetie, 1995, *Therapeutic Immunology* 2:77-94. Interactions of antibodies and antibody-antigen complexes with cells of the immune system cause such responses as, for example, antibody-dependent cell-mediated cytotoxicity (ADCC) and complement dependent cytotoxicity (CDC) (reviewed in Daëron, 1997, *Annu. Rev. Immunol.* 15:203-234; Ward et al., supra; Ravetch et al., 1991, *Annu. Rev. Immunol.* 9:457-492; and Ravetch et al, 2000, *Science* 290:84-89.

Because Fc receptors mediate antibody effector function by binding to the Fc region of the receptor's cognate antibody, FcRs are defined by their specificity for immunoglobulin isotypes: Fc receptors specific for IgG antibodies are referred to as FcγR; Fc receptors for IgE antibodies are FcεR; Fc receptors for IgA antibodies are FcαR, and so on.

Three subclasses of FcγR have been identified: FcγRI (CD64), FcγRII (CD32), and FcγRIII (CD16). Each FcγR subclass is encoded by two or three genes that undergo alternative RNA spicing, thereby leading to multiple transcripts and the existence of a broad diversity in FcγR isoforms. The three genes encoding the human FcγRI subclass (FcγRIa, FcγRIb, and FcγRIc) are clustered in region 1q21.1 of the long arm of chromosome 1; the genes encoding human FcγRII isoforms (FcγRIIa, FcγRIIb and FcγRIIc) are in region 1q23-24; and the two genes encoding human FcγRIII (FcγRIIIa and FcγRIIIb) are clustered in region 1q22. FcγRIIC is formed from an unequal genetic cross over between FcγRIIA and FcγRIIB, and consists of the extracellular region of FcRIIB and the cytoplasmic region of FcγRIIA.

FcγRIIA encodes a transmembrane receptor FcγRIIA1. Alternative RNA splicing results in FcγRIIA2 that lacks the transmembrane region. Allelic variants of the FcγRIIA gene give rise to high responder (HR) or low responder (LR) molecules that differ in their ability to bind IgG. The HR and LR FcγRIIA molecules differ in two amino acids corresponding to positions 27 and 131. FcγRIIB encodes splice variants FcγRIIB1, FcγRIIB2 and FcγRIIB3. FcγRIIB1 and FcγRIIB2 differ by a 19 amino acid insertion in the cytoplasmic domain of FcγRIIB1; FcγRIIB3 is identical to FcγRIIB2, but lacks information for the putative signal peptidase cleavage site.

The receptors are also distinguished by their affinity for IgG. FcγRI exhibit a high affinity for IgG, $K_a=10^8-10^9 M^{-1}$ (Ravetch et al., 2001, *Ann. Rev. Immunol.* 19:275-290) and can bind monomeric IgG. In contrast, FcγRII and FcγRIII show a relatively weaker affinity for monomeric IgG $K_a \leq 10^7 M^{-1}$ (Ravetch et al., supra), and only interact effectively with multimeric immune complexes. The different FcγR subtypes are expressed on different cell types (reviewed in Ravetch, J. V. et al, *Annu. Rev. Immunol.* 9:457-492). For example, only FcγRIIIA is expressed on NK cells. Binding of antibodies to this receptor leads to ADCC activity typical of NK cells. Human FcγRIIIB is found only on neutrophils, whereas FcγRIIIA is found on macrophages, monocytes, natural killer (NK) cells, and a subpopulation of T-cells. On the other hand, FcγRII receptors with low affinity for monomeric IgG are the most widely distributed FcRs, and are usually co-expressed on the same cells. FcγRII (encoded by CD32) is expressed strongly on B cells, monocytes, granulocytes, mast cells, and platelets, while some T cells express the receptor at lower levels (Mantzioris, B. X. et al., 1993, *J. Immunol.* 150:5175-5184; and Zola, H. et al., 2000, *J. Biol. Regul. Homeost. Agents,* 14:311-316). For example, human FcγRIIB receptor is distributed predominantly on B cells, myeloid cells, and mast cells (Ravetch J. V. and et al., 2000, *Science* 290:84-89).

FcγRIIA and FcγRIIB isoforms contain very similar extracellular domains (approximately 92% amino acid sequence identity) but differ in their cytoplasmic regions, leading to functional differences as "activating receptors" (FcγRIIA) and "inhibitory receptors" (FcγRIIB). FcγRI and FcγRIII receptors also function as activating receptors. These activating receptors contain a 19 amino acid immunoreceptor tyrosine-based activation motif (ITAM) in the cytoplasmic domain. The ITAM sequences trigger activation of src and syk families of tyrosine kinases, which in turn activate a variety of cellular mediators, such as P13K, PLCγ, and Tec kinases. The net result of these activation steps is to increase intracellular calcium release from the endoplasmic reticulum stores and open the capacitance-coupled calcium channel, thereby generating a sustained calcium response. These calcium fluxes are important for the exocytosis of granular contents, stimulation of phagocytosis, ADCC responses, and activation of specific nuclear transcription factors.

Cellular responses mediated by activating FcγRs are regulated by the inhibitory FcγRIIB receptor in the maintenance of peripheral tolerance, regulation of activation response thresholds, and ultimately in terminating IgG mediated effector stimulation (Ravetch, J. V. et al, *Annu. Rev. Immunol.* 19:275-290 (2001)). Such regulation is initiated by crosslinking of activating receptors with inhibiting FcγRIIB receptors via an antigen-IgG antibody immune complex (See, for example, Ravetch, J. V. et al., 2000, supra). Crosslinking of an ITAM-containing activating receptor leads to tyrosine phosphorylation within the 13 amino acid immunoreceptor tyrosine-based inhibition motif (ITIM) in the FcγRIIB cytoplasmic domain. This "activation" of FcγRIIB initiates recruitment of a specific SH2-containing inositol polyphosphate-5-phosphatase (SHIP). SHIP catalyzes the hydrolysis of the membrane inositol lipid PIP3, thereby preventing activation of PLCγ and Tec kinases and abrogating the sustained calcium flux mediated by influx of calcium through the capacitance-coupled channel. While FcγRIIB negatively regulates ITAM-containing activating receptors (Daëron, M. et al., 1995, *Immunity* 3:635-646), it has also been shown to negatively regulate receptor tyrosine kinase (RTK) c-kit in the control of RTK-mediated-mediated cell proliferation (Malbec, O. et al., 1999 *J. Immunol.* 162:4424-4429).

Antibodies that bind FcγRII receptors have been described in: Looney et al., (1986) *J. Immunol.* 136:1641-1647; Zipf et al., (1983) *J. Immunol.* 131:3064-3072; Pulford et al., (1986) *Immunology* 57:71-76; Greenman et al., (1991) *Mol. Immunol.* 28:1243-1254; Ierino et al., (1993) *J. Immunol.* 150: 1794-1803. Weinrich et al., (1996) *Hybridoma*, 15:109-116; Sonderman et al., (1999) *Biochemistry*, 38:8469-8477; Lyden, T. W. et al. (2001) *J. Immunol.* 166:3882-3889; and International Publication No. WO 2004/016750, published Feb. 26, 2004. The high-affinity IgER1 receptor, FcεRI, mediates signaling for antigen induced histamine release upon binding of IgE during, for example, allergic reaction (von Bubnoff, D. et al., (2003) Clinical & Experimental Dermatology. 28(2):184-187). FcγRIIB receptors have been shown to interact with and inhibit the activity of FcδRI through the FcγRIIB ITIM domain (Daeron, M. et al. (1995) J. Clin. Invest. 95:577-585; Malbec, O. et al. (1998) J. Immunol. 160:1647-1658); and Tam, S. W. et al. (2004) Allergy 59:772-780). Antibodies that specifically bind human FcγRIIB are needed, not only for research, but also to manipulate FcγRIIB and FcεRI activity to treat disease.

SUMMARY OF THE INVENTION

The invention provides an antigen binding polypeptide or antibody that selectively binds human FcγRIIB. An antigen binding polypeptide or antibody of the invention binds human FcγRIIB with significantly better affinity than it binds to other human FcγRs, and in some embodiments is essentially unable to cross-react with human FcγRIIA.

In some embodiments, an antigen binding polypeptide or antibody of the invention that selectively binds human FcγRIIB comprises at least one or more CDRs (Antibody Complementarity—determining regions of SEQ ID NOs:1, 2, 3, 4, 5, and 6, and in further embodiments, comprises the heavy chain CDRs of SEQ ID NOs:1, 2, and 3 and/or the light chain CDRs of SEQ ID NO:4, 5, and 6. In further embodiments, an antibody of the invention comprises one or more CDRs which is a variant of one or more of the CDRs of SEQ ID NOs:1, 2, 3, 4, 5, and 6, which variant has at least 80%, at least 85%, at least 90%, at least 95%, at least 97%, at least 98%, or at least 99% amino acid sequence identity with one or more of the CDRs of SEQ ID NOs:1, 2, 3, 4, 5, and 6. In further embodiments, the variant antigen binding polypeptide or antibody binds FcγRIIB with an affinity that is from approximately 10-fold less to approximately at least 2-fold, at least 3 fold, at least 5-fold, at least 10-fold, at least 50-fold greater than the affinity of antibody 5A6 for FcγRIIB, while still being essentially unable to cross-react with human FcγRIIA. In further embodiments, an antigen binding polypeptide or antibody of the invention comprises a heavy chain variable domain of SEQ ID NO:7 and/or a light chain variable domain of SEQ ID NO:8.

In some embodiments, an antigen binding polypeptide or antibody of the invention is a monoclonal antibody, a chimeric antibody or a humanized antibody, or a fragment of a monoclonal, chimeric or humanized antibody. In some embodiments, an antigen binding polypeptide or antibody of the invention, including monoclonal, chimeric, humanized or multispecific antibodies, or fragments thereof, is derived from an antibody produced from a hybridoma cell line having ATCC accession number PTA-4614.

Antigen binding polypeptides or antibodies of the invention are administered with therapeutic antibodies or chemotherapeutic agents in methods of treatment of a disease or disorder treated by the therapeutic antibody or chemotherapeutic agent.

The invention provides isolated bispecific antibodies comprising an antibody or antigen binding polypeptide that selectively binds FcγRIIB, including those described above, and a second antibody or antigen binding polypeptide that specifically binds an activating receptor, such as FcεRI. In some embodiments, bispecific antibodies comprise a variant heavy chain hinge region incapable of inter-heavy chain disulfide linkage.

Bispecific antibodies of the invention are useful in methods of inhibiting immune responses and suppressing histamine release, for example, associated with allergy, asthma, and inflammation. In some embodiments of the invention, bispecific antibodies of the invention are useful for activating FcγRIIB receptor in mammalian cells by coaggregating the FcγRIIB receptor with an activating receptor in a cell. In some embodiments, the mammalian cells are human cells; in further embodiments, the human cells are T cells, B cells, mast cells, basophils, antigen presenting cells, macrophages and/or monocytes. For embodiments involving general ITIM protein-mediated inhibition, such inhibition typically occurs in T cells, B cells, mast cells, basophils, and antigen presenting cells. For embodiments in which inhibition is mediated by FcγRIIB, such inhibition typically occurs in mast cells, basophils, antigen presenting cells, monocytes, macrophage, and B cells. In some embodiments, bispecific antibodies of the invention are useful for inactivating, inhibiting the activity of or downregulating expression of the FcεRI receptor. For embodiments in which FcεRI is inhibited or downregulated, the inhibition or downregulation typically occurs in mammalian mast cells, basophils, and antigen presenting cells.

In an aspect, the invention encompasses a composition comprising an isolated anti-huFcγRIIB/anti-huFcεRI bispecific antibody in a pharmaceutical carrier. In another embodiment, the invention encompasses a composition comprising an isolated anti-huFcγRIIB/anti-huFcεRI bispecific antibody and an isolated anti-IgE antibody. A useful ratio of anti-huFcγRIIB/anti-huFcεRI bispecific antibody to anti-IgE antibody in a combination composition is readily determined for each patient. The ratio is typically within the range from approximately 0.01:1 to 100:1. The antibodies of the composition can be monoclonal, human, humanized, or chimeric antibodies.

In another aspect, the invention encompasses a therapeutic method of treating an immune disorder in a mammal by administering an anti-huFcγRIIB/anti-huFcεRI bispecific antibody. In an embodiment the mammal is a human patient, such as a human patient in need of treatment for an allergic disorder, asthma and/or inflammation. In another embodiment, the therapeutic method further comprises administering to a mammal experiencing an immune disorder, an allergy, asthma, or in need of inhibition of histamine release, the anti-huFcγRIIB/anti-huFcεRI bispecific antibody of the invention. In a still further embodiment, the anti-huFcγRIIB/anti-huFcεRI bispecific antibody of the invention is administered in combination with an anti-IgE antibody, where administration is separate in time or simultaneous. In an embodiment, the anti-IgE antibody is a monoclonal antibody. In a further embodiment, the anti-IgE antibody is Xolair®. In a still further embodiment, the bispecific antibody is administered in combination with the anti-IgE antibody as part of a therapeutic treatment for an ongoing immune disorder (for example, as part of the same therapeutic regimen), where the bispecific antibody is administered separately from (not at the same time as) the anti-IgE antibody. In another embodiment, the bispecific antibody of the invention and an anti-IgE antibody are administered at the same time. A useful ratio of anti-huFcγRIIB/anti-huFcεRI bispecific antibody to anti-IgE antibody in a combination administration (whether administration is performed separate times or at the same time) is readily determined for each patient. For purposes of the invention, the ratio is from approximately 0.01:1 to 100:1 and any useful ratio within that range as determined for a patient. Useful ratios may be, for example, 0.05:1, 0.1:1, 0.5:1, 1:1, 1:0.5, 1:0.1, and 1:0.05, although no useful ratio is excluded which may be determined by standard clinical techniques.

The invention additionally provides isolated nucleic acid encoding the antibody, a vector or host cell comprising that nucleic acid, and a method of making an antibody comprising culturing the host cell and, optionally, further comprising recovering the antibody from the host cell culture (e.g. from the host cell or host cell culture medium).

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 2A is an alignment of the preferred human FcγRIIA (SEQ ID NO:9); human FcγRIIB2 (SEQ ID NO:10) amino acid sequences. FIG. 2B shows the amino acid sequence of FcγRIIB1 (SEQ ID NO:11).

FIG. 3 depicts an alignment of native sequence human antibody Fc region sequences. The sequences are native-sequence human IgG1 (SEQ ID NO:31), non-A allotype; native-sequence human IgG2 (SEQ ID NO:32); native sequence human IgG3 (SEQ ID NO:33); and native-sequence human IgG4 (SEQ ID NO:34).

FIG. 10 depicts the amino acid sequences of light and heavy chains of monoclonal antibody 5A6.2.1.

FIG. 25 depicts a nucleic acid sequence (SEQ ID NO:35) encoding the alkaline phosphatase promoter (phoA), STII signal sequence and the entire (variable and constant domains) light chain of the 5A6 antibody.

FIG. 26 depicts a nucleic acid sequence (SEQ ID NO:36) encoding the alkaline phosphatase promoter (phoA), STII signal sequence and the entire (variable and constant domains) light chain of the 22E7 antibody.

FIG. 27 depicts a nucleic acid sequence (SEQ ID NO:37) encoding the last 3 amino acids of the STII signal sequence and approximately 119 amino acids of the murine heavy variable domain of the 5A6 antibody.

FIG. 28 depicts a nucleic acid sequence (SEQ ID NO:38) encoding the last 3 amino acids of the STII signal sequence and approximately 123 amino acids of the murine heavy variable domain of the 22E7 antibody.

FIG. 62 presents results of an assay in which anti-IgE-induced histamine release in primary human basophils was inhibited by the anti-FcγRIIB-anti-FcεRI bispecific antibody 5A6/22E7.

FIG. 65 presents the results of assays in which IgE/antigen-induced arachidonic acid cascade stimulation in RBL FcεRI+FcγRIIB1 cells was inhibited by the anti-FcγRIIB-anti-FcεRI bispecific antibody 5A6/22E7.

FIG. 67A depicts a map of the human FcεRIα gene and its exons 1-6. A 766 bp probe comprising the sequence of exon 6 was used to probe the gel shown in FIG. 67B showing surface expression of human FcεRIα in cells of transgenic mice injected with human FcεRIα DNA.

FIG. 68 shows representative fluorescent antibody staining of mouse basophils from BAC transgenic founder lines 72-I-4 and 304-P-16 (as indicated) with positive surface expression of human FcεR1α protein.

DETAILED DESCRIPTION

I. Definitions

Figure 1:
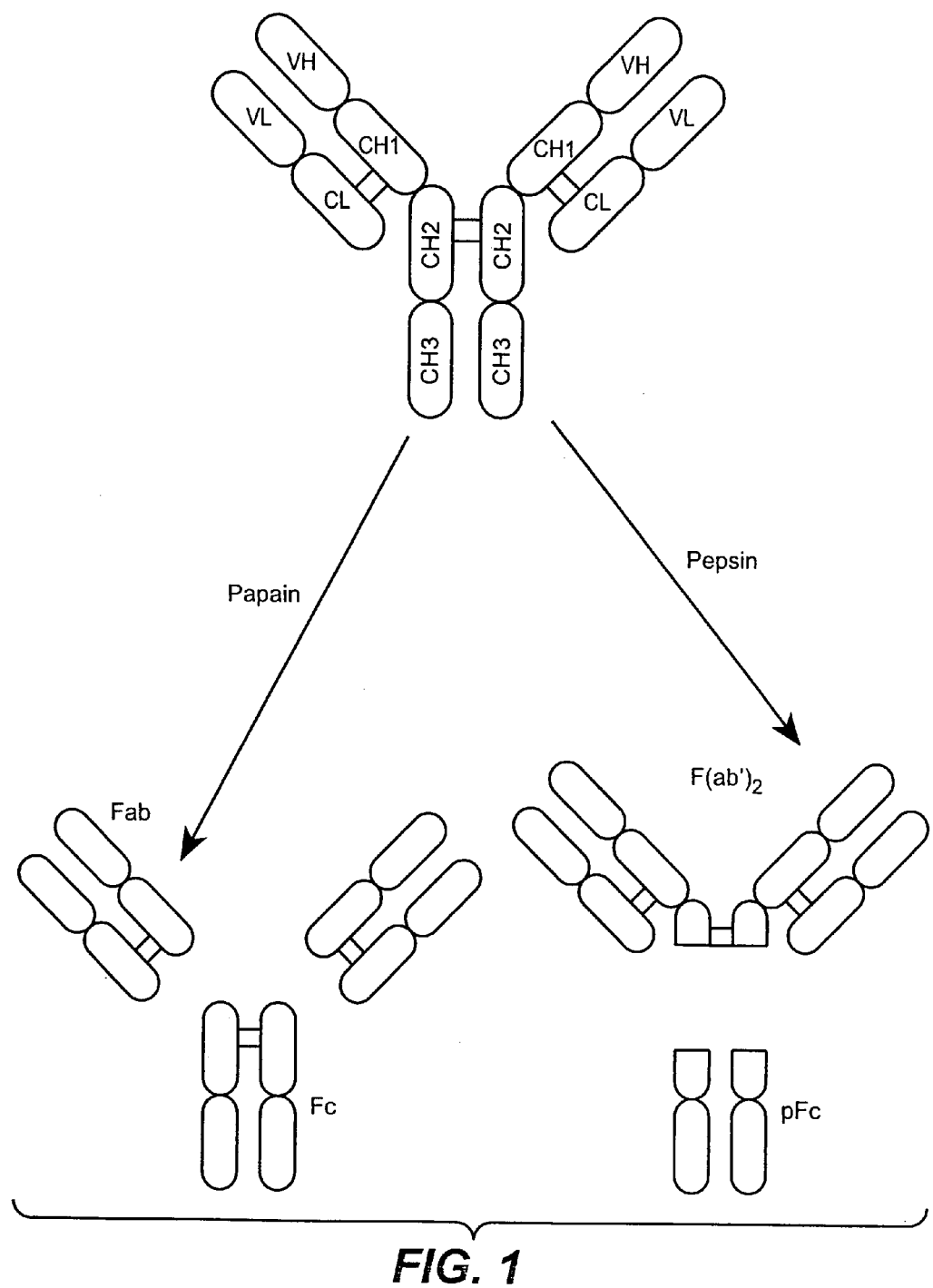
FIG. 1 is a schematic representation of a native IgG. Disulfide bonds are represented by heavy lines between CH1 and $C_L$ domains and the two CH2 domains. V is variable domain; C is constant domain; L stands for light chain and H stands for heavy chain.

Allergy refers to certain diseases in which immune responses to environmental antigens cause tissue inflammation and organ dysfunction. An allergen is any antigen that causes allergy. As such, it can be either the antigenic molecule itself or its source, such as pollen grain, animal dander, insect venom, or food product. IgE plays a central role in allergic disorders. IgE high affinity receptors (FcεRI) are located on mast cells and basophils, which serve as antigenic targets stimulating the further release of inflammatory mediators producing many of the manifestations of allergic disease.

IgE-mediated inflammation occurs when antigen binds to the IgE antibodies that occupy the FcεRI receptor on mast cells. Within minutes, this binding causes the mast cell to degranulate, releasing certain preformed mediators. Subsequently, the degranulated cell begins to synthesize and release additional mediators de novo. The result is a two-phase response: an initial immediate effect on blood vessels, smooth muscle, and glandular secretion (immediate hypersensitivity), followed by a few hours later by cellular infiltration of the involved site. IgE-mediated inflammation is the mechanism underlying atopic allergy (such as hay fever, asthma and atopic dermatitis), systemic anaphylactic reactions and allergic urticaria (hives). It may normally play a role as a first line of immunologic defense, since it causes rapid vasodilation, facilitating entry of circulating soluble factors and cells to the site of antigen contact. Many of the most destructive attributes of allergic disease are due to the actions of the chemoattracted leukocytes.

The terms "antibody" and immunoglobulin are used interchangeably in the broadest sense and include monoclonal antibodies (e.g., full length or intact monoclonal antibodies), polyclonal antibodies, multispecific antibodies (e.g., bispecific antibodies so long as they exhibit the desired biological activity), and may also include certain antibody fragments (as described in greater detail herein), such as, for example, antigen binding polypeptides which polypeptides may be fragments of an antibody. In one embodiment, antibodies and immunoglobulins of the present invention have reduced (fewer) disulfide linkages. In one embodiment, antibodies and immunoglobulins of the invention comprise a hinge region in which at least one cysteine residue is rendered incapable of forming a disulfide linkage, wherein the disulfide linkage is preferably intermolecular, preferably between two heavy chains. A hinge cysteine can be rendered incapable of forming a disulfide linkage by any of a variety of suitable methods known in the art, some of which are described herein, including but not limited to deletion of the cysteine residue or substitution of the cysteine with another amino acid.

Antibodies (immunoglobulins) are assigned to different classes, depending on the amino acid sequences of the heavy chain constant domains. Five major classes of immunoglobulins have been described: IgA, IgD, IgE, IgG and IgM. These may be further divided into subclasses (isotypes), e.g., IgG-1, IgG-2, IgA-1, IgA-2, and the like. The heavy chain constant domains corresponding to each immunoglobulin class are termed $\alpha$, $\delta$, $\epsilon$, $\gamma$ and $\mu$ for IgA, D, E, G, and M, respectively. The subunit structures and three-dimensional configurations of the different classes of immunoglobulins are well known and described generally, for example, in Abbas et al., 2000, *Cellular and Mol. Immunology*, 4th ed. An antibody may be part of a larger fusion molecule, formed by covalent or non-covalent association of the antibody with one or more other protein or peptide.

The terms "full length antibody," "intact antibody" and "whole antibody" are used herein interchangeably, to refer to an antibody in its substantially intact form, and not antibody fragments as defined below. The terms particularly refer to an antibody with heavy chains contains Fc regions. An antibody variant of the invention can be a full length antibody. A full length antibody can be human, humanized, chimeric, and/or affinity matured.

An "affinity matured" antibody is one having one or more alteration in one or more CDRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by known procedures. See, for example, Marks et al., 1992, *Biotechnology* 10:779-783 that describes affinity maturation by variable heavy chain (VH) and variable light chain (VL) domain shuffling. Random mutagenesis of CDR and/or framework residues is described in: Barbas, et al. 1994, *Proc. Nat. Acad. Sci, USA* 91:3809-3813; Shier et al., 1995, *Gene* 169:147-155; Yelton et al., 1995, *J. Immunol.* 155:1994-2004; Jackson et al., 1995, *J. Immunol.* 154(7):3310-9; and Hawkins et al, 1992, *J. Mol. Biol.* 226:889-896, for example.

An "agonist antibody" is an antibody that binds and activates an antigen, such as a receptor. Generally, receptor activation capability of the agonist antibody will be at least qualitatively similar (and may be essentially quantitatively similar) to that of a native agonist ligand of the receptor.

"Antibody fragments" comprise only a portion of an intact antibody, where the portion retains at least one, and may retain most or all, of the functions normally associated with that portion when present in an intact antibody. An antibody fragment of the invention may comprise a sufficient portion of the constant region to permit dimerization (or multimerization) of heavy chains that have reduced disulfide linkage capability, for example where at least one of the hinge cysteines normally involved in inter-heavy chain disulfide linkage is altered as described herein. In one embodiment, an antibody fragment comprises an antigen binding site or variable domains of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function, and/or complement binding (for example, where the antibody has a glycosylation profile necessary for ADCC function or complement binding). Examples of antibody fragments include linear antibodies; single-chain antibody molecules; and multispecific antibodies formed from antibody fragments.

"Antibody-dependent cell-mediated cytotoxicity" and "ADCC" refer to a cell-mediated reaction in which nonspecific cytotoxic cells that express FcRs (such as Natural Killer (NK) cells, neutrophils, and macrophages) recognize bound antibody on a target cell and subsequently cause lysis of the target cell. NK cells, the primary cells for mediating ADCC, express only FcγRIII, whereas monocytes express FcγRI, FcγRII, and FcγRIII. FcR expression on hematopoietic cells is summarized in Table 3 on page 464 of Ravetch et al., 1991, *Annu. Rev. Immunol* 9:457-92. To assess ADCC activity of a molecule of interest, an in vitro ADCC assay such as that described in U.S. Pat. No. 5,500,362 or U.S. Pat. No. 5,821, 337 may be performed. Useful effector cells for such assays include peripheral blood mononuclear cells (PBMC) and Natural Killer (NK) cells. Alternatively, or additionally, ADCC activity of the molecule of interest may be assessed in vivo, for example, in a animal model such as that disclosed in Clynes et al., 1998, PNAS (USA) 95:652-656.

An "antibody-immunoadhesin chimera" comprises a molecule which combines at least one binding domain of an antibody (as herein defined) with at least one immunoadhesin (as defined in this application). Exemplary antibody-immunoadhesin chimeras are the bispecific CD4-IgG chimeras described in Berg et al., 1991, *PNAS (USA)* 88:4723- and Chamow et al., 1994, *J. Immunol.* 153:4268.

An "autoimmune disease" as used herein is a non-malignant disease or disorder arising from and directed against an individual's own tissues. The autoimmune diseases described herein specifically exclude malignant or cancerous diseases or conditions, particularly excluding B cell lymphoma, acute lymphoblastic leukemia (ALL), chronic lymphocytic leukemia (CLL), Hairy cell leukemia, and chronic myeloblastic leukemia. Examples of autoimmune diseases or disorders include, but are not limited to, inflammatory responses such as inflammatory skin diseases including psoriasis and dermatitis (for example, atopic dermatitis); systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); diabetes mellitus (e.g. Type I diabetes mellitus or insulin dependent diabetes mellitus); multiple sclerosis; Reynaud's syndrome; autoimmune thyroiditis; allergic encephalomyelitis; Sjorgen's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Behcet disease; giant cell arteritis; immune complex nephritis; IgA nephropathy; IgM polyneuropathies; immune thrombocytopenic purpura (ITP) or autoimmune thrombocytopenia etc.

A "biologically active" or "functional" immunoglobulin is one capable of exerting one or more of its natural activities in structural, regulatory, biochemical or biophysical events. For example, a biologically active antibody may have the ability to specifically bind an antigen and the binding may elicit or alter a cellular or molecular event such as signaling transduction or enzymatic activity. A biologically active antibody may also block ligand activation of a receptor or act as an agonist antibody. The capability of an antibody to exert one or more of its natural activities depends on several factors, including proper folding and assembly of the polypeptide chains.

"Binding affinity" generally refers to the strength of the sum total of noncovalent interactions between a single binding site of a molecule (e.g., an antibody) and its binding partner (e.g., an antigen or FcRn receptor). The affinity of a molecule X for its partner Y can generally be represented by the dissociation constant (Kd). Affinity can be measured by common methods known in the art, including those described herein. Low-affinity antibodies bind antigen (or FcRn receptor) weakly and tend to dissociate readily, whereas high-affinity antibodies bind antigen (or FcRn receptor) more tightly and remain bound longer.

A "blocking" antibody or an "antagonist" antibody is one that inhibits or reduces biological activity of the antigen it binds. Such blocking can occur by any means, for example, by interfering with: ligand binding to the receptor, receptor complex formation, tyrosine kinase activity of a tyrosine kinase receptor in a receptor complex and/or phosphorylation of tyrosine kinase residue(s) in or by the receptor. For example, an FcγRIIB antagonist antibody binds FcγRIIB and inhibits the ability of IgG to bind FcγRIIB thereby inhibiting immune effector response. Preferred blocking antibodies or antagonist antibodies substantially or completely inhibit the biological activity of the antigen.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, and various types of head and neck cancer.

The term "chimeric" antibodies refer to antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (See, for example, U.S. Pat. No. 4,816,567 and Morrison et al., 1984, Proc. Natl. Acad. Sci. USA 81:6851-6855).

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

A "disorder" is any condition that would benefit from treatment with a therapeutic antibody. This includes chronic and acute disorders or diseases including those pathological conditions which predispose the mammal to the disorder in question. In one embodiment, the disorder is cancer or an autoimmune disease.

An "extracellular domain" is defined herein as that region of a transmembrane polypeptide, such as an FcR, that is external to a cell.

The terms "Fc receptor" or "FcR" are used to describe a receptor that binds to the Fc region of an antibody. The preferred FcR is a native sequence human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. Other FcRs, including those to be identified in the future, are encompassed by the term "FcR" herein. The term also includes the neonatal receptor, FcRn, that is responsible for the transfer of maternal IgGs to the fetus (See Guyer et al., 1976, *J. Immunol.* 117:587 and Kim et al., 1994, *J. Immunol.* 24:249).

The term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226 or from Pro230, to the carboxyl-terminus thereof. The Fc region of an immunoglobulin generally comprises two constant domains, CH2 and CH3, as shown in FIG. 1. A "functional Fc region" possesses an "effector function" of a native sequence Fc region. Exemplary "effector functions" include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), and the like. Such effector functions generally require the Fc region to be combined with a binding domain (e.g. an antibody variable domain) and can be assessed using various assays as, for example, those disclosed herein. A "native sequence Fc region" comprises an amino acid sequence identical to the amino acid sequence of a Fc region found in nature. Native sequence human Fc regions are shown in FIG. 3 and include a native sequence human IgG1 Fc region (non-A and A allotypes); native sequence human IgG2 Fc region; native sequence human IgG3 Fc region; and native sequence human IgG4 Fc region as well as naturally occurring variants thereof. A "variant Fc region" comprises an amino acid sequence that differs from a native sequence Fc region by virtue of at least one "amino acid modification" as herein defined. The variant Fc region can have at least one amino acid substitution compared to a native sequence Fc region or to the Fc region of a parent antibody, and may have, for example, from about one to about ten amino acid substitutions, or from about one to about five amino acid substitutions in a native sequence Fc region or in the Fc region of the parent antibody. The variant Fc region can possess at least about 80% identity with a native sequence Fc region and/or with an Fc region of a parent antibody, and may have at least about 90% identity therewith, or have at least about 95% identity therewith.

The term "FcγRIIA", unless otherwise indicated, refers to human FcγRIIA (huFcγRIIA), a polypeptide encoded by the human FcγRIIa gene and, includes, but is not limited to, FcγRIIA1 and FcγRIIA2, and allelic variants thereof. The Human FcγRIIA is an "activating" FcR and contains an immunoreceptor tyrosine-based activation motif (ITAM) in a cytoplasmic domain thereof. The most preferred human FcγRIIA is human FcRIIA1 comprising the amino acid sequence of SEQ ID NO:9 or allelic variants thereof, including high responder (HR) and low responder (LR) allelic variants thereof.

The term "FcγRIIB", unless otherwise indicated, refers to a polypeptide encoded by the human FcRIIB gene, and includes, but is not limited to, FcγRIIB1, FcγRIIB2, FcγRIIB3, and allelic variants thereof. The preferred FcγRIIB is an "inhibiting" FcR receptor that contains an immunoreceptor tyrosine-based inhibition motif (ITIM) (I/V/LxYxxL/V) (Sathish, et al., 2001, *J. Immunol.* 166, 1763) in a cytoplasmic domain thereof. The preferred human FcγRIIB is human FcγRIIB2 (huFcγRIIB2) or FcγRIIB (huFcγRIIB1) having the amino acid sequence of SEQ ID NO:10, or SEQ ID NO:11, respectively, and allelic variants thereof. The FcγRIIB1 and B2 sequences differ from each other in a 19 amino acid sequence insertion in the cytoplasmic domain of FcγRIIB1, LPGYPECREMGETLPEKPA (SEQ ID NO:29).

An "FcR dependent condition" as used herein includes type II inflammation, IgE-mediated allergy, asthma, anaphylaxis, autoimmune disease, IgG-mediated cytotoxicity, or a rash.

A "hinge region," and variations thereof, as used herein, includes the meaning known in the art, which is illustrated in, for example, Janeway et al., 1999, *Immuno Biology: The Immune System in Health and Disease*, Elsevier Science Ltd., NY. 4th ed.; Bloom et al., 1997, *Protein Science*, 6:407-415; Humphreys et al., 1997, *J. Immunol. Methods*, 209:193-202.

"Homology" is defined as the percentage of residues in the amino acid sequence variant that are identical after aligning the sequences and introducing gaps, if necessary, to achieve the maximum percent homology. Methods and computer programs for the alignment are well known in the art. One such computer program is "Align 2," authored by Genentech, Inc., and filed with user documentation in the United States Copyright Office, Washington, D.C. 20559, on Dec. 10, 1991.

The term "host cell" (or "recombinant host cell"), as used herein, refers to a cell that has been genetically altered, or is capable of being genetically altered, by introduction of an exogenous polynucleotide, such as a recombinant plasmid or vector. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

"Human effector cells" are leukocytes that express one or more FcRs and perform effector functions. Preferably, the cells express at least FcγRIII and perform ADCC effector function. Examples of human leukocytes that mediate ADCC include peripheral blood mononuclear cells (PBMC), natural killer (NK) cells, monocytes, cytotoxic T cells, and neutrophils; with PBMCs and NK cells being preferred. The effector cells may be isolated from a native source, for example, from blood or PBMCs (Peripheral blood mononuclear cells) as described herein.

"Humanized" forms of non-human (for example, murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332: 323-329 (1988); and Presta, *Curr. Op. Struct. Biol.* 2:593-596 (1992).

A "human antibody" is an antibody that possesses an amino acid sequence corresponding to that of an antibody produced by a human and/or has been made using any of the techniques for making human antibodies disclosed herein. This definition specifically excludes a humanized antibody that comprises non-human antigen-binding residues.

As used herein, the term "hyperglycemic disorders" refers to all forms of diabetes and disorders resulting from insulin resistance, such as Type I and Type II diabetes, as well as severe insulin resistance, hyperinsulinemia, and hyperlipidemia, e.g., obese subjects, and insulin-resistant diabetes, such as Mendenhall's Syndrome, Werner Syndrome, leprechaunism, lipoatrophic diabetes, and other lipoatrophies. A particular hyperglycemic disorder disclosed herein is diabetes, especially Type 1 and Type II diabetes. "Diabetes" itself refers to a progressive disease of carbohydrate metabolism involving inadequate production or utilization of insulin and is characterized by hyperglycemia and glycosuria.

The term "hypervariable region," as used herein, refers to the amino acid residues of an antibody which are responsible for antigen-binding. The hypervariable region comprises amino acid residues from a "complementarity determining region" or "CDR," defined by sequence alignment, for example residues 24-34 (L1), 50-56 (L2) and 89-97 (L3) in the light chain variable domain and 31-35 (H1), 50-65 (H2) and 95-102 (H3) in the heavy chain variable domain; see Kabat et al., 1991, *Sequences of Proteins of Immunological Interest,* 5th Ed. Public Health Service, National Institutes of Health, Bethesda, Md. and/or those residues from a "hypervariable loop" (HVL), as defined structurally, for example, residues 26-32 (L1), 50-52 (L2) and 91-96 (L3) in the light chain variable domain and 26-32 (H1), 53-55 (H2) and 96-101 (H3) in the heavy chain variable domain; see Chothia and Leskl, 1987, *J. Mol. Biol.* 196:901-917. "Framework" or "FR" residues are those variable domain residues other than the hypervariable region residues as herein defined.

Immune and inflammatory diseases include: rheumatoid arthritis, osteoarthritis, juvenile chronic arthritis, spondyloarthropathies, systemic sclerosis (scleroderma), idiopathic inflammatory myopathies (dermatomyositis), systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis) autoimmune inflammatory diseases (e.g., allergic encephalomyelitis, multiple sclerosis, insulin-dependent diabetes mellitus, autoimmune uveoretinitis, thyrotoxicosis, autoimmune thyroid disease, pernicious anemia, autograft rejection, diabetes mellitus, and immune-mediated renal disease (glomerulonephritis, tubulointerstitial nephritis)), demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, vernal conjunctivitis, eczema, food hypersensitivity and urticaria; immunologic diseases of the lung such as eosinophilic pneumonia, idiopathic pulmonary fibrosis and hypersensitivity pneumonitis; transplantation associated disease including graft rejection and graft-versus-host-disease;

As used herein, the term "immunoadhesin" designates antibody-like molecules that combine the "binding-domain" of a heterologous "adhesin" protein (for example, a receptor, ligand, or enzyme) with the effector functions of an immunoglobulin constant domain. Structurally, the immunoadhesins comprise a fusion of the adhesin amino acid sequence with the desired binding specificity that is other than the antigen recognition and binding site (antigen combining site) of an antibody (i.e. is "heterologous") and an immunoglobulin constant domain sequence. The immunoglobulin constant domain sequence in the immunoadhesin is preferably derived from γ1, γ2, or γ4 heavy chains, since immunoadhesins comprising these regions can be purified by Protein A chromatography. See, for example, Lindmark et al., 1983, *J. Immunol. Meth.* 62:1-13.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In some embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The term "mammal" includes any animals classified as mammals, including humans, cows, horses, dogs, and cats. In one embodiment of the invention, the mammal is a human.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., 1975, *Nature* 256:495, or may be made by recombinant DNA methods (see, for example, U.S. Pat. No. 4,816,567). The "monoclonal antibodies" may also be isolated from phage antibody libraries using the techniques described in Clackson et al., 1991, *Nature* 352:624-628 and Marks et al., 1991, *J. Mol. Biol.* 222:581-597, for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., 1984, *Proc. Natl. Acad. Sci. USA* 81:6851-6855).

A nucleic acid is "operably linked," as used herein, when it is placed into a functional relationship with another nucleic acid sequence. For example, DNA for a presequence or secretory leader is operably linked to DNA for a antibody if it is expressed as a preprotein that participates in the secretion of the antibody; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, an enhancer may not have to be contiguous. Linking is accomplished by ligation at convenient restriction sites. If such sites do not exist, synthetic oligonucleotide adaptors or linkers are used in accordance with conventional practice.

For the purposes herein, a "pharmaceutical composition" is one that is adapted and suitable for administration to a mammal, especially a human. Thus, the composition can be used to treat a disease or disorder in the mammal. Moreover, the protein in the composition has been subjected to one or more purification or isolation steps, such that contaminant(s) that might interfere with its therapeutic use have been separated therefrom. Generally, the pharmaceutical composition comprises the therapeutic protein and a pharmaceutically acceptable carrier or diluent. The composition is usually sterile and may be lyophilized. Pharmaceutical preparations are described in more detail below.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs, and abasic nucleoside analogs such as methyl riboside. One or more phosphodiester linkage may be replaced by alternative linking groups. These alternative linking groups include, but are not limited to, embodiments wherein phosphate is replaced by P(O)S ("thioate"), P(S)S ("dithioate"), "(O)NR2 ("amidate"), P(O)R, P(O)OR', CO or CH2 ("formacetal"), in which each R or R' is independently H or substituted or unsubstituted alkyl (1-20 C.) optionally containing an ether (-0-) linkage, aryl, alkenyl, cycloalkyl, cycloalkenyl, or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

"Secretion signal sequence" or "signal sequence" refers to a nucleic acid sequence encoding a short signal peptide that can be used to direct a newly synthesized protein of interest through a cellular membrane, usually the inner membrane or both inner and outer membranes of prokaryotes. As such, the protein of interest such as the immunoglobulin light or heavy chain polypeptide is secreted into the periplasm of the prokaryotic host cells or into the culture medium. The signal peptide encoded by the secretion signal sequence may be endogenous to the host cells, or they may be exogenous, including signal peptides native to the polypeptide to be expressed. Secretion signal sequences are typically present at the amino terminus of a polypeptide to be expressed, and are typically removed enzymatically between biosynthesis and secretion of the polypeptide from the cytoplasm. Thus, the signal peptide is usually not present in a mature protein product.

The term "receptor binding domain" is used to designate any native ligand for a receptor, including cell adhesion molecules, or any region or derivative of such native ligand retaining at least a qualitative receptor binding ability of a corresponding native ligand. This definition, among others, specifically includes binding sequences from ligands for the above-mentioned receptors.

As used herein, a "therapeutic antibody" is an antibody that is effective in treating a disease or disorder in a mammal with or predisposed to the disease or disorder. Exemplary therapeutic antibodies include the 5A6 anti-FcγRIIB antibody of the invention and the bispecific anti-FcγRIIB/anti-FcεRI antibody of the invention, as well as antibodies including rhuMAb 4D5 (HERCEPTIN®) (Carter et al., 1992, *Proc. Natl. Acad. Sci. USA,* 89:4285-4289, U.S. Pat. No. 5,725,856); anti-CD20 antibodies such as chimeric anti-CD20 "C2B8" as in U.S. Pat. No. 5,736,137 (RITUXAN®), a chimeric or humanized variant of the 2H7 antibody as in U.S. Pat. No. 5,721,108, B1 or Tositumomab (BEXXAR®); anti-IL-8 (St John et al., 1993, *Chest,* 103:932, and International Publication No. WO 95/23865); anti-VEGF antibodies including humanized and/or affinity matured anti-VEGF antibodies such as the humanized anti-VEGF antibody huA4.6.1 AVASTIN™ (Kim et al., 1992, *Growth Factors,* 7:53-64, International Publication No. WO 96/30046, and WO 98/45331, published Oct. 15, 1998); anti-PSCA antibodies (WO01/40309); anti-CD40 antibodies, including S2C6 and humanized variants thereof (WO00/75348); anti-CD11a (U.S. Pat. No. 5,622,700, WO 98/23761, Steppe et al., 1991, *Transplant Intl.* 4:3-7, and Hourmant et al., 1994, *Transplantation* 58:377-380); anti-IgE (Presta et al., 1993, *J. Immunol.* 151:2623-2632, and International Publication No. WO 95/19181); anti-CD18 (U.S. Pat. No. 5,622,700, issued Apr. 22, 1997, or as in WO 97/26912, published Jul. 31, 1997); anti-IgE (U.S. Pat. No. 5,714,338, issued Feb. 3, 1998 or U.S. Pat. No. 5,091,313, issued Feb. 25, 1992, WO 93/04173 published Mar. 4, 1993, or International Application No. PCT/US98/13410 filed Jun. 30, 1998, U.S. Pat. No. 5,714,338); anti-Apo-2 receptor antibody (WO 98/51793 published Nov. 19, 1998); anti-TNF-α antibodies including cA2 (REMICADE®), CDP571 and MAK-195 (See, U.S. Pat. No. 5,672,347 issued Sep. 30, 1997, Lorenz et al. 1996, *J. Immunol.* 156(4): 1646-1653, and Dhainaut et al. 1995, *Crit. Care Med.* 23(9):1461-1469); anti-Tissue Factor (TF) (European Patent No. 0 420 937 B1 granted Nov. 9, 1994); anti-human $\alpha_4$-$\beta_7$ integrin (WO 98/06248 published Feb. 19, 1998); anti-EGFR (chimerized or humanized 225 antibody as in WO 96/40210 published Dec. 19, 1996); anti-CD3 antibodies such as OKT3 (U.S. Pat. No. 4,515,893 issued May 7, 1985); anti-CD25 or anti-tac antibodies such as CHI-621 (SIMULECT®) and (ZENAPAX®) (See U.S. Pat. No. 5,693,762 issued Dec. 2, 1997); anti-CD4 antibodies such as the cM-7412 antibody (Choy et al. 1996, *Arthritis Rheum* 39(1):52-56); anti-CD52 antibodies such as CAMPATH-1H (Riechmann et al. 1988, *Nature* 332:323-337; anti-Fc receptor antibodies such as the M22 antibody directed against FcγRI as in Graziano et al. 1995, *J. Immunol.* 155(10):4996-5002; anti-carcinoembryonic antigen (CEA) antibodies such as hMN-14 (Sharkey et al. 1995, *Cancer Res.* 55(23Suppl): 5935s-5945s; antibodies directed against breast epithelial cells including huBrE-3, hu-Mc 3 and CHL6 (Ceriani et al. 1995, *Cancer Res.* 55(23): 5852s-5856s; and Richman et al. 1995, *Cancer Res.* 55(23 Supp): 5916s-5920s); antibodies that bind to colon carcinoma cells such as C242 (Litton et al. 1996, *Eur J. Immunol.* 26(1): 1-9); anti-CD38 antibodies, e.g. AT 13/5 (Ellis et al. 1995, *J. Immunol.* 155(2):925-937); anti-CD33 antibodies such as Hu M195 (Jurcic et al. 1995, *Cancer Res* 55(23 Suppl):5908s-5910s and CMA-676 or CDP771; anti-CD22 antibodies such as LL2 or LymphoCide (Juweid et al. 1995, *Cancer Res* 55(23 Suppl):5899s-5907s; anti-EpCAM antibodies such as 17-IA (PANOREX®); anti-GpIIb/IIIa antibodies such as abciximab or c7E3 Fab (REOPRO®); anti-RSV antibodies such as MEDI-493 (SYNAGIS®); anti-CMV antibodies such as PROTOVIR®; anti-HIV antibodies such as PRO542; anti-hepatitis antibodies such as the anti-Hep B antibody OSTAVIR®; anti-CA 125 antibody OvaRex; anti-idiotypic GD3 epitope antibody BEC2; anti-αvβ3 antibody VITAXIN®; anti-human renal cell carcinoma antibody such as ch-G250; ING-1; anti-human 17-IA antibody (3622W94); anti-human colorectal tumor antibody (A33); anti-human melanoma antibody R24 directed against GD3 ganglioside; anti-human squamous-cell carcinoma (SF-25); and anti-human leukocyte antigen (HLA) antibodies such as Smart ID10 and the anti-HLA DR antibody Oncolym (Lym-1).

The term "therapeutically effective amount" refers to an amount of a composition of this invention effective to "alleviate" or "treat" a disease or disorder in a subject or mammal. In one embodiment, if the immune-disease to be treated is a B-cell mediated disease, it is an amount that results in the reduction in the number of B cells (B cell depletion) in the mammal.

"Treatment" refers to use of this invention effective to "treatment" or "treat" a disease or disorder in a subject or mammal. Generally, treatment of a disease or disorder involves the lessening of one or more symptoms or medical problems associated with the disease or disorder. In some embodiments, antibodies and compositions of this invention can be used to prevent the onset or reoccurrence of the disease or disorder in a subject or mammal. For example, in a subject with autoimmune disease, an antibody of this invention can be used to prevent or treat flare-ups. Consecutive treatment or administration refers to treatment on at least a daily basis without interruption in treatment by one or more days. Intermittent treatment or administration, or, treatment or administration in an intermittent fashion, refers to treatment that is not consecutive, but rather cyclic in nature. The treatment regime herein may be either consecutive or intermittent.

A "variant" or "altered" heavy chain, as used herein, generally refers to a heavy chain with reduced disulfide linkage capability, for e.g., wherein at least one cysteine residue has been rendered incapable of disulfide linkage formation. Preferably, said at least one cysteine is in the hinge region of the heavy chain.

The term "vector," as used herein, is intended to refer to a nucleic acid molecule capable of transporting another nucleic acid to which it has been linked. One type of vector is a "plasmid", a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (for example, bacterial vectors having a bacterial origin of replication and episomal mammalian vectors). Other vectors (for example, non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

An antibody that "selectively binds human FcγRIIB" binds to human FcγRIIB with significantly better affinity than it binds to other human FcγRs. In some embodiments, an antibody that selectively binds human FcγRIIB, binds both FcγRIIB1 and FcγRIIB2 and demonstrates little or no binding to FcγRIIA, FcγRI and FcγRIII, and allelic variants thereof. The relative binding and/or binding affinity may be demonstrated in a variety of methods accepted in the art including, but not limited to: enzyme linked immunosorbent assay (ELISA) and fluorescence activated cell sorting (FACS).

Generally, this means that the antibody of the invention binds FcγRIIB with at least about 1 log higher concentration reactivity than it binds FcγRIIA, as determined for an ELISA. Preferably, the antibody that binds human FcγRIIB selectively over human FcγRIIA is essentially unable to cross-react with human FcγRIIA.

As used herein, an antibody that is "essentially unable to cross-react with human FcγRIIA" is one in which the extent of binding to human FcγRIIA will be less than 10% of the level of FcγRIIB binding, alternatively less than 8%, alternatively less than 6%, alternatively less than 4%, alternatively less than 2%, alternatively less than 1% binding to human FcγRIIA relative to binding to FcγRIIB as determined by fluorescence activated cell sorting (FACS) analysis or radioimmunoprecipitation assay (RIA).

As used herein, an antibody that "antagonizes binding of an Fc region to human FcγRIIB" blocks or interferes with the binding of an Fc region (for example, the Fc region of an antibody, such as IgG, or immunoadhesin, or other Fc containing construct) to human FcγRIIB. Such antagonistic activity may be determined, for example, by ELISA.

II. Modes for Carrying Out the Invention

A. Production of the Anti-FcγRIIB Antibody (i) FcγRIIB Antigen

Soluble human FcγRIIB or fragments thereof, optionally conjugated to other molecules, can be used as immunogens for generating antibodies. Example immunogens include fusion proteins comprising an extracellular domain of FcγRIIB1 or FcγRIIB2 with a carrier protein or affinity tag such as GST or $His_6$. Alternatively, or additionally, cells expressing human FcγRIIB can be used as the immunogen. Such cells can be derived from a natural source or may be cells that have been transformed by recombinant techniques to express human FcγRIIB. Other forms of human FcγRIIB useful for preparing antibodies will be apparent to those in the art.

(ii) Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, for example, 100 μg or 5 μg of the protein or conjugate (for rabbits or mice, respectively) with 3 volumes of Freund's complete adjuvant and injecting the solution intradermally at multiple sites. Approximately one month later, the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(iii) Monoclonal Antibodies

Monoclonal antibodies may be made using the hybridoma method first described by Kohler et al., 1975, *Nature,* 256: 495, or may be made by recombinant DNA methods (See, for example, U.S. Pat. No. 4,816,567).

In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, 1986, *Monoclonal Antibodies: Principles and Practice,* pp. 59-103 (Academic Press)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, 1984, *J. Immunol.,* 133:3001; Brodeur et al., 1987, *Monoclonal Antibody Production Techniques and Applications,* pp. 51-63 (Marcel Dekker, Inc., New York)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA; Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

In a further embodiment, antibodies or antibody fragments can be isolated from antibody phage libraries generated using the techniques described in McCafferty et al., 1990, *Nature,* 348:552-554. Clackson et al., 1991, *Nature,* 352:624-628, and Marks et al., 1991, *J. Mol. Biol.,* 222:581-597 describe the isolation of murine and human antibodies, respectively, using phage libraries. Subsequent publications describe the production of high affinity (nM range) human antibodies by chain shuffling (Marks et al., 1992, *Bio/Technology,* 10:779-783), as well as combinatorial infection and in vivo recombination as a strategy for constructing very large phage libraries (Waterhouse et al., 1993, *Nuc. Acids. Res.,* 21:2265-2266). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., 1984, *Proc. Natl. Acad. Sci. USA,* 81:6851), or by covalently joining to the immunoglobulin coding sequence all or part of the coding sequence for non-immunoglobulin material (e.g., protein domains).

Typically such non-immunoglobulin material is substituted for the constant domains of an antibody, or is substituted for the variable domains of one antigen-combining site of an antibody to create a chimeric bivalent antibody comprising one antigen-combining site having specificity for an antigen and another antigen-combining site having specificity for a different antigen.

(iv) Humanized and Human Antibodies

A humanized antibody has one or more amino acid residues from a source that is non-human. The non-human amino acid residues are often referred to as "import" residues, and are typically taken from an "import" variable domain. Humanization can be performed generally following the method of Winter and co-workers (Jones et al., 1986, *Nature,* 321:522-525; Riechmann et al., 1988, *Nature,* 332:323-327; Verhoeyen et al., 1988, *Science,* 239:1534-1536), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in non-human, for example, rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., 1987, *J. Immunol.,* 151:2296; Chothia et al., 1987, *J. Mol. Biol.,* 196:901). Another method uses a particular framework derived from the consensus sequence of all human antibodies of a particular subgroup of light or heavy chains. The same framework may be used for several different humanized antibodies (Carter et al., 1992, *Proc. Natl. Acad. Sci. USA,* 89:4285; Presta et al., 1993, *J. Immunol.,* 151:2623).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., 1993, *Proc. Natl. Acad. Sci. USA,* 90:2551; Jakobovits et al., 1993, *Nature,* 362:255-258; Bruggermann et al., 1993, *Year in Immuno.,* 7:33; and Duchosal et al., 1992, *Nature* 355:258. Human antibodies can also be derived from phage-display libraries (Hoogenboom et al., 1991, *J. Mol. Biol.,* 227:381; Marks et al., *J. Mol. Biol.,* 1991, 222:581-597; Vaughan et al., 1996, *Nature Biotech* 14:309).

(v) Multispecific Antibodies

Multispecific antibodies have binding specificities for at least two different antigens. While such molecules normally will only bind two antigens (i.e. bispecific antibodies, BsAbs), antibodies with additional specificities such as trispecific antibodies are encompassed by this expression when used herein. Examples of BsAbs include those with one antigen binding site directed against FcγRIIB and another antigen binding site directed against, for example: B-cell receptor (BCR), CD79α and/or CD79β, an antigen expressed on a tumor cell, IgE receptor (FcεR), IgE coupled to IgER such as on mast cells and/or basophils, IgG receptors RI (FcγRI) and RIII (FcγRIII) such as on NK and monocytes and macrophages, receptor tyrosine kinase c-kit. In some embodiments, the BsAbs comprise a first binding specificity for FcγRIIB and a second binding specificity for an activating receptor having a cytoplasmic ITAM motif. An ITAM motif structure possesses two tyrosines separated by a 9-11 amino acid spacer. A general consensus sequence is YxxL/I(x)$_{6-8}$YxxL (Isakov, N., 1997, *J. Leukoc. Biol.,* 61:6-16). Exemplary activating receptors include FcεRI, FcγRIII, FcγRI, FcγRIIA, and FcγRIIC. Other activating receptors include, e.g., CD3, CD2, CD10, CD161, DAP-12, KAR, KARAP, FcεRII, Trem-1, Trem-2, CD28, p44, p46, B cell receptor, LMP2A, STAM, STAM-2, GPVI, and CD40 (See, e.g., Azzoni, et al., 1998, *J. Immunol.* 161:3493; Kita, et al., 1999, *J. Immunol.* 162:6901; Merchant, et al., 2000, *J. Biol. Chem.* 74:9115; Pandey, et al., 2000, *J. Biol. Chem.* 275: 38633; Zheng, et al., 2001, *J. Biol. Chem.* 276:12999; Propst, et al., 2000, *J. Immunol.* 165:2214).

In one embodiment, a BsAb comprises a first binding specificity for FcγRIIB and a second binding specificity for FcεRI. Bispecific antibodies can be prepared as full length antibodies or antibody fragments (for example, F(ab')$_2$ bispecific antibodies). Bispecific antibodies may additionally be prepared as knobs-in-holes or hingeless antibodies. Bispecific antibodies are reviewed in Segal et al., 2001, *J. Immunol. Methods* 248:1-6.

Methods for making bispecific antibodies are known in the art. Traditional production of full length bispecific antibodies is based on the coexpression of two immunoglobulin heavy chain-light chain pairs, where the two chains have different specificities (Millstein et al., 1983, *Nature*, 305:537-539). Because of the random assortment of immunoglobulin heavy and light chains, these hybridomas (quadromas) produce a potential mixture of 10 different antibody molecules, of which only one has the correct bispecific structure. Purification of the correct molecule, usually done by affinity chromatography steps, is rather cumbersome, and the product yields are low. Similar procedures are disclosed in WO 93/08829, and in Traunecker et al., 1991, *EMBO J.*, 10:3655-3659.

According to a different approach, antibody variable domains with the desired binding specificities (antibody-antigen combining sites) are fused to immunoglobulin constant domain sequences. The fusion can be with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three antibody fragments in embodiments when unequal ratios of the three antibody chains used in the construction provide the optimum yields. It is, however, possible to insert the coding sequences for two or all three antibody chains in one expression vector when the expression of at least two antibody chains in equal ratios results in high yields or when the ratios are of no particular significance.

In another embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile method of separation. This approach is disclosed in WO 94/04690. For further details of methods for generating bispecific antibodies, see, for example, Suresh et al., 1986, *Methods in Enzymology*, 121:210.

According to another approach described in WO96/27011, the interface between a pair of antibody molecules can be engineered to maximize the percentage of heterodimers that are recovered from recombinant cell culture. The preferred interface comprises at least a part of the CH3 domain of an antibody constant domain. In this method, one or more small amino acid side chains from the interface of the first antibody molecule are replaced with larger side chains (for example, tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360, WO 92/200373, and EP 03089). Heteroconjugate antibodies may be made using any convenient cross-linking methods. Suitable cross-linking agents are well known in the art, and are disclosed, for example, in U.S. Pat. No. 4,676,980, along with a number of cross-linking techniques.

Antibodies with more than two valencies are also contemplated. For example, trispecific antibodies can be prepared According to Tutt et al., 1991, *J. Immunol.* 147: 60.

(vi) Antibodies with Variant Hinge Regions

The antibodies of the present invention may also comprise variant heavy chains, for example as described in application Ser. No. 10/697,995, filed Oct. 30, 2003. Antibodies comprising variant heavy chains comprise an alteration of at least one disulfide-forming cysteine residue, such that the cysteine residue is incapable of forming a disulfide linkage. In one aspect, said cysteine(s) is of the hinge region of the heavy chain (thus, such a hinge region is referred to herein as a "variant hinge region" and may additionally be referred to as "hingeless").

In some aspects, such immunoglobulins lack the complete repertoire of heavy chain cysteine residues that are normally capable of forming disulfide linkages, either intermolecularly (such as between two heavy chains) or intramolecularly (such as between two cysteine residues in a single polypeptide chain). Generally and preferably, the disulfide linkage formed by the cysteine residue(s) that is altered (i.e., rendered incapable of forming disulfide linkages) is one that, when not present in an antibody, does not result in a substantial loss of the normal physicochemical and/or biological characteristics of the immunoglobulin. Preferably, but not necessarily, the cysteine residue that is rendered incapable of forming disulfide linkages is a cysteine of the hinge region of a heavy chain.

An antibody with variant heavy chains or variant hinge region is generally produced by expressing in a host cell an antibody in which at least one, at least two, at least three, at least four, or between two and eleven inter-heavy chain disulfide linkages are eliminated, and recovering said antibody from the host cell. Expression of said antibody can be from a polynucleotide encoding an antibody, said antibody comprising a variant heavy chain with reduced disulfide linkage capability, followed by recovering said antibody from the host cell comprising the polynucleotide. Preferably, said heavy chain comprises a variant hinge region of an immunoglobulin heavy chain, wherein at least one cysteine of said variant hinge region is rendered incapable of forming a disulfide linkage.

It is further anticipated that any cysteine in an immunoglobulin heavy chain can be rendered incapable of disulfide linkage formation, similarly to the hinge cysteines described herein, provided that such alteration does not substantially reduce the biological function of the immunoglobulin. For example, IgM and IgE lack a hinge region, but each contains an extra heavy chain domain; at least one (in some embodiments, all) of the cysteines of the heavy chain can be rendered incapable of disulfide linkage formation in methods of the invention so long as it does not substantially reduce the biological function of the heavy chain and/or the antibody which comprises the heavy chain.

Heavy chain hinge cysteines are well known in the art, as described, for example, in Kabat, 1991, "Sequences of proteins of immunological interest," supra. As is known in the art, the number of hinge cysteines varies depending on the class and subclass of immunoglobulin. See, for example, Janeway, 1999, *Immunobiology*, 4th Ed., (Garland Publishing, NY). For example, in human IgGIs, two hinge cysteines are separated by two prolines, and these are normally paired with their counterparts on an adjacent heavy chain in intermolecular disulfide linkages. Other examples include human IgG2 that contains 4 hinge cysteines, IgG3 that contains 11 hinge cysteines, and IgG4 that contains 2 hinge cysteines.

Accordingly, methods of the invention include expressing in a host cell an immunoglobulin heavy chain comprising a variant hinge region, where at least one cysteine of the variant hinge region is rendered incapable of forming a disulfide linkage, allowing the heavy chain to complex with a light chain to form a biologically active antibody, and recovering the antibody from the host cell.

Alternative embodiments include those where at least 2, 3, or 4 cysteines are rendered incapable of forming a disulfide linkage; where from about two to about eleven cysteines are rendered incapable; and where all the cysteines of the variant hinge region are rendered incapable.

Light chains and heavy chains constituting antibodies of the invention as produced according to methods of the invention may be encoded by a single polynucleotide or by separate polynucleotides.

Cysteines normally involved in disulfide linkage formation can be rendered incapable of forming disulfide linkages by any of a variety of methods known in the art, or those that would be evident to one skilled in the art in view of the criteria described herein. For example, a hinge cysteine can be substituted with another amino acid, such as serine that is not capable of disulfide bonding. Amino acid substitution can be achieved by standard molecular biology techniques, such as site directed mutagenesis of the nucleic acid sequence encoding the hinge region that is to be modified. Suitable techniques include those described in Sambrook et al., 1989, *Molecular Cloning: A Laboratory Manual*, 2nd Ed., Other techniques for generating an immunoglobulin with a variant hinge region include synthesizing an oligonucleotide that encodes a hinge region, where the codon for the cysteine to be substituted is replaced with a codon for the substitute amino acid. This oligonucleotide can then be ligated into a vector backbone comprising other appropriate antibody sequences, such as variable regions and Fc sequences, as appropriate.

In another embodiment, a hinge cysteine can be deleted. Amino acid deletion can be achieved by standard molecular biology techniques, such as site directed mutagenesis of the nucleic acid sequence encoding the hinge region that is to be modified. Suitable techniques include those described in Sambrook et al., Supra. Other techniques for generating an immunoglobulin with a variant hinge region include synthesizing an oligonucleotide comprising a sequence that encodes a hinge region in which the codon for the cysteine to be modified is deleted. This oligonucleotide can then be ligated into a vector backbone comprising other appropriate antibody sequences, such as variable regions and Fc sequences, as appropriate.

(vii) Bispecific Antibodies Formed Using "Protuberance-into-Cavity" Strategy.

In some embodiments, bispecific antibodies of the invention are formed using a "protuberance-into-cavity" strategy, also referred to as "knobs into holes" that serves to engineer an interface between a first and second polypeptide for hetero-oligomerization. The preferred interface comprises at least a part of the CH3 domain of an antibody constant domain. The "knobs into holes" mutations in the CH3 domain of an Fc sequence has been reported to greatly reduce the formation of homodimers (See, for example, Merchant et al., 1998, Nature Biotechnology, 16:677-681). "Protuberances" are constructed by replacing small amino acid side chains from the interface of the first polypeptide with larger side chains (e.g. tyrosine or tryptophan). Compensatory "cavities" of identical or similar size to the protuberances are optionally created on the interface of the second polypeptide by replacing large amino acid side chains with smaller ones (e.g. alanine or threonine). Where a suitably positioned and dimensioned protuberance or cavity exists at the interface of either the first or second polypeptide, it is only necessary to engineer a corresponding cavity or protuberance, respectively, at the adjacent interface. The protuberance and cavity can be made by synthetic means such as altering the nucleic acid encoding the polypeptides or by peptide synthesis. For further description of knobs into holes, see U.S. Pat. Nos. 5,731,168; 5,807, 706; 5,821,333.

In some embodiments "knobs into holes" technology is used to promote heterodimerization to generate full length bispecific anti-FcγRIIB and anti-"activating receptor" (e.g., IgER) antibody. In one embodiment, constructs were prepared for the anti-FcγIIB component (e.g., p5A6.11.Knob) by introducing the "knob" mutation (T366W) into the Fc region, and the anti-IgER component (e.g., p22E7.11.Hole) by introducing the "hole" mutations (T366S, L368A, Y407V). In another embodiment, constructs are prepared for the anti-FcγIIB component (e.g., p5A6.11.Hole) by introducing a "hole" mutation into its Fc region, and the anti-IgER component (e.g., p22E7.11.Knob) by introducing a "knob" mutation in its Fc region such as by the procedures disclosed herein or the procedures disclosed by Merchant et al., (1998), supra, or in U.S. Pat. Nos. 5,731,168; 5,807,706; 5,821,333.

A general method of preparing a heteromultimer using the "protuberance-into-cavity" strategy comprises expressing, in one or separate host cells, a polynucleotide encoding a first polypeptide that has been altered from an original polynucleotide to encode a protuberance, and a second polynucleotide encoding a second polypeptide that has been altered from the original polynucleotide to encode the cavity. The polypeptides are expressed, either in a common host cell with recovery of the heteromultimer from the host cell culture, or in separate host cells, with recovery and purification, followed by formation of the heteromultimer. In some embodiments, the heteromultimer formed is a multimeric antibody, for example a bispecific antibody.

In some embodiments, antibodies of the present invention combine a knobs into holes strategy with variant hinge region constructs to produce hingeless bispecific antibodies.

B. Vectors, Host Cells and Recombinant Methods

The invention also provides isolated polynucleotides encoding the antibodies as disclosed herein, vectors and host cells comprising the polynucleotides, and recombinant techniques for the production of the antibodies.

For recombinant production of the antibody, a polynucleotide encoding the antibody is isolated and inserted into a replicable vector for further cloning (amplification of the DNA) or for expression. DNA encoding the antibody is readily isolated and sequenced using conventional procedures, for example, by using oligonucleotide probes capable of binding specifically to genes encoding the antibody. Many vectors are available. The vector components generally include, but are not limited to, one or more of the following: a signal sequence, an origin of replication, one or more marker genes, an enhancer element, a promoter, and a transcription termination sequence.

(i) Signal Sequence Component

The antibodies of this invention may be produced recombinantly, not only directly, but also as fusion antibodies with heterologous antibodies. In one embodiment, the heterologous antibody is a signal sequence or other antibody having a specific cleavage site at the N-terminus of the mature protein or antibody. The heterologous signal sequence selected preferably is one that is recognized and processed (i.e., cleaved by a signal peptidase) by the host cell. For prokaryotic host cells that do not recognize and process the native antibody signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, α factor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available. The DNA for such precursor region is ligated in reading frame to DNA encoding the antibody.

In another embodiment, production of antibodies can occur in the cytoplasm of the host cell, and therefore does not require the presence of secretion signal sequences within each cistron. In that regard, immunoglobulin light and heavy chains are expressed, folded, and assembled to form functional immunoglobulins within the cytoplasm. Certain host strains (for example, the *E. coli* trxB strains) provide cytoplasm conditions that are favorable for disulfide bond formation, thereby permitting proper folding and assembly of expressed protein subunits. (Proba and Plukthun, 1995, *Gene*, 159:203.)

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV, or BPV) are useful for cloning vectors in mammalian cells. Generally, the origin of replication component is not needed for mammalian expression vectors (the SV40 origin may typically be used only because it contains the early promoter).

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, preferably primate metallothionein genes, adenosine deaminase, ornithine decarboxylase, an the like.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., 1979, *Nature*, 282:39). The trp1 gene provides a selection marker for a mutant strain of yeast lacking the ability to grow in tryptophan, for example, ATCC No. 44076 or PEP4-1. Jones, 1977, *Genetics*, 85:12. The presence of the trp1 lesion in the yeast host cell genome then provides an effective environment for detecting transformation by growth in the absence of tryptophan. Similarly, Leu2-deficient yeast strains (for example, strains having ATCC accession number 20,622 or 38,626) are complemented by known plasmids bearing the Leu2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis*. See Van den Berg, 1990, *Bio/Technology*, 8:135. Stable multi-copy expression vectors for secretion of mature recombinant human serum albumin by industrial strains of *Kluyveromyces* have also been disclosed. See Fleer et al., 1991, *Bio/Technology*, 9:968-975.

(iv) Promoter Component

Expression and cloning vectors usually contain a promoter that is recognized by the host organism and is operably linked to the antibody nucleic acid. Promoters suitable for use with prokaryotic hosts include the phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419, 446. A modification of this system is described in U.S. Pat. No. 4,601,978. See also Reyes et al., 1982, *Nature* 297:598-601 on expression of human β-interferon cDNA in mouse cells under the control of a thymidine kinase promoter from herpes simplex virus. Alternatively, the rous sarcoma virus long terminal repeat can be used as the promoter.

(v) Enhancer Element Component

Transcription of a DNA encoding the antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, 1982, *Nature* 297:17-18 on enhancing elements for activation of eukaryotic promoters. The enhancer may be spliced into the vector at a position 5' or 3' to the antibody-encoding sequence, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the antibody. One useful transcription termination component is the bovine growth hormone polyadenylation region. See WO94/11026 and the expression vector disclosed therein.

(vii) Modulation of Translational Strength

Immunoglobulins of the present invention can also be expressed from an expression system in which the quantitative ratio of expressed light and heavy chains can be modulated in order to maximize the yield of secreted and properly assembled full length antibodies. Such modulation is accomplished by simultaneously modulating translational strengths for light and heavy chains.

One technique for modulating translational strength is disclosed in Simmons et al., U.S. Pat. No. 5,840,523 and Simmons et al., 2002, *J. Immunol. Methods,* 263: 133-147. It utilizes variants of the translational initiation region (TIR) within a cistron. For a given TIR, a series of amino acid or nucleic acid sequence variants can be created with a range of translational strengths, thereby providing a convenient means by which to adjust this factor for the desired expression level of the specific chain. TIR variants can be generated by conventional mutagenesis techniques that result in codon changes which can alter the amino acid sequence, although silent changes in the nucleotide sequence are preferred. Alterations in the TIR can include, for example, alterations in the number or spacing of Shine-Dalgarno sequences, along with alterations in the signal sequence. One preferred method for generating mutant signal sequences is the generation of a "codon bank" at the beginning of a coding sequence that does not change the amino acid sequence of the signal sequence (i.e., the changes are silent). This can be accomplished by changing the third nucleotide position of each codon; additionally, some amino acids, such as leucine, serine, and arginine, have multiple first and second positions that can add complexity in making the bank. This method of mutagenesis is described in detail in Yansura et al., 1992, *METHODS: A Companion to Methods in Enzymol.,* 4:151-158.

Preferably, a set of vectors is generated with a range of TIR strengths for each cistron therein. This limited set provides a comparison of expression levels of each chain as well as the yield of full length products under various TIR strength combinations. TIR strengths can be determined by quantifying the expression level of a reporter gene as described in detail in Simmons et al., U.S. Pat. No. 5,840,523 and Simmons et al., 2002, *J. Immunol. Methods,* 263: 133-147. For the purpose of this invention, the translational strength combination for a particular pair of TIRs within a vector is represented by (N—light, M—heavy), wherein N is the relative TIR strength of light chain and M is the relative TIR strength of heavy chain. For example, (3—light, 7—heavy) means the vector provides a relative TIR strength of about 3 for light chain expression and a relative TIR strength of about 7 for heavy chain expression. Based on the translational strength comparison, the desired individual TIRs are selected to be combined in the expression vector constructs of the invention.

(vii) Selection and Transformation of Host Cells

Suitable host cells for cloning or expressing the DNA in the vectors herein are the prokaryote, yeast, or higher eukaryote cells described above. Suitable prokaryotes for this purpose include Archaebacteria and Eubacteria, such as Gram-negative or Gram-positive organisms, for example, Enterobacteriaceae such as *Escherichia,* e.g., *E. coli, Enterobacter, Erwinia, Klebsiella, Proteus, Salmonella,* e.g., *Salmonella typhimurium, Serratia,* e.g., *Serratia marcescans,* and *Shigella,* as well as Bacilli such as *B. subtilis* and *B. licheniformis* (e.g., *B. licheniformis* 41P disclosed in DD 266,710, published 12 Apr. 1989), *Pseudomonas* such as *P. aeruginosa,* and *Streptomyces.* One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting. It is also preferably for the host cell to secrete minimal amounts of proteolytic enzymes, and additional protease inhibitors may desirably be incorporated in the cell culture. Prokaryotic host cells may also comprise mutation(s) in the thioredoxin and/or glutathione pathways.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183, 070); *Candida*; *Trichoderma reesia* (EP 244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*.

Suitable host cells for the expression of glycosylated antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

Vertebrate host cells are widely used, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/–DHFR (CHO, Urlaub et al., 1980, *Proc. Natl. Acad. Sci. USA* 77:4216); mouse sertoli cells (TM4, Mather, 1980, *Biol. Reprod.* 23:243-251); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., 1982, *Annals N.Y. Acad. Sci.* 383:44-68); MRC 5 cells; FS4 cells; mouse myeloma cells, such as NSO (e.g. RCB0213, 1992, *Bio/Technology* 10:169) and SP2/0 cells (e.g. SP2/0-Ag14 cells, ATCC CRL 1581); rat myeloma cells, such as YB2/0 cells (e.g. YB2/3HL.P2.G11.6Ag.20 cells, ATCC CRL 1662); and a human hepatoma line (Hep G2). CHO cells are a preferred cell line for practicing the invention, with CHO-K1, DUK-B11, CHO-DP12, CHO-DG44 (Somatic Cell and Molecular Genetics 12:555 (1986)), and Lec13 being exemplary host cell lines. In the case of CHO-K1, DUK-B11, DG44 or CHO-DP12 host cells, these may be altered such that they are deficient in their ability to fucosylate proteins expressed therein.

The invention is also applicable to hybridoma cells. The term "hybridoma" refers to a hybrid cell line produced by the fusion of an immortal cell line of immunologic origin and an antibody producing cell. The term encompasses progeny of heterohybrid myeloma fusions, which are the result of a fusion with human cells and a murine myeloma cell line subsequently fused with a plasma cell, commonly known as a trioma cell line. Furthermore, the term is meant to include any immortalized hybrid cell line that produces antibodies such as, for example, quadromas (See, for example, Milstein et al., 1983, *Nature*, 537:3053). The hybrid cell lines can be of any species, including human and mouse.

In a most preferred embodiment the mammalian cell is a non-hybridoma mammalian cell, which has been transformed with exogenous isolated nucleic acid encoding the antibody of interest. By "exogenous nucleic acid" or "heterologous nucleic acid" is meant a nucleic acid sequence that is foreign to the cell, or homologous to the cell but in a position within the host cell nucleic acid in which the nucleic acid is ordinarily not found.

(viii) Culturing the Host Cells

Host cells are transformed with the above-described expression or cloning vectors for antibody production and cultured in conventional nutrient media modified as appropriate for inducing promoters, selecting transformants, or amplifying the genes encoding the desired sequences.

The host cells used to produce the antibody of this invention may be cultured in a variety of media. Commercially available media such as Ham's F10 (Sigma), Minimal Essential Medium ((MEM), (Sigma), RPMI-1640 (Sigma)), and Dulbecco's Modified Eagle's Medium ((DMEM), Sigma) are suitable for culturing the host cells. In addition, any of the media described in Ham et al., 1979, *Meth. Enz.* 58:44, Barnes et al., 1980, *Anal. Biochem.* 102:255, U.S. Pat. No. 4,767, 704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

All culture medium typically provides at least one component from one or more of the following categories:

1) an energy source, usually in the form of a carbohydrate such as glucose;

2) all essential amino acids, and usually the basic set of twenty amino acids plus cystine;

3) vitamins and/or other organic compounds required at low concentrations;

4) free fatty acids; and 5) trace elements, where trace elements are defined as inorganic compounds or naturally occurring elements that are typically required at very low concentrations, usually in the micromolar range.

The culture medium is preferably free of serum, e.g. less than about 5%, preferably less than 1%, more preferably 0 to 0.1% serum, and other animal-derived proteins. However, they can be used if desired. In a preferred embodiment of the invention the cell culture medium comprises excess amino acids. The amino acids that are provided in excess may, for example, be selected from Asn, Asp, Gly, Ile, Leu, Lys, Met, Ser, Thr, Trp, Tyr, and Val. Preferably, Asn, Asp, Lys, Met, Ser, and Trp are provided in excess. For example, amino acids, vitamins, trace elements and other media components at one or two times the ranges specified in European Patent EP 307,247 or U.S. Pat. No. 6,180,401 may be used. These two documents are incorporated by reference herein.

For the culture of the mammalian cells expressing the desired protein and capable of adding the desired carbohydrates at specific positions, numerous culture conditions can be used paying particular attention to the host cell being cultured. Suitable culture conditions for mammalian cells are well known in the art (W. Louis Cleveland et al., 1983, *J. Immunol. Methods* 56:221-234) or can be easily determined by the skilled artisan (see, for example, *Animal Cell Culture: A Practical Approach* 2$^{nd}$ Ed., Rickwood, D. and Hames, B. D., eds. Oxford University Press, New York (1992)), and vary according to the particular host cell selected.

(ix) Antibody Purification

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., 1992, *Bio/Technology* 10: 163-167 describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc region that is present in the antibody. Protein A can be used to purify antibodies that are based on human γ1, γ2, or γ4 heavy chains (Lindmark et al., 1983, *J. Immunol. Meth.* 62:1-13). Protein G is recommended for all mouse isotypes and for human γ3 (Guss et al., 1986, *EMBO J.* 5:15671575). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSET™ chromatography on an anion or cation exchange resin (such as a polyaspartic acid column), chromatofocusing, SDS-PAGE, and ammonium sulfate precipitation are also available depending on the antibody to be recovered.

In one embodiment, the glycoprotein may be purified using adsorption onto a lectin substrate (e.g. a lectin affinity column) to remove fucose-containing glycoprotein from the preparation and thereby enrich for fucose-free glycoprotein.

(x) Antibody Activity Assays

The immunoglobulins of the present invention can be characterized for their physical/chemical properties and biological functions by various assays known in the art. In one aspect of the invention, it is important to compare the selectivity of an antibody of the present invention to bind the immunogen versus other binding targets. Particularly, an antibody to that selectively binds FcγRIIB will preferably not bind or exhibit poor binding affinity to other FcγRs, particularly, FcγRIIA.

In certain embodiments of the invention, the immunoglobulins produced herein are analyzed for their biological activity. In some embodiments, the immunoglobulins of the present invention are tested for their antigen binding activity. The antigen binding assays that are known in the art and can be used herein include without limitation any direct or competitive binding assays using techniques such as western blots, radioimmunoassays, ELISA (enzyme linked immunosorbent assay), "sandwich" immunoassays, immunoprecipitation assays, fluorescent immunoassays, and protein A immunoassays. Illustrative antigen binding assays are provided below in the Examples section.

The purified immunoglobulins can be further characterized by a series of assays including, but not limited to, N-terminal sequencing, amino acid analysis, non-denaturing size exclusion high pressure liquid chromatography (HPLC), mass spectrometry, ion exchange chromatography, and papain digestion. Methods for protein quantification are well known in the art. For example, samples of the expressed proteins can be compared for their quantitative intensities on a Coomassie-stained SDS-PAGE. Alternatively, the specific band(s) of interest (e.g., the full length band) can be detected by, for example, western blot gel analysis and/or AME5-RP assay.

C. Pharmaceutical Formulations

Therapeutic formulations of the antibody can be prepared by mixing the antibody having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) antibody; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. For instance, the formulation may further comprise another antibody or a chemotherapeutic agent. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

D. Non-Therapeutic Uses for the Antibody

The antibody of the invention may be used as an affinity purification agent. In this process, the antibody is immobilized on a solid phase such a Sephadex™ resin or filter paper, using methods well known in the art. The immobilized antibody is contacted with a sample containing the antigen to be purified, and thereafter the support is washed with a suitable solvent that will remove substantially all the material in the sample except the antigen to be purified, which is bound to the immobilized antibody. Finally, the support is washed with another suitable solvent, such as glycine buffer, pH 5.0, that will release the antigen from the antibody.

The antibody may also be useful in diagnostic assays, e.g., for detecting expression of an antigen of interest in specific cells, tissues, or serum. For diagnostic applications, the antibody typically will be labeled with a detectable moiety. Numerous labels are available which can be generally grouped into the following categories:

(a) Radioisotopes, such as $^{35}S$, $^{14}C$, $^{125}I$, $^{3}H$, and $^{131}I$. The antibody can be labeled with the radioisotope using the techniques described in *Current Protocols in Immunology*, Volumes 1 and 2, Coligen et al., Ed. Wiley-Interscience, New York, N.Y., Pubs. (1991), for example, and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in *Current Protocols in Immunology*, supra, for example. Fluorescence can be quantified using a fluorimeter.

(c) Various enzyme-substrate labels are available and U.S. Pat. No. 4,275,149 provides a review of some of these. The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light that can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in *Methods in Enzym.* (ed J. Langone and H. Van Vunakis), Academic press, New York, 73:147-166 (1981).

Examples of enzyme-substrate combinations include, for example:

1) Horseradish peroxidase (HRPO) utilizes hydrogen peroxide to oxidize a dye precursor (e.g., orthophenylene diamine (OPD) or 3,3',5,5'-tetramethyl benzidine hydrochloride (TMB));

2) alkaline phosphatase (AP) with para-Nitrophenyl phosphate as chromogenic substrate; and 3) β-D-galactosidase (β-D-Gal) with a chromogenic substrate (e.g., p-nitrophenyl-β-D-galactosidase) or fluorogenic substrate 4-methylumbelliferyl-β-D-galactosidase.

Numerous other enzyme-substrate combinations are available to those skilled in the art. For a general review of these, see U.S. Pat. Nos. 4,275,149 and 4,318,980.

Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g., digoxin) and one of the different types of labels mentioned above is conjugated with an anti-hapten antibody (e.g., anti-digoxin antibody). Thus, indirect conjugation of the label with the antibody can be achieved.

In another embodiment of the invention, the antibody need not be labeled, and the presence thereof can be detected using a labeled antibody which binds to the antibody.

The antibody of the present invention may be employed in any known assay method, such as competitive binding assays, direct and indirect sandwich assays, and immunoprecipitation assays. Zola, *Monoclonal Antibodies: A Manual of Techniques*, pp. 147-158 (CRC Press, Inc. 1987).

The antibody may also be used for in vivo diagnostic assays. Generally, the antibody is labeled with a radionuclide (such as $^{111}$In, $^{99}$Tc, $^{14}$C, $^{131}$I, $^{125}$I, $^{3}$H, $^{32}$P or $^{35}$S) so that the antigen or cells expressing it can be localized using immunoscintiography.

E. In Vivo Uses for the Antibody (i) Reducing Inhibitory Activity of FcγRIIB (CD32B): Interfering with Antibody Fc Binding In another embodiment, the anti-FcγRIIB antibody is co-administered with a therapeutic agent to enhance the function of the therapeutic agent. For example, anti-FcγRIIB is administered to a mammal to block IgG binding to FcγRIIB, thereby preventing FcγRIIB-mediated inhibition of an immune response. This results in enhanced cytotoxicity of an IgG therapeutic antibody. For example, where a therapeutic antibody is specific for a tumor antigen, co-administration of anti-FcγRIIB of the invention with the anti-tumor antigen antibody enhances cytotoxicity of the anti-tumor antigen antibody.

Therapeutic antibodies, a number of which are described above, have been developed and approved for treatment of a variety of diseases, including cancer. For example, RITUXAN® (Rituximab) (IDEC Pharm/Genentech, Inc.) is used to treat B cell lymphomas, AVASTIN™ (bevacizumab) (Genentech, Inc.) is used to treat metastatic colorectal cancer and HERCEPTIN® (Trastumab) (Genentech, Inc.) is a humanized anti-HER2 monoclonal antibody used to treat metastatic breast cancer. Although, the mechanisms for treatment of cancer by all monoclonal antibodies developed for such treatment may not be completely understood, at least in some cases, a portion of the effectiveness of antibody therapy can be attributed to the recruitment of immune effector function (Houghton et al., 2000, *Nature Medicine*, 6:373-374; Clynes et al., 2000, *Nature Medicine*, 6:433-446). XOLAIR® (Omalizumab) (Genentech, Inc.) is an anti-IgE antibody used to treat allergies.

FcγRIIB is expressed on lymphoid and myeloid lineage cells, but not on natural killer cells and is an inhibitory receptor. When activated, FcγRIIB can, for example, inhibit FcγRIII signaling, which would otherwise activate macrophages, natural killer and mast cells. Inhibition of FcγRIIB, (e.g, blocking Fc binding to FcγRIIB) attenuates its inhibitory effect on immune effector function, thereby assisting MAb therapies. Ravetch, J., (WO01/79299) described a method for enhancing the cytotoxicity of an anti-tumor antibody by reducing the affinity of the Fc region for FcγRIIB and thereby limiting SHIP-mediated inhibition of cellular activation.

In one embodiment, an antibody that selectively binds FcγRIIB is administered with an anti-tumor antibody in a mammal in need of such treatment. Selectivity for FcγRIIB is desired so that the immune effector response activation by other FcγRs, including FcγRIIA is not impaired. By failing to cross-react with FcγRIIA, the inhibitory function of FcγRIIB is more efficiently blocked, thereby further enhancing the effect of the co-therapeutic agent.

In one embodiment, the anti-FcγRIIB antibody of the invention is administered to a mammal to block binding of IgG antibodies, thereby blocking the inhibitory effects of FcγRIIB and, for example, enhancing B cell proliferation.

(ii) Enhancing Inhibitory Activity of FcγRIIB: Co-Aggregation with Activating Receptor:

In vivo, FcγRIIB can be co-aggregated with a variety of activating receptors including, as non-limiting examples, the B cell antigen receptor (BCR), the high affinity receptor for IgE (IgER or FcεRI), FcγRIIA, and the c-kit receptor (FcγRIII). The activating receptors, as non-limiting examples are transmembrane proteins with activating activity for immune effector response and comprise an ITAM activation motif. FcγRIIB is activated by co-aggregation of FcγRIIB with an activating receptor attenuates the signals delivered through the activating receptors. To date, FcγRIIB has not been shown to be phosphorylated by self aggregation or homodimerization. The FcγRIIB receptor has been experimentally heterodimerized or co-aggregated (or co-ligated) with other receptors expressing a phosphorylated ITAM (activation motif) and by indirect association with protein tyrosine kinases (PTKs), the FcγRIIB ITIM can be phosphorylated. The phosphorylated FcγRIIB ITIM recruits the SH2 domain containing phosphatase SHIP (inositol polyphosphate 5'-phosphatase) and inhibits ITAM-triggered calcium mobilization and cellular proliferation (Daeron et al., 1995, *Immunity* 3, 635; Malbec et al., 1998, *J. Immunol.* 169, 1647; Ono et al., 1996, *Nature*, 383, 263). The net effect is to block calcium influx and prevent sustained calcium signaling, which prevents calcium-dependent processes such as degranulation, phagocytosis, ADCC, and cytokine release (Ravetch et al., 2000, *Science*, 290:84-89) although some FcγRIIB-mediated blocks of signaling may also be calcium independent. The arrest of proliferation in B cells is also dependent on the ITIM pathway.

Activation of FcγRIIB inhibitory activity has been accomplished by indirect crosslinking of monoclonal antibodies specific for the FcγRIIB and an associated activating receptor. Indirect crosslinking reagents include avidin for biotinylated monoclonals, polyclonal antibodies specific for the Fc portion of murine monoclonal IgG and multivalent antigen which forms an immune complex that links both inhibitor and activating receptors. Most experimental models have described the use of murine B cells or mast cells and a monoclonal antibody (rat G4.2) that cross-reacts with both murine FcγRII and FcγRIII receptors.

According to the invention, a hetero-bifunctional antibody comprising a monoclonal anti-human FcγRIIB Fab and a monoclonal Fab specific for an activating receptor is prepared by chemical or genetic engineering methods well known in the art.

The therapeutic potential for such a bifunctional antibody would include attenuation of signals involved in inflammation and allergy. When activated by IgE and allergen (via the FcεR), mast cells and basophils secrete inflammatory mediators and cytokines that act on vascular and muscular cells and recruit inflammatory cells. The inflammatory cells in turn secrete inflammatory mediators and recruit inflammatory cells, in a continuing process resulting in long-lasting inflammation. Consequently, means of controlling IgE induced mast cell activation provides a therapeutic approach to treating allergic diseases by interrupting the initiation of the inflammatory response. As described above, a bifunctional antibody further comprising an antibody, or fragment thereof that selectively binds FcγRIIB and comprising an antibody, or fragment thereof, that binds, for example FcεRI or FcεRI bound by IgE, attenuates IgE-mediated activation via the inhibitory activity of FcεRIIB.

Additional bifunctional antibody examples (e.g, bispecific antibodies) comprise combinations of an antibody or fragment thereof that selectively binds FcγRIIB, and a second antibody or fragment thereof, that binds an activating receptor involved in: asthma (monoclonal anti-human FcγRIIB Fab and a monoclonal Fab specific for FcεRI, FcεRI bound by IgE, or CD23), rheumatoid arthritis and systemic lupus erythematosus (monoclonal anti-human FcγRIIB Fab and a monoclonal Fab specific for FcγRI), psoriasis (monoclonal anti-human FcγRIIB Fab and a monoclonal Fab specific for CD11a), immune mediated thrombocytopenia, rheumatoid arthritis and systemic lupus erythematosus (monoclonal anti-human FcγRIIB Fab and a monoclonal Fab specific for FcγRIII (CD16) or CD4), Crohn's disease and Ulcerative colitis (monoclonal anti-human FcγRIIB Fab and a monoclonal Fab specific for alpha4beta7 integrin, beta7 integrin subunit, or alpha 4 integrin subunit, or a binding portion of these monoclonal antibodies), and other autoimmune disorders in which cells such as mast cells, basophils, B cells, monocytes, natural killer cells, neutrophils and dendritic cells are actively engaged. Various autoimmune diseases are described in the definitions section above. The antibody may also be used treat autoimmune diseases for which there is a significant immune complex component associated with the disease.

In some embodiments, the antibody of the invention is used to activate inhibitory FcγRIIB receptors in a mammal treated with the antibody so as to inhibit pro-inflammatory signals and/or B cell activation mediated by activating receptors. Hence, the antibody is used to treat inflammatory disorders and/or autoimmune diseases such as those identified above. Activation of the FcγRIIB inhibitory function is accomplished by a bispecific antibody of the invention that directly cross-links FcγRIIB and an activating receptor or by an antibody that indirectly cross-links FcγRIIB and an activating receptor.

In some embodiments, the antibody of the invention inhibits activation-associated degranulation. Inhibition of activation-associated degranulation is associated with and can be measured by suppression of histamine release. In some embodiments, the antibody of the invention inhibits histamine release at least 70% relative to total histamine. In further embodiments, inhibition of histamine release is at least 75%, at least 80%, at least 85%, at least 90%, at least 95%, including each successive integer from 70% to 100%, wherein 100% reduction of histamine release is equivalent to background histamine release.

For the prevention or treatment of disease, the appropriate dosage of antibody will depend on the type of disease to be treated, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 1 μg/kg to 15 mg/kg (e.g., 0.1-20 mg/kg) of antibody is an initial candidate dosage for administration to the patient, whether, for example, by one or more separate administrations, or by continuous infusion. A typical daily dosage might range from about 1 μg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

The antibody composition should be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody to be administered will be governed by such considerations, and is the minimum amount necessary to prevent, ameliorate, or treat a disease or disorder. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as used hereinbefore or about from 1 to 99% of the heretofore employed dosages.

Therapeutic antibody compositions generally are placed into a container having a sterile access port, for example, an intravenous solution bag or vial having a stopper pierceable by a hypodermic injection needle.

The invention further provides an article of manufacture and kit containing materials useful for the treatment of cancer, for example. The article of manufacture comprises a container with a label. Suitable containers include, for example, bottles, vials, and test tubes. The containers may be formed from a variety of materials such as glass or plastic. The container holds a composition comprising the antibody described herein. The active agent in the composition is the particular antibody. The label on the container indicates that the composition is used for the treatment or prevention of a particular disease or disorder, and may also indicate directions for in vivo, such as those described above.

The kit of the invention comprises the container described above and a second container comprising a buffer. It may further include other materials desirable from a commercial and user standpoint, including other buffers, diluents, filters, needles, syringes, and package inserts with instructions for use.

For example, for treating autoimmune diseases where there is the involvement of an inflammatory cell (e.g., leukocyte) adhesion, migration and activation, such as rheumatoid arthritis and lupus, the antibody herein can be co-administered with, e.g., anti-LFA-1 antibody (such as an anti-CD11a or anti-CD18 antibody) or an anti-ICAM antibody such as ICAM-1, -2, or -3. Additional agents for treating rheumatoid arthritis in combination with the antibody herein include Enbrel™, DMARDS, e.g., methotrexate, and NSAIDs (non-steroidal anti-inflammatory drugs). More than one of such other active agents than the antibody herein may also be employed. Additionally, insulin can be used for treating diabetes, anti-IgE for asthma, anti-CD11a for psoriasis, anti-alpha4beta7 and growth hormone (GH) for inflammatory bowel disease.

Furthermore, the formulation is suitably administered along with an effective amount of a hypoglycemic agent. For purposes herein, the term "hypoglycemic agent" refers to compounds that are useful for regulating glucose metabolism, preferably oral agents. More preferred herein for human use are insulin and the sulfonylurea class of oral hypoglycemic agents, which cause the secretion of insulin by the pancreas. Examples include glyburide, glipizide, and gliclazide. In addition, agents that enhance insulin sensitivity or are insulin sensitizing, such as biguanides (including metformin and phenformin) and thiazolidenediones such as REZULINTM™ (troglitazone) brand insulin-sensitizing agent, and other compounds that bind to the PPAR-gamma nuclear receptor, are within this definition, and also are preferred.

The hypoglycemic agent is administered to the mammal by any suitable technique including parenterally, intranasally, orally, or by any other effective route. Most preferably, the administration is by the oral route. For example, MICRONASE™ tablets (glyburide) marketed by Upjohn in 1.25, 2.5, and 5 mg tablet concentrations are suitable for oral administration. The usual maintenance dose for Type II diabetics, placed on this therapy, is generally in the range of from or about 1.25 to 20 mg per day, which may be given as a single dose or divided throughout the day as deemed appropriate. Physician's Desk Reference, 2563-2565 (1995). Other examples of glyburide-based tablets available for prescription include GLYNASE™ brand drug (Upjohn) and DIABETA™ brand drug (Hoechst-Roussel). GLUCOTROL™ (Pratt) is the trademark for a glipizide (1-cyclohexyl-3-(p-(2-(5-methylpyrazine carboxamide)ethyl)phenyl)sulfonyl) urea) tablet available in both 5- and 10-mg strengths and is also prescribed to Type II diabetics who require hypoglycemic therapy following dietary control or in patients who have ceased to respond to other sulfonylureas. Physician's Desk Reference, 1902-1903 (1995). Other hypoglycemic agents than sulfonylureas, such as the biguanides (e.g., metformin and phenformin) or thiazolidinediones (e.g., troglitozone), or other drugs affecting insulin action may also be employed. If a thiazolidinedione is employed with the peptide, it is used at the same level as currently used or at somewhat lower levels, which can be adjusted for effects seen with the peptide alone or together with the dione. The typical dose of troglitazone (REZULINTM™) employed by itself is about 100-1000 mg per day, more preferably 200-800 mg/day, and this range is applicable herein. See, for example, Ghazzi et al., Diabetes, 46: 433-439 (1997). Other thiazolidinediones that are stronger insulin-sensitizing agents than troglitazone would be employed in lower doses.

F. Deposit of Materials

The following hybridoma cell line has been deposited with the American Type Culture Collection, 10801 University Blvd., Manassas, Va. 20110-2209 USA (ATCC):

| Hybridoma/Antibody Designation | ATCC No. | Deposit Date |
|---|---|---|
| FcγRIIB 5A6.2.1 | PTA-4614 | Aug. 28, 2002 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture for 30 years from the date of deposit. The cell line will be made available by ATCC under the terms of the Budapest Treaty, and subject to an agreement between Genentech, Inc. and ATCC, which assures (a) that access to the culture will be available during pendency of the patent application to one determined by the Commissioner to be entitled thereto under 37 CFR §1.14 and 35 USC §122, and (b) that all restrictions on the availability to the public of the culture so deposited will be irrevocably removed upon the granting of the patent.

The assignee of the present application has agreed that if the culture on deposit should die or be lost or destroyed when cultivated under suitable conditions, it will be promptly replaced on notification with a viable specimen of the same culture. Availability of the deposited cell line is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the culture deposited, since the deposited embodiment is intended as a single illustration of one aspect of the invention and any culture that is functionally equivalent is within the scope of this invention. The deposit of material herein does not constitute an admission that the written description herein contained is inadequate to enable the practice of any aspect of the invention, including the best mode thereof, nor is it to be construed as limiting the scope of the claims to the specific illustration that it represents. Indeed, various modifications of the invention in addition to those shown and described herein will become apparent to those skilled in the art from the foregoing description and fall within the scope of the appended claims.

The invention will be more fully understood by reference to the following examples. They should not, however, be construed as limiting the scope of this invention. All literature and patent citations mentioned herein are expressly incorporated by reference.

III. EXAMPLES

Although functionally opposed, human FcγRIIA (activating receptor) and human FcγRIIB (inhibitory receptor) are highly homologous proteins (regions of homology are boxed in FIG. 2A), differing in about nine amino acids in the IgG1 and 3 binding domains. Commercially available monoclonal antibodies bind both human FcγRIIA and FcγRIIB. A monoclonal antibody that specifically binds FcγRIIB would be useful, and the additional ability to block IgG binding is also desirable.

In the Examples and supporting figures, FcγRIIB is human FcγRIIB, and generally refers to human FcγRIIB1, unless specifically noted. FcγRIIB may be interchangeably referred to as FcgRIIB, FcGRIIb, huFcγRIIB, hu FcGRIIb, hFcRIIB, Fcγ-RIIb, FcγR2B, FcγR2b, or IgGR. Specific allelic variants are designated by the addition of a numeral 1, 2, or 3, e.g, hu FcGRIIb1. FcεRI is human FcεRI, and refers to human FcεRIα. FcεRI may be interchangeably referred to as FcεRI, FcεRIa, FcεRI, IgER, IgE-R FcεRIα, Fcε-RI or FcεRIa.

Antibodies of any of the above proteins are designated either by name, or generally, by prepending "anti"- to the related protein antigen, e.g, anti-FcγRIIB, anti-IgER, etc. . . . Extracellular domains of a protein are designated by the addition of ECD to the protein name, e.g, FcγRIIB ECD. Cells expressing protein(s) of interest may be named descriptively to include variations of the protein name in the cell line name and are designated "cells".

Example 1.0

Materials and Methods 1.1 Materials

Reverse transcriptase-PCR was performed using GeneAmp™ from Perkin Elmer Life Sciences. pGEX-4T2 plasmid, Protein A columns and reagents, and Protein G FcγRIII: columns and reagents, were obtained from Amersham Pharmacia Biotech. Ni-NTA columns and reagents were from Qiagen, Valencia, Calif. Centriprep-30 concentrators were from Millipore, Bedford, Mass. SDS-polyacrylamide gels and polyvinylidene difluoride membranes were obtained from NOVEX, San Diego, Calif. FuGENE® 6 was obtained from Roche.

The cDNAs encoding extracellular and transmembrane domains of human FcγRIIA (CD32A; $His_{131}$ allotype), FcγRIIB (CD32B), and FcγRIIIA (CD16A; $Val_{158}$ allotype); and glucose-6-phosphate-isomerase (GPI) isoforms of FcγRIIB, and FcγRIIA were provided by Dr. J. Ravetch (Rockefeller University, New York). FcγRIIA-Arg$_{131}$ allotype and FcγRIIA-Phe$_{158}$ allotype were generated by site-directed mutagenesis (31). Sequence information for: FcγRIIB1 (SEQ ID NO:11) is also available at Accession No: NP_003992; FcγRIIB2 (SEQ ID NO:10) and at Accession No: NP_001002273; FcγRIIA (SEQ ID NO:9) and at Accession No: NP_067674, and FcγRIII (two isoforms) at Accession Nos: NP_000560 and NP_000561.

Antibody AT10 was obtained from Biosource International, Camirillo, Calif. Antibody mopc21 was obtained from BD Pharmagen. Murine monoclonal antibodies were obtained from the following sources: 32.2 (anti-FcγRI), IV.3 (anti-FcγRII), and 3G8 (anti-FcγRIII) from Medarex, Annandale, N.J.; and B1G6 (anti-b2-microglobulin) from Beckman Coulter, Palo Alto, Calif. Anti-GST antibody was from Zymed Laboratories Inc. Anti-GST-biotin was Genentech clone 15H4.1.1. JW8.5.13 was obtained from Serotec Inc., Raleigh, N.C.

ELISA plates, for example, Nunc® maxisorb plates, were obtained from (Nalge-Nunc, Naperville, Ill.). Tissue culture plates may be obtained, for example, from Linbro or Fisher. Bovine serum albumin (BSA), Tween 20®, Triton X-100, EMEM (Eagle's Minimal Essential Media, ionomycin, protamine sulfate and o-phenylenediamine dihydrochloride (OPD), propidium iodide were from Sigma (St. Louis, Mo.). Streptavidin and casein blocker (Prod #37528) were from Pierce (Rockford, Ill.). Horseradish peroxidase rabbit anti-mouse IgG antibody conjugate, and peroxidase-conjugated F(ab')$^2$ fragment of goat anti-human F(ab')$^2$-specific IgG, were obtained from Jackson ImmunoResearch Laboratories, West Grove, Pa. Peroxidase-conjugated protein G was from Bio-Rad. Streptavidin-HRP was from either Boehringer Mannheim or Zymed. TMB substrate (Prod #TMBW-0100-01) and stop solution (Prod #BSTP-0100-01) were from BioFx Laboratory. Goat anti-mouse IgG-Fluorescein was obtained from American Qualex Labs. NP-(11)-OVA and TNP-(11)-OVA were obtained from Biosearch Technologies, Inc., Novado, Calif. Streptavidin-PE and rat anti-mouse IgG-PE or Fluorescein conjugates were obtained from BD Pharmagen, Franklin, Lakes, N.J.

Flow cytometry was performed on a FACScan™ or FACSCalibur™ flow cytometer from BD, Franklin Lakes, N.J. Absorbances were read using a Vmax plate reader from Molecular Devices, MountainView, Calif. Histamine ELISA was performed using a Histamine ELISA Kit obtained from IBL Immunobiological Labs (Hamburg, Germany), distributed by RDI, Inc (NJ).

1.2 Producing GST—Fc Receptor Fusion Proteins

The cDNA for FcγRI (CD64) was isolated by reverse transcriptase-PCR of oligo(dT)-primed RNA from U937 cells using primers that generated a fragment encoding the α-chain extracellular domain. The coding regions of all receptors were subcloned into previously described pRK mammalian cell expression vectors (Eaton, D. et al., 1986, *Biochemistry* 25:8343-8347). For all FcγR pRK plasmids, the transmembrane and intracellular domains were replaced by DNA encoding a Gly-His$_6$ tag and human glutathione S-transferase (GST). The 234-amino acid GST sequence was obtained by PCR from the pGEX-4T2 plasmid with NheI and XbaI restriction sites at the 5' and 3' ends, respectively. Thus, the expressed proteins contained the extracellular domains of the α-chain fused at their carboxyl termini to Gly/His$_6$/GST at amino acid positions as follows: FcγRI, His292; FcγRIIA, Met216; FcγRIIB, Met195; FcγRIIIA, Gln191 (residue numbers include signal peptides).

Plasmids were transfected into the adenovirus-transformed human embryonic kidney cell line 293 by calcium phosphate precipitation (Gorman et al., 1990, *DNA Prot. Eng. Tech.* 2:3-10). Supernatants were collected 72 hours after conversion to serum-free PSO$_4$ medium supplemented with 10 mg/liter recombinant bovine insulin, 1 mg/liter human transferrin, and trace elements. Proteins were purified by nickel-nitrilotriacetic acid (Ni-NTA) chromatography and buffer exchanged into phosphate-buffered saline (PBS) using Centriprep-30 concentrators. Proteins were analyzed on 4-20% SDS-polyacrylamide gels, transferred to polyvinylidene difluoride membranes, and their amino termini sequenced to ensure proper signal sequence cleavage. Receptor conformation was evaluated by ELISA using murine monoclonals 32.2 (anti-FcγRI), IV.3 (anti-FcγRII), 3G8 (anti-FcγRIII), and B1G6 (anti-b2-microglobulin). Receptor concentrations were determined by absorption at 280 nm using extinction coefficients derived by amino acid composition analysis.

1.3 Producing FcγRIIB Antibodies

Human FcγRIIB-specific antibodies that block IgG Fc binding by the receptor were generated against FcγRIIB-His$_6$-GST fusion proteins. BALB/c mice were immunized in the footpad with 2 μg of huFcγRIIB-His$_6$-GST. Splenocytes from the immunized mice were fused with P3X63Ag8UI myeloma cells (cells described in Oi V T, Herzenberg L A., 1981, *Immunoglobulin producing hybrid cell lines. In: Selected methods in cellular immunology* (Mishell B B, Shiigi S M, eds), pp 351-372. San Francisco: Freeman.) resulting in approximately 900 hybridomas.

ELISA is generally performed as follows: the receptor fusion protein at approximately 1.5 mg/ml in PBS, pH 7.4, was coated onto ELISA plates for 18 hours at 4° C. Plates were blocked with assay buffer at 25° C. for 1 hour. Serial 3-fold dilutions of antibodies to be screened and control antibodies (10.0-0.0045 mg/ml) were added to plates and incubated for 2 hours. After washing plates with assay buffer, IgG bound to the receptors was detected with peroxidase-conjugated F(ab')$^2$ fragment of goat anti-human F(ab')-specific IgG or with peroxidase-conjugated protein G. The substrate used was o-phenylenediamine dihydrochloride. Absorbance at 490 nm was read using a Vmax plate reader.

1.4 Primary Screen for FcγRIIB Specific Antibodies

In a primary screen, supernatants containing antibodies expressed from the hybridoma sub-clones were screened for positive binding to FcγRIIB-His$_6$-GST. Antibodies reactive to FcγRIIB-His$_6$-GST by ELISA were rescreened for binding to FcγRIIB-His$_6$-GST and negative binding to FcγRIIA (R131 variant)-His$_6$-GST and FcγRIII (F158 variant)-His$_6$-GST by ELISA.

Approximately 50 antibodies were selected from the primary screen for further analysis.

1.5 Secondary Screen for FcγRIIB Specific Antibodies

Figure 4:
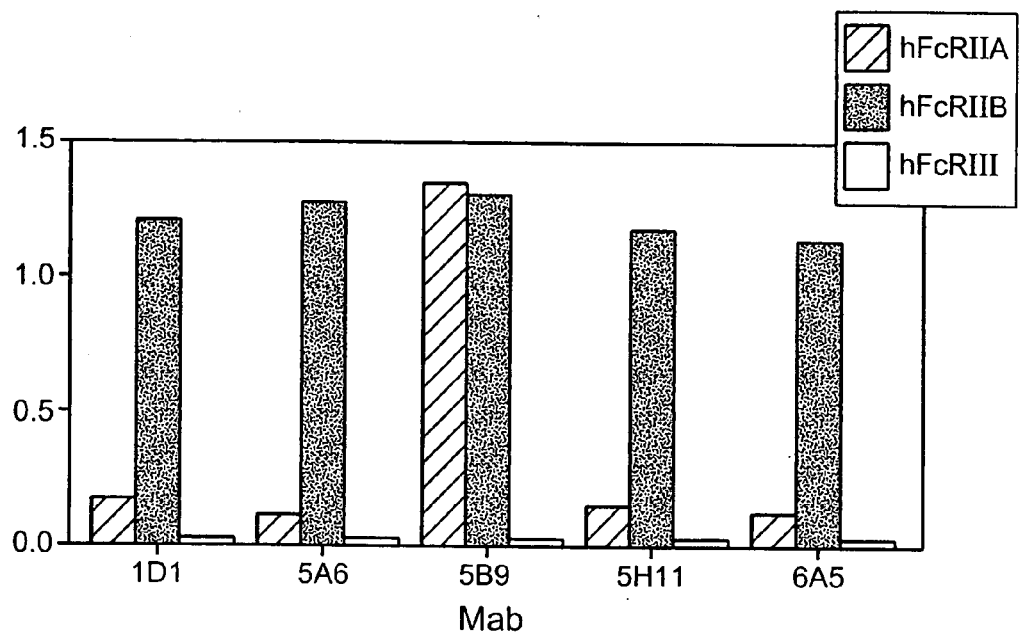
FIG. 4 provides a bar graph indicating relative binding of antibodies to GST-huFcγRIIB relative to GST-huFcγRIIA and GST-huFcγRIII fusion proteins.

In a secondary screen, the antibodies were re-screened for receptor specificity by ELISA, and cell binding assays utilizing CHO cell lines expressing glucose-6-phosphate-isomerase (GPI) linked FcγRIIB, and FcγRIIA. ELISA was performed and described above and results are depicted in FIG. 4. In FIG. 4, a bar graph indicates relative binding of the antibodies to GST-huFcγRIIB relative to GST-huFcγRIIA and GST-huFcγRIII fusion proteins. Antibodies 1D1, 5A6, 5H11 and 6A5 selectively bind GST-huFcγRIIB over GST-huFcγRIIA and GST-huFcγRIII fusion proteins. Antibody 5B9 binds both GST-huFcγRIIB and GST-huFcγRIIA selectively over GST-huFcγRIII.

Figure 5:
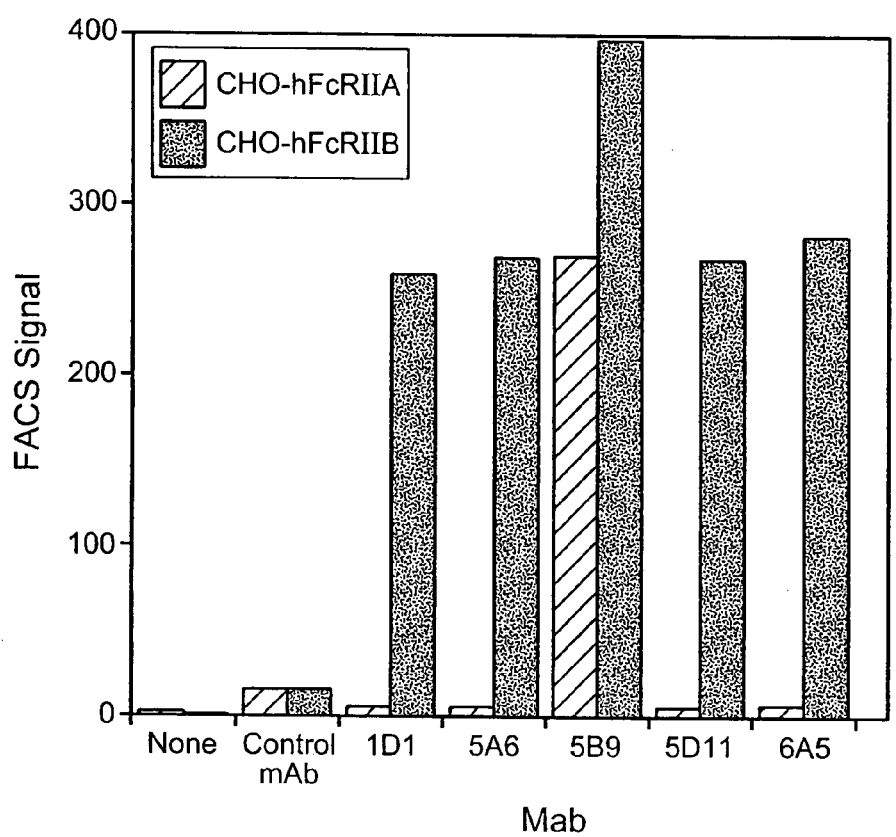
FIG. 5 shows binding specificity by immunofluorescence binding of the antibodies to CHO cells expressing GPI-huFcγRIIB relative to CHO cells expressing GPI-huFcγRIIA.
Figure 6:
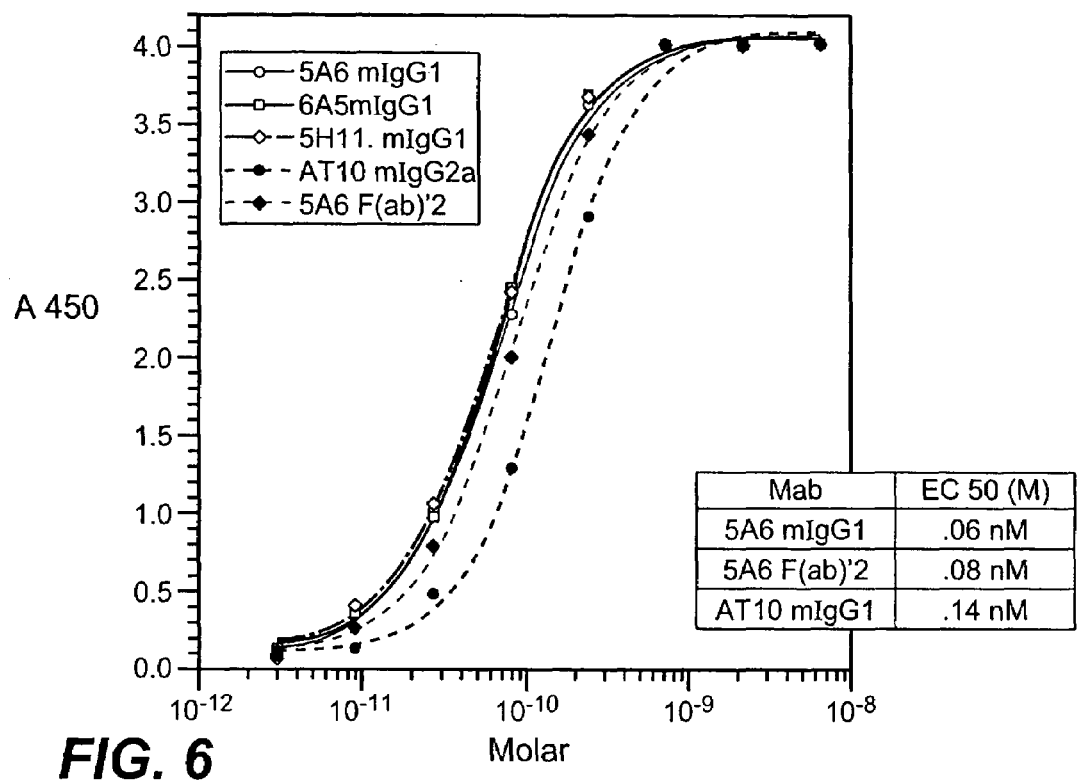
FIGS. 6-9 present binding affinity curves for binding of various anti-FcγRII (CD32) MAbs to GST-huFcγRIIB, GST-huFcγRIIA (H131), or GST-huFcγRIIA (R131).
Figure 7:
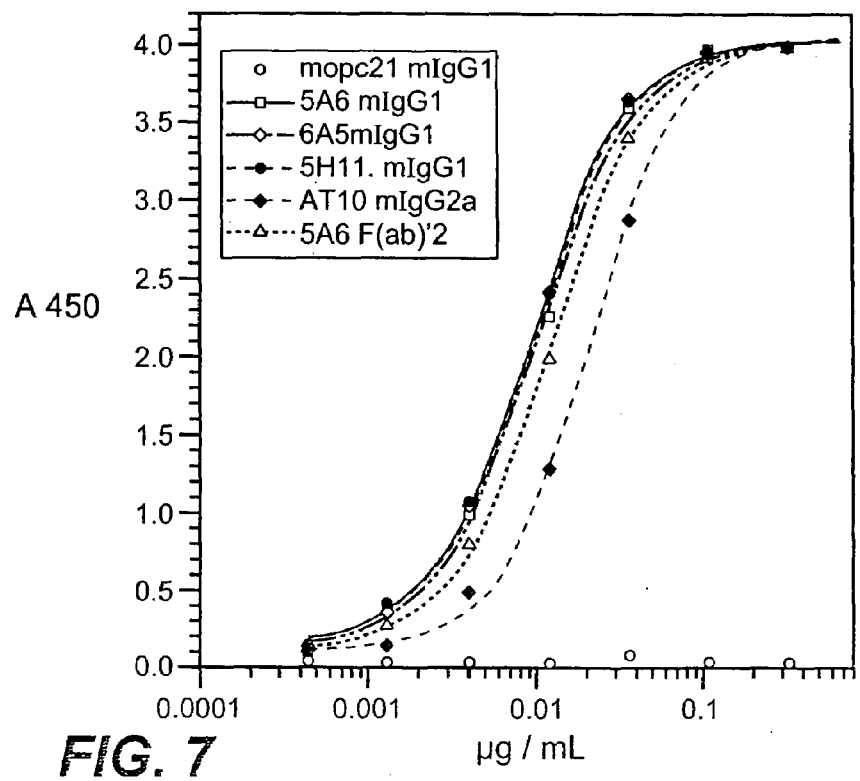

FIG. 5 shows binding specificity by immunofluorescence binding of the antibodies to CHO cells expressing GPI-huFcγRIIB relative to CHO cells expressing GPI-huFcγRIIA.

Separated aliquots of CHO cells were stained with either a mIgG1 isotype control (mopc 21), or (anti-human FcγRIIB) monoclonal antibodies, 1D1, 5A6, 5B9, 5D11 and 6A5. Binding was detected indirectly by a second incubation with Fluorescein conjugated F(ab)'2 goat anti-mouse IgG (F(ab)'2 specific antibody) and analyzed by flow cytometry. Antibody 5A6 preferentially binds to CHO cells expressing GPI-huFcγRIIB relative to CHO cells expressing GPI-huFcγRIRA. Results are similar to binding to GST constructs.

Figure 8:
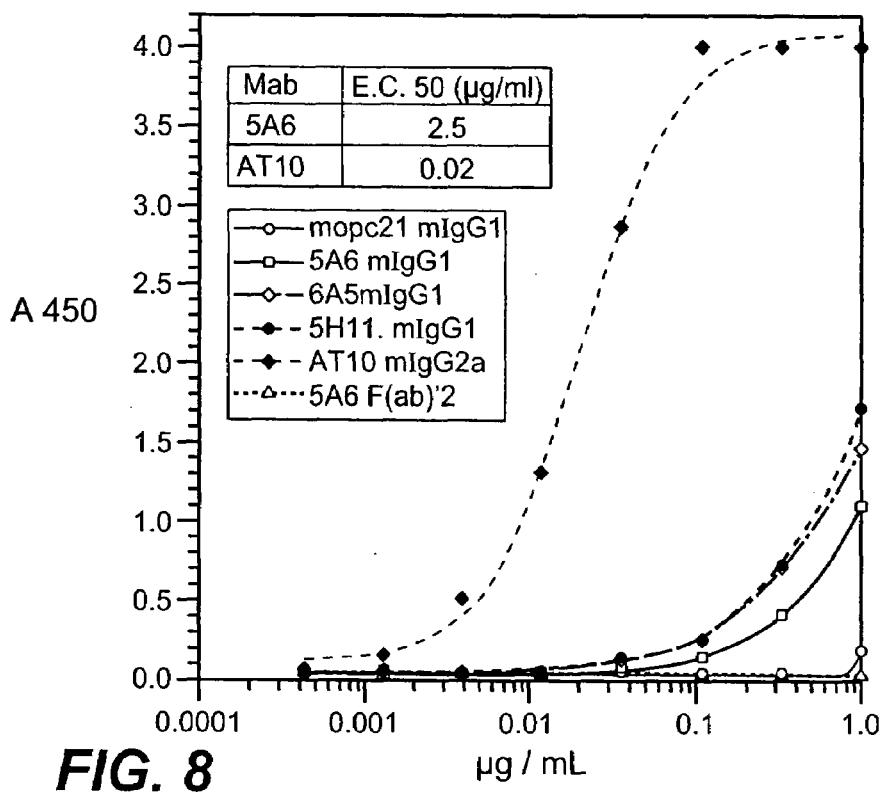
Figure 9:
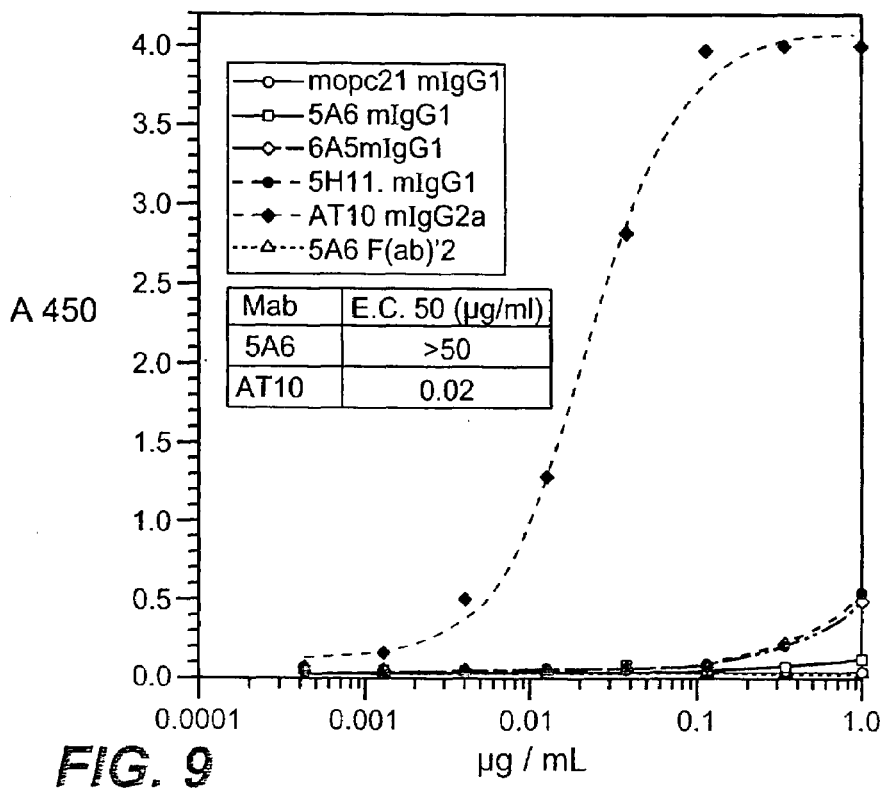

Additional ELISA binding data is illustrated in FIGS. 6-9. FIGS. 6-9 present binding affinity curves for binding of various anti-FcγRII (CD32) MAbs to GST-huFcγRIIB, GST-huFcγRIIA (H131), or GST-huFcγRIIA (R131). AT10 is a mIgG specific for FcγRIIA and mopc21 is mIgG isotype control. 5A6 mIgG1 has a measured EC50 of 0.06 nM for binding to GST-huFcγRIIB shown in FIG. 6. In contrast, the EC50 of 5A6 mIgG1 for binding to GST-huFcγRIIA (H131) is greater than 50 µg/ml (FIG. 9) and for binding to GST-huFcγRIIA (R131) is 2.5 µg/ml (FIG. 8).

1.6 Antibody Expression and Purification

Antibody 5A6.2.1 (herein referred to interchangeably as 5A6.2.1 or 5A6) was selected for ascites and purified using protein G chromatography (Amersham Pharmacia Biotech). DNA encoding the 5A6.2.1 was isolated and sequenced using conventional procedures. The amino acid sequences and CDRs of the heavy chain (SEQ ID NO:7) and light chain (SEQ ID NO:8) are provided in FIG. 10. The heavy chain CDRs are: DAWMD (SEQ ID NO:1), EIRSKPN-NHATYYAESVKG (SEQ ID NO:2), and FDY (SEQ ID NO:3). The light chain CDRs are: RASQEISGYLS (SEQ ID NO:4), AASALDS (SEQ ID NO:5), and LQYVSYPL (SEQ ID NO:6).

The putative binding epitopes for 5A6 monoclonal antibody include amino acid residues K158-V161 and F174-N180, where the numbering is indicated for FcγRIIB2 in FIG. 2A (FcγRIIB2, SEQ ID NO:10). The FcγRIIB1 and FcγRIIB2 receptors have structural domains indicated in FIGS. 2A and 2B (illustrated by FcγRIIB2) as an IgG-like Domain 1 at residues T43-P123 and IgG-like domain 3 at residues W132-P217. The ITIM motif is shown in FIG. 2A for FcγRIIB2 and comprises residues N269-M277. It was recently reported that the amino acid sequence of FcγRIIA F165-T171 indicated as FSRLDPT (SEQ ID NO:39) in FIG. 2A, may be FSHLDPT (SEQ ID NO:40), thereby indicating a greater sequence difference between FcγRIIA and FcγRIIB in the FcγRIIB putative binding epitope for antibody 5A6 (see FIG. 2 and Accession No:NP_067674, SEQ ID NO:30, which amino acid sequence also includes residues changes in the N-terminal portion of FcγRIIA).

1.7 Competition with E27:IgE Complexes

Figure 11:
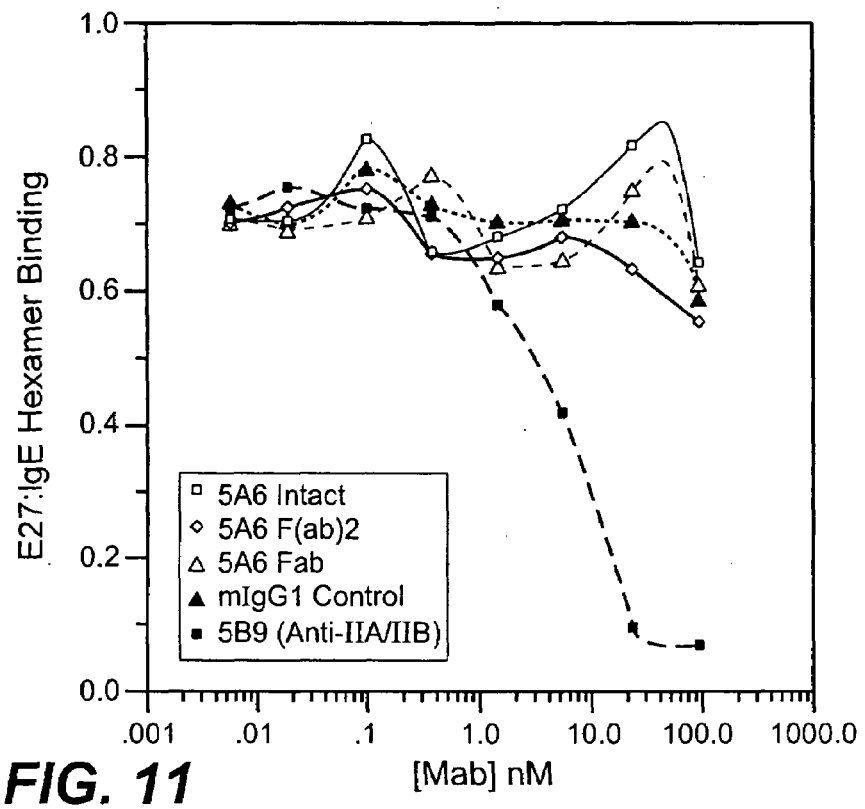
FIGS. 11-15 show that 5A6 does not block E27-IgE hexamer binding to huFcγRIIA and 5A6 does block binding of E27-IgE hexamer binding to huFcγRIIB.
Figure 12:
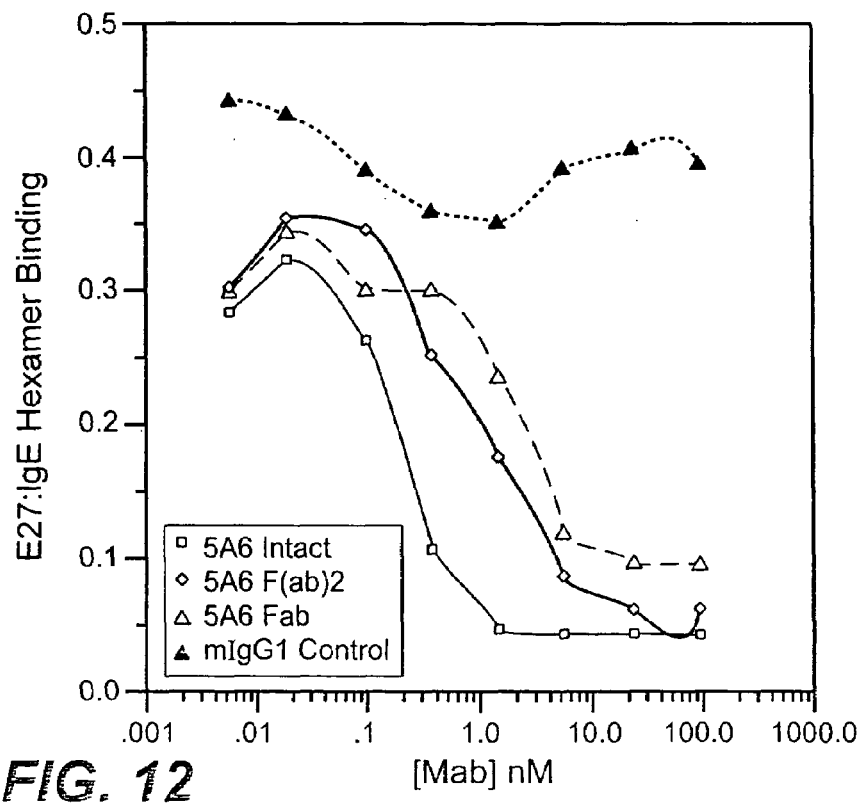

This assay screens the ability of the 5A6 MAb to interfere with binding of IgG1 to FcγRIIA and FcγRIIB. FcγRIIs have a weak affinity for monomeric IgG1, consequently, IgG1 binding is assayed using a stable hexameric complex of three IgE and three anti-IgE molecules, e.g. E27, a humanized IgG1 antibody that binds IgE (Shields, R. L., et al., *J. Biol. Chem.*, 276:6591-6604 (2001)). The 5A6 MAb was screened for neutralizing IgG binding by assessing the ability of the antibody to compete with binding of E27-IgE hexamer complexes to human FcγRIIA and FcγRIIB. The competition assay was performed as follows and results are illustrated in FIGS. 11 and 12.

Figure 13:
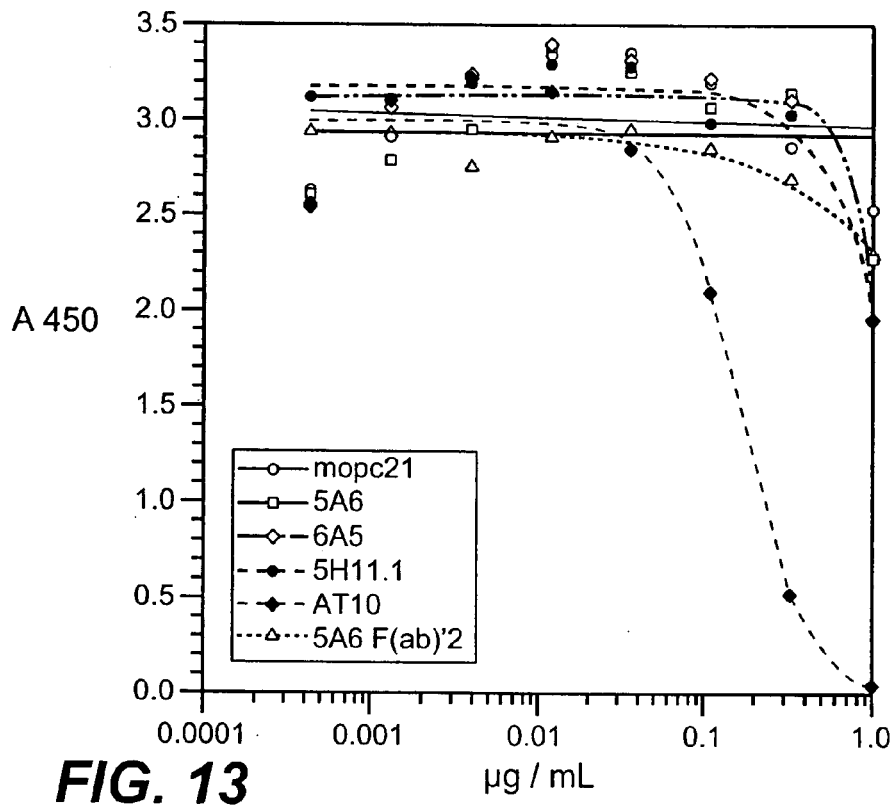
Figure 14:
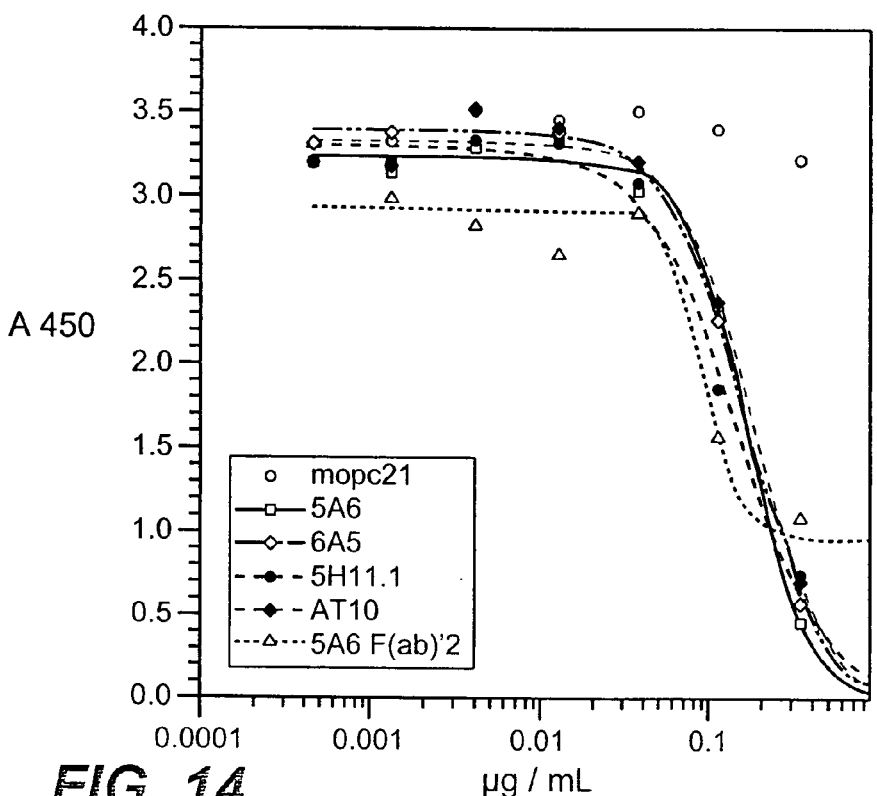
Figure 15:
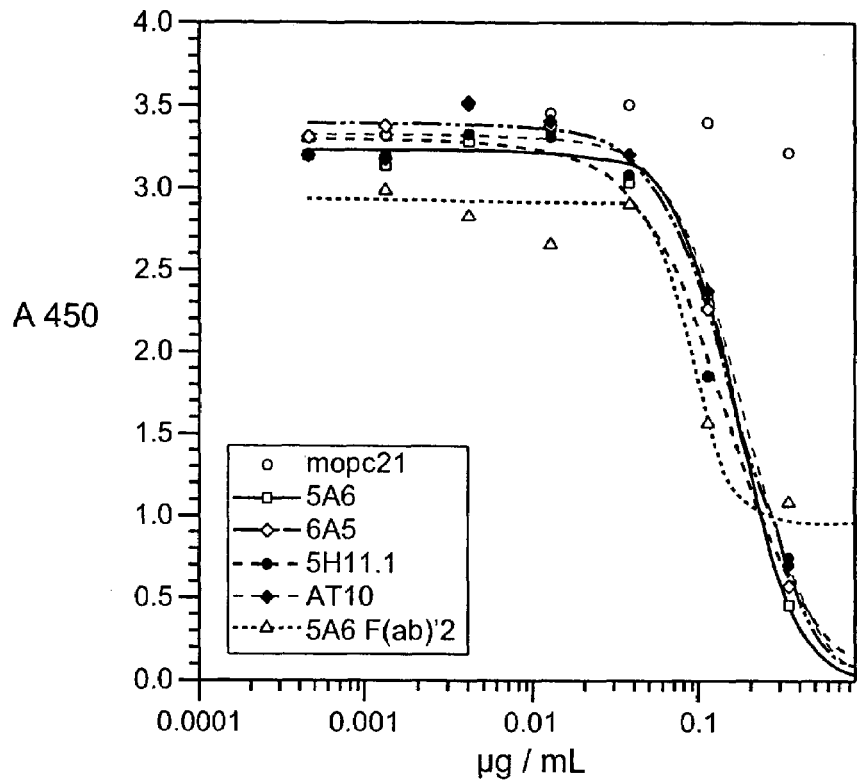

FcγRIIB and FcγRIIA fusion proteins at 1 mg/ml in PBS, pH 7.4, were coated onto ELISA plates for 48 hours at 4° C. Plates were blocked with Tris-buffered saline, 0.5% bovine serum albumin, 0.05% polysorbate-20, 2 mM EDTA, pH 7.45 (assay buffer), at 25° C. for 1 hour. E27-IgE hexameric complexes were prepared in assay buffer by mixing equimolar amounts of E27 and human myeloma IgE (Nilsson, K., Bennich, H., Johansson, S. G. O., and Ponten, J., (1970) *Clin. Exp. Immunol.* 7:477-489) at 25° C. for 1 hour. E27-IgE (10.0 mg/ml in assay buffer) was added to plates and incubated for 2 hours. The plates were washed to remove unbound E27-IgE. 5A6 MAb, 5A6 F(ab)², 5A6 Fab, mIgG1 (control), and 5B9 (anti-FcγRIIIB) were prepared in assay buffer at various concentrations from 0.01 nM to 100 nM. The antibodies were added to individual wells and incubated for 1 hour. After washing plates with assay buffer, detection of E27-IgE hexameric complexes that remained bound to FcγRIIA or FcγRIIB in the presence of competing antibody was performed. Detection involved binding to the IgG1 portion of E27 a peroxidase-conjugated F(ab')² fragment of goat anti-human F(ab')-specific IgG. The detectable peroxidase substrate used was o-phenylenediamine dihydrochloride. Absorbance at 490 nm was read using a Vmax plate reader. FIG. 11 shows that 5A6 does not block E27-IgE hexamer binding to huFcγRIIA as indicated by the continued binding of E27-IgE hexamer to FcγRIIA with increasing concentration of competition antibody (5A6 MAb, 5A6 F(ab)², 5A6 Fab, mIgG1, and 5B9). Only antibody 5B9, known to bind both FcγRIIA and FcγRIIB (see FIGS. 4 and 5) was able to compete with E27-IgE hexamer binding. FIG. 12 shows that 5A6 does compete with E27-IgE hexamer binding to FcγRIIB as indicated by the reduction in E27-IgE hexamer binding with increasing 5A6 antibody, Fab or F(ab)₂. As expected, control IgG1 antibody did not compete. Binding of antibodies to huFcγIIB (5A6, 5A5, 5H11.1 and 5A6 Fab'2) and IgG1 (E27-IgE hexamer) to FcγRIIB, FcγRIIA (R131), or FcγRIIA (H131) is additionally shown in FIGS. 13-16. FIG. 14 shows IgG was prevented from binding to FcγRIIB in the presence of antibodies 5A6.2.1 and 6A5 while IgG binding to FcγRIIA (R131), shown in FIG. 13, and IgG binding to FcγRIIA (H131), shown in FIG. 15 is not blocked.

1.8 Immunofluorescence Binding Analysis

Figure 16:
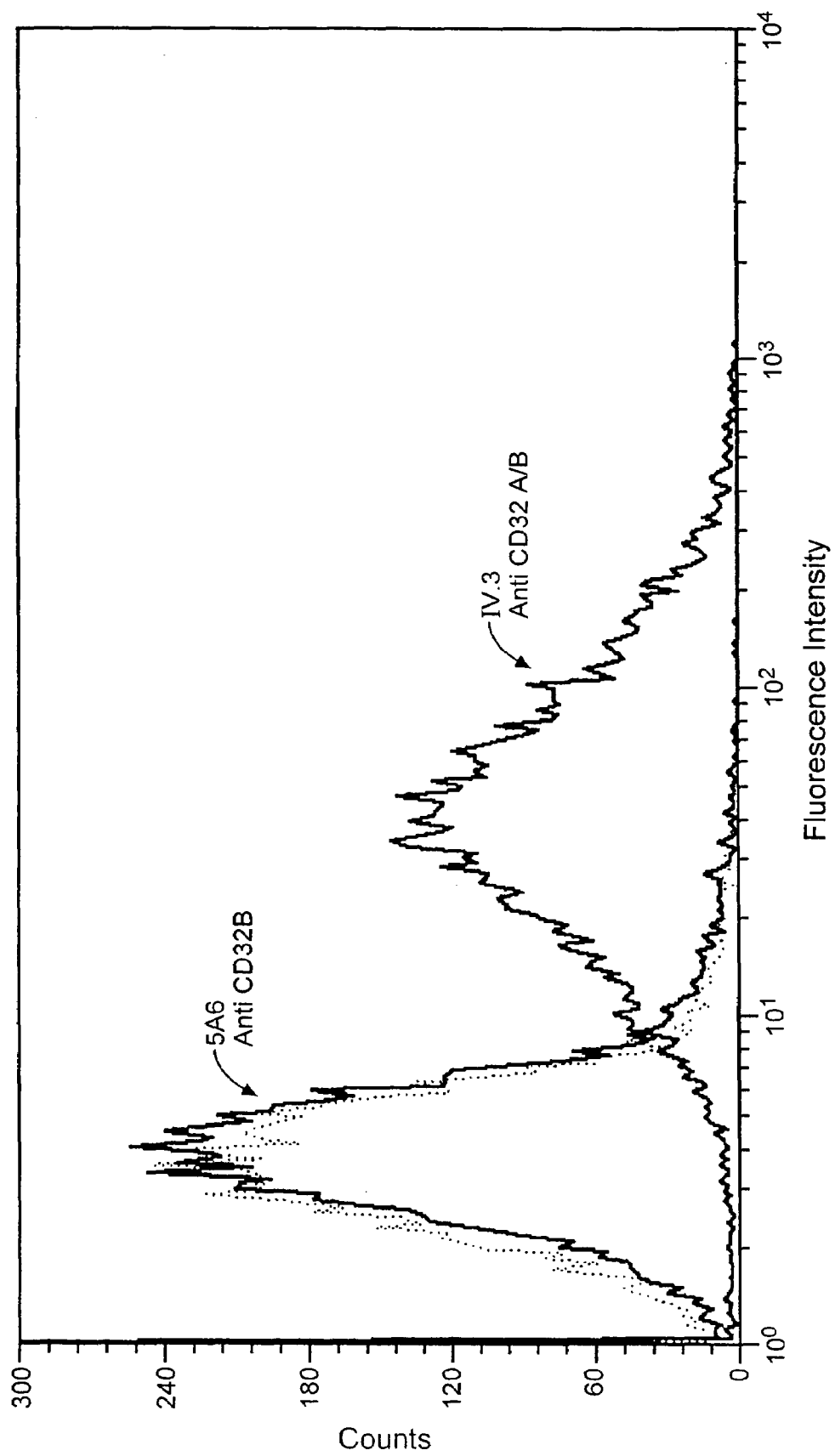
FIG. 16 presents indirect immunofluorescence binding analysis of 5A6 MAb on native FcγRIIA expressing K562 erythroleukemia line (ATCC No. CCL-243).

Indirect immunofluorescence binding analysis of 5A6 MAb to native FcγRIIA expressed on K562 erythroleukemia cells (ATCC No. CCL-243) is presented in FIG. 16. Separated aliquots of K562 cells were stained with either a mIgG1 isotype control (mopc 21), 5A6 (anti-human FcγRIIB) monoclonal antibody or Medarex 4.3 MAb (anti-human FcγRIIA/B) monoclonal antibody. Binding was detected indirectly by a second incubation with Fluorescein conjugated F(ab)'2 goat anti-mouse IgG (F(ab)'2 specific antibody) and analyzed by flow cytometry. Medarex 4.3 MAb bound to huFcγRIIA (CD32A) as shown in FIG. 16. 5A6, anti-huFcγRIIB (anti-CD32B) antibody, did not bind huFcγRIIA (CD32A), consistent with isotype control, mopc 21 antibody, which also did not bind huFcγRIIA (CD32A) as shown by the dotted line in FIG. 4.

Example 2.0

Properties of the Anti-FcγRIIB Antibody 2.1 Materials

Anti-FcεRI MAb, 22E7 MAb binds FcεRI with or without IgE bound at the receptor. 22E7 MAb was purified from Hoffman-LaRoche cell line IGE4R:22E7.2D2.1D11 (Risek, F., et al., 1991, *J. Biol. Chem.* 266: 11245-11251). Hoffman-LaRoche cells expressing 22E7 MAb were grown in Iscove's Modified Dulbecco's Media, with 10×FBS, 1× Pen-Strep, and 1× Glutamine. The 22E7 MAb was purified using protein A and protein G chromatography. The 22E7 extracts were pooled and affinity for FcεRI was verified.

2.2 RBL Cell Lines

RBL48 cell line, derived from parental rat mast cell line RBL-2H3 (ATCC#CRL-2256), expresses the α-subunit of the high affinity human IgE receptor (FcεRI). (Gilfillian A. M. et al., 1992, *Immunology*, 149, 2445-2451). RBL48 cell line was transfected by electroporation with a cDNA clone of full length α-subunit of human FcγRIIB1 (Muta T., et al., 1994, *Nature* 368:70-73.) which had been subcloned into a puromycin selectable expression vector (Morgenstern, J. P., et al., 1990, *Nucleic Acid Research*, 18:3587-3596). Clones were selected in 1 μM puromycin and analyzed for FcγRIIB cell surface expression by immunofluorescence staining with anti-human FcγRIIB monoclonal antibody, 5A6.2.1. The selected sub-clone was designated RBL48.C.4.

2.3 Histamine Release

Figure 17:
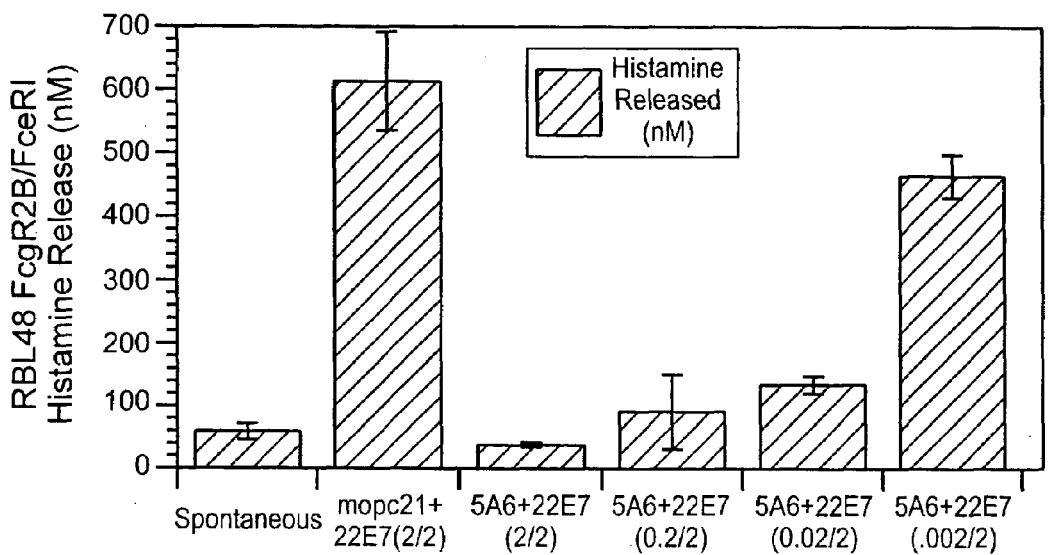
FIG. 17 shows effects of FcγRIIB cross-linking to activating receptors measured quantitatively by blocking of histamine release.

Effects of FcγRIIB cross-linking (also referred interchangeably to herein as co-cross-linking, co-aggregation, or co-ligation) on activating receptors is measured quantitatively based on the ability of the antibody to block histamine release from allergen sensitized RBL48.C.4 cells. Assay methods are described below, with results additionally depicted in FIG. 17.

The RBL48.C.4 clone was incubated in a 96 well, flat bottom, microtiter plate in assay buffer (EMEM (Eagle's Minimum Essential Medium with Earle's BSS) with 2 mM L-glutamine, 1 mM sodium pyruvate, 0.1 mM non-essential amino acids, 1.5 g/L sodium bicarbonate, penicillin, streptomycin, 15% fetal bovine serum) with 2 μg/ml anti-FcεRI MAb 22E7 and either an mIgG1 isotype control (mopc21) or 5A6 MAb at varying concentrations from 0.002 to 2 μg/nm at 37° C. for 30 minutes in a $CO_2$ incubator. Cells were washed twice in assay buffer and incubated with F(ab)'2 goat anti-mouse Fc specific crosslinking antibody for 30 minutes at 37° C. Supernatants were harvested and assayed for histamine content by ELISA as described generally above using a histamine ELISA kit.

Histamine release values are expressed as the mean and SEM from triplicate wells and presented graphically in FIG. 5. Both 5A6 and 22E7 with the crosslinking antibody were required for inhibition of histamine release. Histamine release was suppressed by binding of 5A6 to FcγRIIB and binding of 22E7 to FcεRI where 5A6 and 22E7 are also crosslinked by the goat anti-mouse Fc specific crosslinking antibody. A 1:1 ratio of 5A6 to 22E7 was the most effective at inhibiting histamine release, with discernable suppression also seen at ratios of 1:10, 1:100 and 1:1000.

Example 3.0

Producing Bispecific Antibody

This example describes construction and purification of bispecific antibodies having a variant hinge region lacking disulfide-forming cysteine residues ("hingeless"). Construction of bispecific antibodies having wild type hinge sequence is also described; these antibodies can be used to assess efficiency of obtaining various species of antibody complexes.

3.1 Construction of Expression Vectors

All plasmids for the expression of full-length antibodies were based on a separate cistron system (Simmons et al., 2002, *J. Immunol. Methods*, 263: 133-147; Simmons et al., U.S. Pat. No. 5,840,523) which relied on separate phoA promoters (AP) (Kikuchi et al., 1981, *Nucleic Acids Res.*, 9: 5671-5678) for the transcription of heavy and light chains, followed by the trp Shine-Dalgarno sequences for translation initiation (Yanofsky et al., 1981, *Nucleic Acids Res.*, 9: 6647-6668 and Chang et al., 1987, *Gene*, 55: 189-196). Additionally, the heat-stable enterotoxin II signal sequence (STII) (Picken et al., 1983, *Infect. Immun.*, 42: 269-275 and Lee et al., 1983, *Infect. Immun.*, 42: 264-268) was used for periplasmic secretion of heavy and light chains. Fine control of translation for both chains was achieved with previously described STII signal sequence variants of measured relative translational strengths, which contain silent codon changes in the translation initiation region (TIR) (Simmons and Yansura, 1996, *Nature Biotechnol.*, 14: 629-634 and Simmons et al., supra). For the purpose of this invention, the translational strength combination for a particular pair of TIRs within a vector is represented by (N—light, M—heavy), wherein N is the relative TIR strength of light chain and M is the relative TIR strength of heavy chain. Finally, the $\lambda_{t0}$ transcriptional terminator (Schlosstissek and Grosse, 1997, *Nucleic Acids Res.*, 15: 3185) was placed downstream of the coding sequences for both chains. All plasmids use the framework of a pBR322-based vector system (Sutcliffe, 1978, *Cold Spring Harbor Symp. Quant. Biol.*, 43: 77-90).

To enhance association of bispecific polypeptide chains, "knob-and-hole" mutations were introduced into dimerization regions. It is understood that either chain may comprise a "knob" mutation while the other chain comprises a complementary "hole" mutation. The invention comprises both embodiments. In the present illustrative example, the 5A6 arm of the bispecific antibody is constructed to comprise a "knob" mutation and the 22E7 arm of the bispecific antibody is constructed to comprise a complementary "hole" mutation.

(i) Plasmid p5A6.11.Knob.Hg—

Two intermediate plasmids were required to generate the desired p5A6.11.Knob.— plasmid. The variable domain of the 5A6 (anti-FcγRIIB) chimeric light chain was first transferred onto the pVG11.VNERK.Knob plasmid to generate the intermediate plasmid p5A6.1.L.VG.1.H.Knob. The variable domain of the 5A6 chimeric heavy chain was then transferred onto the p5A6.1.L.VG.1.H.Knob plasmid to generate the intermediate plasmid p5A6.11.Knob plasmid. The following describes the preparation of these intermediate plasmids p5A6.1.LC.VG.1.HC.Knob and p5A6.11.Knob followed by the construction of p5A6.11.Knob.— p5A6.1.L.VG.1.H.Knob

This plasmid was constructed in order to transfer the murine light variable domain of the 5A6 antibody to a plasmid compatible for generating the full-length antibody heavy chain-light chain (H/L) monomeric antibody. The construction of this plasmid involved the ligation of two DNA fragments. The first was the pVG11.VNERK.Knob vector in which the small EcoRI-PacI fragment had been removed. The plasmid pVG11.VNERK.Knob is a derivative of the separate cistron vector with relative TIR strengths of 1—light and 1—heavy (Simmons et al., 2002, supra) in which the light and heavy variable domains have been changed to an anti-VEGF antibody (VNERK) with the "knob" mutation (T366W) (Merchant et al., 1998, *Nature Biotechnology*, 16:677-681) and all the control elements described above. The second part of the ligation involved ligation of the sequence depicted in FIG. 25 (SEQ ID NO:35) into the EcoRI-PacI digested pVG11.VNERK.Knob vector described above. The sequence encodes the alkaline phosphatase promoter (phoA), STII signal sequence and the entire (variable and constant domains) light chain of the 5A6 antibody. p5A6.11.Knob This plasmid was constructed to introduce the murine heavy variable domain of the 5A6 antibody into a human heavy chain framework to generate the chimeric full-length heavy chain/light chain (H/L) monomeric antibody. The construction of p5A6.11.Knob involved the ligation of two DNA fragments. The first fragment was the p5A6.1.L.VG.1.H.Knob vector, from above, in which the small MluI-PspOMI fragment had been removed. The second fragment involved ligation of the sequence depicted in FIG. 27 (SEQ ID NO:37) into the MluI-PspOMI digested p5A6.1.L.VG.1.H.Knob vector. The sequence encodes the last 3 amino acids of the STII signal sequence and approximately 119 amino acids of the murine heavy variable domain of the 5A6 antibody.

p5A6.11.Knob.Hg—

The p5A6.11.Knob.Hg— plasmid was constructed to express the full-length chimeric 5A6 hingeless Knob heavy chain/light (H/L) chain monomeric antibody. The construction of the plasmid involved the ligation of two DNA fragments. The first fragment was the p5A6.11.Knob vector, from above, in which the small PspOMI-SacII fragment had been removed. The second fragment was an approximately 514 base-pair PspOMI-SacII fragment from p4D5.22.— encoding approximately 171 amino acids of the human heavy chain in which the two hinge cysteines have been converted to serines (C226S, C229S, EU numbering scheme of Kabat, E. A. et al. (eds.), 1991, page 671 in *Sequences of proteins of Immunological interest*, 5th ed. Vol. 1. NIH, Bethesda Md.). The plasmid p4D5.22.— is a derivative of the separate cistron vector with relative TIR strengths of 2—light and 2—heavy (Simmons et al., *J. Immunol. Methods*, 263: 133-147 (2002)) in which the light and heavy variable domains have been changed to an anti-HER2 antibody and the two hinge cysteines have been converted to serines (C226S, C229S).

(ii) Plasmid p5A6.22.Knob.Hg—

One intermediate plasmid was required to generate the desired p5A6.22. Hg— plasmid. The phoA promoter and the STII signal sequence (relative TIR strength of 2 for light chain) were first transferred onto the p5A6.11.Knob.Hg— plasmid to generate the intermediate plasmid p5A6.21.Knob.Hg—. The following describes the preparation of the intermediate plasmid p5A6.21.Knob.Hg— followed by the construction of p5A6.22.Knob.Hg— p5A6.21.Knob.Hg—

This plasmid was constructed to introduce the STII signal sequence (relative TIR strength of 2) for the light chain. The construction of p5A6.21.Knob.Hg—involved the ligation of three DNA fragments. The first fragment was the p5A6.11.Knob.Hg—vector in which the small EcoRI-PacI fragment had been removed. The second fragment was an approximately 658 base-pair NsiI-PacI fragment from the p5A6.11.Knob.Hg— plasmid encoding the light chain for the chimeric 5A6 antibody. The third part of the ligation was an approximately 489 base-pair EcoRI-NsiI PCR fragment generated from the p1H1.22.Hg— plasmid, using the following primers:

```
                                         (SEQ ID NO:27)
5'-AAAGGGAAAGAATTCAACTTCTCCAGACTTTGGATAAGG (SEQ ID NO:28)
5'-AAAGGGAAAATGCATTTGTAGCAATAGAAAAAACGAA
```

The plasmid p1H1.22.Hg— is a derivative of the separate cistron vector with relative TIR strengths of 2—light and 2—heavy (Simmons et al., J. Immunol. Methods, 263: 133-147 (2002)) in which the light and heavy variable domains have been changed to a rat anti-Tissue Factor antibody in which the two hinge cysteines have been converted to serines (C226S, C229S).

p5A6.22.Knob.Hg—

This plasmid was constructed to introduce the STII signal sequence—with a relative TIR strength of 2 for the heavy chain. The construction of p5A6.22.Knob involved the ligation of two DNA fragments. The first was the p5A6.21.Knob.Hg— vector in which the small PacI-MluI fragment had been removed. The second part of the ligation was an approximately 503 base-pair PacI-MluI fragment from the p1H1.22.Hg— plasmid encoding the $\lambda_{t0}$ transcriptional terminator for the light chain, the phoA promoter, and the STII signal sequence (relative TIR strength of 2 for the heavy chain).

(iii) Plasmid p22E7.11.Hole.Hg—

Two intermediate plasmids were required to generate the desired p22E7.11.Hole.Hg— plasmid. The variable domain of the 22E7 (anti-FcεRI) chimeric light chain was first transferred onto the pVG11.VNERK.Hole plasmid to generate the intermediate plasmid p22E7.1.L.VG.1.H.Hole. The variable domain of the 22E7 chimeric heavy chain was then transferred onto the p22E7.1.L.VG.1.H.Hole plasmid to generate the intermediate plasmid p22E7.11.Hole plasmid. The following describes the preparation of these intermediate plasmids p22E7.1.L.VG.1.H.Hole and p22E7.11.Hole followed by the construction of p22E7.11.Hole.Hg— p22E7.1.L.VG.1.H.Hole

This plasmid was constructed in order to transfer the murine light variable domain of the 22E7 antibody to a plasmid compatible for generating the full-length heavy chain/ light chain (H/L) monomeric antibody. The construction of this plasmid involved the ligation of two DNA fragments. The first fragment was the pVG11.VNERK.Hole vector in which the small EcoRI-PacI fragment had been removed. The plasmid pVG11.VNERK.Hole is a derivative of the separate cistron vector with relative TIR strengths of 1—light and 1—heavy (Simmons et al., J. Immunol. Methods, 263: 133-147 (2002)) in which the light and heavy variable domains have been changed to an anti-VEGF antibody (VNERK) having the "hole" mutations (T366S, L368A, Y407V) (Merchant et al., Nature Biotechnology, 16:677-681 (1998)) and all the control elements described above. The second part of the ligation involved ligating the sequence depicted in FIG. 26 (SEQ ID NO:36) into the EcoRI-PacI digested pVG11.VNERK.Hole vector described above. The sequence encodes the alkaline phosphatase promoter (phoA), STII signal sequence and the entire (variable and constant domains) light chain of the 22E7 antibody.

p22E7.11.Hole

This plasmid was constructed to introduce the murine heavy variable domain of the 22E7 antibody into a human heavy chain framework to generate the chimeric full-length heavy chain/light chain H/L monomeric antibody. The construction of p22E7.11.Knob involved the ligation of two DNA fragments. The first was the p22E7.1.L.VG.1.H.Hole vector in which the small MluI-PspOMI fragment had been removed. The second part of the ligation involved ligating the sequence depicted in FIG. 28 (SEQ ID NO:38) into the MluI-PspOMI digested p22.E7.1.L.VG.1.H.Hole vector. The sequence encodes the last 3 amino acids of the STII signal sequence and approximately 123 amino acids of the murine heavy variable domain of the 22E7 antibody.

p22E7.11.Hole.Hg—

The p22E7.11.Hole.Hg— plasmid was constructed to express the full-length chimeric 22E7 hingeless Hole heavy chain/light chain (H/L) monomeric antibody. The construction of the plasmid involved the ligation of two DNA fragments. The first was the p22E7.11.Hole vector in which the small PspOMI-SacII fragment had been removed. The second part of the ligation was an approximately 514 base-pair PspOMI-SacII fragment from p4D5.22.Hg— encoding approximately 171 amino acids of the human heavy chain in which the two hinge cysteines have been converted to serines (C226S, C229S).

(iv) Plasmid p22E7.22.Hole.Hg—

One intermediate plasmid was required to generate the desired p22E7.22.Hole.Hg— plasmid. The phoA promoter and the STII signal sequence (relative TIR strength of 2) for light chain were first transferred onto the p22E7.11.Hole.Hg— plasmid to generate the intermediate plasmid p22E7.21.Hole.Hg—. The following describes the preparation of the intermediate plasmid p22E7.21.Hole.Hg— followed by the construction of p22E7.22.Hole.Hg— p22E7.21.Hole.Hg—

This plasmid was constructed to introduce the STII signal sequence (with a relative TIR strength of 2) for the light chain. The construction of p22E7.21.Hole.Hg— involved the ligation of three DNA fragments. The first fragment was the p22E7.11.Hole.Hg— vector in which the small EcoRI-PacI fragment had been removed. The second fragment was an approximately 647 base-pair EcoRI-PacI fragment from the p22E7.11.Hole.Hg— plasmid encoding the light chain for the chimeric 22E7 antibody. The third fragment was an approximately 500 base-pair EcoRI-EcoRV fragment from the p1H1.22.Hg— plasmid encoding the alkaline phosphatase promoter (phoA) and STII signal sequence.

p22E7.22.Hole.Hg—

This plasmid was constructed to introduce the STII signal sequence (with a relative TIR strength of 2) for the heavy chain. The construction of p22E7.22.Hole.Hg— involved the ligation of three DNA fragments. The first fragment was the p22E7.21.Hole.Hg— vector in which the small EcoRI-MluI fragment had been removed. The second fragment was an approximately 1141 base-pair EcoRI-PacI fragment from the p22E7.21.Hole.Hg— plasmid encoding the alkaline phosphatase promoter, STII signal sequence, and the light chain for the chimeric 22E7 antibody. The third fragment was an approximately 503 base-pair PacI-MluI fragment from the p1H1.22.Hg— plasmid encoding the $\lambda_{t0}$ transcriptional terminator for the light chain and the STII signal sequence (with a relative TIR strength of 2) for the heavy chain.

3.2 Antibody Expression—5A6 Knob and 22E7 Hole

Full-length bispecific antibody was formed by exploiting "knobs into holes" technology to promote heterodimerization in the generation of anti-FcγRIIB (5A6)/anti-FcεRI (22E7) antibody. The "knobs into holes" mutations in the CH3 domain of Fc sequence has been reported to greatly reduce the formation of homodimers (Merchant et al., Nature Biotechnology, 16:677-681 (1998)). Constructs were prepared for the anti-FcγRIIB component (p5A6.11.Knob) by introducing the "knob" mutation (T366W) into the Fc region, and the anti-FcεRI component (p22E7.11.Hole) by introducing the "hole" mutations (T366S, L368A, Y407V) (Merchant, 1998, supra).

Small-scale synthesis of the antibodies were carried out using the plasmids p5A6.11.Knob for production of knob anti-FcγRIIB monomeric antibody and p22E7.11.Hole for hole anti-FcεRI monomeric antibody. Each plasmid possessed relative TIR strengths of 1 for both light and heavy chains. For small scale expression of each construct, the *E. coli* strain 33D3 (W3110 ΔfhuA (ΔtonA) ptr3 lac Iq lacL8 ΔompT Δ(nmpc-fepE) degP41 kan$^R$) was used as host cells. Following transformation, selected transformants were inoculated into 5 mL Luria-Bertani medium supplemented with carbenicillin (50 μg/mL) and grown at 30° C. on a culture wheel overnight. Each culture was then diluted (1:100) into C.R.A.P. phosphate-limiting media (Simmons et al., J. Immunol. Methods 263:133-147 (2002)). Carbenicillin was then added to the induction culture at a concentration of 50 μg/mL and the culture was grown for approximately 24 hours at 30° C. on a culture wheel. Unless otherwise noted, all shake flask inductions were performed in a 5 mL volume.

Non-reduced whole cell lysates from induced cultures were prepared as follows: (1) 1 $OD_{600}$-mL induction samples were centrifuged in a microfuge tube; (2) each pellet was resuspended in 90 μL TE (10 mM Tris pH 7.6, 1 mM EDTA); (3) 10 μL of 100 mM iodoacetic acid (Sigma I-2512) was added to each sample to block any free cysteines and prevent disulfide shuffling; (4) 20 μL of 10% SDS was added to each sample. The samples were vortexed, heated to about 90° C. for 3 minutes and then vortexed again. After the samples had cooled to room temperature, 750 μL acetone was added to precipitate the protein. The samples were vortexed and left at room temperature for about 15 minutes. Following centrifugation for 5 minutes in a microcentrifuge, the supernatant of each sample was removed by aspiration, and each protein pellet was resuspended in 50 μL $dH_2O$ plus 50 μL 2×NOVEX SDS sample buffer. The samples were then heated for four minutes at about 90° C., vortexed and allowed to cool to room temperature. A final five minute centrifugation was performed and the supernatants were transferred to clean tubes.

Reduced whole cell lysates from induced cultures were prepared as follows: (1) 1 $OD_{600}$-mL induction samples were centrifuged in a microfuge tube; (2) each pellet was resuspended in 90 μL TE (10 mM Tris pH 7.6, 1 mM EDTA); (3) 10 μL of 1 M dithiothreitol (Sigma D-5545) was added to each sample to reduce disulfide bonds; (4) 20 μL of 10% SDS was added to each sample. The samples were vortexed, heated to about 90° C. for 3 minutes and then vortexed again. After the samples had cooled to room temperature, 750 μL acetone was added to precipitate the protein. The samples were vortexed and left at room temperature for about 15 minutes. Following centrifugation for 5 minutes in a microcentrifuge, the supernatant of each sample was removed by aspiration and each protein pellet was resuspended in 10 μL 1 M dithiothreitol plus 40 μL dH20 plus 50 μL 2×NOVEX SDS sample buffer. The samples were then heated for 4 minutes at about 90° C., vortexed and allowed to cool to room temperature. A final five minute centrifugation was performed and the supernatants were transferred to clean tubes.

Following preparation, 5 to 8 μL of each sample was loaded onto a 10 well, 1.0 mm 12% Tris-Glycine SDS-PAGE (NOVEX and electrophoresed at ~120 volts for 1.5-2 hours. The resulting gels were then either stained with Coomassie Blue or used for Western blot analysis.

For Western blot analysis, the SDS-PAGE gels were electroblotted onto a nitrocellulose membrane (NOVEX) in 10 mM CAPS buffer, pH 11+3% methanol. The membrane was blocked using a solution of 1×NET (150 mM NaCl, 5 mM EDTA, 50 mM Tris pH 7.4, 0.05% Triton X-100) plus 0.5% gelatin for approximately 30 min-1 hours rocking at room temperature. Following the blocking step, the membrane was placed in a solution of 1×NET/0.5% gelatin/anti-Fab antibody (peroxidase-conjugated goat IgG fraction to human IgG Fab; CAPPEL #55223) for an anti-Fab Western blot analysis. The anti-Fab antibody dilution ranged from 1:50,000 to 1:1,000,000 depending on the lot of antibody. Alternatively, the membrane was placed in a solution of 1×NET/0.5% gelatin/anti-Fc antibody (peroxidase-conjugated goat IgG fraction to human Fc fragment; BETHYL #A80-104P-41) for an anti-Fc Western blot analysis. The anti-Fc antibody dilution ranged from 1:50,000 to 1:250,000 depending on the lot of the antibody. The membrane in each case was left in the antibody solution overnight at room temperature with rocking. The next morning, the membrane washed a minimum of 3×10 minutes in 1×NET/0.5% gelatin and then 1×15 minutes in TBS (20 mM Tris pH 7.5, 500 mM NaCl). The protein bands bound by the anti-Fab antibody and the anti-Fc antibody were visualized using Amersham Pharmacia Biotech ECL detection kit, followed by exposure of the membrane to X-Ray film.

Figure 18:
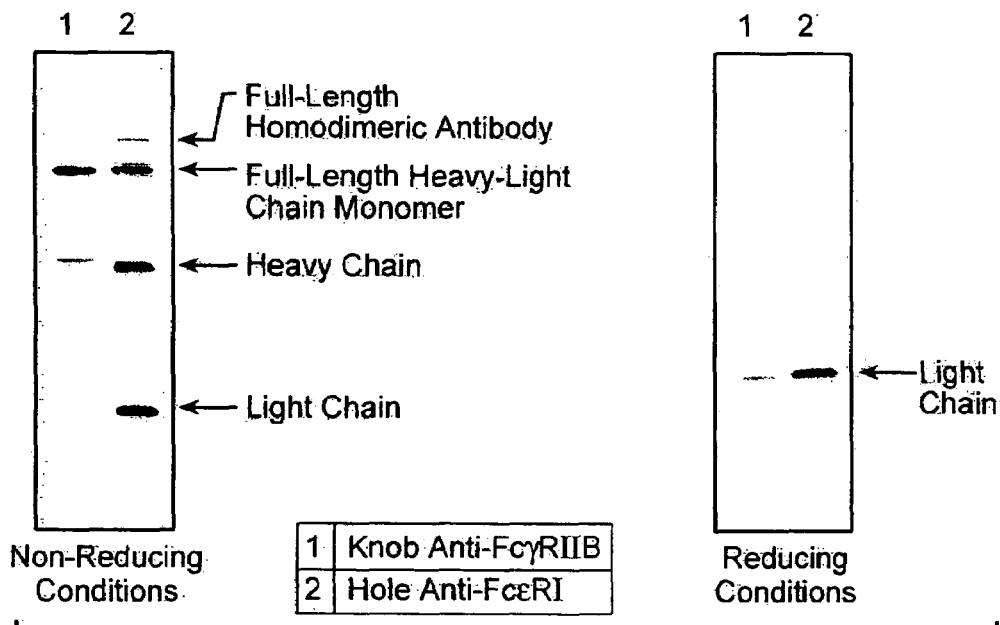
FIG. 18 depicts anti-Fab Western blot results for p5A6.11.Knob (knob anti-FcγRIIB) and p22E7.11.Hole (hole anti-FcεRI) antibody component expression.

The anti-Fab Western blot results for the p5A6.11.Knob (knob anti-FcγRIIB) and p22E7.11.Hole (hole anti-FcεRI) antibody expression are shown in FIG. 18. They reveal the expression of fully folded and assembled heavy-light (HL) chain species for the knob anti-FcγRIIB antibody in lane 1 and the hole anti-FcεRI antibody in lane 2. The anti-Fab antibody has different affinities for different variable domains of the light chain. The anti-Fab antibody generally has a lower affinity for the heavy chain. For the non-reduced samples, the expression of each antibody results in the detection of the heavy-light chain species. Notably, the full-length antibody homodimer species is detectable for the hole anti-FcεRI antibody, however it is only a small proportion of total fully folded and assembled antibody species. The folding and assembly of the full-length antibody homodimer species is not favored as a result of the inclusion of the "knob" mutation for the anti-FcγRIIB antibody and the "hole" mutations for the anti-FcεRI antibody. For the reduced samples, the light chain is detected for the knob anti-FcγRIIB antibody and the hole anti-FcεRI antibody.

Figure 19:
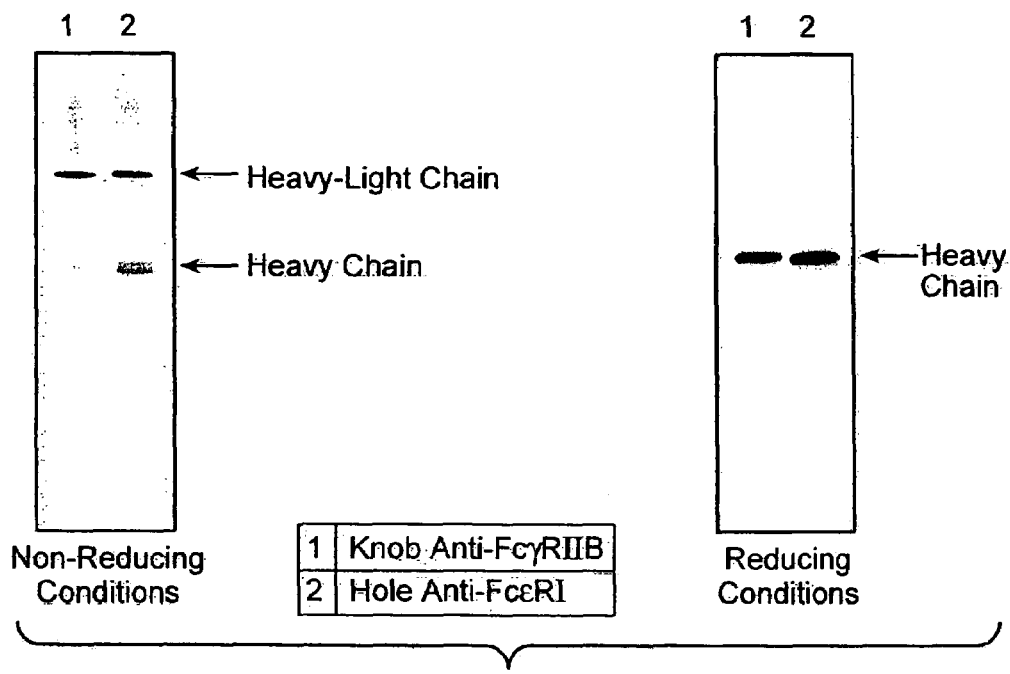
FIG. 19 depicts anti-Fc Western blot results for p5A6.11.Knob (knob anti-FcγRIIB) and p22E7.11.Hole (hole anti-FcεRI) antibody component expression.

Similarly, the anti-Fc Western blot results are shown in FIG. 19 and they also reveal the expression of fully folded and assembled heavy-light (HL) chain species for the knob anti-FcγRIIB antibody in lane 1 and the hole anti-FcεRI antibody in lane 2. The anti-Fc antibody is not able to bind light chain, and therefore the light chain is not detected. For the non-reduced samples, the expression of each antibody again results in the detection of the heavy-light chain species, but not the full-length antibody homodimer species. For the reduced samples, there are similar quantities of heavy chain detected for the knob anti-FcγRIIB antibody and the hole anti-FcεRI antibody.

3.3 Expression of 5A6 Knob Hinge Variant and 22E7 Hole Hinge Variant Antibodies

The primary antibody species obtained from expression of the p5A6.11.Knob and p22E7.11.Hole constructs were the fully folded and assembled heavy-light (HL) chain species. However, in order to facilitate the method of preparation herein described for the bispecific anti-FcγRIIB/anti-FcεRI (5A6/22E7) antibody, the hinge sequence of the two heavy chains were modified by substituting the two hinge cysteines with serines (C226S, C229S, EU numbering scheme of Kabat, E. A. et al., supra). Hinge variants are also referred to below as "hingeless".

Plasmid constructs were prepared for the knob anti-FcγRIIb (5A6) antibody and the hole anti-FcεRI (22E7) antibody comprising hinge variants having C226S, C229S substitutions. Two plasmid constructs were prepared for each antibody. One construct had a relative TIR strength of 1 for both light and heavy chains and the second construct had a relative TIR strength of 2 for both light and heavy chains.

The knob anti-FcγRIIB antibody (from p5A6.11.Knob plasmid), the hole anti-FcεRI antibody (p22E7.11.Hole), the knob hingeless anti-Fcγ-RIIb antibodies (p5A6.11.Knob.Hg— and p5A6.22.Knob.—), and the hole hingeless anti-FcεRI antibodies (p22E7.11.Hole.Hg— and p22E7.22.Hole.Hg—) were then expressed from their respective plasmids as described herein above. Whole cell lysates were prepared, separated by SDS-PAGE, transferred to nitrocellulose, and detected with the goat anti-human Fab conjugated antibody and goat anti-human Fc conjugated antibody described above.

Figure 20:
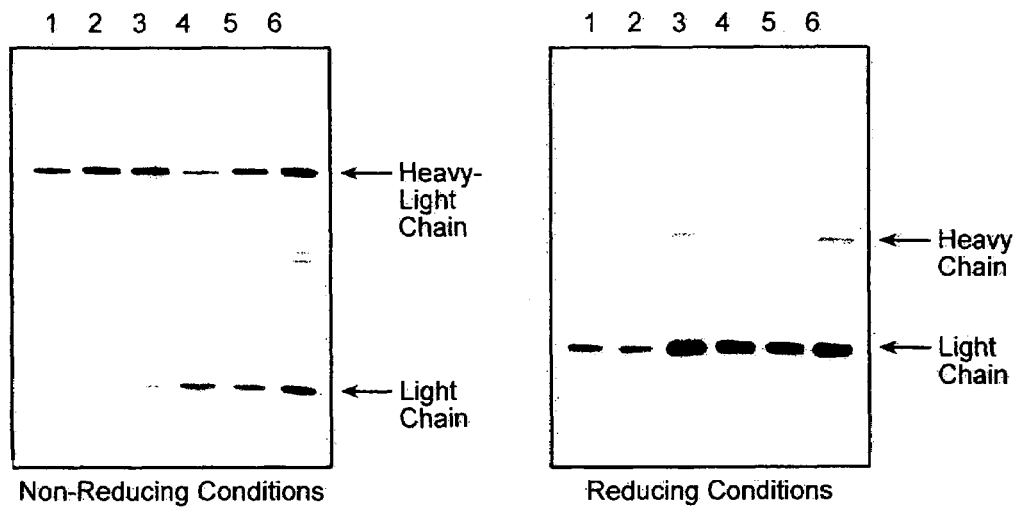
FIG. 20 depicts anti-Fab Western blot results for expression of antibody components with wild type or variant hinge sequences.

The anti-Fab Western blot results are shown in FIG. 20 and they show a significant improvement in folding and assembly of the heavy-light (HL) chain species for the knob hingeless anti-Fcγ-RIIB monomeric antibody (relative TIR strengths—1 for light chain and 1 for heavy chain) in lane 2 and the hole hingeless anti-FcεRI monomeric antibody (relative TIR strengths—1 for light chain and 1 for heavy chain) in lane 5. In addition, the anti-Fab Western blot results show an increase in the folding and assembly of the heavy-light (HL) chain species for the monomeric HL knob hingeless anti-Fcγ-RIIB antibody (lane 3) and the monomeric HL hole hingeless anti-FcεRI antibody (lane 6) when the relative TIR strengths for light and heavy chain are increased from 1 to 2. The anti-Fab antibody has different affinities for different variable domains of the light chain and generally has a lower affinity for the heavy chain. For the non-reduced samples, the expression of each antibody results in the detection of the heavy-light chain species, but not the full-length antibody species as a result of the conversion of the hinge cysteines to serines. There are significant improvements in the folding and assembly of the heavy-light (HL) chain species for each of the knob hingeless anti-Fcγ-RIIb and hole hingeless anti-FcεRI antibodies when the two hinge cysteines are converted to serines and again when the relative TIR strengths for light and heavy chains are increased from 1 to 2. For the reduced samples, the heavy, as well as light chains, are detected for the different anti-Fcγ-RIIb and anti-FcεRI antibodies. The increase in the quantities of heavy and light chains is detected when the relative TIR strengths are increased from 1 to 2.

Figure 21:
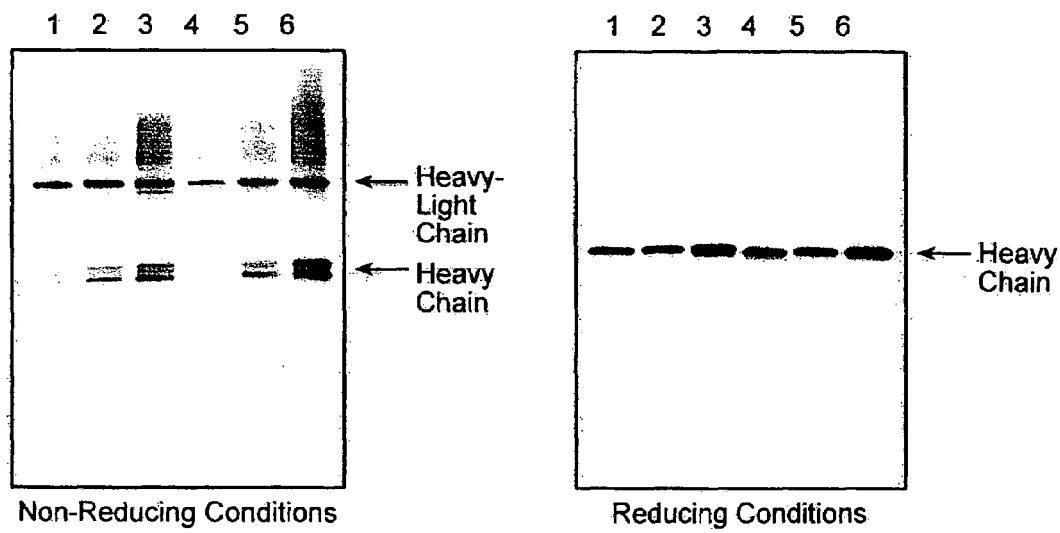
FIG. 21 depicts anti-Fc Western blot results for expression of antibody components with wild type or variant hinge sequences.

Similarly, the anti-Fc Western blot results in FIG. 21 show significant improvement in the folding and assembly of the heavy-light (HL) chain monomeric species for both the knob hingeless anti-Fcγ-RIIB and hole hingeless anti-FcεRI antibody when the two heavy chain (HC) hinge cysteines are converted to serines and again when the relative TIR strengths for light and heavy chains are increased from 1 to 2. The anti-Fc antibody is not able to bind light chain, and therefore the light chain is not detected. For the reduced samples, the heavy chain is detected for the different anti-Fcγ-RIIb and anti-FcεRI antibodies. The increase in the quantities of heavy chains is detected when the relative TIR strengths are increased from 1 to 2.

3.4 Purification of Bispecific Antibody Components

Ease and efficiency of obtaining purified and functional bispecific antibodies was further assessed in the context of antibodies having a variant hinge region as described above.

1. Extraction from *E. coli* Paste

Frozen *E. coli* paste was thawed and suspended in 5 volumes (v/w) distilled water, adjusted to pH 5 with HCl, centrifuged, and the supernatant discarded. The insoluble pellet was resuspended in 5-10 volumes of a buffer at pH 9 using a polytron (Brinkman), and the supernatant retained following centrifugation. This step was repeated once.

The insoluble pellet was then resuspended in 5-10 volumes of the same buffer, and the cells disrupted by passage through a microfluidizer (Microfluidics). The supernatant was retained following centrifugation.

The supernatants were evaluated by SDS polyacrylamide gel electrophoresis (SDS-PAGE) and Western blots, and those containing the single-armed antibody (i.e. a band corresponding to the molecular weight of a single heavy chain plus light chain) were pooled.

2. Protein-A Affinity Chromatography

The pooled supernatants were adjusted to pH8, and ProSep™-A beads (Millipore) were added (approximately 250 ml beads per 10 liters). The mixture was stirred for 24-72 hours at 4° C., the beads allowed to settle, and the supernatant poured off. The beads were transferred to a chromatography column (Amersham Biosciences XK50™), and washed with 10 mM tris buffer pH7.5. The column was then eluted using a pH gradient in 50 mM citrate, 0.1M NaCl buffer. The starting buffer was adjusted to pH6, and the gradient formed by linear dilution with pH2 buffer.

Fractions were adjusted to pH5 and 2M urea by addition of 8M urea and tris base, then evaluated by SDS-PAGE and pooled.

3. Cation Exchange Chromatography

An S-Sepharose Fast Flow™ column (Amersham Biosciences) was equilibrated with 2M urea, 25 mM MES pH5.5. The ProSep™-A eluate pool was diluted with an equal volume of equilibration buffer, and loaded onto the column. After washing with equilibration buffer, then with 25 mM MES pH5.5, the column was developed with a linear gradient of 0-1M NaCl in 25 mM MES, pH5.5. Fractions were pooled based on SDS-PAGE analysis.

4. Hydrophobic Interaction Chromatography

A HI-Propyl™ column (J. T. Baker) was equilibrated with 0.5M sodium sulfate, 25 mM MES pH6. The S-Fast Flow™ eluate was adjusted to 0.5M Sodium sulfate, pH6, loaded onto the column, and the column developed with a gradient of 0.5-0M sodium sulfate in 25 mM MES, pH6. Fractions were pooled based on SDS-PAGE analysis.

5. Size Exclusion Chromatography

The HI-Propyl™ eluate pool was concentrated using a CentriPrep™ YM10 concentrator (Amicon), and loaded onto a Superdex™ SX200 column (Amersham Biosciences) equilibrated with 10 mM succinate or 10 mM histidine in 0.1M NaCl, pH6, and the column developed at 2.5 ml/m. Fractions were pooled based on SDS-PAGE.

3.5 Annealing of Antibody Components to Generate Bispecific Antibodies

Two similar (but not identical) annealing methods are described below, both of which resulted in good yields of bispecific antibodies. Heavy chains of the antibodies and antibody components described below contain a variant hinge region as described above.

Annealing Hinge Variant 5A6Knob and Hinge Variant 22E7Hole—Method 1

Purified 5A6Knob and 22E7Hole heavy chain/light chain monomeric antibodies in 25 mM MES pH5.5, 0.5 M NaCl, were mixed in equal molar ratios based on their concentrations. The mixture was then heated at 50° C. for 5 minutes to 1 hour. This annealing temperature was derived from the melting curves previously described for these CH3 variants (Atwell, S., et al, 1997, *J. Mol. Biol.*, 270:26-35). The annealed antibody was then subjected to analysis to determine its bispecificity.

Analysis of Bispecificity

1) Isoelectric Focusing

Figure 22:
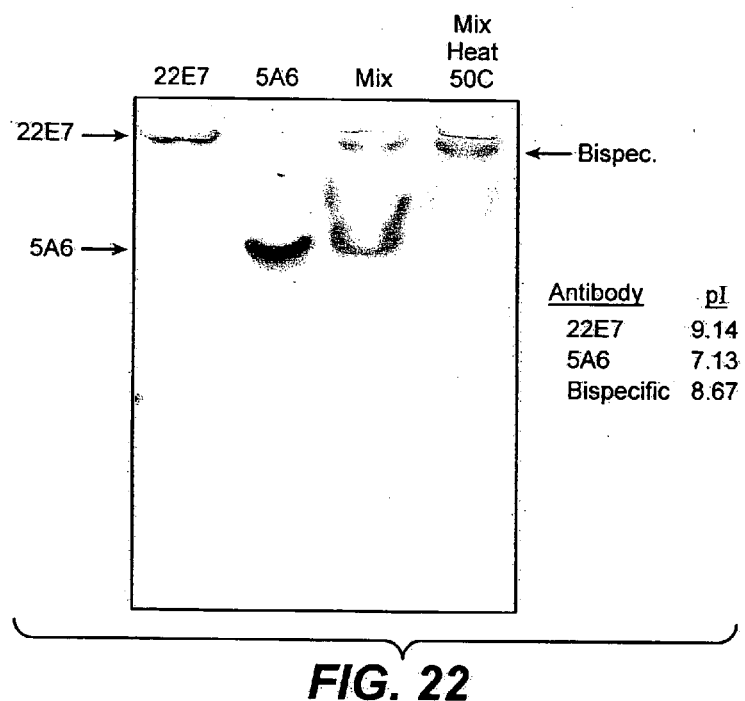
FIG. 22 depicts isoelectric focusing analysis of 5A6Knob, 22E7Hole, mixed 5A6Knob and 22E7Hole at room temperature, and the mixture heated to 50° C. for 5 minutes.

Annealed antibody was verified as bispecific by applying samples for isoelectric focusing analysis. The 5A6Knob antibody has a pI of 7.13 while the 22E7Hole has a pI of 9.14. The bispecific 5A6Knob/22E7Hole antibody has a pI of 8.67. FIG. 22 shows the movement of the 5A6Knob, 22E7Hole and bispecific 5A6Knob/22E7Hole (before and after heating) antibodies on an isoelectric focusing gel (Invitrogen, Novex pH3-10 IEF) after staining with Coomassie Blue. While there is some annealing upon mixing at room temperature, the heating to 50° C. appears to promote completion of the process. The appearance of a new protein band with a pI in between that of 5A6Knob and 22E7Hole verifies the formation of the bispecific antibody.

2) Affinity Column Analysis

The behaviors of the 5A6Knob, 22E7Hole, and bispecific 5A6Knob/22E7Hole antibodies were observed on FcγRIIB affinity columns. A human FcγRIIB (extracellular domain)-GST fusion protein was coupled to a solid support in a small column according to the manufacturer's instructions (Pierce, UltraLink™ Immobilization Kit #46500). 5A6Knob, 22E7Hole, and bispecific 5A6Knob/22E7Hole antibodies in PBS (137 mM NaCl, 2.7 mM KCl, 8 mM $Na_2HPO_4$, 1.5 mM $KH_2PO_4$, pH 7.2) were loaded onto three separate FcγRIIB affinity columns at approximately 10-20% of the theoretical binding capacity of each column. The columns were then washed with 16 column volumes of PBS. The column flow-throughs for the loading and wash were collected, combined, and concentrated approximately 10-fold in Centricon™ Microconcentrators (Amicon). Each concentrate in the same volume was then diluted 2 fold with 2×SDS sample buffer and analyzed by SDS-PAGE (Invitrogen, Novex Tris-Glycine). The protein bands were transferred to nitrocellulose by electroblotting in 20 mM $Na_2HPO_4$ pH 6.5, and probed with an anti-human IgG Fab peroxidase conjugated antibody (CAPPELL#55223). The antibody bands were then detected using Amersham Pharmacia Biotech ECL™ kit according to the manufacturer's instructions.

Figure 23:
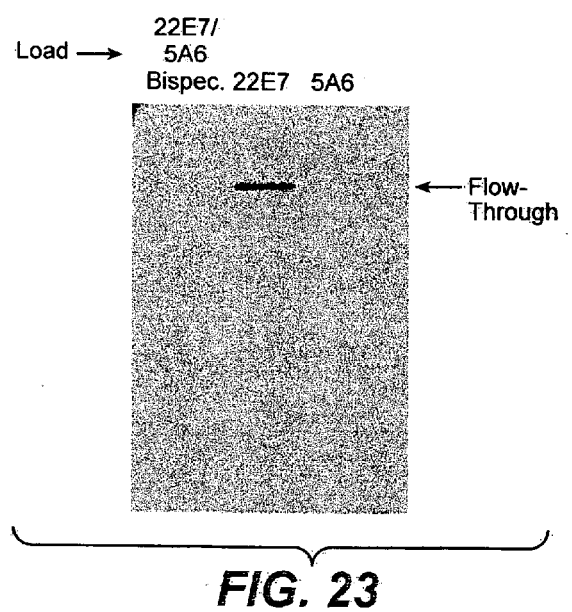
FIG. 23 depicts FcγRIM affinity column flow-throughs for 5A6Knob/22E7Hole bispecific, 22E7Hole, and 5A6Knob antibodies.

The results of this analysis are shown in FIG. 23. The FcγRIIB affinity column should retain the 5A6Knob antibody and the 5A6Knob/22E7Hole bispecific antibody. The 22E7Hole antibody should flow through as is shown in FIG. 23. The lack of antibody detected in the 5A6Knob/22E7Hole bispecific lane indicated bispecificity.

The behaviors of the 5A6Knob, 22E7Hole, and bispecific 5A6Knob/22E7Hole antibodies may also be observed on FcεRI affinity columns. IgE fusion affinity column may be prepared and utilized as described above for the FcγRIIB affinity column. The FcεRI affinity column should retain the 22E7Hole antibody and 5A6Knob/22E7Hole antibody. The 5A6Knob antibody should flow through. Lack of antibody detected in the 5A6Knob/22E7Hole antibody lane indicated bispecificity.

Annealing Hinge Variant 5A6Knob and Hinge Variant 22E7Hole—Method 2

The antibody components (single arm 5A6Knob and 22E7Hole) were purified as described above.

The 'heterodimer' was formed by annealing at 50° C., using a slight molar excess of 5A6, then purified on a cation exchange column.

5A6(Knob) 5 mg and 22E7(Hole) 4.5 mg H/L monomeric antibodies were combined in a total volume of 10 ml 8 mM succinate, 80 mM NaCl buffer, adjusted to 20 mM tris, pH7.5.

The monomeric antibodies were annealed by heating the mixture to 50° C. in a water bath for 10 minutes, then cooled to 4° C. to form the bispecific antibody.

Analysis of Bispecificity

1. Isoelectric Focusing

Figure 24:
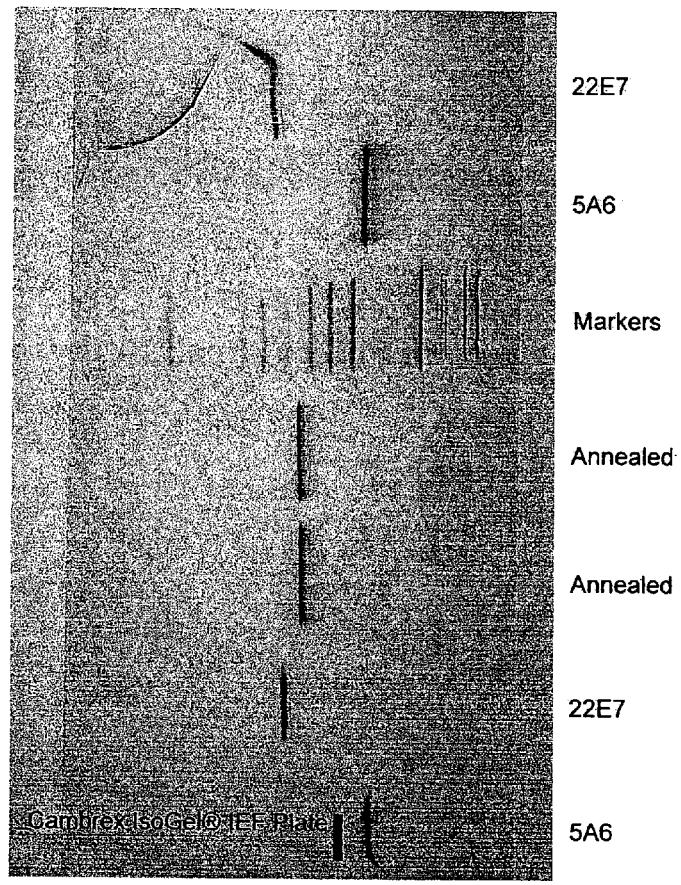
FIG. 24 isoelectric focusing analysis of 5A6Knob, 22E7Hole, and 5A6Knob and 22E7Hole mixture heated to 50° C. for 10 minutes.

Analysis on an isoelectric focusing gel (Cambrex, pH7-11) showed formation of a single band at pI ~8.5 in the annealing mixture, corresponding to bispecific antibody (which has a calculated pI of 8.67). See FIG. 24.

2. Purification on a Cation Exchange Column

A 5 ml CM-Fast Flow column (HiTrap, Amersham Biosciences) was equilibrated with a buffer at pH5.5 (30 mM MES, 20 mM hepes, 20 mM imidazole, 20 mM tris, 25 mM NaCl). The annealed pool was diluted with an equal volume of equilibration buffer and adjusted to pH5.5, loaded onto the column, and washed with equilibration buffer. The column was developed at 1 ml/m with a gradient of pH5.5 to pH9.0 in the same buffer, over 30 minutes.

Fractions were analyzed by IEF, which revealed that 5A6 was eluted ahead of the heterodimer. Analysis by light scattering of the pooled fractions containing heterodimer revealed no monomer.

Example 4.0

Characterization of 5A6/22E7 Knob in Holes Bispecific Antibody

The purpose of this example is to demonstrate 5A6/22E7, not 5A6 or 22E7 alone, is a bispecific antibody. 5A6/22E7 has dual binding specificity to human FcγRIIB-His$_6$-GST and FcεRI-ECD-Fc in a sandwich Elisa assay. Results are presented in FIGS. 29 and 30. 5A6(A) and 5A6(B) designate two protein preps of 5A6.5A6/22E7 bispecific antibodies described below are knob in holes heterodimeric antibodies with either wild type hinge or are hingeless. Bispecific antibody is interchangeably referred to as BsAb.

Figure 29:
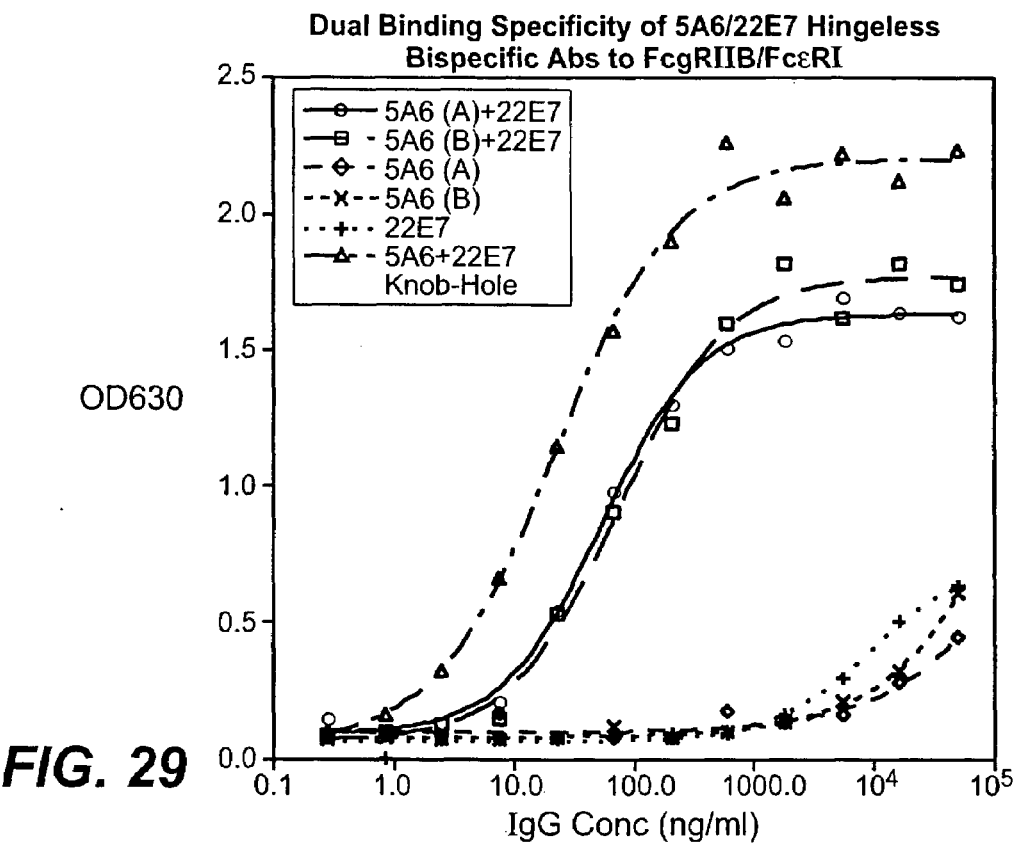
FIGS. 29 and 30 provide ELISA results illustrating the dual binding specificity of a 5A6/22E7 hingeless bispecific antibody.

Dual binding specificity of 5A6/22E7 hingeless bispecific antibody to huFcγRIIB-His$_6$-GST and huFcεRI-ECD-Fc (IgE receptor fusion) was demonstrated by ELISA with results presented in FIG. 29. ELISA plates were coated overnight at 4° C. with 100 µl of a 1 µg/ml solution of FcγRIIB-His$_6$-GST in PBS, pH 7.4. The plate washed with PBS and blocked with 1% Casein blocker in PBS. The wells were washed three times with PBS/0.05% TWEEN®. 10 µg/ml of CD4-IgG was prepared in Elisa Diluent buffer (50 mM Tris-HCl, pH7.5, 150 mM NaCl, 0.05% Tween-20, 0.5% BSA, 2 mM EDTA) and added to wells at 100 µl/well to block FcγRIIB-His$_6$-GST binding to Fc portion of each of the test antibodies: 5A6 (A)/22E7 knob in holes, wild type hinge, bispecific antibody; 5A6 (B)/22E7 knob in holes, wild type hinge, BsAb; 5A6/22E7 knob in holes, hingeless BsAb; 5A6 MAb; and 22E7 MAb. After washing the plate three times with PBS/0.05% TWEEN®, serial dilutions of the three 5A6/22E7 BsAb, 5A6 MAb, and 22E7 MAb were prepared in ELISA Diluent buffer and added to wells at 100 µl/well of each dilution. The plates were incubated for 1 hour at room temperature. After washing the plate three times with PBS/0.05% TWEEN®, 100 µl of 1 µg/ml huFcεRI-ECD-Fc was added to each well and the plates were incubated for 1 hour at room temperature. After washing the plate three times with PBS/0.05% TWEEN®, 100 µl of 1 µg/ml IgE-biotin was added to each well and incubated for 1 hour at room temperature. The plate washed with PBS/0.05% TWEEN® and incubated 30 minutes with 100 µl/well of 1:2000 Streptavidin-HRP in ELISA diluent buffer. After washing with PBS/0.05% TWEEN®, the plate was incubated 5 minutes with 100 µl TMB substrate. The reaction was quenched with 100 µl/well stop solution and the plate read at 630 nm on a 96-well plate densitometer (Molecular Devices). Results show IgE bound in wells containing the 5A6/22E7 bispecific antibodies. The bispecific antibodies: 5A6 (A)+22E7 BsAb, 5A6 (B)+22E7 BsAb, and 5A6+22E7 hingeless knob-hole BsAb successfully bound to FcγRIIB-GST and IgE-biotin. See FIG. 29.

A complementary ELISA experiment was performed as follows with results presented in FIG. 30. ELISA plates were coated overnight at 4° C. with 100 µl of a 1 µg/ml solution of huFcεRI-ECD-Fc in PBS, pH 7.4. The plate washed with PBS and blocked with 1% Casein blocker in PBS. The wells were washed three times with PBS/0.05% TWEEN®. Serial dilutions of 5A6/22E7 bispecific antibodies, 5A6 antibodies, or 22E7 antibody were prepared in ELISA Diluent buffer and added to wells at 100 µl/well of each dilution. The plates were incubated for 1 hour at room temperature. After washing the plate three times with PBS/0.05% TWEEN®, FcγRIIB-His$_6$-GST was added to each well at 100 µl of 1 µg/ml in the presence of 10 µg/ml of CD4-IgG to block FcγRIIB-His$_6$-GST binding to Fc portion of the test antibody, huFcεRI-ECD-Fc and secondary antibody (anti-GST-biotin) and incubated for 1 hour at room temperature. After washing the plate three times with PBS/0.05% TWEEN®, 100 µl of 1 µg/ml anti-GST-biotin was added to each well and incubated for 1 hour at room temperature. The plate washed with PBS/0.05% TWEEN® and incubated 30 minutes with 100 µl/well of 1:2000 Streptavidin-HRP in Elisa diluent buffer. After washing with PBS/0.05% TWEEN®, the plate was incubated 5 minutes with 100 µl TMB substrate. The reaction was quenched with 100 µl/well stop solution and the plate read at 630 nm. Results show anti-GST biotin bound in wells containing the 5A6/22E7 bispecific antibodies. The bispecific antibodies: 5A6 (A)+22E7 and 5A6 (B)+22E7 hingeless bispecific antibodies, and 5A6+22E7 knob-hole bispecific antibody successfully bound to huFcεRI-ECD-Fc and FcγRIIB-GST. See FIG. 30.

Figure 30:
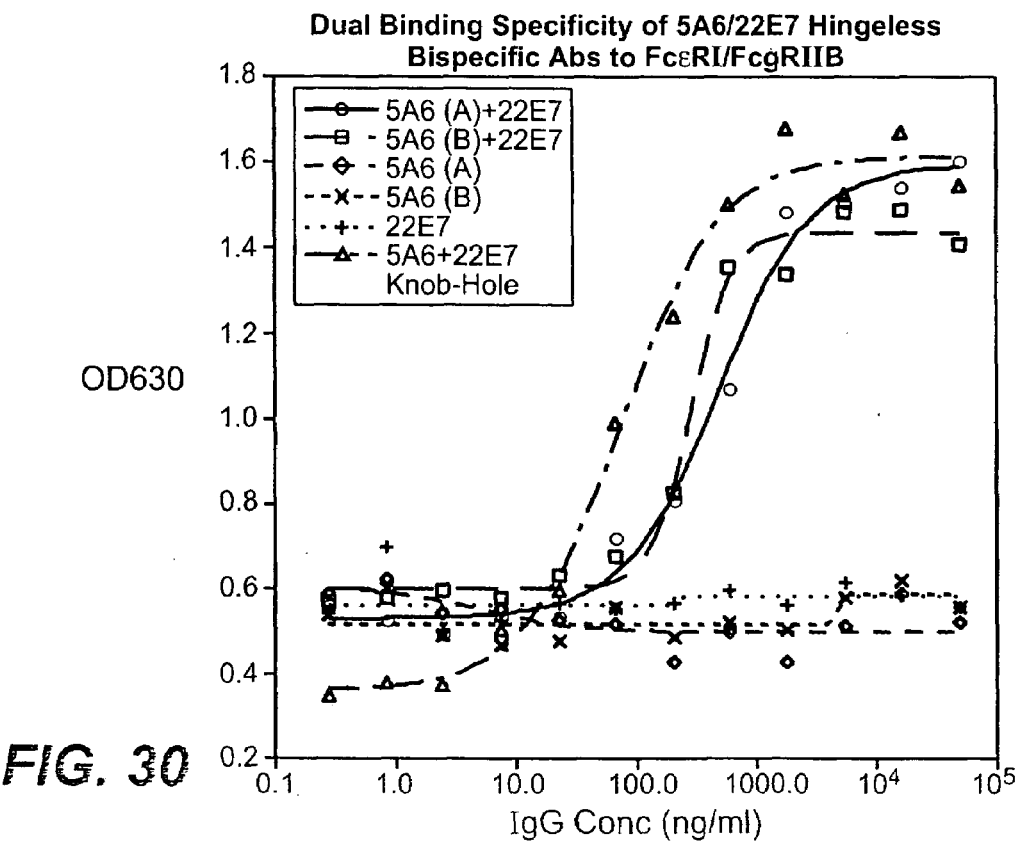

Graphs of the curves for both experiments are presented in FIGS. 29 and 30. Successful binding to both FcγRIIB-GST and huFcεRI-ECD-Fc was demonstrated only by 5A6 (A)+22E7 and 5A6 (B)+22E7 hingeless bispecific antibodies. IC 50 values for the results shown in FIGS. 29 and 30 are provided in Table 1.

TABLE 1

| IC50 values for FcγRIIB-GST (ng/ml) (FIG. 29) | |
|---|---|
| BsAb-knob in hole, wild type hinge | |
| 5A6 (A)+22E7: | 55.2 |
| 5A6 (B)+22E7: | 76.0 |
| MAb | |
| 5A6 (A): | 3.3e+06 |
| 5A6 (B): | 1.4e+07 |
| 22E7: | 1.0e+05 |
| BsAb-knob in hole, hingeless | |
| 5A6+22E7 hingeless Knob-hole: | 23 |
| IC50 values for huFcεRI-ECD-Fc (ng/ml) (FIG. 30) | |
| BsAb-knob in hole, wild type hinge | |
| 5A6 (A)+22E7: | 490 |
| 5A6 (B)+22E7: | 291.5 |
| MAb | |
| 5A6 (A): | 5.3e+06 |
| 5A6 (B): | 1.0e+07 |
| 22e7: | 2.8e+06 |
| BsAb-knob in hole, hingeless | |
| 5A6+22E7 Knob-hole: | 76.5 |

Example 5.0

Properties of 5A6/22E7 Hingeless, Knob in Holes, Bispecific Antibody 5.1 Materials In the previous examples, FcγRIIB referred to huFcγRIIB1, one of three human FcγRIIB splice variants. In the remaining examples, FcγRIIB1 and an additional splice variant, FcγRIIB2 are utilized and are so designated.

JW8.5.13 is a chimeric antibody consisting of a mouse variable region specific for NP (Nitrophenol, an antigen) and a human IgE Fc region. The variable region of JW8.5.13 IgE is specific for NP and does not cross-react with TNP. The human IgE portion of JW8.5.13 binds specifically to huFcεRI and does not bind to endogenous rat FcεRI in the RBL derived cell lines. Binding of JW8.5.13 to huFcεRI upregulates its expression and loads it with antigen-specific IgE. RBL-2H3 (ATCC#CRL-2256) cells expressing FcεRIα, the α-subunit of the high affinity human IgE receptor (FcεRI) (Gilfillan et al., (1995) Int Arch Allergy Immunol. 107(1-3):66-68) were transfected with combinations of (i.e. with and without), huFcγRIIB1 and/or huFcγRIIB2 to generate RBL derivative cell lines. RBL 2H3 cell line variants were generated by retroviral transduction of RBL 2H3 cells with human FcγRIIB1 or FcγRIIB2 using a retroviral expression vector obtained from Washington University, MO, that is similar to the pQCXIR (Retro-X Q vectors) vector series available from BD-Clontech. cDNA of the full length human genes was subcloned into the retroviral vector either singly or in combination with an IRES (Internal Ribosomal Entry Sequence) to allow for bicistronic co-transfection and co-expression of two genes. Further description of the method of retroviral transduction is provided below.

PG13 packaging cells (ATCC CRL-10686) were seeded on a 10 cm tissue culture plate at $2\times10^6$ cells per plate (DMEM high glucose, 10% FCS, penicillin, streptomycin, 2 mM L-glutamine) for 24 hours. Cells were transfected with pMSCV DNA constructs using FuGENE 6 and cultured for 2 days at 37° C., 5%. CO2. Cell culture supernatant containing retroviral particles was harvested and filtered through a 0.4 micron filter. Sterile protamine sulfate was added to a final concentration of 10 μg/ml, and 4 ml of supernatant was used to infect approximately $1\times10^6$ RBL cells by spin infection at 32° C. for 90 minutes, followed by continued culture in retroviral supernatant for 3-4 hours at 37° C. in 5% $CO_2$. Infected RBL cells were recovered, transferred to RBL medium, and expanded for sorting. Positively transfected cells were identified by FACS using 22E7 and/or 5A6 antibodies to detect human FcεRIA and human FcγRIIB, respectively.

The resulting cell lines were designated as follows: RBL huFcεRI cells surface expressed human FcεRIα; RBL huFcγRIIB cells surface expressed human FcγRIIB1, RBL huFcεRI+huFcγRIIB1 cells surface expressed human FcεRIα and human FcγRIIB1; and RBL huFcεRI+huFcεRIIB2 cells surface expressed human FcεRIα and human FcγRIIB2.

Biotinylated 5A6/22E7 bispecific antibody (knob in holes, hingeless) was prepared by coupling a 20× molar excess of EZ-link™ NHS-PEO$_4$-Biotin (Pierce, Rockford, Ill.) to bispecific antibody in PBS.

The huFcεRIα extracellular domain (huFcεRIα ECD) was produced by subcloning into a baculovirus expression system and purified using CNBr-sepharose linked column and sephadex size exclusion column. The huFcεRIIB extracellular domain (huFcγRIIB ECD) was produced by subcloning in frame with a C-terminal His$_6$ tag with subsequent expression in a baculovirus expression system. The huFcγRIIB ECD was purified by NiNTA resin.

5.2 Histamine Release Assay

The ability of the 5A6/22E7 bispecific antibody to crosslink huFcγRIIB1 or huFcγRIIB2 to huFcεRI on a cell surface was demonstrated by selectively blocking histamine release according to the following assay. The description below is additionally supported by FIGS. 31-33.

Transfected RBL 48 cells (supra) were grown in (EMEM (Eagle's Minimum Essential Medium with Earle's BSS) with 2 mM L-glutamine, 1 mM sodium pyruvate, 0.1 mM non-essential amino acids, 1.5 g/L sodium bicarbonate, penicillin, streptomycin, 15% fetal bovine serum) in a standard tissue culture flask at 37° C. in a humidified 5% $CO_2$ incubator. The cells were harvested by exposure to 4 mL solution of PBS/ 0.05% trypsin/0.53 mM EDTA for 2 minutes at 37° C., followed by centrifugation (400×g, 10 minutes.) and resuspension in fresh EMEM. The cells in suspension were counted with a hemocytometer (Reichert-Jung) and the density was adjusted to approximately $10^5$ to $10^6$ cells/ml.

Transfected RBL cells described above, RBL huFcεRI, RBL huFcεRI+huFcγRIIB1 cells, and RBL huFcεRI+huFcγRIIB2 cells, were seeded onto a 96-well, flat bottom tissue culture plate at $10^5$ cells/well in 200 μl of EMEM. The cells were incubated for 24 hours at 37° C. either with or without 1 μg/ml of JW8.5.13 ("NP-specific human IgE"). Next, the cells were washed three times with fresh media to remove unbound NP-specific human IgE. Some cells were treated with 1-5 μg/ml of bispecific antibody, under saturating conditions, and incubated for 1 hour at 37° C., prior to activation with antigen.

Cells were incubated with Nitrophenol (NP)-conjugated ovalbumin (NP (11)-OVA), an antigen that binds JW8.5.13, an IgE, or TNP (11)-OVA, an irrelevant antigen, for 1 hour at 37° C. Activation-associated degranulation (histamine release) of RBL huFcεRI, RBL huFcεRI+huFcγRIIB1 cells, and RBL huFcεRI+huFcγRIIB2 cells, with or without bispecific antibody, by NP-(11)-OVA and TNP was tested over a range of antigen concentrations from 0.0001 to 10 μg/ml. Following incubation, the histamine level in the cell supernatants (cell culture medium) was measured by ELISA as described above. Total histamine levels for the cells, to serve as positive controls independent of activation, were also obtained by either lysing cells with either Triton X-100 or triggering total histamine release by stimulation with ionomycin. Background histamine release by RBL cells was also obtained. Histamine release levels were quantitated by ELISA using a Histamine ELISA kit (KMI, Diagnostics Minneapolis, Minn.).

Figure 31A:
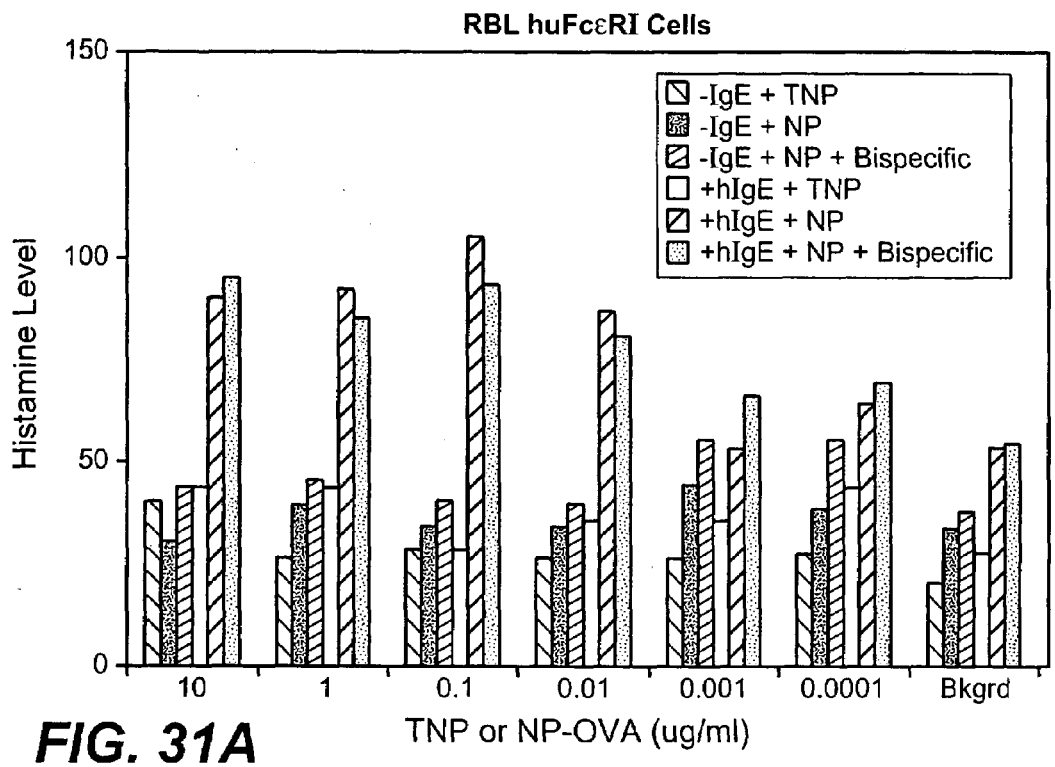
FIG. 31-33 present histamine release assay ELISA data illustrating the ability of the 5A6/22E7 bispecific antibody to crosslink huFcγRIIB to huFcεRI.
Figure 31B:
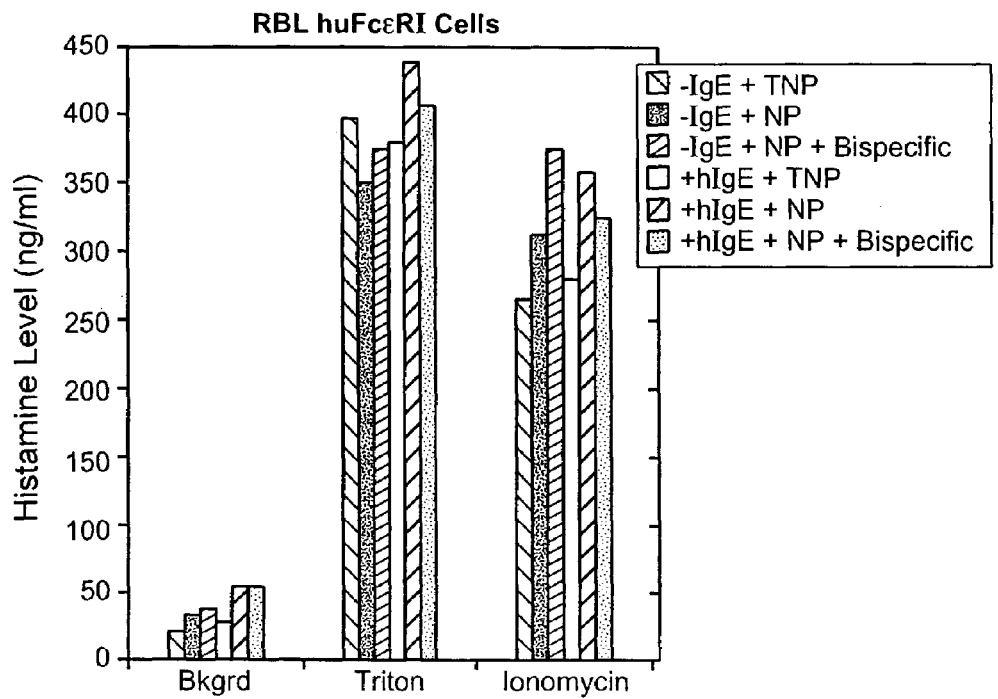
Figure 32A:
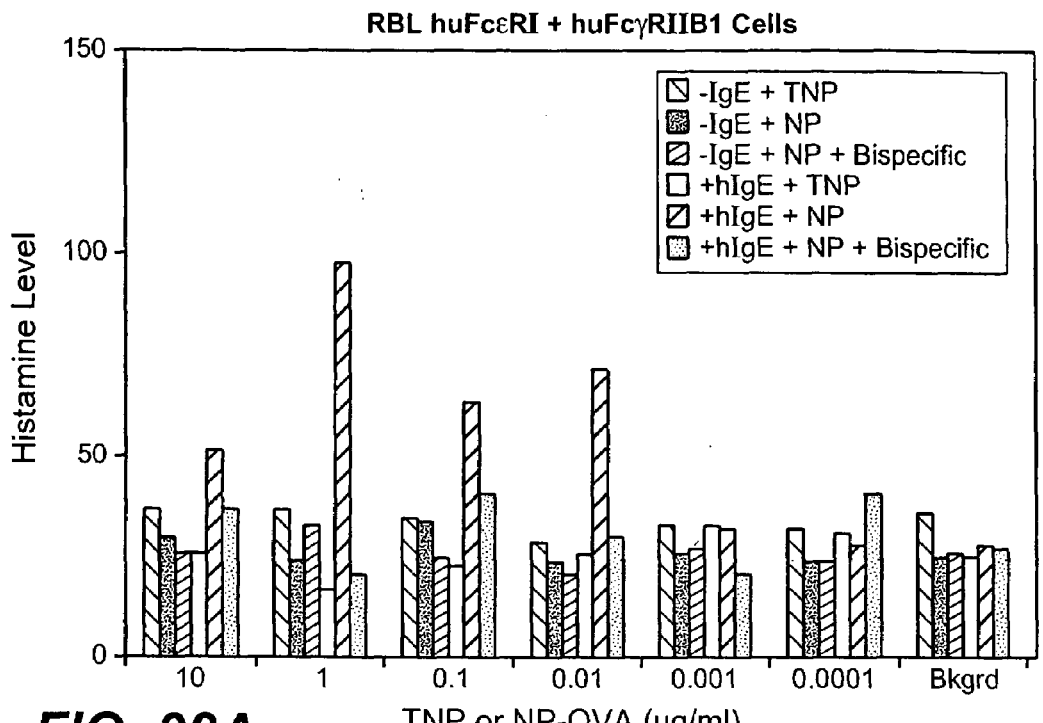
Figure 32B:
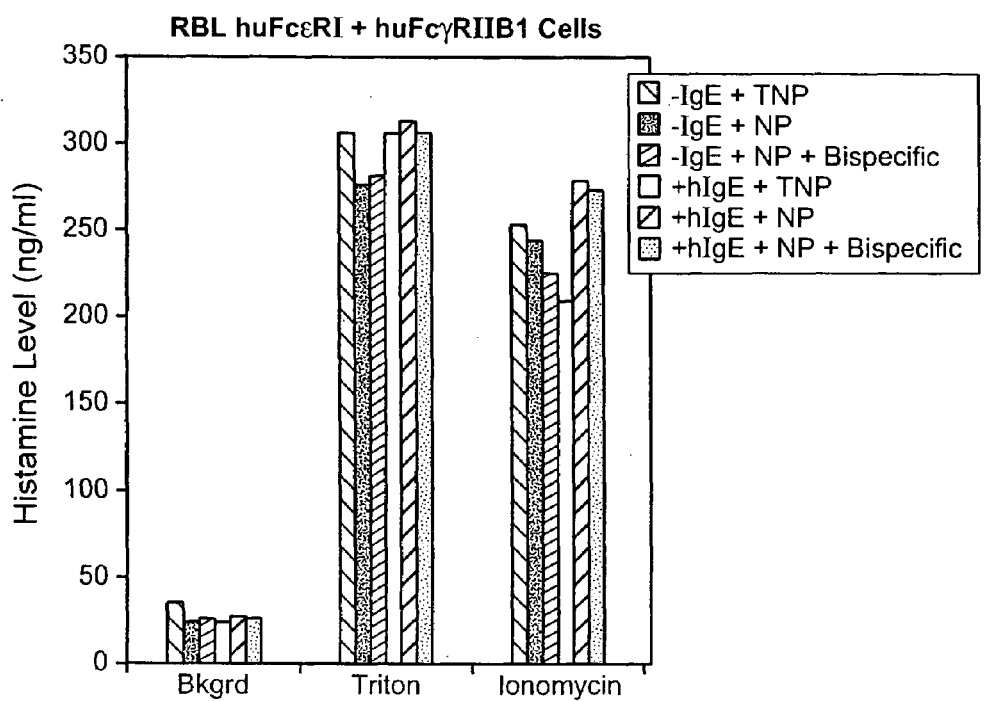
Figure 33A:
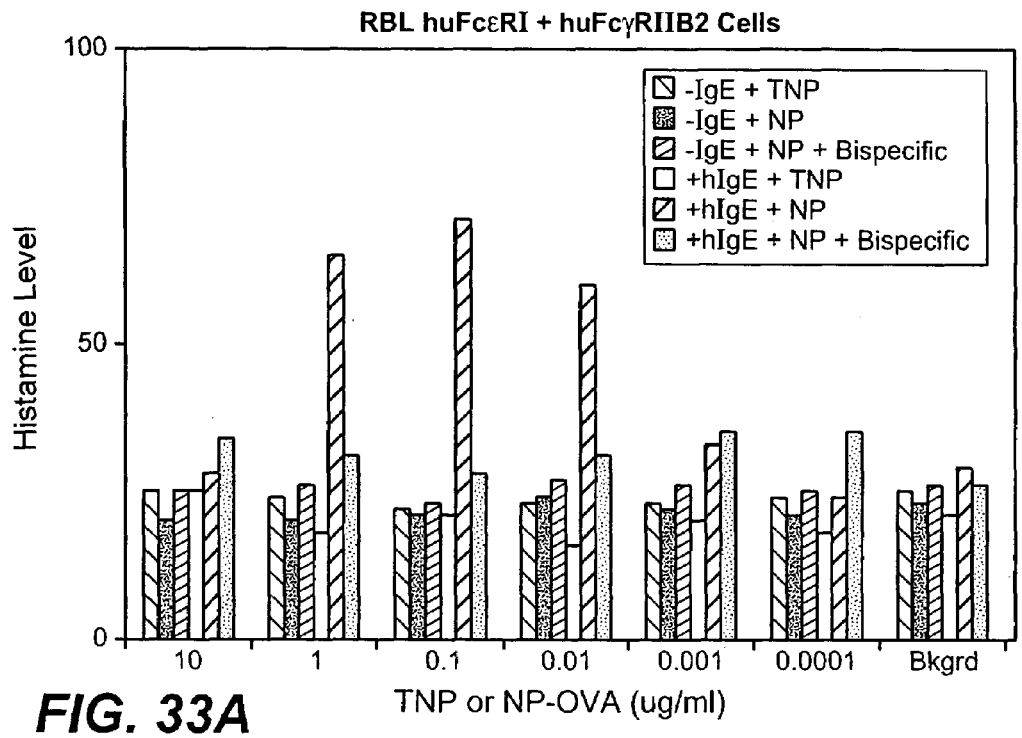
Figure 33B:
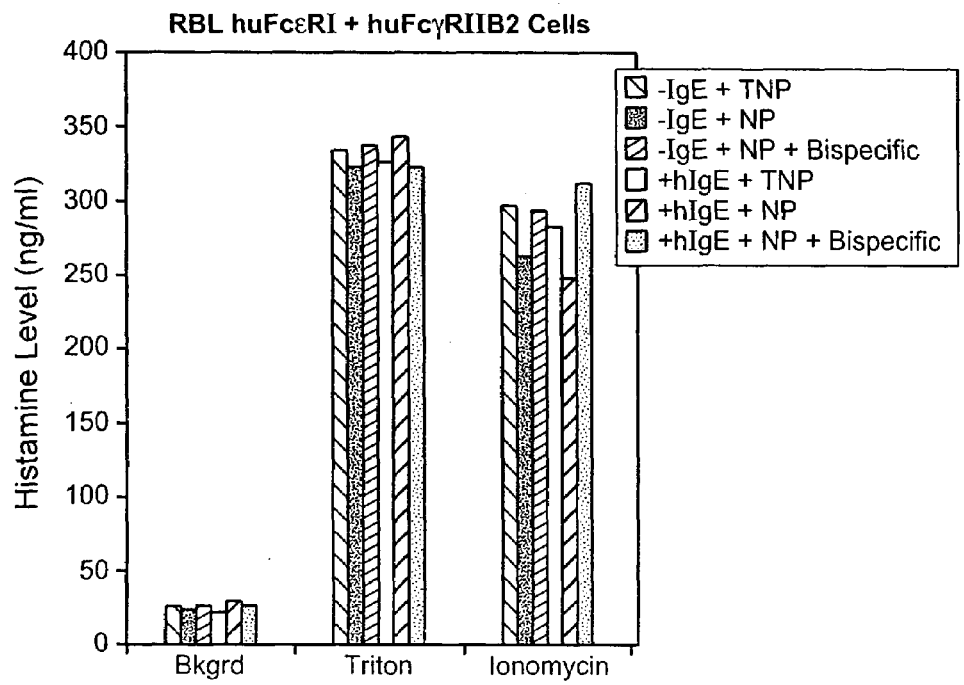

Results of the Histamine Release Assay are presented in FIGS. 31-33. Histamine release is expected to be increased in the presence of hIgE (JW8.5.13) and NP (11)-OVA antigen ("NP"), unless specifically inhibited. FIG. 31 presents histamine release data in RBL huFcεRI cells at varying concentrations of TNP or NP (11)-OVA. In RBL huFcεRI cells, histamine release is triggered by NP and hIgE. As expected, the bispecific antibody does not affect (i.e. suppress or inhibit) histamine release in the absence of huFcγRIIB (see "+hIgE+NP+bispecific", dark grey column on far right for each sample in FIG. 31 graph A).

FIG. 32 presents histamine release data in RBL huFcγRI+ huFcγRIIB1 cells and FIG. 33 presents histamine release data in RBL huFcεRI+huFcγRIIB2 cells. In RBL huFcεRI+huFcγRIIB1 and RBL huFcεRI+huFcγRIIB2 cells, the bispecific antibody inhibits histamine release (compare light grey "+hIgE+NP" bar to dark grey "+hIgE+NP+bispecific" bar in graph A of FIG. 32 and in graph A of FIG. 33).

Activation of histamine release in all RBL cell lines is antigen specific in a dose-dependent manner through human IgE bound to human FcεRI. Cells were not activated in the absence of human IgE, nor were they activated when triggered with an irrelevant antigen (i.e. TNP). Addition of 5A6/22E7 bispecific antibody inhibits histamine release (to background levels) in RBL huFcεRI+huFcγRIIB1 and RBL huFcεRI+huFcγRIIB2 cells, but not RBL huFcεRI cells, indicating that the presence of FcγRIIB is necessary for inhibitory function. Similar results are seen by both huFcγRIIB1 and huFcγRIIB2 in the presence of huFcεRI.

The bispecific antibody of the invention also inhibits anti-IgE-induced histamine release in primary human basophils. Primary basophils were isolated from six normal human blood donors from whom informed consent had been obtained. Basophils were enriched from human blood using a dextran sedimentation protocol. Briefly, for every 40 ml of donor blood to be sedimented, mix in a 50 ml conical tube, 375 mg of dextrose, 5.0 ml 0.1 M EDTA and 12.5 ml 6% clinical dextran. Divide the mixture into two 50 ml conical tubes and add 20 ml blood per tube. The blood is allowed to sediment for 60-90 minutes, at which time the plasma layer is withdrawn and centrifuged at 110×g for 8 minutes, 4° C. and the pelleted cells are retained, resuspended, washed with PAG (dextrose 1 g/L: 1×PIPES, pH7.3:0.003% human serum albumin), and resuspended in PAG. Cells were stimulated with anti-IgE antibody either as a dextran-enriched preparation or after subsequent purification using Miltenyi magnetic bead separation (Miltenyi Biotec, Auburn, Calif.; see, for example, Kepley, C. et al., J. Allergy Clin. Immunol. 102:304-315 (1998)) by incubation at 37° C. for one hour followed by centrifugation to pellet the cells. The supernatant was retained for analysis. Basophils may be isolated by standard procedures such as those described by Kepley, C. L. et al., J. Allergy Clin. Immunol. 106(2): 337-348 (2000). Enriched basophils may be further purified by magnetic bead separation (Miltenyi Biotec, Auburn, Calif.; Kepley, C. et al., J. Allergy Clin. Immunol. 102:304-315 (1998) and/or by flow cytometry sorting (Kepley, C. et al. (1994), supra). Goat anti-human IgE was obtained from Caltag (Caltag Laboratories, Burlingame, Calif., USA). The isolated basophils, co-expressing huFcγRIIB and huFcεRI, were incubated with anti-IgE (goat anti-human IgE (Caltag Laboratories)) or with the further addition of 5A6/22E7 bispecific antibody for one hour at 37° C. A 1:100 dilution (by volume) of goat anti-IgE was used to stimulate the basophils in the presence of 5A6/22E7 bispecific antibody ranging from 0 to 20000 ng/ml in the test solution. Histamine release was assayed as disclosed herein above. The bar graph of FIG. 62 indicates that histamine release was induced in the presence of anti-human IgE. The addition of 5A6/22E7 bispecific antibody inhibited histamine release in a roughly dose-dependent manner. There was limited background histamine release in the absence of either antibody or in the presence of 5A6/22E7 bispecific antibody alone. Based on analyses of basophil samples from six normal human blood donors, the mean inhibition of histamine release by the 5A6/22E7 bispecific antibody was 67%±9. It has been reported that average histamine release from basophils of Xolair® patients was inhibited to approximately 50% after 90 days (MacGlashan, D. W. et al., J. Immunol. 158:1438-1445 (1997) based on downregulation of FcεRI expression. These results demonstrate that an anti-huFcγRIIB/anti-huFcεRI bispecific antibody is useful as a therapeutic molecule to rapidly inhibit an immune reaction (such as histamine release in basophils) of a human patient by inhibiting the activity of FcεRI through cross-linking with FcγRIIB. An anti-huFcγRIIB/anti-huFcεRI bispecific antibody is also useful in combination therapy with an anti-IgE antibody. By use of combination therapy, an anti-huFcγRIIB/anti-huFcεRI bispecific antibody acts to rapidly inhibit histamine release by crosslinking with FcγRIIB followed by downregulation of FcεRI expression by the anti-IgE antibody (such as Xolair® anti-IgE antibody, Genentech, Inc.).

5.3 Crosslinking of huFcεRI and huFcγRIIB by Bispecific Antibody

The purpose of this example is to show the dependency of inhibition of histamine upon co-crosslinking of human FcεRI and human FcγRIIB on the surface of cells by 5A6/22E7 bispecific antibody. The assay method is described below with results further illustrated in FIGS. 34-41.

Figure 34:
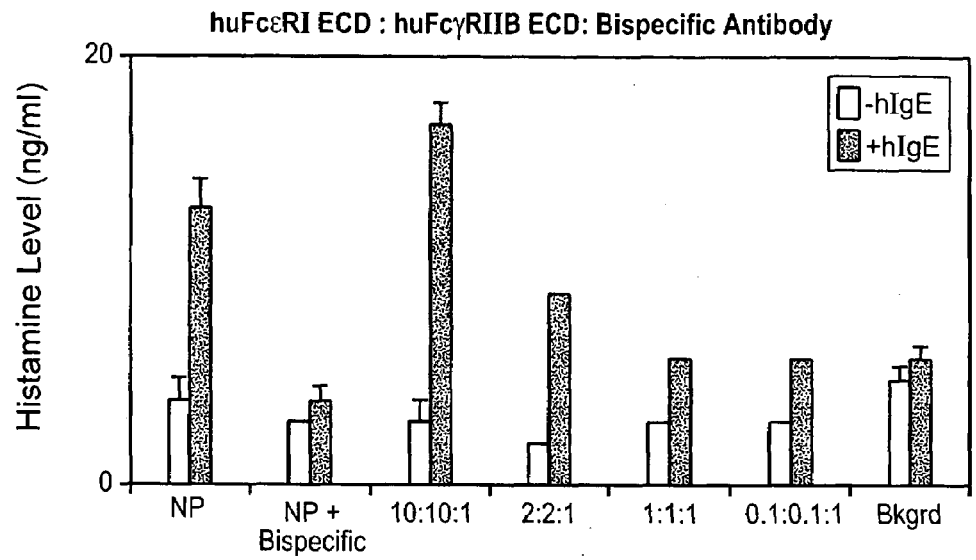
FIG. 34 is a graph of ELISA histamine release assay results demonstrating blocking of inhibition of antigen-induced histamine release in RBL-huFcεRI+FcγRIIB1 cells by preincubation of 5A6/22E7 bispecific antibody with huFcεRI ECD and huFcγRIIB ECD.

RBL huFcεRI+huFcγRIIB1 and RBL huFcεRI+huFcγRIIB2 cells were incubated for 24 hours at 37° C. with 5 μg/ml of NP-specific human IgE and subsequently washed three times with fresh media EMEM to remove unbound NP-specific human IgE. Prior to addition to RBL cells, 5A6/22E7 bispecific antibody was preincubated for 30 minutes with purified huFcεRIα ECD and huFcγRIIB ECD at various molar ratios. Preincubated 5A6/22E7 bispecific antibody was added to RBL cell culture medium at a final concentration of 5 μg/ml 5A6/22E7 bispecific antibody and further incubated for 1 hour at 37° C. Cells were activated by incubation with NP-conjugated ovalbumin for 1 hour at 37° C. Activation-associated degranulation was measured by quantitating histamine release into the cell culture medium using ELISA procedures described generally above. The dependency of histamine release inhibition on human FcεRI and human FcγRIIB co-crosslinking by the bispecific antibody of the invention is shown in FIG. 34 (for RBL huFcεRI+huFcγRIIB1 cells) and in FIG. 36 (RBL huFcεRI+huFcγRIIB2 cells).

Figure 35:
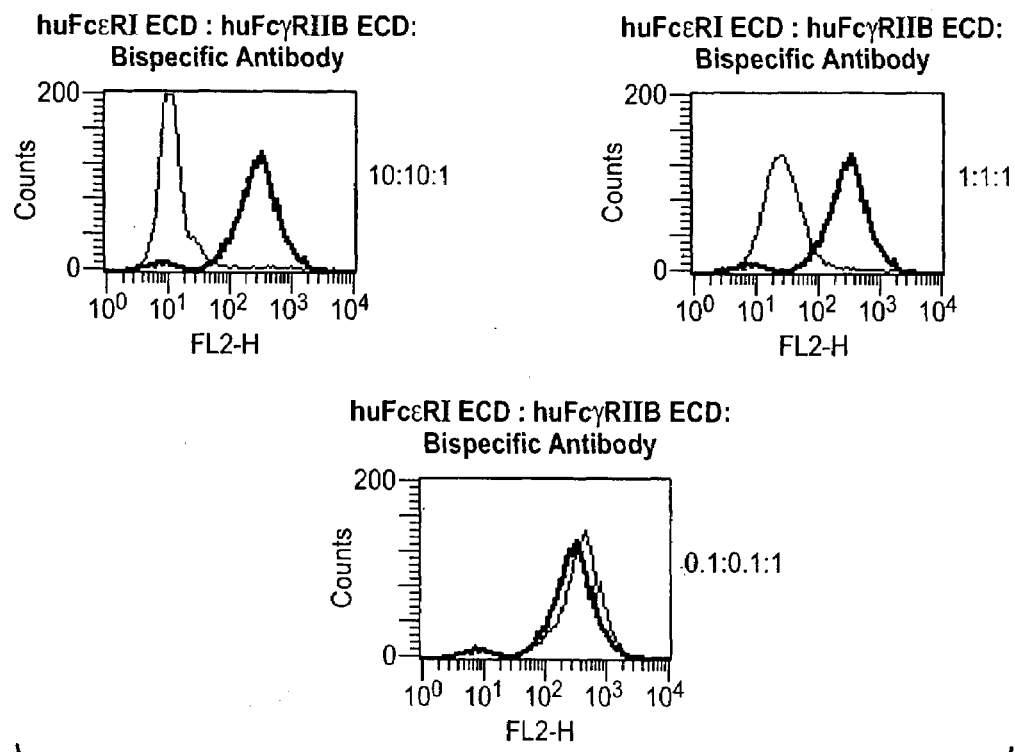
FIG. 35 includes graphs of FACS data for the binding of 5A6/22E7 bispecific antibody in the presence of huFcεRI ECD and huFcγRIIB ECD to RBL-huFcεRI+FcγRIIB1 cells.
Figure 36:
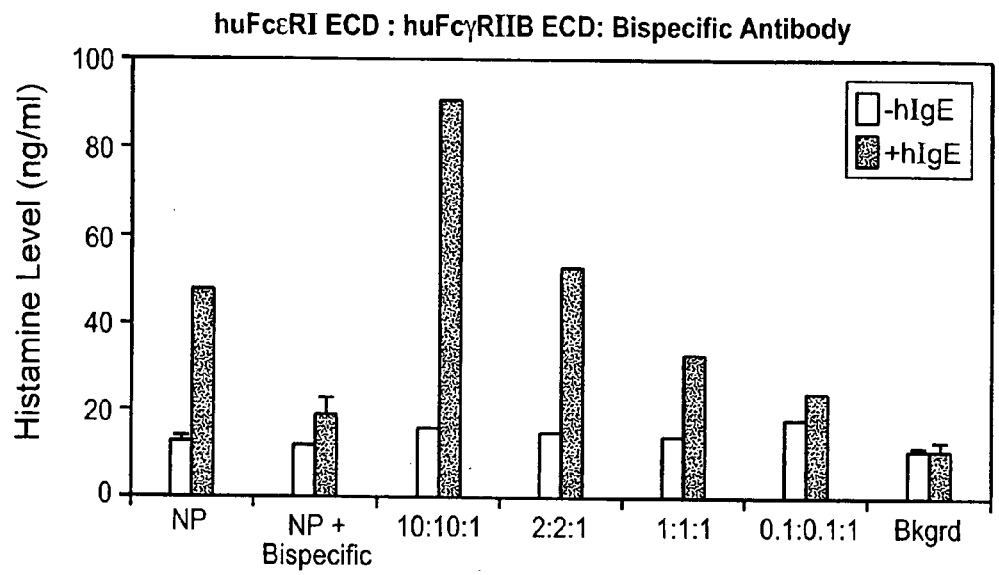
FIG. 36 is a graph of ELISA histamine release assay results demonstrating blocking of inhibition of antigen-induced histamine release in RBL-huFcεRI+FcγRIIB2 cells by preincubation of 5A6/22E7 bispecific antibody with huFcεRI ECD and huFcγRIIB ECD.
Figure 37:
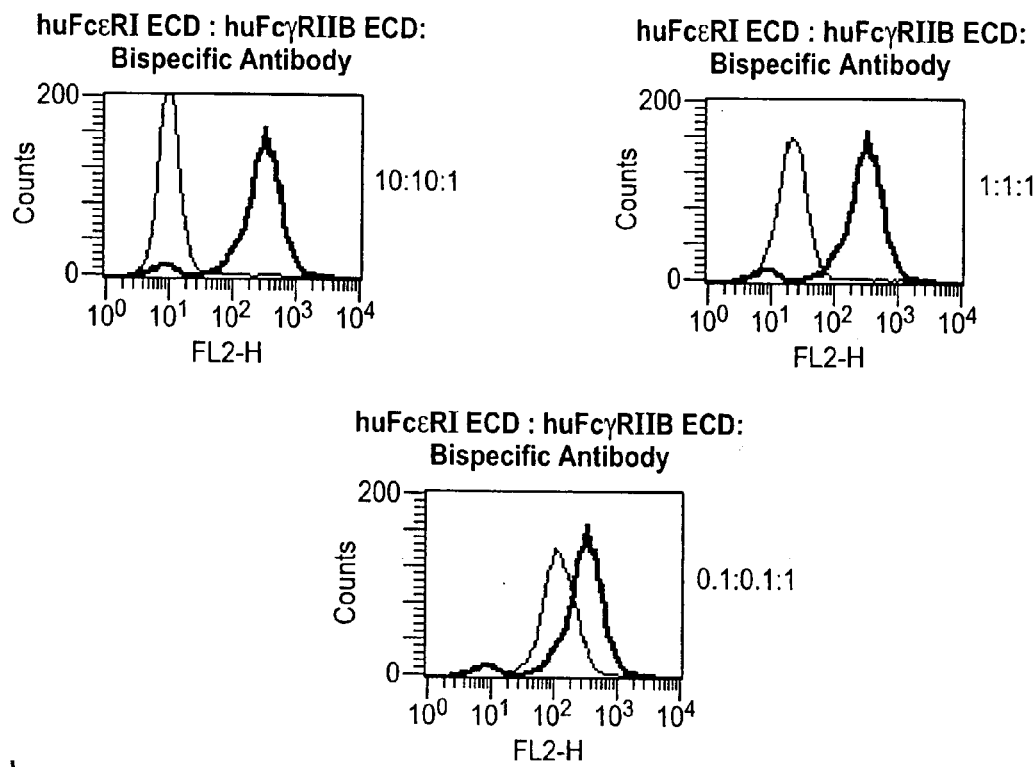
FIG. 37 includes graphs of FACS data for the binding of 5A6/22E7 bispecific antibody in the presence of huFcεRI ECD and huFcγRIIB ECD to RBL huFcεRI+FcγRIIB2 cells.
Figure 38:
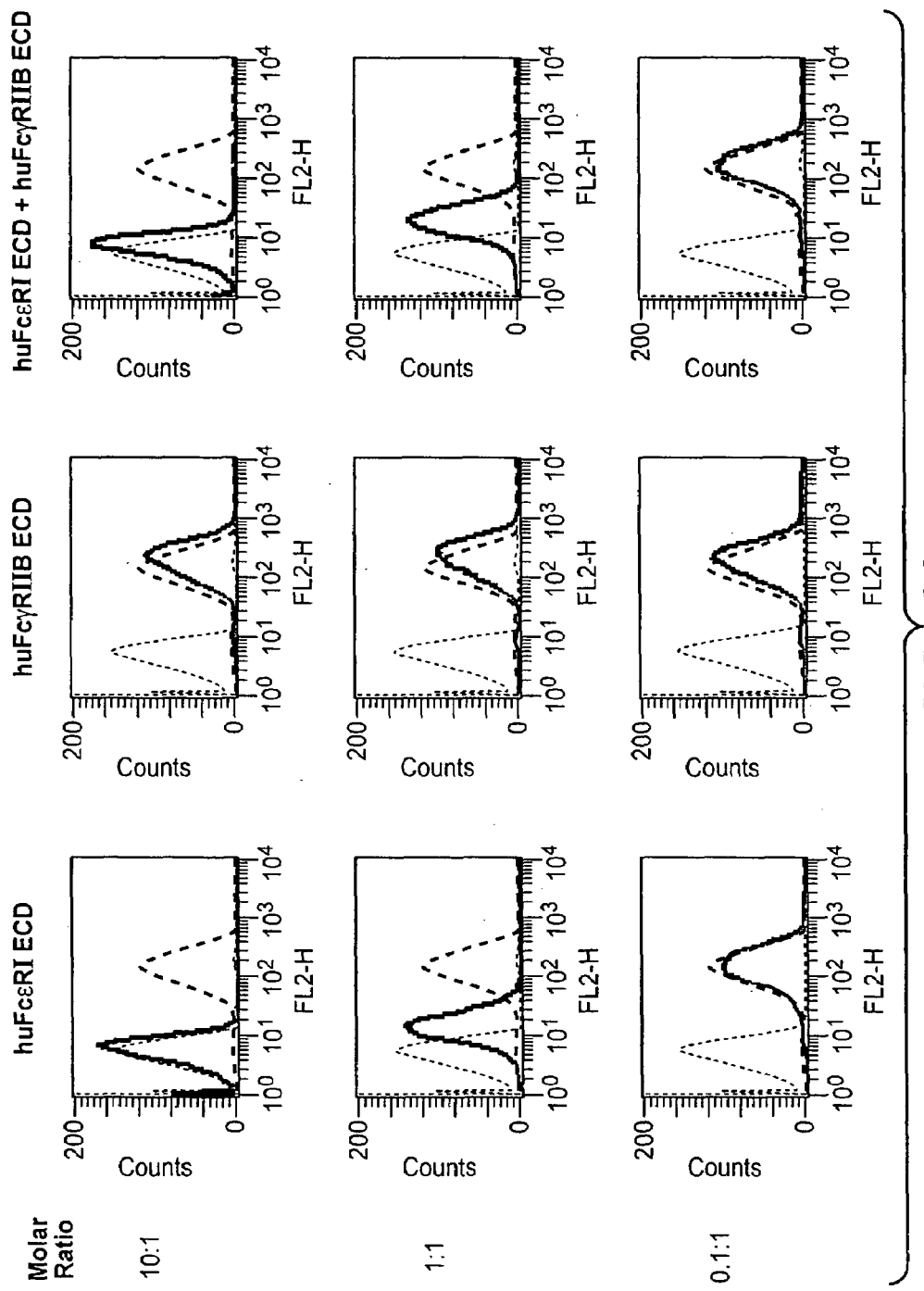
FIG. 38 includes graphs of FACS data illustrating blocking of 5A6/22E7 bispecific antibody binding to RBL huFcεRI cells by huFcεRI ECD, huFcγRIIB ECD, or both ECDs.
Figure 39:
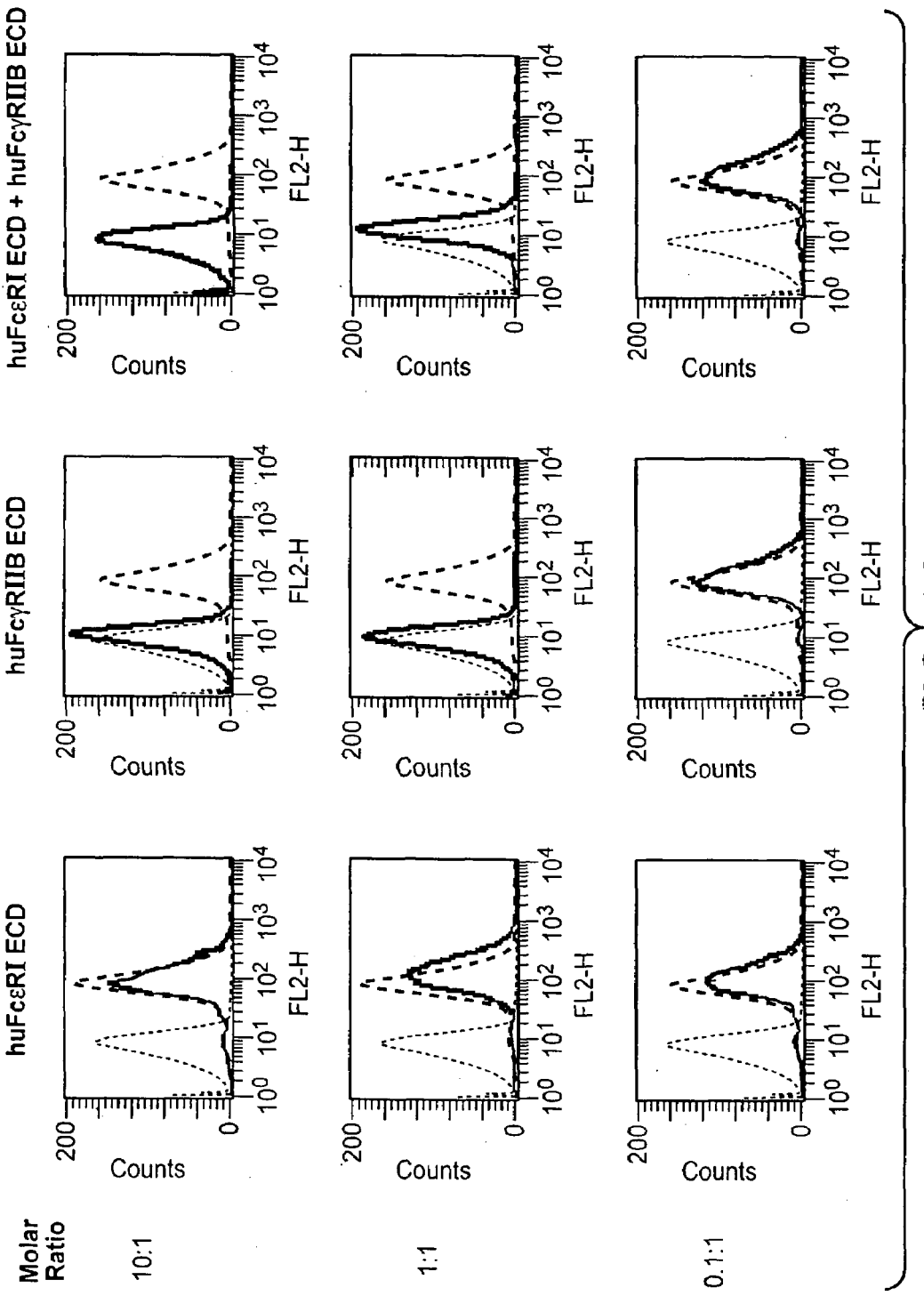
FIG. 39 includes graphs of FACS data illustrating blocking of 5A6/22E7 bispecific antibody binding to RBL huFcγRIIB cells by huFcεRI ECD, huFcγRIIB ECD, or both ECDs.
Figure 40:
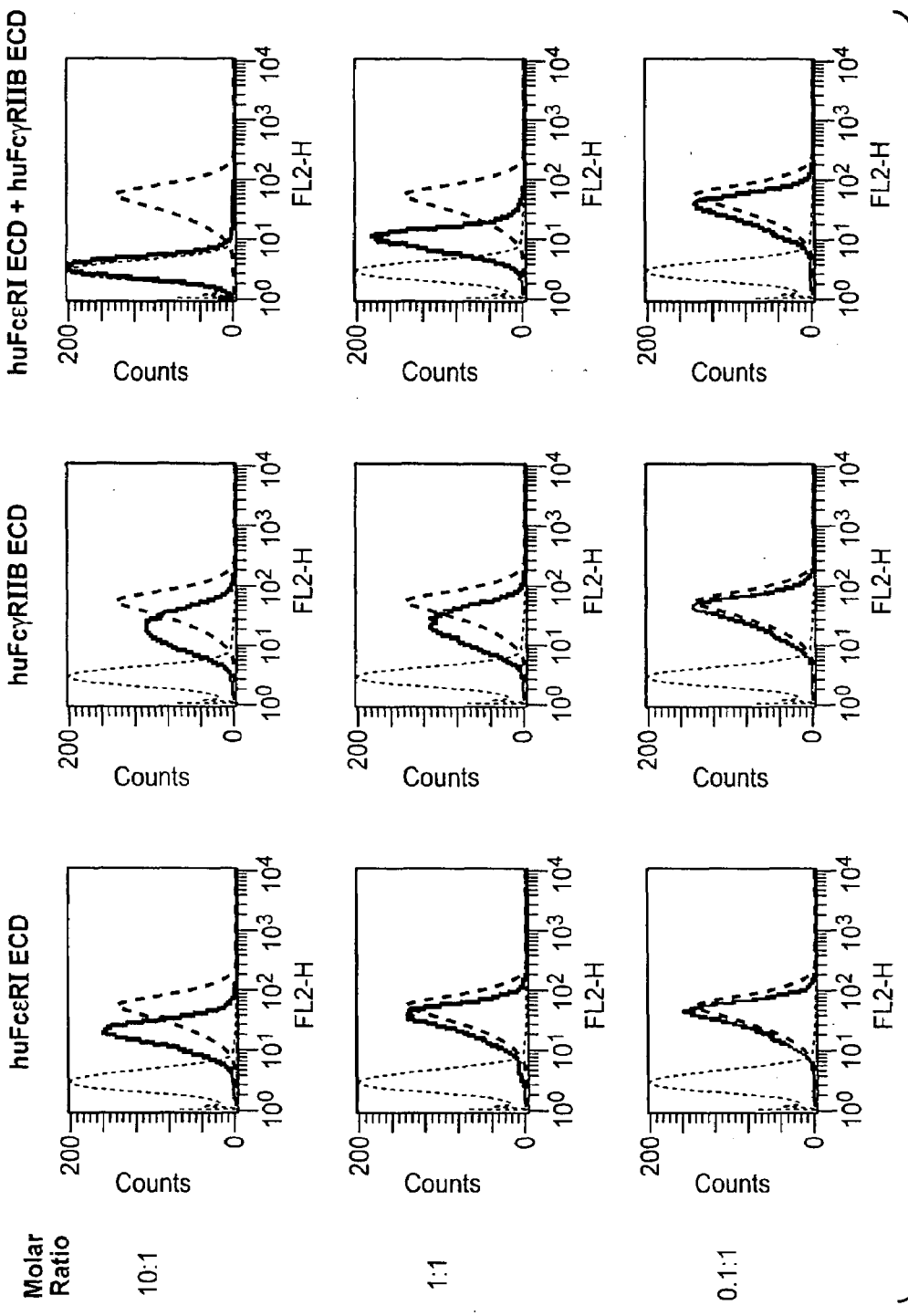
FIG. 40 includes graphs of FACS data illustrating blocking of 5A6/22E7 bispecific antibody binding to RBL huFcεRI+huFcγRIIB1 cells by huFcεRIIB ECD, huFcγRIIB ECD, or both ECDs.

Binding of bispecific antibody to RBL-derived cells was also assessed in the presence of huFcεRIα ECD and huFcγRIIB ECD using flow cytometry. The cells and materials are as described above. The cells are harvested and sorted into aliquots of $10^5$-$10^6$ cells. The cells were washed and resuspended in FACS buffer (PBS with 2% FCS). The cells were washed a second time and resuspended in FACS buffer supplemented with 10% rat serum, 2 μg/ml human IgG and 1 μg/mL biotinylated bispecific antibody. The cells were incubated for 30' on ice, washed and resuspended in FACS buffer with streptavidin-PE. After incubation for an additional 30' on ice, the mixture was washed cold FACS buffer, spun down and resuspended in FACS buffer with 0.1% propidium iodide. The samples were analyzed flow cytometry and results expressed as relative fluorescence units (RFU). The results of these binding studies are shown in FIGS. 35, and 37-41, with ratios of ECD to bispecific antibody indicated. FIGS. 35 and 37 include graphs of flow cytometry data for the binding of 5A6/22E7 bispecific antibody to either RBL huFcεRI+FcγRIIB1 cells (FIG. 35) or RBL huFcεRI+FcγRIIB2 cells (FIG. 37) in the presence of huFcεRI ECD and huFcγRIIB ECD. As expected, higher ratios of ECDs to bispecific antibody reduce the binding the bispecific antibody to the cells. Compare light peak (cell bound by BsAb in presence of ECDs) versus dark peak (positive control-cells bound by BsAb in absence of ECDs).

Figure 41:
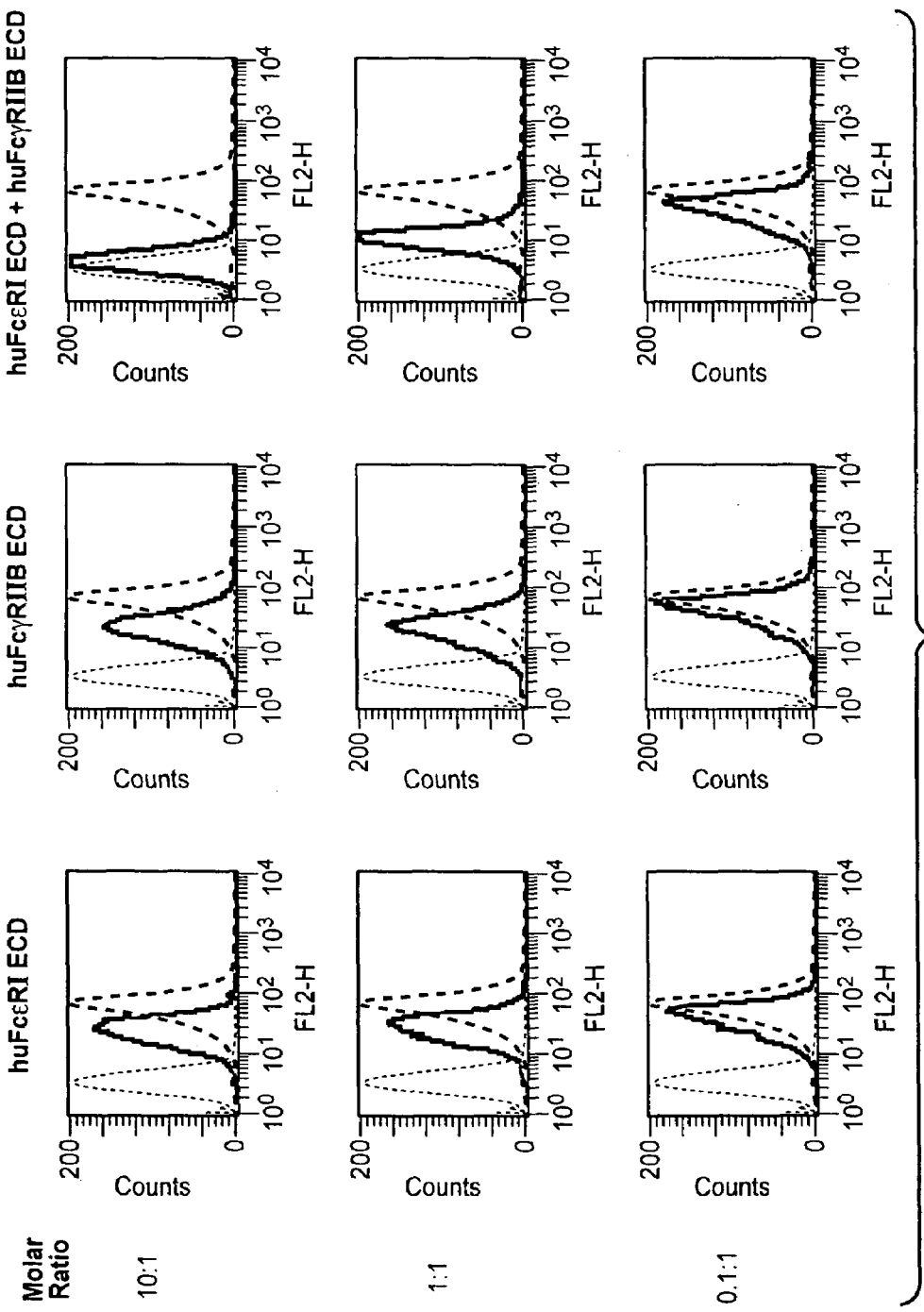
FIG. 41 includes graphs of FACS data illustrating blocking of 5A6/22E7 bispecific antibody binding to RBL huFcεRI+huFcγRIIB2 cells by huFcεRI ECD, huFcγRIIB ECD, or both ECDs.

In FIGS. 38-41, flow cytometry is used to analyze binding of 5A6/22E7 bispecific antibody to various RBL-derived cells in the presence of huFcεRI ECD, huFcγRIIB ECD or both huFcεRI ECD and huFcγRIIB ECD. In FIGS. 38-41, the black peak is cell-surface receptor binding of 5A6/22E7 in the presence of ECDs. Compare to the light grey peak, (cells not bound by BsAb) and the dark grey peak (cells bound by BsAb in absence of ECDs). As expected, 5A6/22E7 binding to RBL huFcεRI cells (see FIG. 38) is blocked by increasing concentrations of huFcεRI ECD, but not huFcγRIIB ECD, with the blocking of both ECDs having similar results to huFcεRI ECD. 5A6/22E7 binding to RBL huFcγRIIB cells (see FIG. 39) is not affected by huFcεRI ECD, with blocking by huFcγRIIB ECD. Similar binding results are seen in RBL huFcϵRI+huFcγRIIB1 cells (FIG. 40) and RBL huFcϵRI+huFcγRIIB2 cells (FIG. 41). As expected, binding of 5A6/22E7 is decreased by a 10:1 ratio of either huFcϵRI ECD or huFcγRIIB ECD, with complete blocking of 5A6/22E7 to RBL huFcϵRI+huFcγRIIB (1 or 2) cells only at a 10:1 ratio (saturating concentration) of both ECDs.

These experiments demonstrate that inhibition of histamine release is dependent upon co-crosslinking of cell surface FcϵRI and FcγRIIB since no inhibition of histamine response was observed upon preincubation of the 5A6/22E7 bispecific antibody with 10-fold molar excess of huFcϵRIα and huFcγRIIB extracellular domains. Under these conditions, binding of 5A6/22E7 bispecific antibody to the cell surface was completely blocked, as assessed by flow cytometry. Preincubation with lower molar ratios of huFcϵRI ECD and huFcγRIIB ECD (2:2:1, 1:1:1, or 0.1:0.1:1 huFcϵRI:huFcγRIIB:bispecific) led to incomplete blocking of 5A6/22E7 bispecific binding to RBL cells and incomplete inhibition of histamine release. Therefore suppression of histamine release in mast cells requires crosslinking of cell surface FcϵRIα and FcγRIIB.

The inhibition of histamine release by 5A6/22E7 bispecific antibody at concentrations below saturation suggests that full occupancy of the receptors is not required to achieve the desired inhibition.

5.4 Inhibition by Bispecific Antibody at Subsaturating Concentrations

5A6/22E7 bispecific antibody inhibition of histamine release and binding of RBL huFcϵRI+huFcγRIIB1 cells were measured at concentrations below binding saturation by the following method with results presented in FIGS. 42-46.

RBL huFcϵRI+huFcγRIIB1 or RBL huFcϵRI+huFcγRIIB2 cells were incubated for 24 hours at 37° C. with 5 µg/ml of NP-specific human IgE and subsequently washed three times with fresh media to remove unbound NP-specific human IgE. Prior to activation with antigen, cells were additionally incubated for 1 hour at 37° C. with varying concentrations of 5A6/22E7 bispecific antibody. The cells were divided for analysis by flow cytometry or histamine expression.

The extent of bispecific antibody binding was assessed by flow cytometry as described above. Flow cytometry was performed using comparable concentrations of biotinylated bispecific antibody detected with streptavidin-PE.

The pre-incubated cells, above, were activated by incubation with either 0.1 µg/ml or 1 µg/ml NP-conjugated ovalbumin for 1 hour at 37° C. Activation-associated degranulation was measured by quantitating histamine levels released into the cell culture medium as described above.

Figure 42:
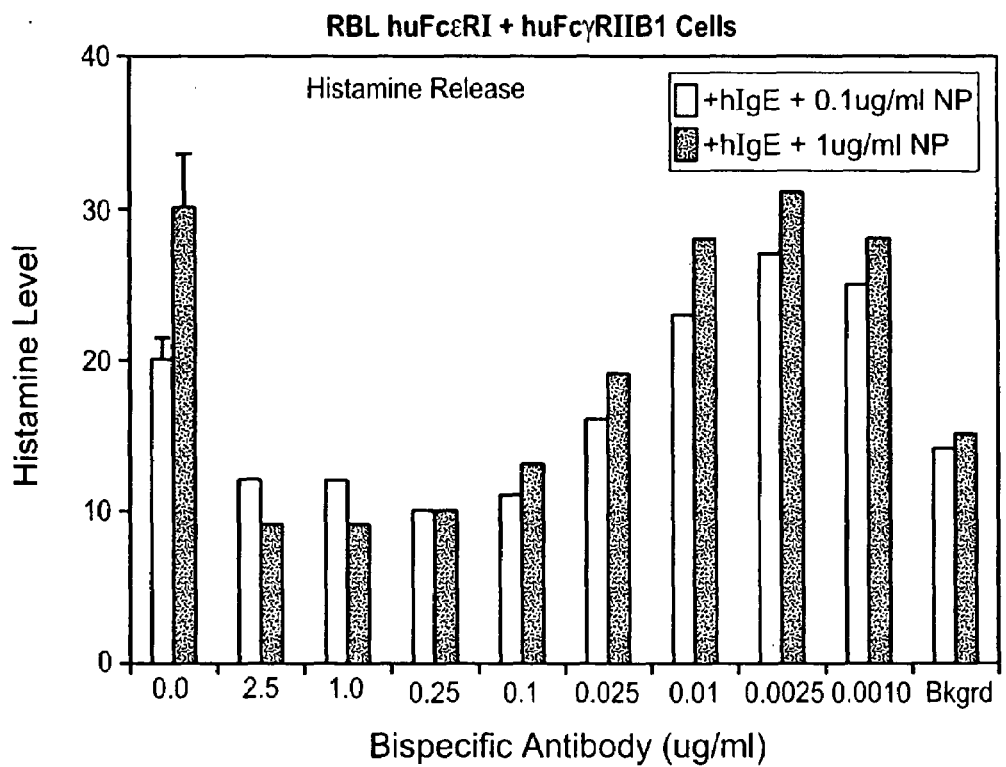
FIG. 42 is a graph of ELISA histamine release assay results demonstrating inhibition of antigen-induced histamine release in RBL huFcεRI+FcγRIIB1 cells by 5A6/22E7 bispecific antibody at subsaturating concentrations.
Figure 43:
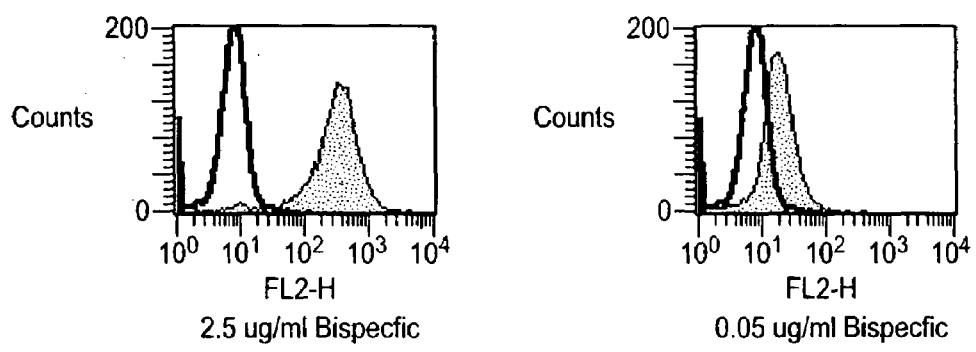
FIG. 43 is flow cytometry data of 5A6/22E7 bispecific antibody binding to RBL huFcεRI+FcγRIIB1 cells.
Figure 44:
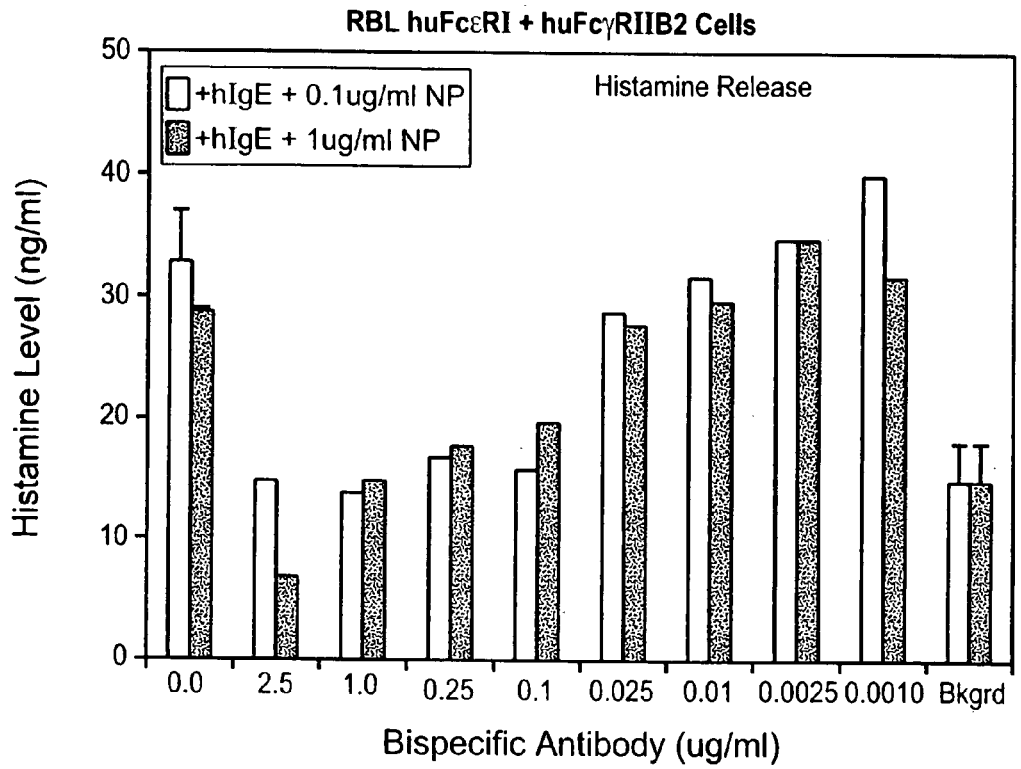
FIG. 44 is a graph of ELISA histamine release assay results demonstrating inhibition of antigen-induced histamine release in RBL huFcεRI+FcγRIIB2 cells by 5A6/22E7 bispecific antibody at subsaturating concentrations.
Figure 45:
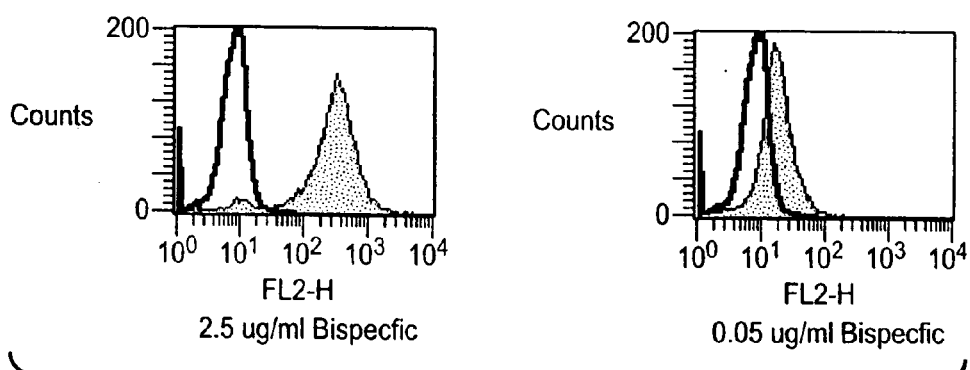
FIG. 45 is flow cytometry data of 5A6/22E7 bispecific antibody binding to RBL huFcεRI+FcγRIIB2 cells.

Histamine release data and 5A6/22E7 bispecific antibody binding for RBL huFcϵRI+huFcγRIIB1 cells are presented in FIGS. 42 and 43 respectively, while histamine release and 5A6/22E7 bispecific antibody binding for RBL huFcϵRI+huFcγRIIB2 cells is presented in FIGS. 44 and 45 respectively. Suppression of histamine release to background levels is demonstrated at bispecific antibody concentrations greater than 0.0025 µg/mL in both RBL huFcϵRI+huFcγRIIB1 cells and RBL huFcϵRI+huFcγRIIB2 cells.

Figure 46A:
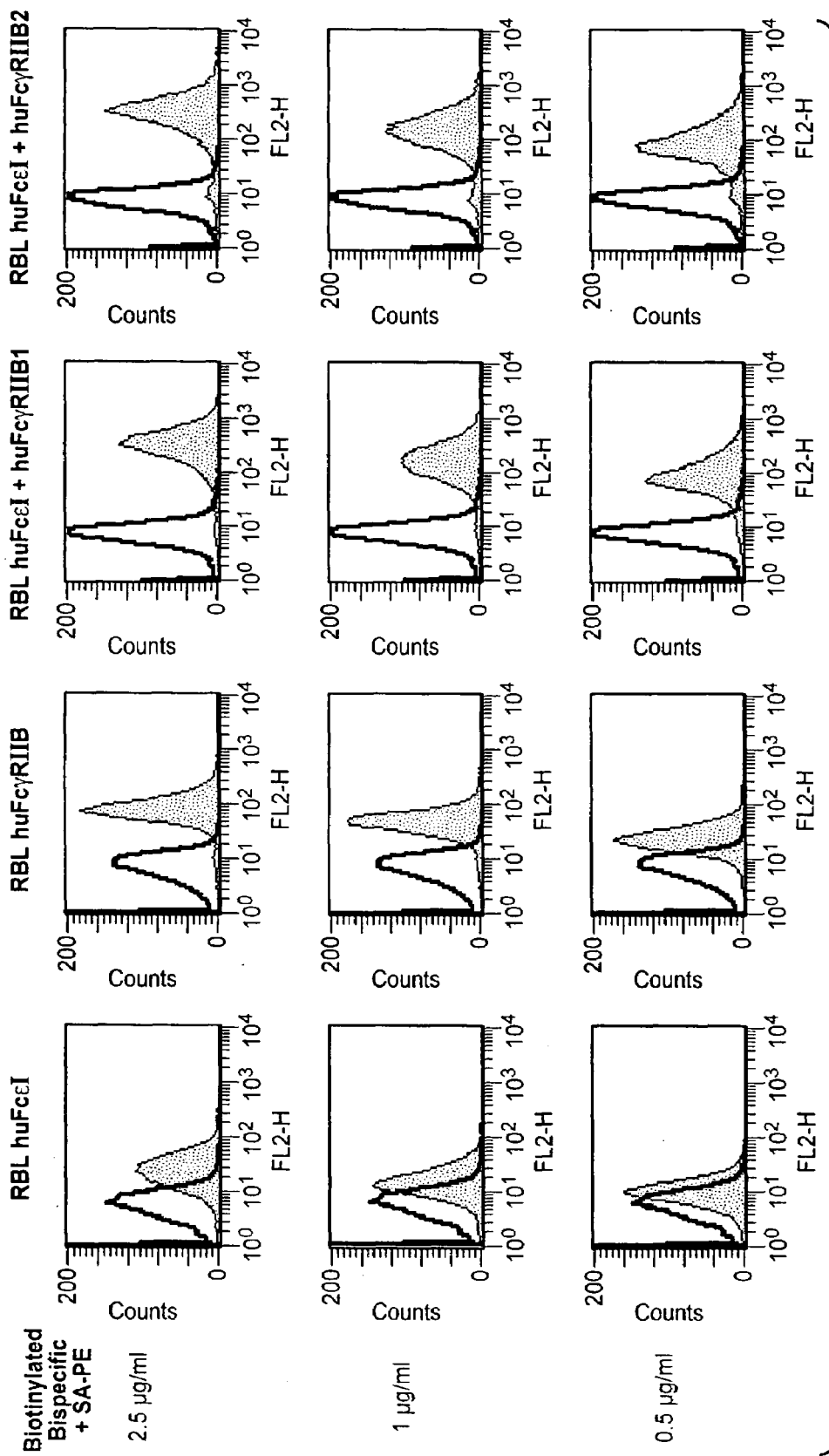
FIG. 46 is flow cytometry data of the titration of 5A6/22E7 bispecific antibody binding to RBL huFcεRI, RBL FcγRIIB cells, RBL huFcεRI+FcγRIIB1 cells, and RBLhuFcε+FcγRIIB2 cells.
Figure 46B:
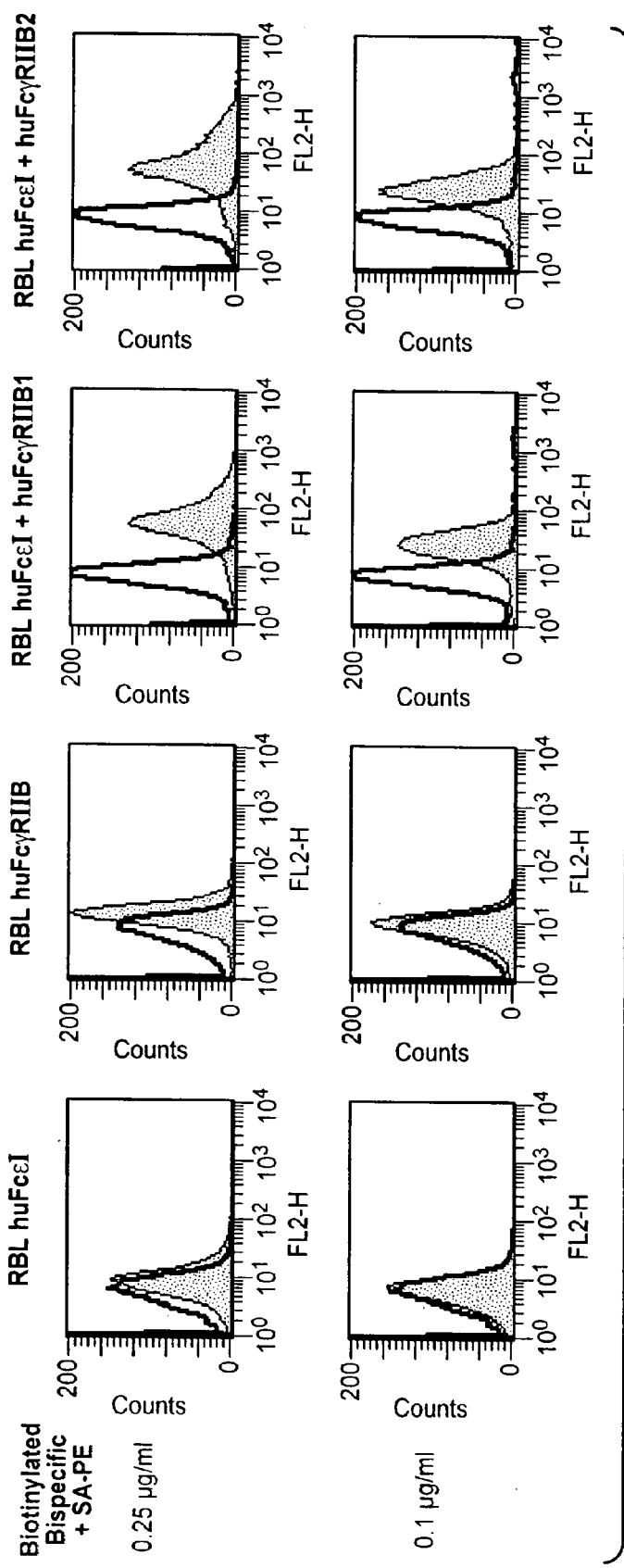

Flow cytometry studies of bispecific antibody binding to RBL huFcϵRI+huFcγRIIB1 and RBL huFcϵRI+huFcγRIIB2 cells indicated that binding saturation is reached at approximately 2.5 µg/ml of bispecific antibody. FIG. 46 presents titration by flow cytometry of bispecific antibody from 0.1 µg/nm to 2.5 µg/ml across four RBL-derived cell lines, RBL huFcϵRI cells, RBL huFcγRIIB cells, RBL huFcϵRI+huFcγRIIB1 cells, and RBL huFcϵRI+huFcγRIIB2 cells. The solid peak corresponds to cells bound with biotinylated bispecific antibody. Titration of bispecific antibody binding to RBL-derived cell lines indicates binding of the bispecific antibody to RBL huFcϵRI+huFcγRIIB1 cells and RBL huFcϵRI+huFcγRIIB2 cells was decreased at lower concentrations of bispecific antibody and undetectable at less than 0.0025 µg/ml. Bispecific antibody inhibition of RBL histamine release as shown in FIGS. 42 and 44 was maintained at concentrations of bispecific antibody below binding saturation, using two different concentrations of NP-antigen stimulus.

5.5 Bispecific Effects on FcϵRIα Surface Expression Levels

Downmodulation of FcϵRI expression levels on mast cells and basophils is a means of reducing mast cell and basophil sensitivity towards antigen-induced activation and is one mechanism by which a therapeutic agent could have a beneficial effect in asthma or allergy.

The ability of the bispecific antibody to modulate surface expression levels of FcϵRI was assessed by performing IgE-induced FcϵRI upregulation and downregulation experiments in the presence and absence of bispecific antibody using the following procedures.

Figure 47:
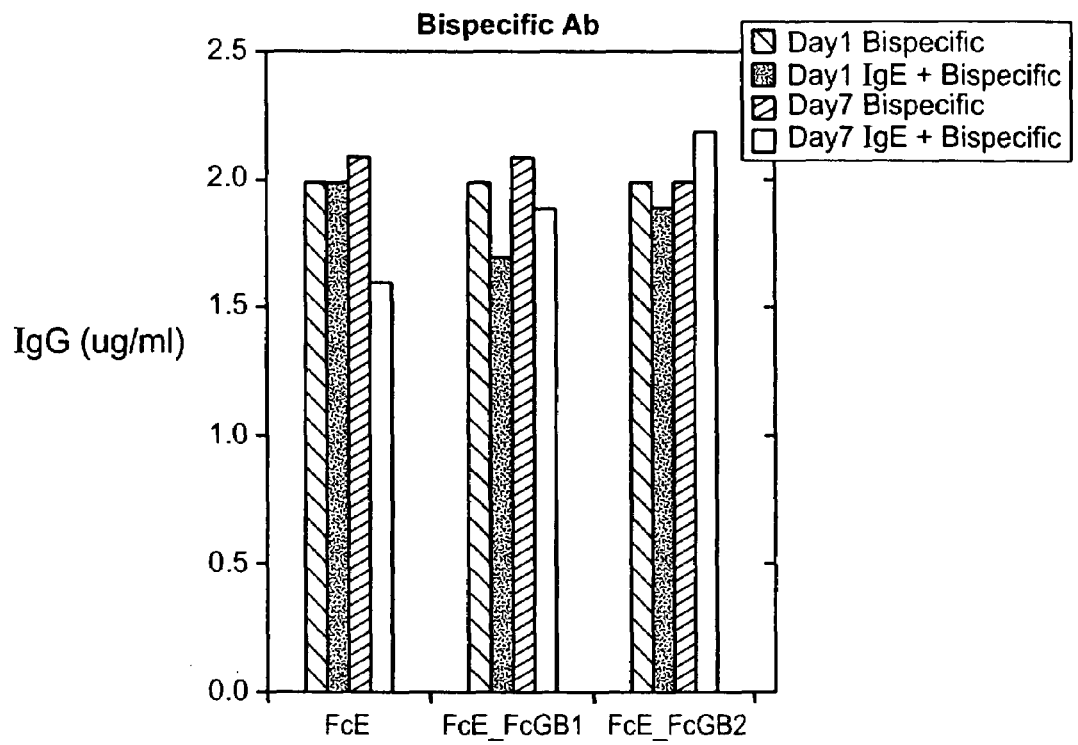
FIG. 47 is a graph of bispecific antibody levels detected by ELISA in cell culture media of RBL FcεRI cells, RBL FcεRI+FcγRIIB1 cells, and RBL FcεRI+FcγRIIB2 cells over the seven day timecourse after treatment with IgE in the presence or absence of bispecific antibody indicating that the antibodies were not depleted.
Figure 48:
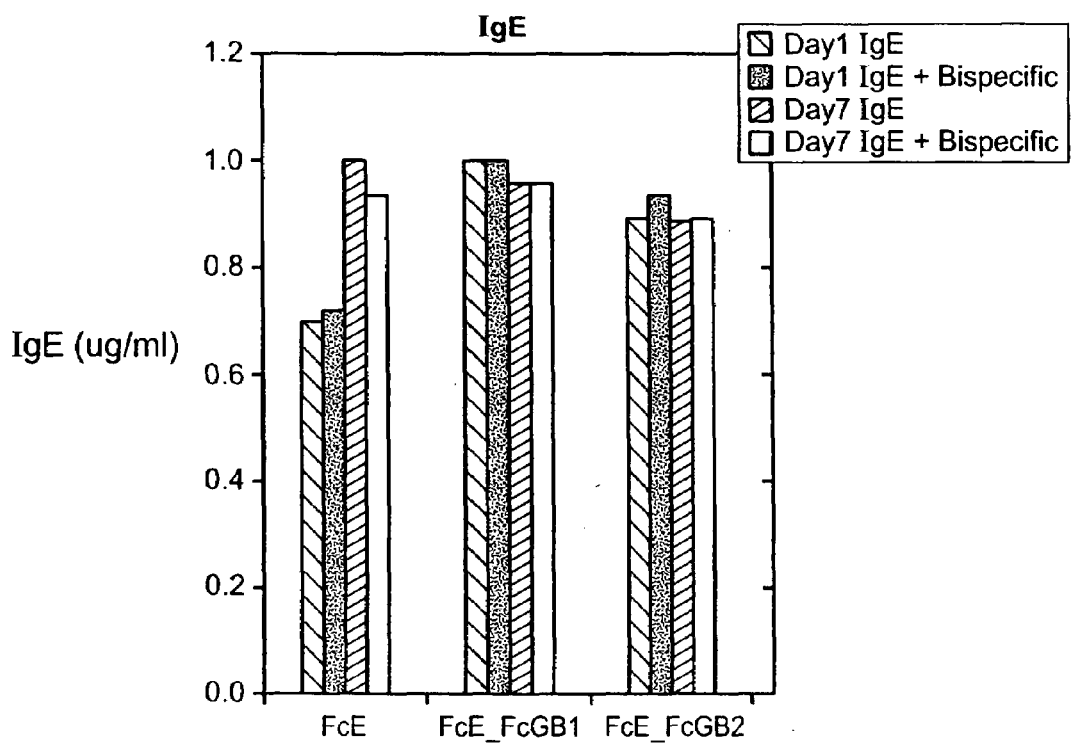
FIG. 48 is a graph of IgE levels detected by ELISA in cell culture media of RBL FcεRI cells, RBL FcεRI+FcγRIIB1 cells, and RBL FcεRI+FcγRIIB2 cells over the seven day timecourse after treatment with IgE in the presence or absence of bispecific antibody indicating that the antibodies were not depleted.

RBL huFcϵRI+huFcγRIIB1 and RBL huFcϵRI+huFcγRIIB2 cells were incubated with 1 µg/ml U266 IgE (ATCC TIB196) in the presence or absence of 2 µg/ml bispecific antibody for 1, 2, 3, or 7 days. FIGS. 47 and 48 shows that 5A6/22E7 bispecific antibody and IgE concentrations remained unchanged, as detected by ELISA using human IgG1 and IgE for detection, during the 7 day time course, indicating that the reagents were not depleted from the cell culture medium. Total levels of cell surface human FcϵRI were determined by flow cytometry using an antibody against human IgE, (Caltag Laboratories) after saturation of all FcϵRI receptors on ice with U266 IgE.

Figure 49:
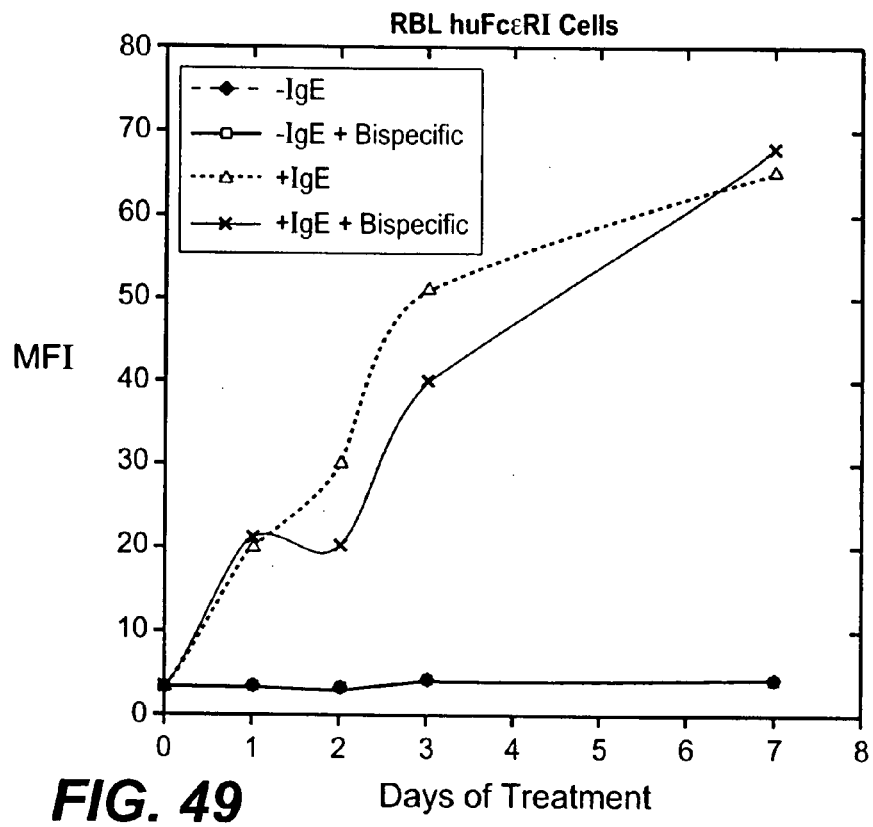
FIGS. 49 and 50 present flow cytometry data for IgE-induced upregulation of FcεRI surface expression in RBL FcεRI cells.
Figure 50:
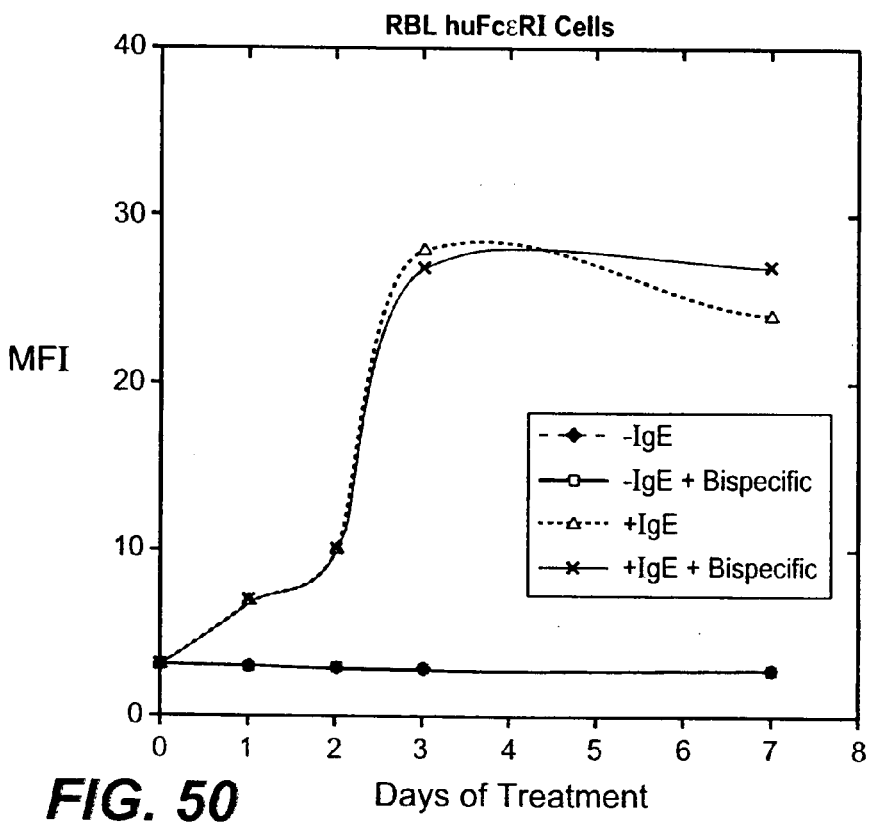
Figure 51:
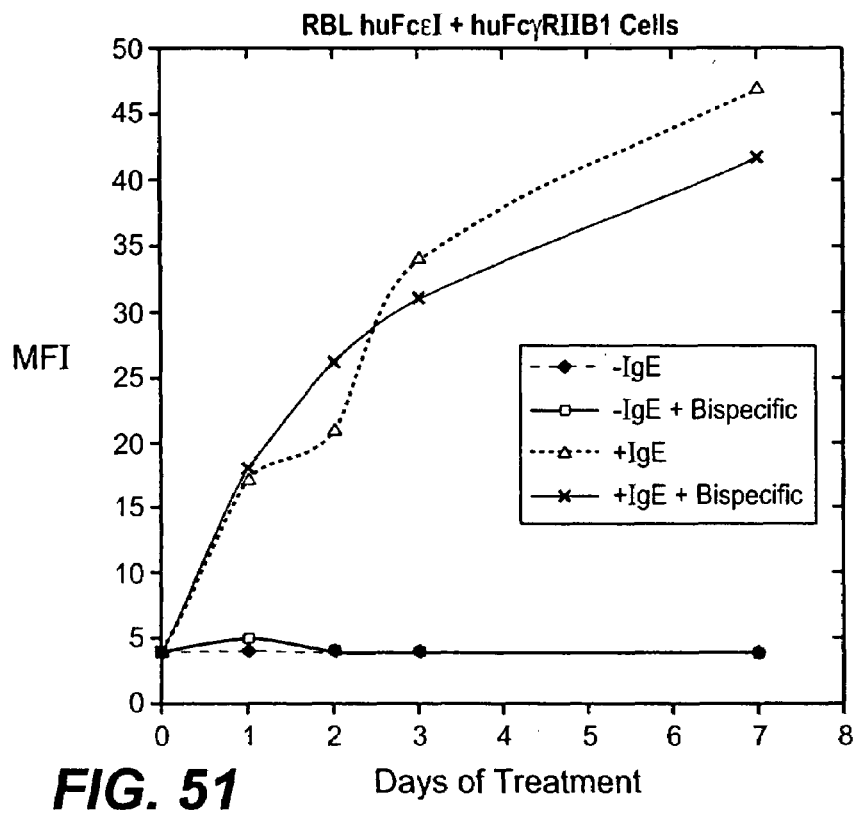
FIGS. 51 and 52 present flow cytometry data for IgE-induced upregulation of FcεRI surface expression in RBL FcεRI+FcγRIIB1 cells.
Figure 52:
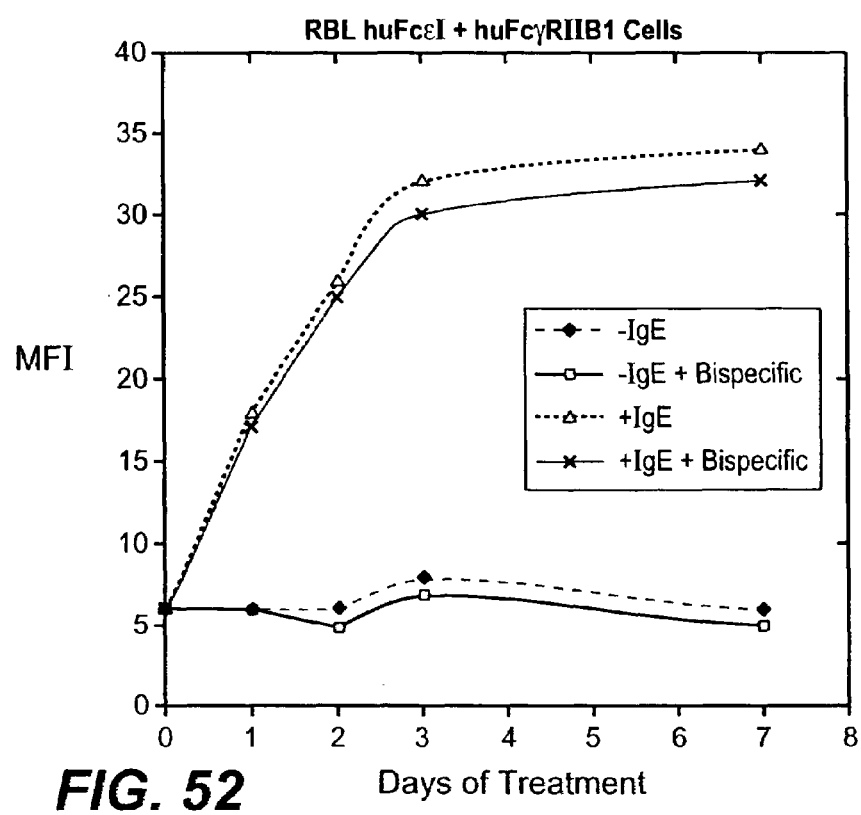
Figure 53:
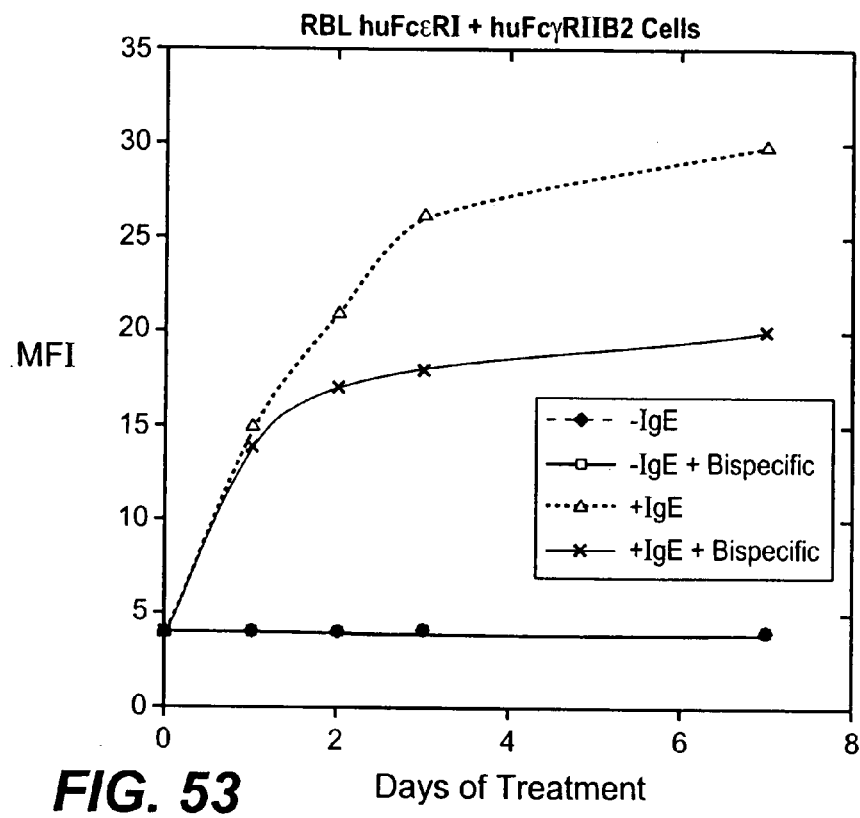
FIGS. 53 and 54 present flow cytometry data for IgE-induced upregulation of FcεRI surface expression in RBL FcεRI+FcγRIIB2 cells.
Figure 54:
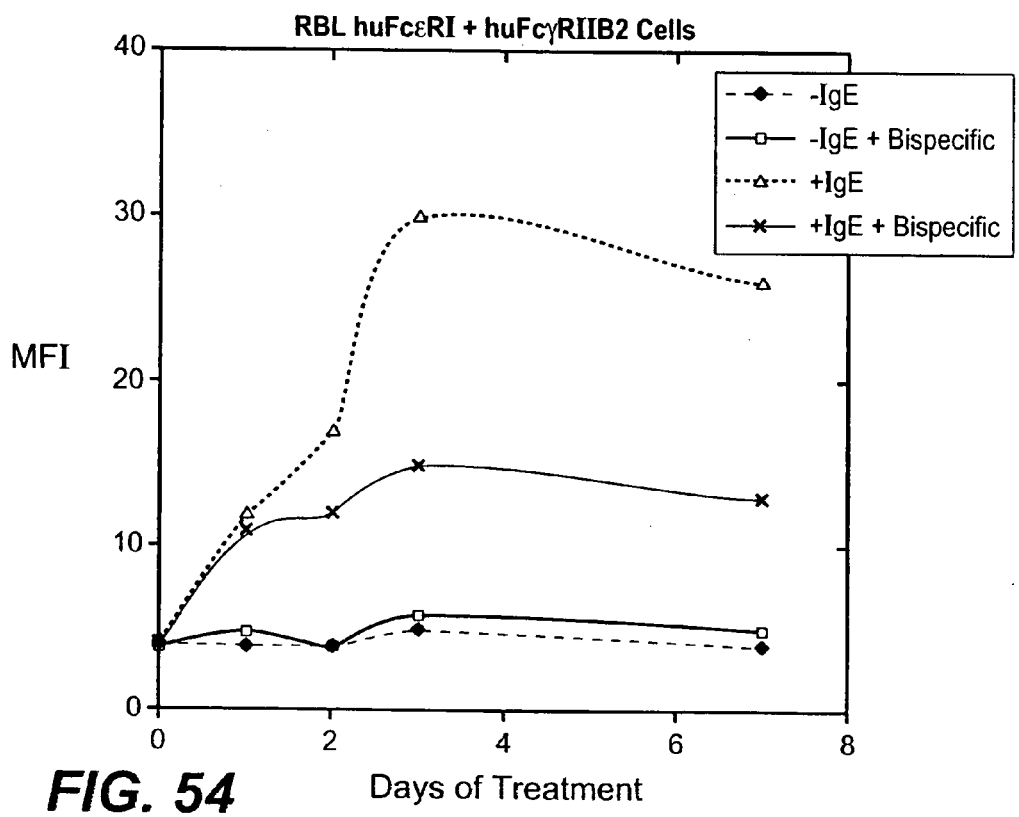

Flow cytometry data for FcϵRI upregulation is shown in FIGS. 49-54. Bispecific antibody has no effect on IgE-induced upregulation of FcϵRI surface expression levels in 2 samples of RBL huFcϵRI cells, as shown in FIGS. 49 and 50, and in 2 samples of RBL huFcϵRI+huFcγRIIB1 cells, as shown in FIGS. 51 and 52. However, bispecific antibody decreased the extent of FcϵRI upregulation upon co-crosslinking huFcϵRI and huFcγRIIB2 in 2 samples of RBL huFcϵRI+huFcγRIIB2 cells as shown in FIGS. 53 and 54.

Figure 55:
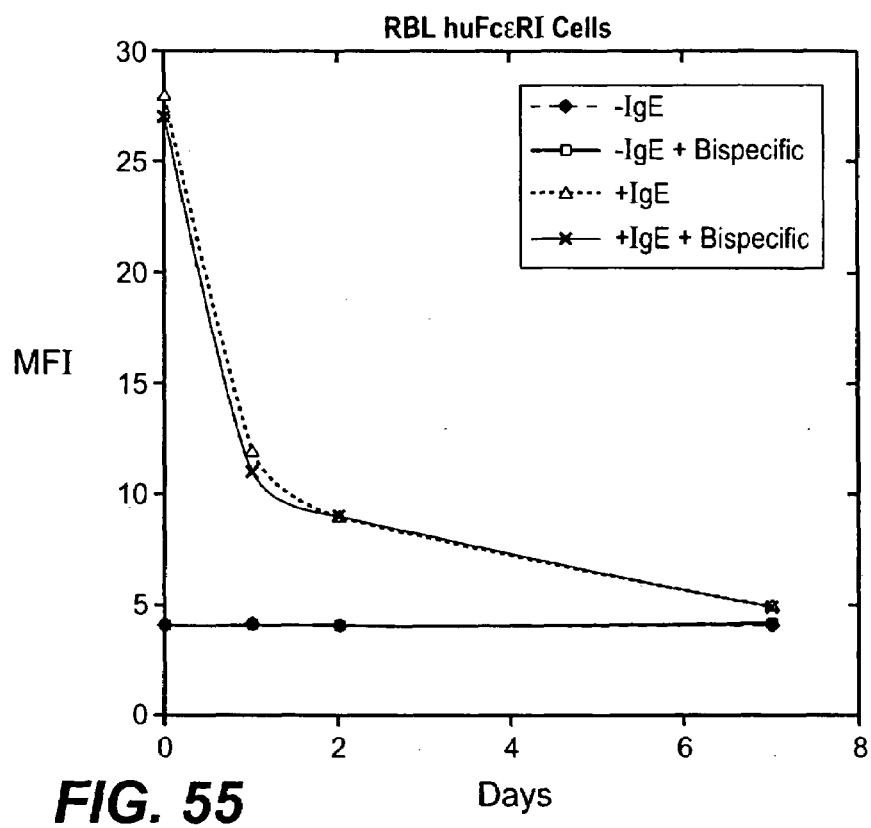
FIG. 55 presents flow cytometry data showing effect of bispecific antibody for downregulation of FcεRI surface expression in RBL FcεRI cells after removal of IgE.
Figure 56:
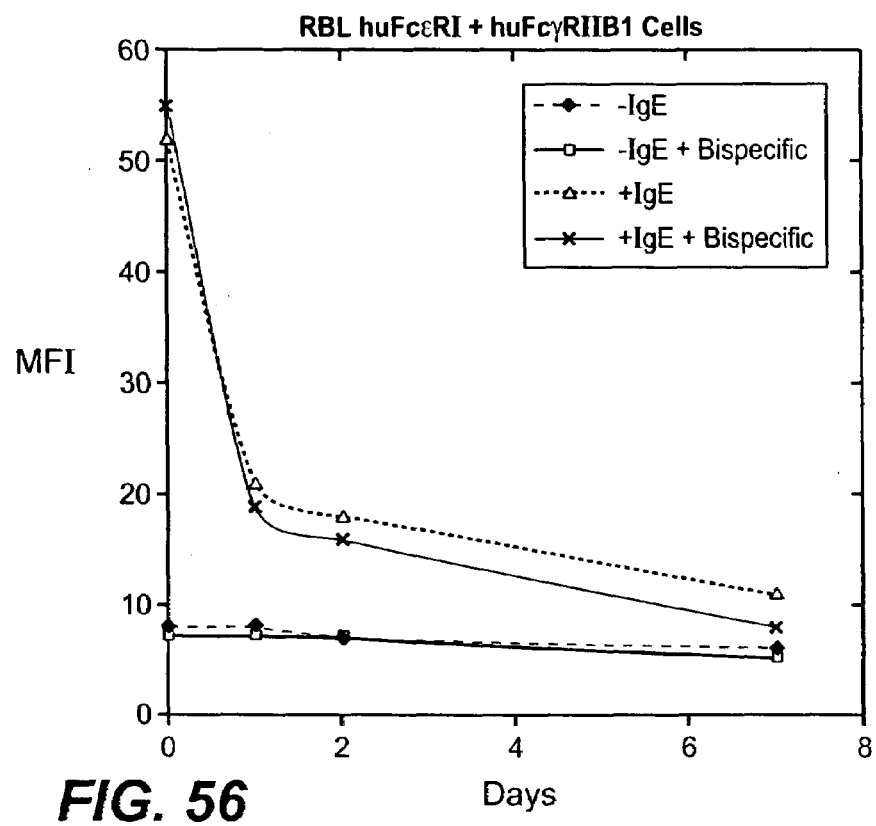
FIG. 56 presents flow cytometry data showing effect of bispecific antibody for downregulation of FcεRI surface expression in RBL FcεRI+FcγRIIB1 cells after removal of IgE.
Figure 57:
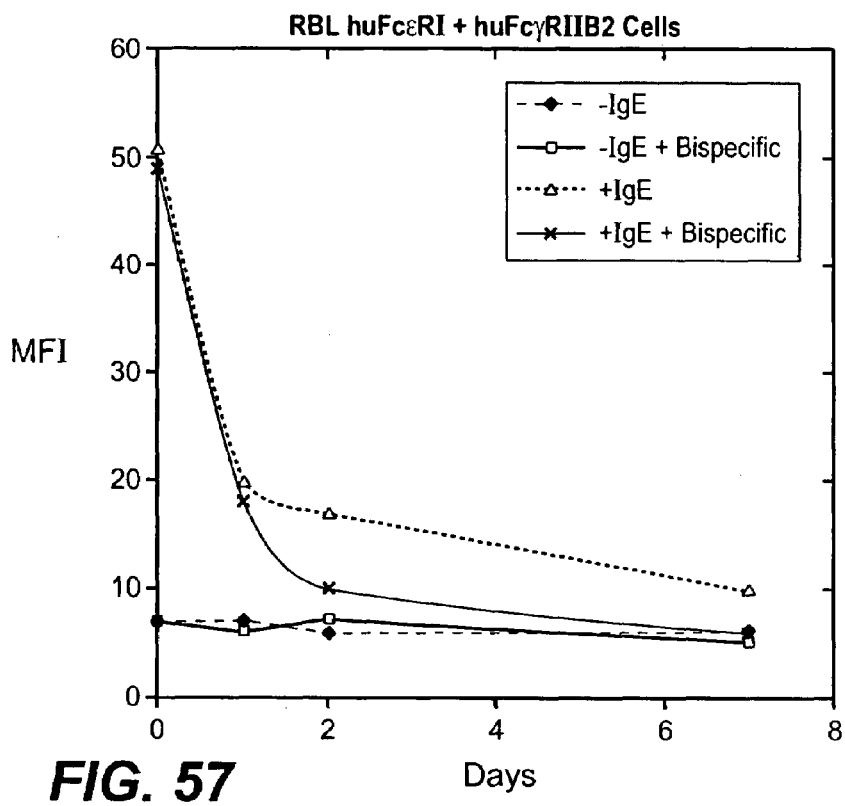
FIG. 57 presents flow cytometry data showing the effect of bispecific antibody on downregulation of FcεRI surface expression in RBL FcεRI+FcγRIIB2 cells after removal of IgE.
Figure 58:
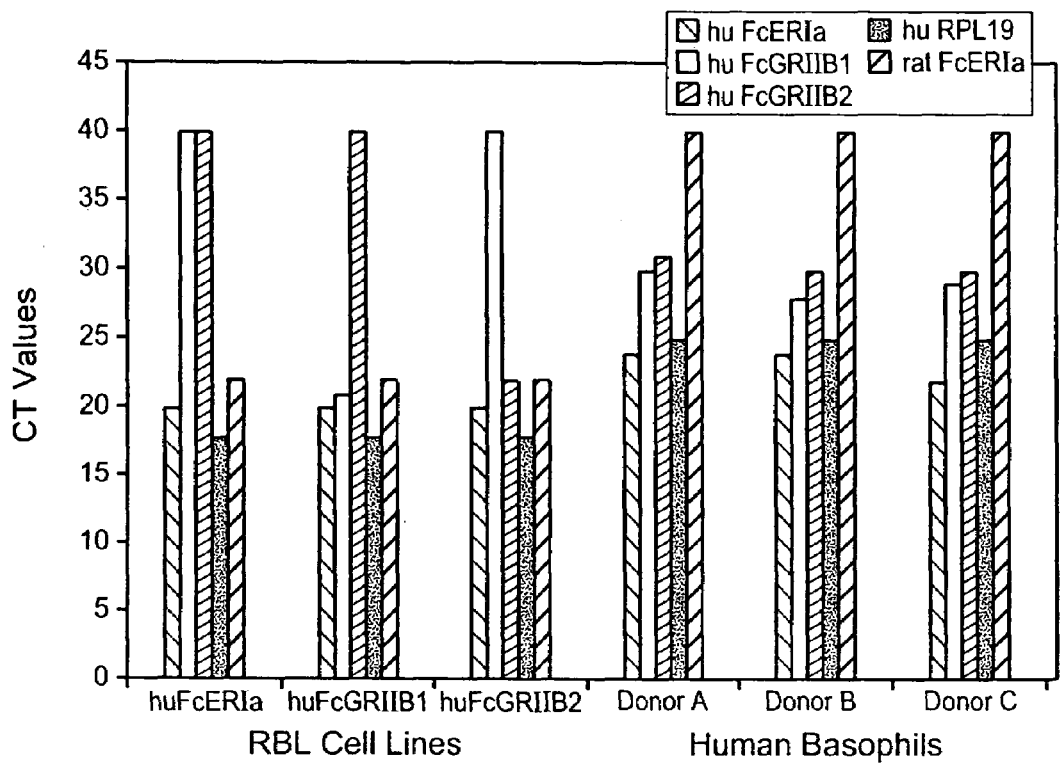
FIGS. 58-61 present RT-PCR data of mRNA expression of huFcεRIα, FcγRIIB1, FcγRIIB2, huRPL19 (control), and rat FcεRIα in mast cells RBL huFcεRI (designated huFcεRIa), RBL huFcεRI+FcγRIIB1 cells (designated huFcGRIIb1), and RBLhuFcεRI+FcγRIIB2 cells (designated huFcGRIIb2) and on human basophils from three different donors.
Figure 59:
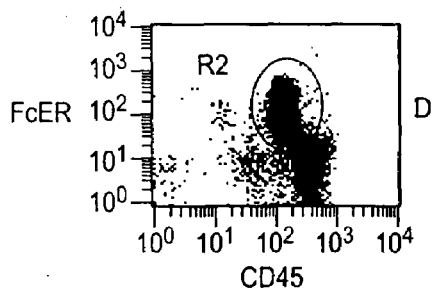
Figure 60:
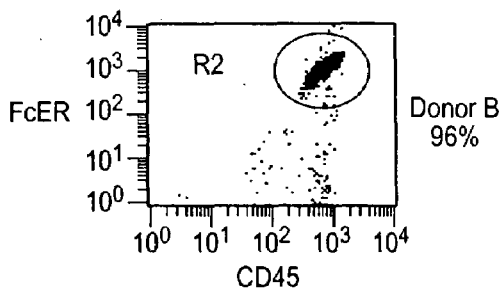
Figure 61:
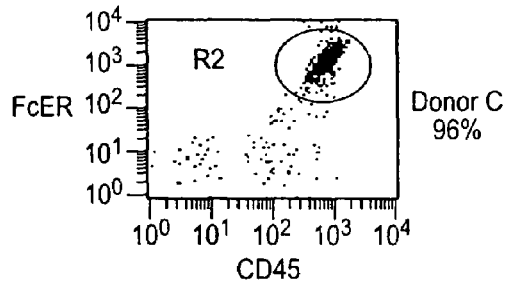
Figure 63:
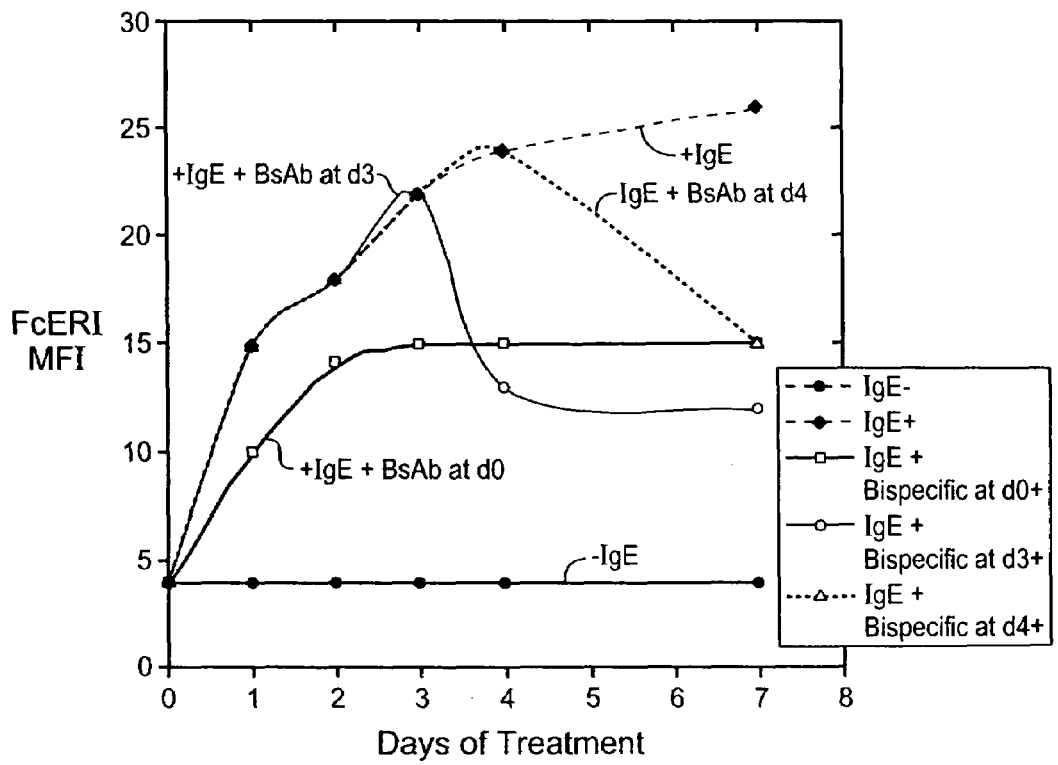
FIG. 63 graphically represents flow cytometry data showing the effect of bispecific antibody on downregulation of IgE-induced FcεRI surface expression in RBL FcεRI+FcγRIIB2 cells when anti-FcγRIIB-anti-FcεRI bispecific antibody 5A6/22E7 is added at day zero, day three and day four.

The effect of bispecific antibody on FcϵRIα downregulation after removal of IgE was also measured with results shown in FIGS. 55-57. FcϵRIα on RBL cells was upregulated for 7 days with 1 µg/ml U266 IgE. The IgE was then washed out of the cell culture medium and FcϵRIα downregulation was observed by flow cytometry in the presence or absence of bispecific antibody at 1, 2, 3, and 7 days after removal of IgE. Bispecific antibody had no effect on FcϵRIα downregulation in RBL huFcϵRI and RBL huFcϵRI+huFcγRIIB1 cells, as shown in FIGS. 55 and 56. However, the rate of FcϵRIα downregulation was increased by bispecific antibody in RBL huFcϵRI+huFcγRIIB2 cells as shown in FIG. 57. The experiment using RBL huFcϵRI+huFcγRIIB2 cells was repeated, but 5A6/22E7 bispecific antibody was added in the presence of IgE at zero, three or four days (see FIG. 63). The results show that the bispecific antibody decreases IgE-induced expression of FcϵRI in these cells. It was also discovered by these studies that the huFcγRIIB1 isoform does not downregulate huFcϵRI expression.

These studies indicate that the bispecific antibody can decrease the surface expression level of FcϵRI on mast cells and basophils upon co-crosslinking FcϵRI with the B2 isoform of FcγRIIB. RT-PCR data of huFcϵRIα, FcγRIIB1, FcγRIIB2, huRPL19 (control), and rat FcεRIα, mRNA expression in mast cells: RBL huFcεRI (designated huFce-RIa), RBL huFcεRI+FcγRIIB1 cells (designated huFc-GRIIb1), and RBLhuFcε+FcγRIIB2 cells (designated huFc-GRIIb2); and on human basophils from three different donors. Real time RT-PCR identification of FcγRIIB1 and FcγRIIB2 isoforms was performed on mRNA prepared from purified peripheral blood basophils from three different human donors. Human blood basophils were isolated from 100 ml of blood using magnetic bead purification (MACs human basophil isolation kit, Miltenyi). mRNA from 106 basophils was prepared using RNeasy™ mini kit (Qiagen). The following primer/probe sets used for real time RT-PCR analysis are listed in Table 2.

TABLE 2

| huFcεRI | Forward: | GGT GAA GCT CTC AAG TAC TGG TAT (SEQ ID NO:12) |
|---|---|---|
| | Reverse: | GTA GGT TCC ACT GTC TTC AAC TGT (SEQ ID NO:13) |
| | Probe: | AGA ACC ACA ACA TCT CCA TTA CAA ATG CC (SEQ ID NO:14) |
| huFcγRIIB1 | Forward: | CCC TGA GTG CAG GGA AAT (SEQ ID NO:15) |
| | Reverse: | CCT CAT CAG GAT TAG TGG GAT T (SEQ ID NO:16) |
| | Probe: | AGA GAC CCT CCC TGA GAA ACC AGC C (SEQ ID NO:17) |
| huFcγRIIB2 | Forward: | TGC TGT AGT GGC CTT GAT CT (SEQ ID NO:18) |
| | Reverse: | CCA ACT TTG TCA GCC TCA TC (SEQ ID NO:19) |
| | Probe: | AGC GGA TTT CAG CCA ATC CCA (SEQ ID NO:20) |
| huRPL19 | Forward: | GCG GAT TCT CAT GGA ACA CA (SEQ ID NO:21) |
| | Reverse: | GGT CAG CCA GGA GCT TCT TG (SEQ ID NO:22) |
| | Probe: | CAC AAG CTG AAG GCA GAC AAG GCC C (SEQ ID NO:23) |
| rat FcεRI | Forward: | CAA TTA TTT CCC ACA GTA TCT TCA A (SEQ ID NO:24) |
| | Reverse: | GGG GTA CAG ACA TTT CTA TGG AT (SEQ ID NO:25) |
| | Probe: | ACA TGA GTG TCC TTT GAC AGT TGA AAG GCT (SEQ ID NO:26) |

RNA was analyzed on the ABI PRISM® 7700 Sequence Detection System using TaqMan® One-Step RT-PCR Master Mix (Applied Biosystems) following the manufacturer's recommended protocol. Both B1 and B2 isoforms of FcγRIIB are expressed in human basophils as shown in FIGS. 58-61, the demonstrated ability of the bispecific antibody to down-modulate FcεRI surface expression levels when co-crosslinked to FcγRIIB2 in cells makes methods of using the anti-FcγRIIB-anti-FcεRI bispecific antibody of the invention particularly useful for treatment of patients experiencing a disorder for which inhibition and/or downregulation of FcεRI provides relief from such disorder.

5.6 The Bispecific Antibody Inhibits Cytokine Release in RBL Cell Line

Figure 64:
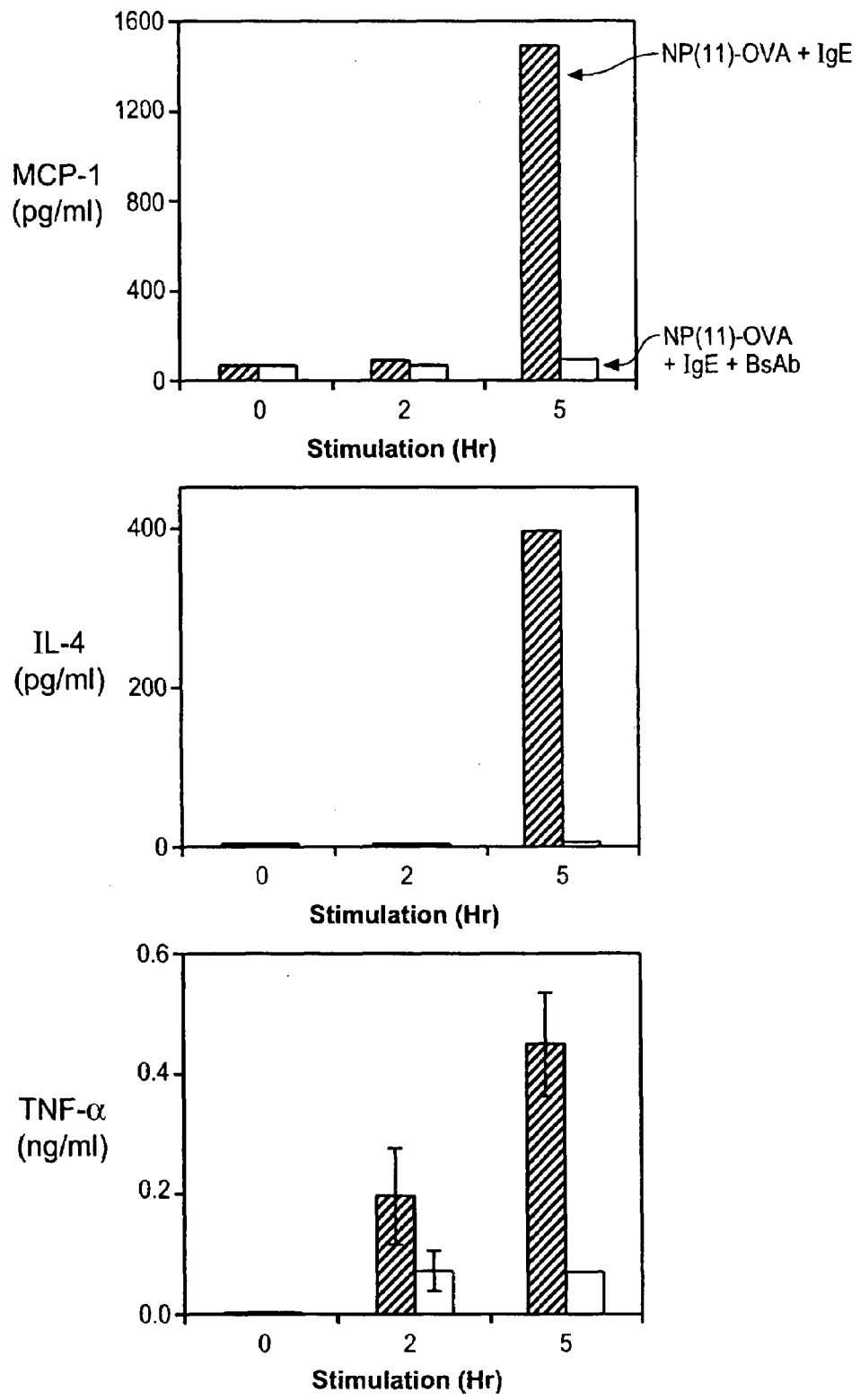
FIG. 64 presents results of assays in which IgE/antigen-induced cytokine release in RBL FcεRI+FcγRIIB2 cells was inhibited by the anti-FcγRIIB-anti-FcεRI bispecific antibody 5A6/22E7. For each bar graph: antigen/IgE alone (NP(11)-OVA+IgE), dark grey bars; antigen/IgE+bispecific antibody (NP(11)-OVA+IgE+BsAb), light grey bars.

The release of cytokines MCP-1 (monocyte chemotactic protein-1), IL-4 (interleukin-4), and TNF-α (tumor necrosis factor-α) was inhibited in the presence of anti-FcγRIIB-anti-FcεRI bispecific antibody 5A6/22E7 as demonstrated by the following assay. RBL cells were transfected with cDNA encoding huFcγRIIB2 or huFcγRIIB1 and huFcεRI and cultured according to the procedures described above in this Example 5. Cells were stimulated to release cytokines by exposure to nitrophenol (NP)-conjugated ovalbumin (NP (11)-OVA) and an IgE (anti-NP human IgE) as described in this Example 5 for the histamine release assay. The 5A6/22E7 bispecific antibody was added to the text samples at a concentration of 5 μg/ml. Detection and quantitation of each of the cytokines of interest was performed as follows for the cytokines of interest. MCP-1 and IL-4 were detected using a Beadlyte Rat Multi-cytokine Beadmaster kit (catalog 48-200, Upstate, Charlottesville, Va., USA. Rat TNF alpha was detected using an anti-rat TNF alpha ELISA kit according to the manufacturer's instructions. The assays were performed according to the manufacturer's instructions. FIG. 64 depicts the results for cytokine release in RBL cells transfected with huFcγRIIB2 and huFcεRI, although the results were the same for RBL cells transfected with huFcγRIIB1 and huFcεRI. Rat mast cells cytokine release was inhibited in the presence of 5A6/22E7 bispecific antibody (5 μg/ml, light bars), whereas cytokine release was not inhibited and increased over a period of five hours in cell culture (dark bars).

5.7 The Bispecific Antibody Inhibits Synthesis and Release of Arachadonic Acid Metabolites in RBL Cell Line The presence of allergen initiates multiple immune responses, including the release of so-called "pre-formed" inflammatory mediators such as histamine from mast cells, the production of arachidonic acid and its conversion into so-called "eicosanoid" mediators such as prostaglandins, and the production and release of cytokines and chemokines. Pre-formed mediators are released immediately upon exposure, whereas eicosanoid mediators are delayed roughly 30 minutes to 2 hours, and cytokines and chemokines are delayed roughly 5 to 24 hours. One of the body's defense mechanisms, referred to as the arachidonic acid cascade, produces three newly-formed inflammatory mediators—prostaglandins, thromboxanes and leukotrienes—which are collectively known as eicosanoids. The release of metabolites of arachidonic acid was monitored to test the ability of the 5A6/22E7 bispecific antibody to inhibit this downstream effect of exposure to allergen. RBL cells were transfected with cDNA encoding huFcγRIIB1 or huFcγRIIB2 and huFcεRI and cultured as described above in this Example 5. The arachidonic acid cascade was stimulated by exposure to nitrophenol (NP)-conjugated ovalbumin (NP(11)-OVA) as an antigen in combination with an IgE (anti-NP human IgE) as described in this Example 5 for the histamine release assay. Quantitation of metabolite leukotriene C4 (LTC4) was performed with an EIA kit (catalog #520211, Cayman Chemical Company, Ann Arbor, Mich., USA) according to the manufacturer's instructions. Quantitation of metabolite prostaglandin D2 (PGD2) was performed with a MOX EIA kit (catalog #212011 (Cayman Chemical Company, supra) according to the manufacturer's instructions. The results in FIG. 65 show that in RBL cells expressing huFcγRIIB1 and FcεRI, arachidonic acid metabolism, as evidenced by the production of LTC4 and PGD2, increased with time in the presence of IgE plus antigen, but not in the presence of an irrelevant antigen (TNP(11)-OVA). In the presence of 5 μg/ml of the 5A6/22E7 bispecific antibody, arachidonic acid metabolism was inhibited. The same results were obtained using RBL cells expressing huFcγRIIB2 and FcεRI (data not shown). These results demonstrate that an important immune pathway is inhibited by the anti-FcγRIIB-anti-FcεRI bispecific antibody.

5.8 The Bispecific Antibody Inhibits IgE-Induced Mast Cell Survival

Human bone marrow derived mast cell (huBMMC) survival is induced by murine IgE. To test whether the 5A6/22E7 bispecific antibody inhibited such survival, the following assay can be performed. Human hematopoietic progenitor stem cells (CD34+) were obtained from Allcells (catalog #ABM012, Allcells, LLC, Berkeley, Calif., USA). The cells from each of three donors were cultured two weeks in Stem-Pro-34® serum-free medium (Gibco Cell Culture Systems, Invitrogen, Carlsbad, Calif., USA) containing IL-3 (at 30 ng/ml), IL-6 (at 200 ng/ml) and stem cell factor (SCF, at 100 ng/ml). Mast cell survival was assessed by Annexin/7-AAD (7-Amino-Actinomycin D) staining (BD/Pharmingen flow cytometry kit, Becton Dickenson & Company, Franklin Lakes, N.J., USA) under the following test conditions: (1) StemPro® medium alone, (2) StemPro® medium+30 ng/ml IL-3, 200 ng/ml L-6, and 100 ng/ml SCF, (3) StemPro® medium+5 µg/ml SPE-7 (mouse IgE anti-DNP monoclonal antibody (SPE-7, Sigma, St. Louis, Mo., USA), (4) StemPro® medium+5 µg/ml boiled, denatured SPE-7, and (5) StemPro® medium+5 µg/ml SPE-7+5 µg/ml 5A6/22E7 bispecific antibody. Cell survival was monitored for 10 days after the initial two-week culturing period. Cells were maintained at 37° C., 5% $CO_2$ during both phases. At a time between 4 and 7 days after the start of the test culturing, cell survival was determined. The average percent inhibition of cell survival for three donor cell samples was 65%±9. These results indicate that inhibition of the FcεRI receptor activity by cross-linking with the FcγRIIB receptor using an anti-FcγRIIB-anti-FcεRI bispecific antibody inhibits murine IgE-induced survival of human bone marrow derived mast cells.

5.9 A Bispecific Antibody Inhibits Mast Cell Activation In Vivo

A mouse model was used to determine the in vivo efficacy of the bispecific antibody. The mouse model was a BAC transgenic mouse expressing the human gene for FcεRIα. Mast cell activation was tested by passive cutaneous anaphylaxis (PCA) assays as described in this example.

Generation of a Mouse Anti-Mouse FcγRIIB Antibody.

For this purpose, a surrogate bispecific antibody capable of binding mouse FcγRIIB was needed. Such an antibody was prepared comprising anti-human FcεRIα antibody clone 22E7 and a mouse-anti-mouse FcγRIIB antibody, designated 14H6. The mouse surrogate bispecific antibody was generated by annealing (1:1 ratio for 5 minutes at 50° C.), bacterially expressed and Protein A purified, 22E7 (comprising heavy chain "hole" mutations T366S, L368A, and Y407V) and 14H6 (comprising heavy chain "knob" mutation T366W) to form heavy chain heterodimers utilizing the "knobs and holes" technology (Merchant et al. (1998), supra, and U.S. Pat. Nos. 5,731,168; 5,807,706; and 5,821,333).

Generation of a BAC Transgenic Mice Expressing hu FcεRIα.

BAC transgenic mice expressing the human gene for FcεRIα were generated as follows. Genomic clones encoding the sequence for human FcεRIα were obtained by screening the RPCI-11 (Rosewell Park Cancer Institute) Human Male BAC (Bacterial Artificial Chromosome) Library (Osoegawa et al. Genomic Res. 11:483 (2001)), with a human FcεRIα-specific probe (SEQ ID NO:41) generated by PCR-amplification of human genomic DNA (Clontech, Mountain View, Calif.) with a forward primer (intron 3,5'-TCTTTCTCCCTGTGT-TGGGCGTTC-3', SEQ ID NO:42) and reverse primer (intron 4, 5'-AGAGGCCTTGAATCCCACTCTGGTG-3', SEQ ID NO:43) located in the neighboring intronic segment approximately 100 nucleotides from the 5' and 3' ends of human FcεR1α exon 4, respectively. The human FcεR1α-specific probe was sent to a commercial BAC Library Hybridization Screening Service (Invitrogen, San Diego, Calif.) that produced three RPCI 11 Human BAC Clones 72-I-4, 304-P-16 and 990-O-21.

The presence of full-length human FcεR1α in the three clones was verified by DNA sequencing using human FcεR1α-specific primers corresponding to each of the 6 exons including 100-200 bp of intervening sequence on either side of a particular exon (SEQ ID NOs:46-55) and primers specific to the 5' and 3' untranslated regions (SEQ ID NOs:44, 45, and 56).

Additional information regarding the primers and probes used in these experiments are shown in Table 3, below.

TABLE 3

EXON4 HYBRIDIZATION PROBE
TGCCCAGTTGGGCACCATCCTGAATATTATCTCTAAAGAAAGAAGCAAAA
CCAGGCACAGCTGATGGGTTAACCAGATATGATACAGAAAACATTTCCTT
CTGCTTTTTGGTTTTAAGCCTATATTTGAAGCCTTAGATCTCTCCAGCAC
AGTAAGCACCAGGAGTCCATGAAGAAGATGGCTCCTGCCATGGAATCCCC
TACTCTACTGTGTAGCCTTACTGTTCTTCGGTAAGTAGAGATTCATTA
CCCCTCCCAGGGAGGCCCAAATGAATTTGGGGAGCAGCTGGGGTAGGAAC
CTTTACTGTGGGTGGTGACTTTTTCTAGGACATGTGCAAACTATTGGGCA
TTTCCCAG, SEQ ID NO:41, where plain text
indicates intron 3, underlined text indicates exon
4, and italicized text indicates intron 4.

INTRON3 FORWARD PRIMER1
5'-TCTTTCTCCCTGTGTTGGGCGTTC-3', SEQ ID NO:42

INTRON4 REVERSE PRIMER
5'-AGAGGCCTTGAATCCCACTCTGGTG-3', SEQ ID NO:43

5'UTRA FORWARD PRIMER
5'-TCTGGGAACTCTAATCAGGAGAC, SEQ ID NO:44

5'UTRB FORWARD PRIMER
5'-GATAAAGACTTGCCTCTGAGG, SEQ ID NO:45

5'UTR-EXON1 FORWARD PRIMER
5'-CTACTACTGCTGTGGACCCATTC, SEQ ID NO:46

EXON1-INTRON1 REVERSE PRIMER
5'-AGCCTCCATTGTGTGGCACCTAC, SEQ ID NO:47

INTRON1-EXON2 FORWARD PRIMER
5'-ATTGCCCAGTTGGGCACCATC, SEQ ID NO:48

EXON3-INTRON3 REVERSE PRIMER
5'-GCCAAGGAACAGATTCATGCTC, SEQ ID NO:49

INTRON3-EXON4 FORWARD PRIMER
5'-GAATAAGGACAGGTTGACCACTG, SEQ ID NO:50

EXON4-INTRON4 REVERSE PRIMER
5'-AGTGCTGGGATTACAGGCGTG, SEQ ID NO:51

INTRON4-EXON5 FORWARD PRIMER
5'-GTTTCTGACACATGCTCTATGC, SEQ ID NO:52

EXON5-INTRON5 REVERSE PRIMER
5'-TCTGTTATGCTTGGGTAGTGC, SEQ ID NO:53

INTRON5-EXON6 FORWARD PRIMER
5'-GAGCACCAACAGAGCAACTCAAC, SEQ ID NO:54

EXON6-INTRON6 REVERSE PRIMER
5'-CCTAGATCGCACTTGCAATAGTC, SEQ ID NO:55

3'UTR REVERSE PRIMER
5'-GTAAGCTATAGGCATCCTGATC, SEQ ID NO:56

Figure 66:
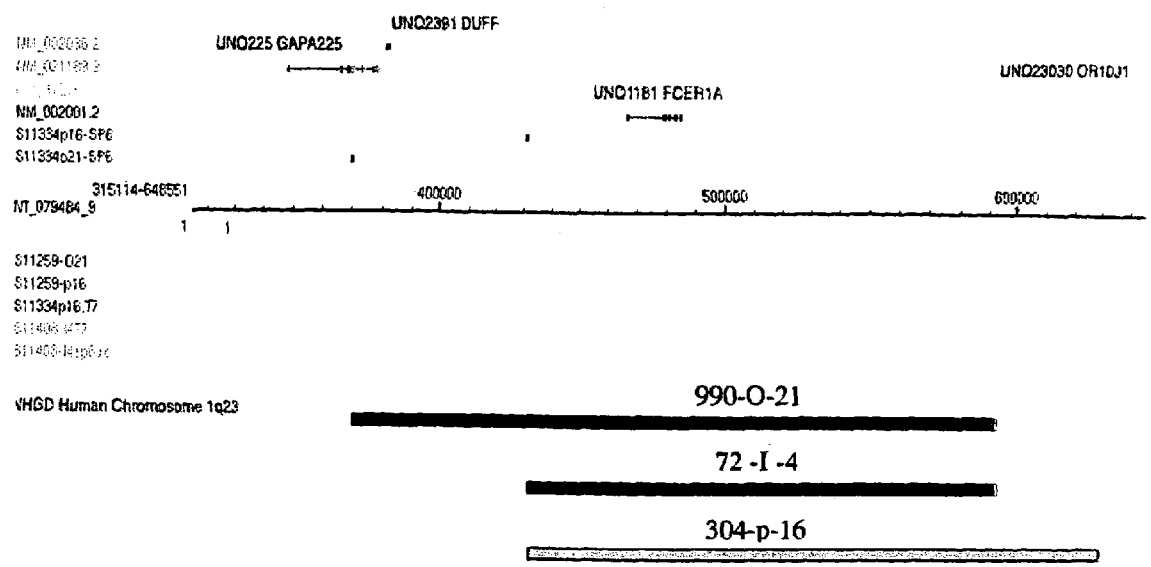
FIG. 66 depicts a map of BAC clones, summarizing the bioinformatic results showing the location of human FcεRIα and neighboring full-length genes, Duffy antigen (DARC Duffy blood group, chemokine receptor), OR10J1 (olfactory receptor, family 10, subfamily J, member 1), and a partial sequence for IGSF4B (immunoglobin superfamily, member 4B).
Figure 67A:
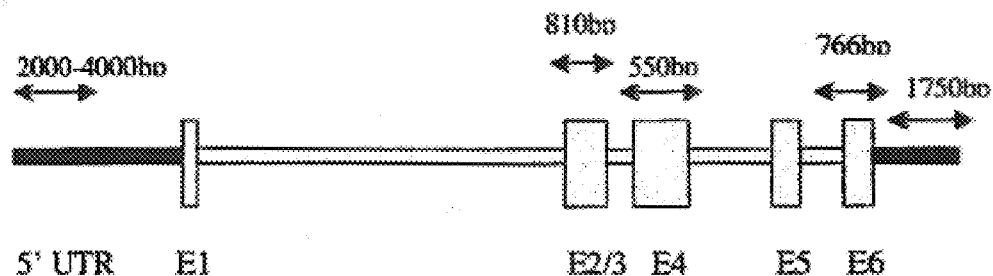
FIGS. 67A and 67B.

The 5' and 3' ends flanking the human genomic sequence of the BAC clones was determined by DNA sequencing and used to map the position of FcεR1α on chromosome 1 and identify other genes in the BAC clones. FIG. 66 depicts a map of BAC clones, summarizing the bioinformatic results showing the location of human FcεR1α and neighboring full-length genes, Duffy antigen (DARC Duffy blood group, chemokine receptor), OR10J1 (olfactory receptor, family 10, subfamily J, member 1), and a partial sequence for IGSF4B (immunoglobin superfamily, member 4B). Clone 72-I-4 contained only the full-length human FcεR1a gene and was the preferred clone for generating the human FcεR1α BAC transgenic mouse. Clone 304-P-16 contained an additional unrelated gene, OR10J1, and was used as a backup clone for the injections. DNA was prepared from Clones 72-I-4 and 304-P-16 using a Large DNA Construct Isolation Kit (Qiagen, Valencia, Calif.) and characterized by Pulse Field Inversion Gel Electrophoresis for size integrity (Sambrook and Russell, *Molecular Cloning: A Laboratory Manual*, 3$^{rd}$ Ed, Cold Spring Harbor Press (2001)). Subsequently, the DNAs were resuspended at 1 ug/ml in sterile microinjection buffer (10 mM Tris pH 7.5, 0.1 mM EDTA pH 8.0, 100 mM NaCl, 30 mM spermine, and 20 mM Spermidine). A map of the human FcεR1α gene showing exons 1-6 is provided in FIG. 67A.

Figure 67B:
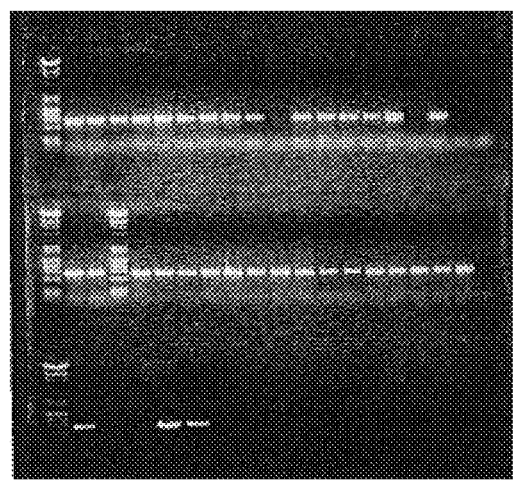

Human FcεR1α BAC transgenic mice were generated by injecting the male pronucleus of a fertilized egg (1 cell stage) with DNA from either BAC clones 72-I-4 or 304-P-16 and transferring the injected egg into to foster mother FVB mouse (Hogan et al, *Manipulating the Mouse Embryo: A Laboratory Manual*. Second Ed. Cold Spring Harbor Press. (1994); (FVB/NTac mouse, Taconic, Hudson, N.Y.)). At approximately the twenty-third day following injection, newborn mice were screened for the presence of human FcεR1α using a PCR assay specific to exon 6 (SEQ ID NO:54 and SEQ ID NO:55). FIG. 67B shows the high rate of inclusion of human FcεR1α in the majority of the newborn mice (− and + denotes DNA from a non-injected FVB mouse and BAC 72-I-4 or 304-P-16 DNA, respectively). Human FcεR1α exon-6 positive mice also tested positive for the presence of 5'UTR (SEQ ID NOs:44 and 45), Exon 2/3 (SEQ ID NOs:48 and 49) and Exon 4 (SEQ ID NOs:50 and 51) of human FcεR1α by polymerase chain reaction. Surface expression of human FcεR1α on the basophils of BAC transgenic PCR-positive mice was determined by staining the cells with an antibody to human FcεR1α, 22E7 (Riske et al. *J. Biol Chem* 266:11245 (1991)). FIG. 68 shows representative fluorescent antibody staining of mouse basophils (CD3$^-$, B220$^-$, CD14$^-$, CD45$^+$, mIgE$^+$; BD Bioscience, San Diego, Calif.) from BAC transgenic founder lines 72-I-4 and 304-P-16 with positive surface expression of human FcεR1α protein.

Monitoring Mast Cell Activation by Passive Cutaneous Anaphylaxis (PCA) Assays.

Figure 69:
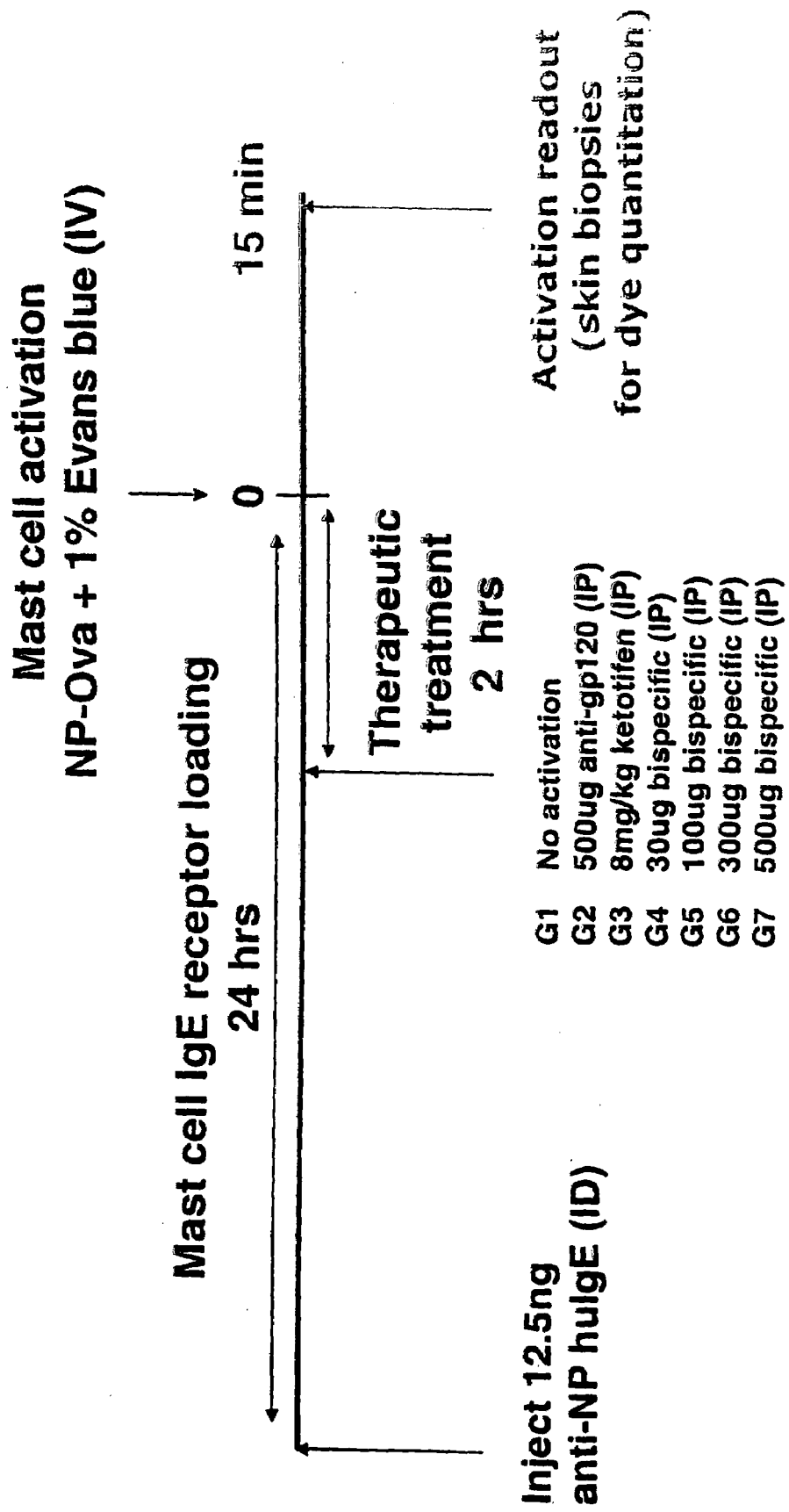
FIG. 69 shows a diagram outlining the protocol for the passive cutaneous anaphylaxis assays performed to monitor mast cell activation in vivo (See Example 5.9, herein).
Figure 70A:
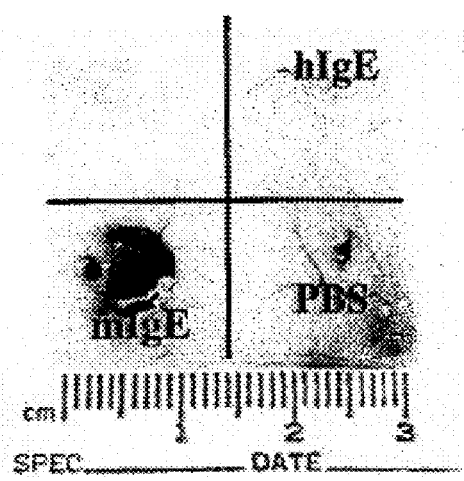
FIGS. 70A and 70B are photographs of mouse skin showing dye migration at sites of extravasation/degranulation resulting from mast cell activation (See Example 5.9, herein).
Figure 70B:
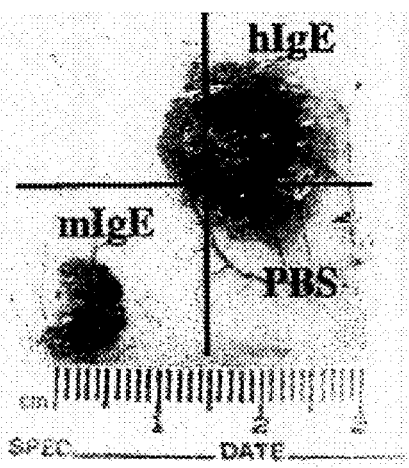

An in vivo assay of IgE-mediated passive cutaneous anaphylaxis (Zhu et al, *Nature Medicine* 8:518 (2002)) was performed on a subset of PCR-(lacking transgene) and surface-positive (expressing transgene) human FcεR1α mice to demonstrate the functionality of the transgene. A diagrammatic outline of the protocol is shown in FIG. 69. In this assay, 25 ng of mouse (anti-DNP SPE7, Sigma) and human (anti-NP JW8.5.13) IgE were administered intradermally and challenged intravenously 24 hours later with antigens NP(15)-ovalbumin (Biosearch Technologies) and DNP-albumin (Sigma), and a blue dye (Evans blue). If mast cells express species-specific FcεR1α, and therefore allow the corresponding mouse or human IgE to bind, antigen-specific triggering by either NP or DNP leads to rapid increase in vascular permeability of the skin that is easily visualized by the influx of blue dye from the circulation. In the FIG. 70A, the skin of a FVB mouse (mFcεR1α$^+$/hFcεRα$^-$) showed no response to NP-ovalbumin challenge, but exhibited a wild-type response to mIgE-DNP albumin challenge (lower left quadrant). When basophils from a transgenic mouse (mFcεR1α$^+$/hFcεR1α$^+$) expressed both mouse and human FcεR1α, hIgE and mIgE antigens induced an increase in blue dye extravasation compared to the PBS control (upper right and lower left quadrants, respectively, of FIG. 70B). This result illustrates that surface expression of a human FcεR1α is functional in the context of a chimeric human FcεR1α-mouse FcεR1βγ IgE receptor complex.

A quantitative in vivo PCA assay was also performed. HuFcεRIα Bac transgenic mice (7 mice per group/1 control and 6 treatment groups) were injected intradermally in the right flank with 12.5 ng anti-NP huIgE (JW8.5.13) in 20 ul of 1×PBS. After 22 hours mice were given an intraperitoneal injection as follows: G1: No activation; G2: Anti-gp120 isotype control antibody (500 μg/mouse); G3: Ketotifen mast cell stabilizer (8 mg/kg per mouse); G4: 22E7/14H6 bispecific antibody (30 μg/mouse); G5: 22E7/14H6 bispecific antibody (100 μg/mouse); G6: 22E7/14H6 bispecific antibody (300 μg/mouse); and G7: 22E7/14H6 bispecific antibody (500 μg/mouse). After 2 hours mice were given an intravenous tail vein injection of 200 μg NP albumin (BioSearch Technology, Inc. Catalog #N-5051-10) plus 1% Evans blue (Sigma Catalog #E2129, lot #104K3717). After 15 minutes, extravasation/degranulation was measure by quantitation of Evans blue dye in the skin. Mouse skin biopsies were incubated at RT for 72 hrs in 1 ml of formamide (Sigma Catalog #F9037) to extract the dye. The optical density of each sample was measured at a fixed wavelength of 620 nM in a 96 well plate format using a Molecular Devices SpectraMax 250 plate reader. The concentration of each sample was determined based a standard curve generated by making 2 fold serial dilutions from the original 1% Evans blue stock (10 ug/ml to 0.2 ug/ml).

Figure 71:
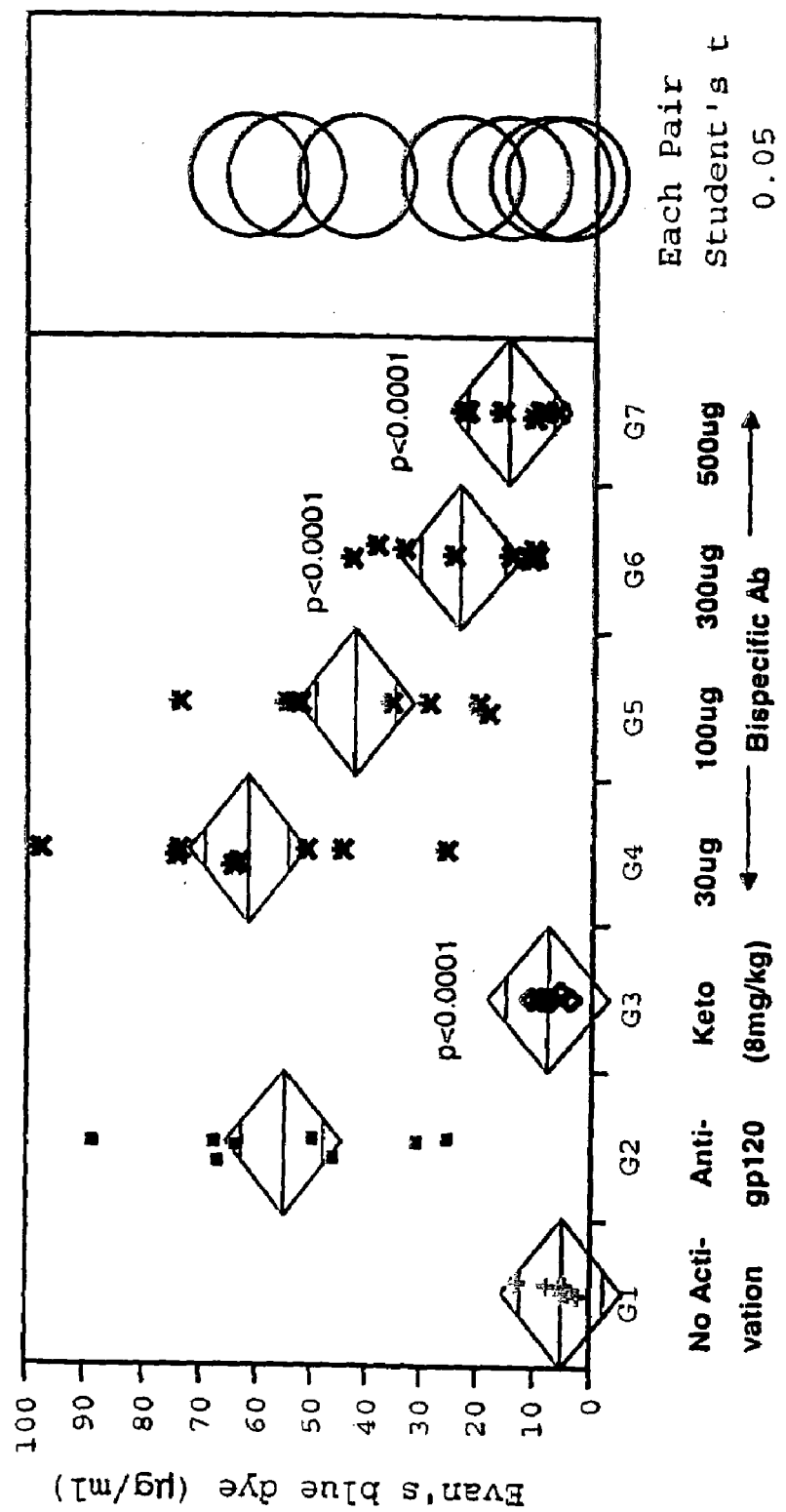
FIG. 71 is a graph showing mast cell activation (as concentration of Evan's blue dye released during PCA assays) as a function of various treatments described in Example 5.9, herein. Mast cell activation decreased with bispecific antibody treatment in a dose dependent manner.

The mouse surrogate bispecific antibody inhibited the PCA reaction in a dose-dependent manner, with almost complete suppression of the reaction at 500 μg of bispecific per mouse (see FIG. 71).

5.10 The 22E7/5A6 Bispecific Antibody Binds FcεRI in the Presence of IgE

Figure 72:
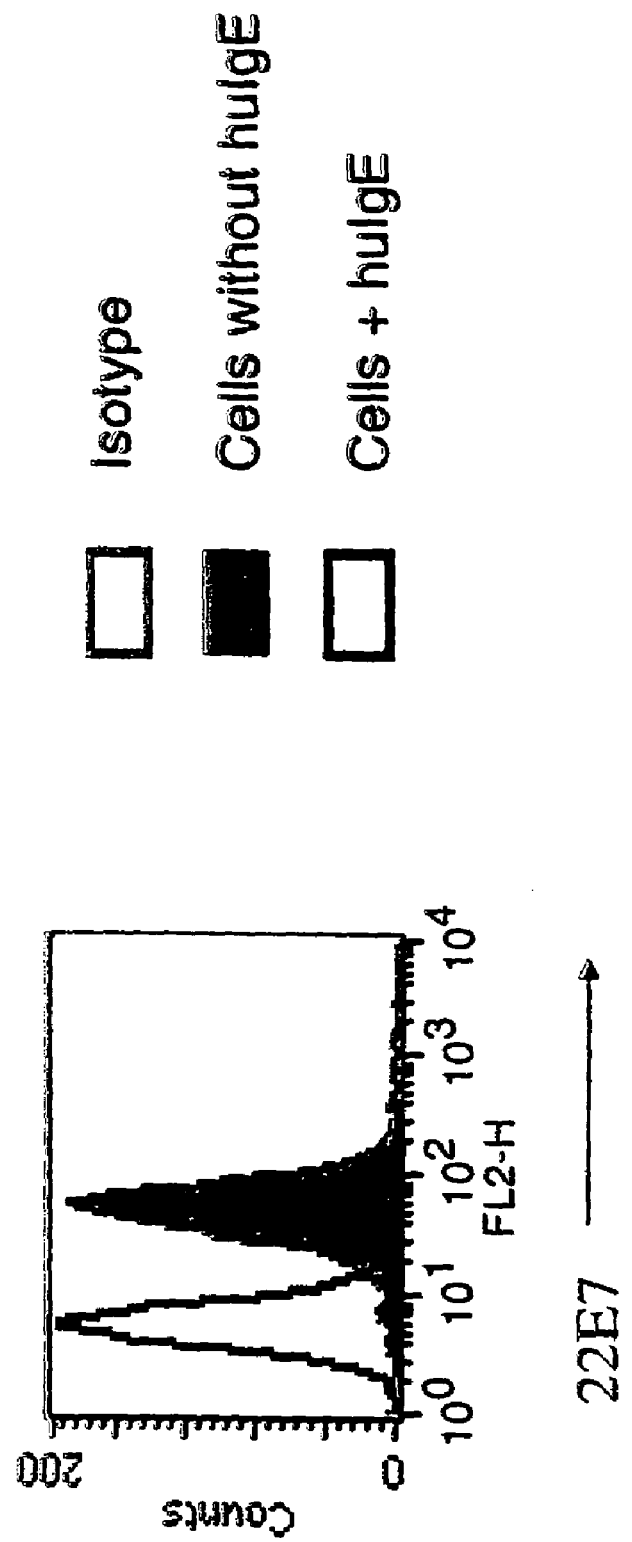
FIG. 72 is a FACS plot showing that anti-human FcεRIα binds human FcεRIα in the presence or absence of human IgE.

Antibody 22E7 has been reported to bind to FcεRI regardless of whether FcεRI is occupied by IgE (Riske et al, JBC (1991) 266:11245-11251). To verify this property, RBL huFcεRI cells were incubated with 1 μg/ml U266 human IgE for 30 min. at 4° C. to load all huFcεRI receptors with IgE, and then assess for 22E7 binding by flow cytometry. Cells were harvested and sorted into aliquots of 10$^5$-10$^6$ cells. The cells were washed and resuspended in FACS buffer (PBS with 2% FCS). The cells were washed a second time and resuspended in FACS buffer supplemented with 10% rat serum and 2.4 μg/ml 22E7 antibody or isotype control antibody. The cells were incubated for 30' on ice, washed and resuspended in FACS buffer with 2 ug/ml rat anti-mouse IgG1-PE (BD Biosciences 55008). After incubation for an additional 30' on ice, the mixture washed with cold FACS buffer, spun down and resuspended in FACS buffer with 0.1% propidium iodide. The samples were analyzed by flow cytometry and results expressed as relative fluorescence units (RFU). The results are plotted in FIG. 72.

Example 5.11

The 22E7/5A6 Bispecific Antibody Inhibits FcεRI Signalling In Vitro

The ability of the 22E7/5A6 bispecific antibody to inhibit FcεRIα signaling in vitro was tested according to the following procedure. A rat basophil leukemia (RBL) cell line generated to express human FcεRIα and human FcγRIIB was grown to 80% confluence in the presence of 1 μg/ml anti-NP human IgE (JW8.5.13). Growth media (MEM with Earle's salts (Gibco Cat#11090), 1 mM glutamine, 1 mM sodium pyruvate (Gibco Cat#11360-070), 0.1 mM nonessential amino acids (Gibco Cat#11140-050), 1.5 g/L sodium bicarbonate (Gibco Cat#25080-094), 15% fetal bovine serum (Hyclone Cat#SH30071.03) was replaced with OptiMem® medium (Invitrogen Cat#31985) containing anti-NP human IgE (1 μg/ml). Cells were cultured for an additional 3-4 hours and then washed 3 times with OptiMem® medium prior to the addition of anti-human FcεRIα/anti human FcγRIIB bispecific antibody (2 μg/ml). After 1-2 hours 0.1 μg/nm NP-OVA was added to the cells for 0, 2, 5, and 10 minutes to trigger cell activation. At the specified time points cell medium was aspirated and cells were lysed on ice with cell lysis buffer (RIPA buffer, Sigma Cat#R0278) containing protease inhibitor cocktail (Roche Cat#11697498001) and phosphatase inhibitor cocktail (Sigma Cat#P5726). Proteins in cell lysates were resolved on 8-16% acrylamide gel, transferred to nitrocellulose and incubated with the following antibodies from Cell Signaling Technology (at a 1:1000 dilution unless noted otherwise); anti-phospho CD32 FcγRIIB (Cat#4141) ("p-FcγRIIB" in FIG. 73), anti-phospho p44/p42 map kinase (ERK) (Cat#9106) ("p-Erk" in FIG. 73), anti p44/p42 map kinase (ERK) (Cat#9102) ("Erk" in FIG. 73), anti-phospho tyrosine (Cat#9411) ("PY" in FIG. 73) at 1:2000 and in house anti-CD32 FcγRIIB clone 5A6 (Genentech, Inc.) ("FcγRIIB" in FIG. 73) at 1 μg/ml.

Figure 73:
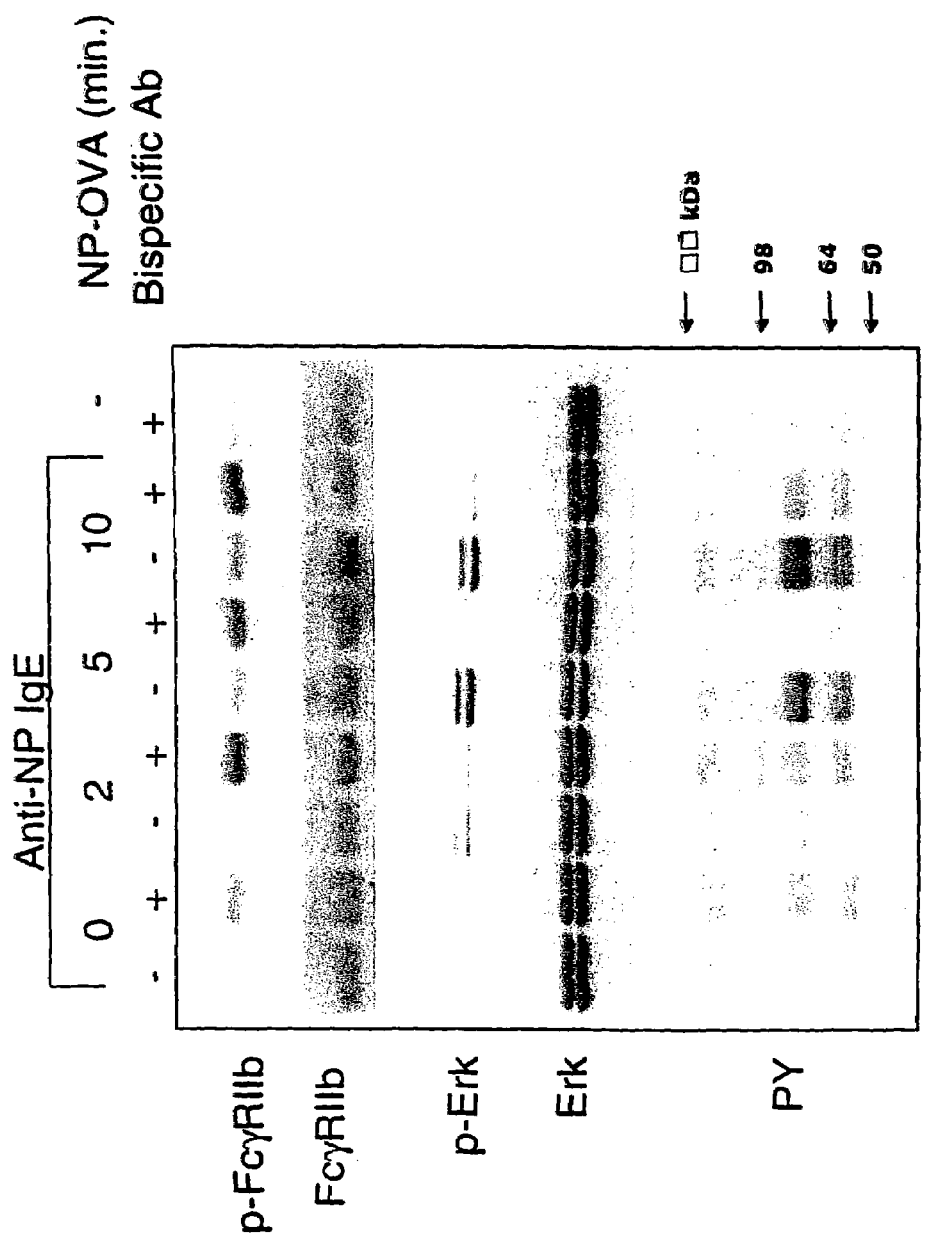
FIG. 73 shows the inhibition of FcεRIα signaling in the presence of the 22E7/5A6 bispecific antibody.

As shown in FIG. 73, the bispecific antibody inhibits the activation of FcεRIα and the phosphorylation of signaling transduction molecules downstream of FcεRIα, including ERK, due to phosphorylation and activation of the inhibitory receptor FcγRIIB.

The above specification, examples and data provide a complete description of the manufacture and use of the composition of the invention. Since many embodiments of the invention can be made without departing from the spirit and scope of the invention, the invention resides in the claims hereinafter appended.

We claim:

1. A method of downregulating FcεRIα expression on a cell comprising crosslinking FcγRIIB2 with FcεRIα by contacting said cell with an effective amount of a bispecific antibody that specifically binds FcγRIIB and FcεRIα, and which does not (a) downregulate FcγRIIA expression, and (b) cross link FcγRIIB1.

2. The method of claim 1, wherein FcεRIα expression is upregulated by prior stimulation from IgE.

3. The method of claim 1, wherein the cell is a B cell or a mast cell.

4. The method of claim 3, wherein the cell is a human cell.

5. The method of claim 2, wherein the stimulation by IgE induces mast cell survival.

6. The method of claim 1, wherein the FcγRIIB binding component of the bispecific antibody blocks binding to FcγRIIB by the anti-FcγRIIB antibody 5A6.

7. The method of claim 1, wherein the FcγRIIB binding component of the bispecific antibody blocks binding to FcγRIIB by the anti-FcγRIIB antibody secreted by the hybridoma having the ATCC accession number PTA-4614.

8. The method of claims 1, 2, 6 or 7, wherein the FcεRIα binding component of the bispecific antibody binds to FcεRIα when FcεRIα is bound to IgE.

9. The method of claim 8, wherein the bispecific antibody comprises a T366W mutation in the anti-FcγRIIB component and a T366S, L368A and Y407V mutation in FcεRIα binding component.

10. The method of claim 9, wherein the bispecific antibody further comprises C226S and C229S mutations in the hinge region.

11. The method of claim 1, 2, 6 or 7, wherein the anti-FcγRIIB binding component of the bispecific antibody comprises a heavy chain sequence further comprising the CDR regions of SEQ ID NOS:1, 2 and 3.

12. The method of claim 1, 2, 6 or 7, wherein the anti-FcγRIIB binding component of the bispecific antibody comprises a light chain sequence further comprising the CDR regions of SEQ ID NOS: 4, 5 and 6.

13. The method of claim 11, wherein the heavy chain comprises the amino acid sequence of SEQ ID NO:7.

14. The method of claim 12, wherein the light chain comprises the amino acid sequence of SEQ ID NO:8.

15. The method of claim 1, 2, 6 or 7, wherein the anti-FcγRIIB binding component of the bispecific antibody comprises (i) a heavy chain sequence further comprising the CDR regions of SEQ ID NOS:1, 2 and 3, (ii) a light chain sequence further comprising the CDR regions of SEQ ID NOS: 4, 5 and 6.

16. The method of claim 15, wherein the heavy chain comprises the amino acid sequence of SEQ ID NO:7.

17. The method of claim 15, wherein the light chain comprises the amino acid sequence of SEQ ID NO:8.

18. A method of inhibiting an immune response comprising administering at least a therapeutically effective amount of a bispecific antibody that: (i) specifically binds both FcγRIIB and FcεRIα, and which does not downregulate FcγRIIA expression; (ii) binds FcεRIα when FcεRIα is bound to IgE, (iii) a knob mutation at position 366 in the one of the binding components of the bispecific antibody and corresponding hole mutations at positions 366, 368 and 407 in the other binding component, and (iv) a C226S and C229S mutation in the hinge region.

19. The method of claim 18, wherein the bispecific antibody administered blocks binding to FcγRIIB by the anti-FcγRIIB antibody 5A6.

20. The method of claim 18, wherein the bispecific antibody administered blocks binding to FcγRIIB by the anti-FcγRIIB antibody secreted by the hybridoma having the ATCC accession number PTA-4614.

21. A method of treating an allergic disorder in a mammal comprising administering at least a therapeutically effective amount of a bispecific antibody that: (i) specifically binds both FcγRIIB and FcεRIα and which does not downregulate FcγRIIA expression; (ii) binds FcεRIα when FcεRIα is bound to IgE, (iii) a knob mutation at position 366 in the one of the binding components of the bispecific antibody and corresponding hole mutations at positions 366, 368 and 407 in the other binding component, and (iv) a C226S and C229S mutation in the hinge region.

22. The method of claim 21, wherein the bispecific antibody administered blocks binding to FcγRIIB by the anti-FcγRIIB antibody 5A6.

23. The method of claim 21, wherein the bispecific antibody administered blocks binding to FcγRIIB by the anti-FcγRIIB antibody secreted by the hybridoma having the ATCC accession number PTA-4614.

24. The method of claim 21, further comprising the administration of an anti-IgE antibody.

25. The method of claim 24, wherein the ratio of bispecific antibody: anti-IgE antibody is from 0.01:1 to 100:1.

26. The method of claim 21 wherein the allergic disorder is atopic allergy.

27. The method of claim 26 wherein the atopic allergy is selected from the group consisting of hay fever, asthma and atopic dermatitis.

28. The method of claim 27, wherein the atopic allergy is hay fever.

29. The method of claim 27, wherein the atopic allergy is asthma.

30. The method of claim 27, wherein the atopic allergy is dermatitis.

31. The method of claim 21 wherein the allergic disorder is systemic anaphylaxis.

32. The method of claim 21, wherein the allergic disorder is urticaria.

33. A method of inhibiting histamine release from a cell comprising contacting said cell with an effective amount of a bispecific antibody that specifically binds FcγRIIB and FcεRIα, and which does not downregulate FcγRIIA expression and wherein FcγRIIB expression is upregulated by stimulation from IgE.

34. The method of claim 33, wherein the histamine release is reduced at least 70% relative to background levels.

35. The method of claim 34, wherein the level reduced is at least 75%.

36. The method of claim 35, therein the level reduced is at least 80%.

37. The method of claim 36, therein the level reduced is at least 85%.

38. The method of claim 37, therein the level reduced is at least 90%.

39. The method of claim 38, therein the level reduced is at least 95%.

40. The method of claim 39, therein the level reduced is 100%.

* * * * *

SEQUENCE LISTING

```
<160> NUMBER OF SEQ ID NOS: 40

<210> SEQ ID NO 1
<211> LENGTH: 5
<212> TYPE: PRT
<213> ORGANISM: Artificial sequence
<220> FEATURE:
<223> OTHER INFORMATION: sequence is synthesized

<400> SEQUENCE: 1

Asp Ala Trp Met Asp
                  5

<210> SEQ ID NO 2
<211> LENGTH: 19
<212> TYPE: PRT
<213> ORGANISM: Artificial sequence
<220> FEATURE:
<223> OTHER INFORMATION: sequence is synthesized

<400> SEQUENCE: 2

Glu Ile Arg Ser Lys Pro Asn Asn His Ala Thr Tyr Tyr Ala Glu
  1               5                  10                  15

Ser Val Lys Gly

<210> SEQ ID NO 3
<211> LENGTH: 3
<212> TYPE: PRT
<213> ORGANISM: Artificial sequence
<220> FEATURE:
<223> OTHER INFORMATION: sequence is synthesized

<400> SEQUENCE: 3

Phe Asp Tyr

<210> SEQ ID NO 4
<211> LENGTH: 11
<212> TYPE: PRT
<213> ORGANISM: Artificial sequence
<220> FEATURE:
<223> OTHER INFORMATION: sequence is synthesized

<400> SEQUENCE: 4
```

Arg Ala Ser Gln Glu Ile Ser Gly Tyr Leu Ser
                5                  10

<210> SEQ ID NO 5
<211> LENGTH: 7
<212> TYPE: PRT
<213> ORGANISM: Artificial sequence
<220> FEATURE:
<223> OTHER INFORMATION: sequence is synthesized

<400> SEQUENCE: 5

Ala Ala Ser Ala Leu Asp Ser
                5

<210> SEQ ID NO 6
<211> LENGTH: 8
<212> TYPE: PRT
<213> ORGANISM: Artificial sequence
<220> FEATURE:
<223> OTHER INFORMATION: sequence is synthesized

<400> SEQUENCE: 6

Leu Gln Tyr Val Ser Tyr Pro Leu
                5

<210> SEQ ID NO 7
<211> LENGTH: 222
<212> TYPE: PRT
<213> ORGANISM: Artificial sequence
<220> FEATURE:
<223> OTHER INFORMATION: sequence is synthesized

<400> SEQUENCE: 7

Glu Val Lys Leu Glu Glu Ser Gly Gly Gly Leu Val Gln Pro Gly
  1               5                  10                  15

Gly Ser Met Lys Leu Ser Cys Val Ala Ser Gly Phe Thr Phe Ser
                 20                  25                  30

Asp Ala Trp Met Asp Trp Val Arg Gln Ser Pro Glu Arg Gly Leu
                 35                  40                  45

Glu Trp Val Ala Glu Ile Arg Ser Lys Pro Asn Asn His Ala Thr
                 50                  55                  60

Tyr Tyr Ala Glu Ser Val Lys Gly Arg Phe Thr Ile Ser Arg Asp
                 65                  70                  75

Asp Ser Lys Ser Ser Val Tyr Leu Gln Met Thr Ser Leu Arg Pro
                 80                  85                  90

Glu Asp Thr Gly Ile Tyr Tyr Cys Thr His Phe Asp Tyr Trp Gly
                 95                  100                 105

Gln Gly Thr Thr Leu Thr Val Ser Ser Ala Lys Thr Thr Gly Pro
                 110                 115                 120

Ser Val Phe Pro Leu Ala Pro Ser Ser Lys Ser Thr Ser Gly Gly
                 125                 130                 135

Thr Ala Ala Leu Gly Cys Leu Val Lys Asp Tyr Phe Pro Glu Pro
                 140                 145                 150

Val Thr Val Ser Trp Asn Ser Gly Ala Leu Thr Ser Gly Val His
                 155                 160                 165

Thr Phe Pro Ala Val Leu Gln Ser Ser Gly Leu Tyr Ser Leu Ser
                 170                 175                 180

Ser Val Val Thr Val Pro Ser Ser Ser Leu Gly Thr Gln Thr Tyr
                 185                 190                 195

```
Ile Cys Asn Val Asn His Lys Pro Ser Asn Thr Lys Val Asp Lys
                200                 205                 210
Lys Val Glu Pro Lys Ser Cys Asp Lys Thr His Thr
                215                 220

<210> SEQ ID NO 8
<211> LENGTH: 214
<212> TYPE: PRT
<213> ORGANISM: Artificial sequence
<220> FEATURE:
<223> OTHER INFORMATION: sequence is synthesized

<400> SEQUENCE: 8

Asp Ile Gln Met Thr Gln Ser Pro Ser Ser Leu Ser Ala Ser Leu
  1               5                  10                  15

Gly Glu Arg Val Ser Leu Thr Cys Arg Ala Ser Gln Glu Ile Ser
                 20                  25                  30

Gly Tyr Leu Ser Trp Phe Gln Gln Lys Pro Asp Gly Thr Ile Lys
                 35                  40                  45

Arg Leu Ile Tyr Ala Ala Ser Ala Leu Asp Ser Gly Val Pro Lys
                 50                  55                  60

Arg Phe Ser Gly Ser Trp Ser Gly Ser Asp Tyr Ser Leu Thr Ile
                 65                  70                  75

Ser Ser Leu Glu Ser Glu Asp Phe Ala Asp Tyr Tyr Cys Leu Gln
                 80                  85                  90

Tyr Val Ser Tyr Pro Leu Thr Phe Gly Ala Gly Thr Lys Leu Glu
                 95                 100                 105

Leu Lys Arg Thr Val Ala Ala Pro Ser Val Phe Ile Phe Pro Pro
                110                 115                 120

Ser Asp Glu Gln Leu Lys Ser Gly Thr Ala Ser Val Val Cys Leu
                125                 130                 135

Leu Asn Asn Phe Tyr Pro Arg Glu Ala Lys Val Gln Trp Lys Val
                140                 145                 150

Asp Asn Ala Leu Gln Ser Gly Asn Ser Gln Glu Ser Val Thr Glu
                155                 160                 165

Gln Asp Ser Lys Asp Ser Thr Tyr Ser Leu Ser Ser Thr Leu Thr
                170                 175                 180

Leu Ser Lys Ala Asp Tyr Glu Lys His Lys Val Tyr Ala Cys Glu
                185                 190                 195

Val Thr His Gln Gly Leu Ser Ser Pro Val Thr Lys Ser Phe Asn
                200                 205                 210

Arg Gly Glu Cys

<210> SEQ ID NO 9
<211> LENGTH: 317
<212> TYPE: PRT
<213> ORGANISM: Homo sapiens

<400> SEQUENCE: 9

Met Ala Met Glu Thr Gln Met Ser Gln Asn Val Cys Pro Arg Asn
  1               5                  10                  15

Leu Trp Leu Leu Gln Pro Leu Thr Val Leu Leu Leu Leu Ala Ser
                 20                  25                  30

Ala Asp Ser Gln Ala Ala Ala Pro Lys Ala Val Leu Lys Leu
                 35                  40                  45

Glu Pro Pro Trp Ile Asn Val Leu Gln Glu Asp Ser Val Thr Leu
                 50                  55                  60
```

```
Thr Cys Gln Gly Ala Arg Ser Pro Glu Ser Asp Ser Ile Gln Trp
                65                  70                  75

Phe His Asn Gly Asn Leu Ile Pro Thr His Thr Gln Pro Ser Tyr
                80                  85                  90

Arg Phe Lys Ala Asn Asn Asp Ser Gly Glu Tyr Thr Cys Gln
                95                 100                 105

Thr Gly Gln Thr Ser Leu Ser Asp Pro Val His Leu Thr Val Leu
                110                 115                 120

Ser Glu Trp Leu Val Leu Gln Thr Pro His Leu Glu Phe Gln Glu
                125                 130                 135

Gly Glu Thr Ile Met Leu Arg Cys His Ser Trp Lys Asp Lys Pro
                140                 145                 150

Leu Val Lys Val Thr Phe Phe Gln Asn Gly Lys Ser Gln Lys Phe
                155                 160                 165

Ser Arg Leu Asp Pro Thr Phe Ser Ile Pro Gln Ala Asn His Ser
                170                 175                 180

His Ser Gly Asp Tyr His Cys Thr Gly Asn Ile Gly Tyr Thr Leu
                185                 190                 195

Phe Ser Ser Lys Pro Val Thr Ile Thr Val Gln Val Pro Ser Met
                200                 205                 210

Gly Ser Ser Ser Pro Met Gly Ile Ile Val Ala Val Val Ile Ala
                215                 220                 225

Thr Ala Val Ala Ala Ile Val Ala Ala Val Val Ala Leu Ile Tyr
                230                 235                 240

Cys Arg Lys Lys Arg Ile Ser Ala Asn Ser Thr Asp Pro Val Lys
                245                 250                 255

Ala Ala Gln Phe Glu Pro Pro Gly Arg Gln Met Ile Ala Ile Arg
                260                 265                 270

Lys Arg Gln Leu Glu Glu Thr Asn Asn Asp Tyr Glu Thr Ala Asp
                275                 280                 285

Gly Gly Tyr Met Thr Leu Asn Pro Arg Ala Pro Thr Asp Asp Asp
                290                 295                 300

Lys Asn Ile Tyr Leu Thr Leu Pro Pro Asn Asp His Val Asn Ser
                305                 310                 315

Asn Asn

<210> SEQ ID NO 10
<211> LENGTH: 291
<212> TYPE: PRT
<213> ORGANISM: Artificial sequence
<220> FEATURE:
<223> OTHER INFORMATION: sequence is synthesized

<400> SEQUENCE: 10

Met Gly Ile Leu Ser Phe Leu Pro Val Leu Ala Thr Glu Ser Asp
 1               5                  10                  15

Trp Ala Asp Cys Lys Ser Pro Gln Pro Trp Gly His Met Leu Leu
                20                  25                  30

Trp Thr Ala Val Leu Phe Leu Ala Pro Val Ala Gly Thr Pro Ala
                35                  40                  45

Ala Pro Pro Lys Ala Val Leu Lys Leu Glu Pro Gln Trp Ile Asn
                50                  55                  60

Val Leu Gln Glu Asp Ser Val Thr Leu Thr Cys Arg Gly Thr His
                65                  70                  75
```

```
Ser Pro Glu Ser Asp Ser Ile Gln Trp Phe His Asn Gly Asn Leu
                80                  85                  90

Ile Pro Thr His Thr Gln Pro Ser Tyr Arg Phe Lys Ala Asn Asn
                95                 100                 105

Asn Asp Ser Gly Glu Tyr Thr Cys Gln Thr Gly Gln Thr Ser Leu
               110                 115                 120

Ser Asp Pro Val His Leu Thr Val Leu Ser Glu Trp Leu Val Leu
               125                 130                 135

Gln Thr Pro His Leu Glu Phe Gln Glu Gly Glu Thr Ile Val Leu
               140                 145                 150

Arg Cys His Ser Trp Lys Asp Lys Pro Leu Val Lys Val Thr Phe
               155                 160                 165

Phe Gln Asn Gly Lys Ser Lys Lys Phe Ser Arg Ser Asp Pro Asn
               170                 175                 180

Phe Ser Ile Pro Gln Ala Asn His Ser His Ser Gly Asp Tyr His
               185                 190                 195

Cys Thr Gly Asn Ile Gly Tyr Thr Leu Tyr Ser Ser Lys Pro Val
               200                 205                 210

Thr Ile Thr Val Gln Ala Pro Ser Ser Ser Pro Met Gly Ile Ile
               215                 220                 225

Val Ala Val Val Thr Gly Ile Ala Val Ala Ala Ile Val Ala Ala
               230                 235                 240

Val Val Ala Leu Ile Tyr Cys Arg Lys Lys Arg Ile Ser Ala Asn
               245                 250                 255

Pro Thr Asn Pro Asp Glu Ala Asp Lys Val Gly Ala Glu Asn Thr
               260                 265                 270

Ile Thr Tyr Ser Leu Leu Met His Pro Asp Ala Leu Glu Glu Pro
               275                 280                 285

Asp Asp Gln Asn Arg Ile
               290

<210> SEQ ID NO 11
<211> LENGTH: 310
<212> TYPE: PRT
<213> ORGANISM: Artificial sequence
<220> FEATURE:
<223> OTHER INFORMATION: sequence is synthesized

<400> SEQUENCE: 11

Met Gly Ile Leu Ser Phe Leu Pro Val Leu Ala Thr Glu Ser Asp
  1               5                  10                  15

Trp Ala Asp Cys Lys Ser Pro Gln Pro Trp Gly His Met Leu Leu
                 20                  25                  30

Trp Thr Ala Val Leu Phe Leu Ala Pro Val Ala Gly Thr Pro Ala
                 35                  40                  45

Ala Pro Pro Lys Ala Val Leu Lys Leu Glu Pro Gln Trp Ile Asn
                 50                  55                  60

Val Leu Gln Glu Asp Ser Val Thr Leu Thr Cys Arg Gly Thr His
                 65                  70                  75

Ser Pro Glu Ser Asp Ser Ile Gln Trp Phe His Asn Gly Asn Leu
                 80                  85                  90

Ile Pro Thr His Thr Gln Pro Ser Tyr Arg Phe Lys Ala Asn Asn
                 95                 100                 105

Asn Asp Ser Gly Glu Tyr Thr Cys Gln Thr Gly Gln Thr Ser Leu
                110                 115                 120
```

-continued

```
Ser Asp Pro Val His Leu Thr Val Leu Ser Glu Trp Leu Val Leu
            125                 130                 135

Gln Thr Pro His Leu Glu Phe Gln Glu Gly Glu Thr Ile Val Leu
            140                 145                 150

Arg Cys His Ser Trp Lys Asp Lys Pro Leu Val Lys Val Thr Phe
            155                 160                 165

Phe Gln Asn Gly Lys Ser Lys Lys Phe Ser Arg Ser Asp Pro Asn
            170                 175                 180

Phe Ser Ile Pro Gln Ala Asn His Ser His Ser Gly Asp Tyr His
            185                 190                 195

Cys Thr Gly Asn Ile Gly Tyr Thr Leu Tyr Ser Ser Lys Pro Val
            200                 205                 210

Thr Ile Thr Val Gln Ala Pro Ser Ser Ser Pro Met Gly Ile Ile
            215                 220                 225

Val Ala Val Val Thr Gly Ile Ala Val Ala Ala Ile Val Ala Ala
            230                 235                 240

Val Val Ala Leu Ile Tyr Cys Arg Lys Lys Arg Ile Ser Ala Leu
            245                 250                 255

Pro Gly Tyr Pro Glu Cys Arg Glu Met Gly Glu Thr Leu Pro Glu
            260                 265                 270

Lys Pro Ala Asn Pro Thr Asn Pro Asp Glu Ala Asp Lys Val Gly
            275                 280                 285

Ala Glu Asn Thr Ile Thr Tyr Ser Leu Leu Met His Pro Asp Ala
            290                 295                 300

Leu Glu Glu Pro Asp Asp Gln Asn Arg Ile
            305                 310

<210> SEQ ID NO 12
<211> LENGTH: 24
<212> TYPE: PRT
<213> ORGANISM: Artificial sequence
<220> FEATURE:
<223> OTHER INFORMATION: sequence is synthesized

<400> SEQUENCE: 12

Gly Gly Thr Gly Ala Ala Gly Cys Thr Cys Thr Cys Ala Ala Gly
 1               5                   10                  15

Thr Ala Cys Thr Gly Gly Thr Ala Thr
                20

<210> SEQ ID NO 13
<211> LENGTH: 24
<212> TYPE: PRT
<213> ORGANISM: Artificial sequence
<220> FEATURE:
<223> OTHER INFORMATION: sequence is synthesized

<400> SEQUENCE: 13

Gly Thr Ala Gly Gly Thr Thr Cys Cys Ala Cys Thr Gly Thr Cys
 1               5                   10                  15

Thr Thr Cys Ala Ala Cys Thr Gly Thr
                20

<210> SEQ ID NO 14
<211> LENGTH: 29
<212> TYPE: PRT
<213> ORGANISM: Artificial sequence
<220> FEATURE:
<223> OTHER INFORMATION: sequence is synthesized
```

-continued

```
<400> SEQUENCE: 14

Ala Gly Ala Ala Cys Cys Ala Cys Ala Ala Cys Ala Thr Cys Thr
 1               5                  10                  15

Cys Cys Ala Thr Thr Ala Cys Ala Ala Ala Thr Gly Cys Cys
                20                  25

<210> SEQ ID NO 15
<211> LENGTH: 18
<212> TYPE: PRT
<213> ORGANISM: Artificial sequence
<220> FEATURE:
<223> OTHER INFORMATION: sequence is synthesized

<400> SEQUENCE: 15

Cys Cys Cys Thr Gly Ala Gly Thr Gly Cys Ala Gly Gly Gly Ala
 1               5                  10                  15

Ala Ala Thr

<210> SEQ ID NO 16
<211> LENGTH: 22
<212> TYPE: PRT
<213> ORGANISM: Artificial sequence
<220> FEATURE:
<223> OTHER INFORMATION: sequence is synthesized

<400> SEQUENCE: 16

Cys Cys Thr Cys Ala Thr Cys Ala Gly Gly Ala Thr Thr Ala Gly
 1               5                  10                  15

Thr Gly Gly Gly Ala Thr Thr
                20

<210> SEQ ID NO 17
<211> LENGTH: 25
<212> TYPE: PRT
<213> ORGANISM: Artificial sequence
<220> FEATURE:
<223> OTHER INFORMATION: sequence is synthesized

<400> SEQUENCE: 17

Ala Gly Ala Gly Ala Cys Cys Cys Thr Cys Cys Thr Gly Ala
 1               5                  10                  15

Gly Ala Ala Ala Cys Cys Ala Gly Cys Cys
                20                  25

<210> SEQ ID NO 18
<211> LENGTH: 20
<212> TYPE: PRT
<213> ORGANISM: Artificial sequence
<220> FEATURE:
<223> OTHER INFORMATION: sequence is synthesized

<400> SEQUENCE: 18

Thr Gly Cys Thr Gly Thr Ala Gly Thr Gly Cys Cys Thr Thr
 1               5                  10                  15

Gly Ala Thr Cys Thr
                20

<210> SEQ ID NO 19
<211> LENGTH: 20
<212> TYPE: PRT
<213> ORGANISM: Artificial sequence
<220> FEATURE:
<223> OTHER INFORMATION: sequence is synthesized
```

-continued

```
<400> SEQUENCE: 19

Cys Cys Ala Ala Cys Thr Thr Thr Gly Thr Cys Ala Gly Cys Cys
  1               5                  10                  15

Thr Cys Ala Thr Cys
                 20

<210> SEQ ID NO 20
<211> LENGTH: 21
<212> TYPE: PRT
<213> ORGANISM: Artificial sequence
<220> FEATURE:
<223> OTHER INFORMATION: sequence is synthesized

<400> SEQUENCE: 20

Ala Gly Cys Gly Gly Ala Thr Thr Cys Ala Gly Cys Cys Ala
  1               5                  10                  15

Ala Thr Cys Cys Cys Ala
                 20

<210> SEQ ID NO 21
<211> LENGTH: 20
<212> TYPE: PRT
<213> ORGANISM: Artificial sequence
<220> FEATURE:
<223> OTHER INFORMATION: sequence is synthesized

<400> SEQUENCE: 21

Gly Cys Gly Gly Ala Thr Thr Cys Thr Cys Ala Thr Gly Gly Ala
  1               5                  10                  15

Ala Cys Ala Cys Ala
                 20

<210> SEQ ID NO 22
<211> LENGTH: 20
<212> TYPE: PRT
<213> ORGANISM: Artificial sequence
<220> FEATURE:
<223> OTHER INFORMATION: sequence is synthesized

<400> SEQUENCE: 22

Gly Gly Thr Cys Ala Gly Cys Cys Ala Gly Gly Ala Gly Cys Thr
  1               5                  10                  15

Thr Cys Thr Thr Gly
                 20

<210> SEQ ID NO 23
<211> LENGTH: 25
<212> TYPE: PRT
<213> ORGANISM: Artificial sequence
<220> FEATURE:
<223> OTHER INFORMATION: sequence is synthesized

<400> SEQUENCE: 23

Cys Ala Cys Ala Ala Gly Cys Thr Gly Ala Ala Gly Gly Cys Ala
  1               5                  10                  15

Gly Ala Cys Ala Ala Gly Gly Cys Cys Cys
                 20                  25

<210> SEQ ID NO 24
<211> LENGTH: 25
<212> TYPE: PRT
<213> ORGANISM: Artificial sequence
<220> FEATURE:
<223> OTHER INFORMATION: sequence is synthesized
```

-continued

<400> SEQUENCE: 24

Cys Ala Ala Thr Thr Ala Thr Thr Thr Cys Cys Ala Cys Ala
1               5                   10                  15

Gly Thr Ala Thr Cys Thr Thr Cys Ala Ala
            20                  25

<210> SEQ ID NO 25
<211> LENGTH: 23
<212> TYPE: PRT
<213> ORGANISM: Artificial sequence
<220> FEATURE:
<223> OTHER INFORMATION: sequence is synthesized

<400> SEQUENCE: 25

Gly Gly Gly Gly Thr Ala Cys Ala Gly Ala Cys Ala Thr Thr Thr
1               5                   10                  15

Cys Thr Ala Thr Gly Gly Ala Thr
            20

<210> SEQ ID NO 26
<211> LENGTH: 30
<212> TYPE: PRT
<213> ORGANISM: Artificial sequence
<220> FEATURE:
<223> OTHER INFORMATION: sequence is synthesized

<400> SEQUENCE: 26

Ala Cys Ala Thr Gly Ala Gly Thr Gly Thr Cys Cys Thr Thr Thr
1               5                   10                  15

Gly Ala Cys Ala Gly Thr Thr Gly Ala Ala Gly Gly Cys Thr
            20                  25                  30

<210> SEQ ID NO 27
<211> LENGTH: 39
<212> TYPE: PRT
<213> ORGANISM: Artificial sequence
<220> FEATURE:
<223> OTHER INFORMATION: sequence is synthesized

<400> SEQUENCE: 27

Ala Ala Ala Gly Gly Gly Ala Ala Ala Gly Ala Ala Thr Thr Cys
1               5                   10                  15

Ala Ala Cys Thr Thr Cys Thr Cys Cys Ala Gly Ala Cys Thr Thr
            20                  25                  30

Thr Gly Gly Ala Thr Ala Ala Gly Gly
            35

<210> SEQ ID NO 28
<211> LENGTH: 37
<212> TYPE: PRT
<213> ORGANISM: Artificial sequence
<220> FEATURE:
<223> OTHER INFORMATION: sequence is synthesized

<400> SEQUENCE: 28

Ala Ala Ala Gly Gly Gly Ala Ala Ala Ala Thr Gly Cys Ala Thr
1               5                   10                  15

Thr Thr Gly Thr Ala Gly Cys Ala Ala Thr Ala Gly Ala Ala Ala
            20                  25                  30

Ala Ala Ala Cys Gly Ala Ala
            35

```
<210> SEQ ID NO 29
<211> LENGTH: 19
<212> TYPE: PRT
<213> ORGANISM: Artificial sequence
<220> FEATURE:
<223> OTHER INFORMATION: sequence is synthesized

<400> SEQUENCE: 29

Leu Pro Gly Tyr Pro Glu Cys Arg Glu Met Gly Glu Thr Leu Pro
  1               5                  10                  15

Glu Lys Pro Ala

<210> SEQ ID NO 30
<211> LENGTH: 317
<212> TYPE: PRT
<213> ORGANISM: Homo sapiens

<400> SEQUENCE: 30

Met Ala Met Glu Thr Gln Met Ser Gln Asn Val Cys Pro Arg Asn
  1               5                  10                  15

Leu Trp Leu Leu Gln Pro Leu Thr Val Leu Leu Leu Leu Ala Ser
                 20                  25                  30

Ala Asp Ser Gln Ala Ala Ala Pro Pro Lys Ala Val Leu Lys Leu
                 35                  40                  45

Glu Pro Pro Trp Ile Asn Val Leu Gln Glu Asp Ser Val Thr Leu
                 50                  55                  60

Thr Cys Gln Gly Ala Arg Ser Pro Glu Ser Asp Ser Ile Gln Trp
                 65                  70                  75

Phe His Asn Gly Asn Leu Ile Pro Thr His Thr Gln Pro Ser Tyr
                 80                  85                  90

Arg Phe Lys Ala Asn Asn Asn Asp Ser Gly Glu Tyr Thr Cys Gln
                 95                 100                 105

Thr Gly Gln Thr Ser Leu Ser Asp Pro Val His Leu Thr Val Leu
                110                 115                 120

Ser Glu Trp Leu Val Leu Gln Thr Pro His Leu Glu Phe Gln Glu
                125                 130                 135

Gly Glu Thr Ile Met Leu Arg Cys His Ser Trp Lys Asp Lys Pro
                140                 145                 150

Leu Val Lys Val Thr Phe Phe Gln Asn Gly Lys Ser Gln Lys Phe
                155                 160                 165

Ser Arg Leu Asp Pro Thr Phe Ser Ile Pro Gln Ala Asn His Ser
                170                 175                 180

His Ser Gly Asp Tyr His Cys Thr Gly Asn Ile Gly Tyr Thr Leu
                185                 190                 195

Phe Ser Ser Lys Pro Val Thr Ile Thr Val Gln Val Pro Ser Met
                200                 205                 210

Gly Ser Ser Ser Pro Met Gly Ile Ile Val Ala Val Val Ile Ala
                215                 220                 225

Thr Ala Val Ala Ala Ile Val Ala Ala Val Val Ala Leu Ile Tyr
                230                 235                 240

Cys Arg Lys Lys Arg Ile Ser Ala Asn Ser Thr Asp Pro Val Lys
                245                 250                 255

Ala Ala Gln Phe Glu Pro Pro Gly Arg Gln Met Ile Ala Ile Arg
                260                 265                 270

Lys Arg Gln Leu Glu Glu Thr Asn Asn Asp Tyr Glu Thr Ala Asp
                275                 280                 285
```

```
Gly Gly Tyr Met Thr Leu Asn Pro Arg Ala Pro Thr Asp Asp
            290                 295                 300

Lys Asn Ile Tyr Leu Thr Leu Pro Pro Asn Asp His Val Asn Ser
            305                 310                 315

Asn Asn

<210> SEQ ID NO 31
<211> LENGTH: 218
<212> TYPE: PRT
<213> ORGANISM: Homo sapiens

<400> SEQUENCE: 31

Pro Ala Pro Glu Leu Leu Gly Gly Pro Ser Val Phe Leu Phe Pro
  1               5                  10                  15

Pro Lys Pro Lys Asp Thr Leu Met Ile Ser Arg Thr Pro Glu Val
                 20                  25                  30

Thr Cys Val Val Val Asp Val Ser His Glu Asp Pro Glu Val Lys
                 35                  40                  45

Phe Asn Trp Tyr Val Asp Gly Val Glu Val His Asn Ala Lys Thr
                 50                  55                  60

Lys Pro Arg Glu Glu Gln Tyr Asn Ser Thr Tyr Arg Val Val Ser
                 65                  70                  75

Val Leu Thr Val Leu His Gln Asp Trp Leu Asn Gly Lys Glu Tyr
                 80                  85                  90

Lys Cys Lys Val Ser Asn Lys Ala Leu Pro Ala Pro Ile Glu Lys
                 95                 100                 105

Thr Ile Ser Lys Ala Lys Gly Gln Pro Arg Glu Pro Gln Val Tyr
                110                 115                 120

Thr Leu Pro Pro Ser Arg Glu Glu Met Thr Lys Asn Gln Val Ser
                125                 130                 135

Leu Thr Cys Leu Val Lys Gly Phe Tyr Pro Ser Asp Ile Ala Val
                140                 145                 150

Glu Trp Glu Ser Asn Gly Gln Pro Glu Asn Asn Tyr Lys Thr Thr
                155                 160                 165

Pro Pro Val Leu Asp Ser Asp Gly Ser Phe Phe Leu Tyr Ser Lys
                170                 175                 180

Leu Thr Val Asp Lys Ser Arg Trp Gln Gln Gly Asn Val Phe Ser
                185                 190                 195

Cys Ser Val Met His Glu Ala Leu His Asn His Tyr Thr Gln Lys
                200                 205                 210

Ser Leu Ser Leu Ser Pro Gly Lys
                215

<210> SEQ ID NO 32
<211> LENGTH: 217
<212> TYPE: PRT
<213> ORGANISM: Homo sapiens

<400> SEQUENCE: 32

Pro Ala Pro Pro Val Ala Gly Pro Ser Val Phe Leu Phe Pro Pro
  1               5                  10                  15

Lys Pro Lys Asp Thr Leu Met Ile Ser Arg Thr Pro Glu Val Thr
                 20                  25                  30

Cys Val Val Val Asp Val Ser His Glu Asp Pro Glu Val Gln Phe
                 35                  40                  45
```

Asn Trp Tyr Val Asp Gly Val Glu Val His Asn Ala Lys Thr Lys
                50                  55                  60

Pro Arg Glu Glu Gln Phe Asn Ser Thr Phe Arg Val Val Ser Val
            65                  70                  75

Leu Thr Val Val His Gln Asp Trp Leu Asn Gly Lys Glu Tyr Lys
        80                  85                  90

Cys Lys Val Ser Asn Lys Gly Leu Pro Ala Pro Ile Glu Lys Thr
    95                 100                 105

Ile Ser Lys Thr Lys Gly Gln Pro Arg Glu Pro Gln Val Tyr Thr
110                 115                 120

Leu Pro Pro Ser Arg Glu Glu Met Thr Lys Asn Gln Val Ser Leu
            125                 130                 135

Thr Cys Leu Val Lys Gly Phe Tyr Pro Ser Asp Ile Ala Val Glu
        140                 145                 150

Trp Glu Ser Asn Gly Gln Pro Glu Asn Asn Tyr Lys Thr Thr Pro
    155                 160                 165

Pro Met Leu Asp Ser Asp Gly Ser Phe Phe Leu Tyr Ser Lys Leu
170                 175                 180

Thr Val Asp Lys Ser Arg Trp Gln Gln Gly Asn Val Phe Ser Cys
            185                 190                 195

Ser Val Met His Glu Ala Leu His Asn His Tyr Thr Gln Lys Ser
        200                 205                 210

Leu Ser Leu Ser Pro Gly Lys
    215

<210> SEQ ID NO 33
<211> LENGTH: 218
<212> TYPE: PRT
<213> ORGANISM: Homo sapiens

<400> SEQUENCE: 33

Pro Ala Pro Glu Leu Leu Gly Gly Pro Ser Val Phe Leu Phe Pro
  1               5                  10                  15

Pro Lys Pro Lys Asp Thr Leu Met Ile Ser Arg Thr Pro Glu Val
            20                  25                  30

Thr Cys Val Val Val Asp Val Ser His Glu Asp Pro Glu Val Gln
        35                  40                  45

Phe Lys Trp Tyr Val Asp Gly Val Glu Val His Asn Ala Lys Thr
    50                  55                  60

Lys Pro Arg Glu Glu Gln Phe Asn Ser Thr Phe Arg Val Val Ser
65                  70                  75

Val Leu Thr Val Leu His Gln Asp Trp Leu Asn Gly Lys Glu Tyr
            80                  85                  90

Lys Cys Lys Val Ser Asn Lys Ala Leu Pro Ala Pro Ile Glu Lys
        95                 100                 105

Thr Ile Ser Lys Thr Lys Gly Gln Pro Arg Glu Pro Gln Val Tyr
    110                 115                 120

Thr Leu Pro Pro Ser Arg Glu Glu Met Thr Lys Asn Gln Val Ser
125                 130                 135

Leu Thr Cys Leu Val Lys Gly Phe Tyr Pro Ser Asp Ile Ala Val
            140                 145                 150

Glu Trp Glu Ser Ser Gly Gln Pro Glu Asn Asn Tyr Asn Thr Thr
        155                 160                 165

Pro Pro Met Leu Asp Ser Asp Gly Ser Phe Phe Leu Tyr Ser Lys
    170                 175                 180

```
Leu Thr Val Asp Lys Ser Arg Trp Gln Gln Gly Asn Ile Phe Ser
            185                 190                 195

Cys Ser Val Met His Glu Ala Leu His Asn Arg Phe Thr Gln Lys
            200                 205                 210

Ser Leu Ser Leu Ser Pro Gly Lys
            215

<210> SEQ ID NO 34
<211> LENGTH: 218
<212> TYPE: PRT
<213> ORGANISM: Homo sapiens

<400> SEQUENCE: 34

Pro Ala Pro Glu Phe Leu Gly Gly Pro Ser Val Phe Leu Phe Pro
  1               5                  10                  15

Pro Lys Pro Lys Asp Thr Leu Met Ile Ser Arg Thr Pro Glu Val
             20                  25                  30

Thr Cys Val Val Val Asp Val Ser Gln Glu Asp Pro Glu Val Gln
             35                  40                  45

Phe Asn Trp Tyr Val Asp Gly Val Glu Val His Asn Ala Lys Thr
             50                  55                  60

Lys Pro Arg Glu Glu Gln Phe Asn Ser Thr Tyr Arg Val Val Ser
             65                  70                  75

Val Leu Thr Val Leu His Gln Asp Trp Leu Asn Gly Lys Glu Tyr
             80                  85                  90

Lys Cys Lys Val Ser Asn Lys Gly Leu Pro Ser Ser Ile Glu Lys
             95                 100                 105

Thr Ile Ser Lys Ala Lys Gly Gln Pro Arg Glu Pro Gln Val Tyr
            110                 115                 120

Thr Leu Pro Pro Ser Gln Glu Glu Met Thr Lys Asn Gln Val Ser
            125                 130                 135

Leu Thr Cys Leu Val Lys Gly Phe Tyr Pro Ser Asp Ile Ala Val
            140                 145                 150

Glu Trp Glu Ser Asn Gly Gln Pro Glu Asn Asn Tyr Lys Thr Thr
            155                 160                 165

Pro Pro Val Leu Asp Ser Asp Gly Ser Phe Phe Leu Tyr Ser Arg
            170                 175                 180

Leu Thr Val Asp Lys Ser Arg Trp Gln Glu Gly Asn Val Phe Ser
            185                 190                 195

Cys Ser Val Met His Glu Ala Leu His Asn His Tyr Thr Gln Lys
            200                 205                 210

Ser Leu Ser Leu Ser Leu Gly Lys
            215

<210> SEQ ID NO 35
<211> LENGTH: 1141
<212> TYPE: PRT
<213> ORGANISM: Artificial sequence
<220> FEATURE:
<223> OTHER INFORMATION: sequence is synthesized

<400> SEQUENCE: 35

Gly Ala Ala Thr Thr Cys Ala Ala Cys Thr Thr Cys Thr Cys Cys
  1               5                  10                  15

Ala Thr Ala Cys Thr Thr Thr Gly Gly Ala Thr Ala Ala Gly Gly
             20                  25                  30
```

-continued

```
Ala Ala Ala Thr Ala Cys Ala Gly Ala Cys Ala Thr Gly Ala Ala
                 35                  40                  45
Ala Ala Ala Thr Cys Thr Cys Ala Thr Thr Gly Cys Thr Gly Ala
                 50                  55                  60
Gly Thr Thr Gly Thr Thr Ala Thr Thr Thr Ala Ala Gly Cys Thr
                 65                  70                  75
Thr Gly Cys Cys Ala Ala Ala Ala Ala Gly Ala Ala Gly Ala
                 80                  85                  90
Ala Gly Ala Gly Thr Cys Gly Ala Ala Thr Gly Ala Ala Cys Thr
                 95                 100                 105
Gly Thr Gly Thr Gly Cys Gly Cys Ala Gly Gly Thr Ala Gly Ala
                110                 115                 120
Ala Gly Cys Thr Thr Thr Gly Gly Ala Gly Ala Thr Thr Ala Thr
                125                 130                 135
Cys Gly Thr Cys Ala Cys Thr Gly Cys Ala Ala Thr Gly Cys Thr
                140                 145                 150
Thr Cys Gly Cys Ala Ala Thr Ala Thr Gly Gly Cys Gly Cys Ala
                155                 160                 165
Ala Ala Ala Thr Gly Ala Cys Cys Ala Ala Cys Ala Gly Cys Gly
                170                 175                 180
Gly Thr Thr Gly Ala Thr Thr Gly Ala Thr Cys Ala Gly Gly Thr
                185                 190                 195
Ala Gly Ala Gly Gly Gly Gly Cys Gly Cys Thr Gly Thr Ala
                200                 205                 210
Cys Gly Ala Gly Gly Thr Ala Ala Ala Gly Cys Cys Cys Gly Ala
                215                 220                 225
Thr Gly Cys Cys Ala Gly Cys Ala Thr Thr Cys Cys Thr Gly Ala
                230                 235                 240
Cys Gly Ala Cys Gly Ala Thr Ala Cys Gly Gly Ala Gly Cys Thr
                245                 250                 255
Gly Cys Thr Gly Cys Gly Cys Gly Ala Thr Thr Ala Cys Gly Thr
                260                 265                 270
Ala Ala Ala Gly Ala Ala Gly Thr Thr Ala Thr Thr Gly Ala Ala
                275                 280                 285
Gly Cys Ala Thr Cys Cys Thr Cys Gly Thr Cys Ala Gly Thr Ala
                290                 295                 300
Ala Ala Ala Ala Gly Thr Thr Ala Ala Thr Cys Thr Thr Thr Thr
                305                 310                 315
Cys Ala Ala Cys Ala Gly Cys Thr Gly Thr Cys Ala Thr Ala Ala
                320                 325                 330
Ala Gly Thr Thr Gly Thr Cys Ala Cys Gly Gly Cys Cys Gly Ala
                335                 340                 345
Gly Ala Cys Thr Thr Ala Thr Ala Gly Thr Cys Gly Cys Thr Thr
                350                 355                 360
Thr Gly Thr Thr Thr Thr Thr Ala Thr Thr Thr Thr Thr Thr Ala
                365                 370                 375
Ala Thr Gly Thr Ala Thr Thr Gly Thr Ala Ala Cys Thr Ala
                380                 385                 390
Gly Thr Ala Cys Gly Cys Ala Ala Gly Thr Thr Cys Ala Cys Gly
                395                 400                 405
Thr Ala Ala Ala Ala Ala Gly Gly Gly Thr Ala Thr Cys Thr Ala
                410                 415                 420
Gly Ala Ala Thr Thr Ala Thr Gly Ala Ala Gly Ala Ala Gly Ala
```

-continued

```
                425                 430                 435
Ala Thr Ala Thr Cys Gly Cys Ala Thr Thr Cys Thr Thr Cys
                440                 445                 450
Thr Thr Gly Cys Ala Thr Cys Thr Ala Thr Gly Thr Thr Cys Gly
                455                 460                 465
Thr Thr Thr Thr Thr Thr Cys Thr Ala Thr Gly Cys Thr Ala
                470                 475                 480
Cys Ala Ala Ala Thr Gly Cys Ala Thr Ala Cys Gly Cys Thr Gly
                485                 490                 495
Ala Cys Ala Thr Cys Cys Ala Gly Ala Thr Gly Ala Cys Cys Cys
                500                 505                 510
Ala Gly Thr Cys Thr Cys Cys Ala Thr Cys Thr Thr Cys Cys Thr
                515                 520                 525
Thr Ala Thr Cys Thr Gly Cys Cys Thr Cys Thr Cys Thr Gly Gly
                530                 535                 540
Gly Ala Gly Ala Ala Gly Ala Gly Thr Cys Ala Gly Thr Cys
                545                 550                 555
Thr Cys Ala Cys Thr Thr Gly Th

Cys Thr Gly Cys Ala Cys Cys Ala Thr Cys Thr Gly Thr Cys Thr
                830                 835                 840

Thr Cys Ala Thr Cys Thr Thr Cys Cys Gly Cys Ala Thr
                845                 850                 855

Cys Thr Gly Ala Thr Gly Ala Gly Cys Ala Gly Thr Thr Gly Ala
                860                 865                 870

Ala Ala Thr Cys Thr Gly Gly Ala Ala Cys Thr Gly Cys Cys Thr
                875                 880                 885

Cys Thr Gly Thr Thr Gly Thr Gly Thr Gly Cys Cys Thr Gly Cys
                890 895 900

Thr Gly Ala Ala Thr Ala Ala Cys Thr Thr Cys Thr Ala Thr Cys
905 910 915

Cys Cys Ala Gly Ala Gly Ala Gly Gly Cys Cys Ala Ala Ala Gly
920 925 930

Thr Ala Cys Ala Gly Thr Gly Gly Ala Ala Gly Gly Thr Gly Gly
935 940 945

Ala Thr Ala Ala Cys Gly Cys Cys Cys Thr Cys Cys Ala Ala Thr
950 955 960

Cys Gly Gly Gly Thr Ala Ala Cys Thr Cys Cys Cys Ala Gly Gly
965 970 975

Ala Gly Ala Gly Thr Gly Thr Cys Ala Cys Ala Gly Ala Gly Cys
980 985 990

Ala Gly Gly Ala Cys Ala Gly Cys Ala Ala Gly Gly Ala Cys Ala
995 1000 1005

Gly Cys Ala Cys Cys Thr Ala Cys Ala Gly Cys Cys Thr Cys Ala
1010 1015 1020

Gly Cys Ala Gly Cys Ala Cys Cys Cys Thr Gly Ala Cys Gly Cys
1025 1030 1035

Thr Gly Ala Gly Cys Ala Ala Ala Gly Cys Ala Gly Ala Cys Thr
1040 1045 1050

Ala Cys Gly Ala Gly Ala Ala Ala Cys Ala Cys Ala Ala Ala Gly
1055 1060 1065

Thr Cys Thr Ala Cys Gly Cys Cys Thr Gly Cys Gly Ala Ala Gly
1070 1075 1080

Thr Cys Ala Cys Cys Cys Ala Thr Cys Ala Gly Gly Gly Cys Cys
1085 1090 1095

Thr Gly Ala Gly Cys Thr Cys Gly Cys Cys Cys Gly Thr Cys Ala
1100 1105 1110

Cys Ala Ala Ala Gly Ala Gly Cys Thr Thr Cys Ala Ala Cys Ala
1115 1120 1125

Gly Gly Gly Gly Ala Gly Ala Gly Thr Gly Thr Thr Ala Ala Thr
1130 1135 1140

Thr

<210> SEQ ID NO 36
<211> LENGTH: 1141
<212> TYPE: PRT
<213> ORGANISM: Artificial sequence
<220> FEATURE:
<223> OTHER INFORMATION: sequence is synthesized

<400> SEQUENCE: 36

Gly Ala Ala Thr Thr Cys Ala Ala Cys Thr Thr Cys Thr Cys Cys
1 5 10 15

-continued

```
Ala Thr Ala Cys Thr Thr Thr Gly Gly Ala Thr Ala Gly Gly
                 20                  25                  30

Ala Ala Ala Thr Ala Cys Ala Gly Ala Cys Ala Thr Gly Ala Ala
                 35                  40                  45

Ala Ala Ala Thr Cys Thr Cys Ala Thr Thr Gly Cys Thr Gly Ala
                 50                  55                  60

Gly Thr Thr Gly Thr Thr Ala Thr Thr Ala Ala Gly Cys Thr
             65                  70                  75

Thr Gly Cys Cys Cys Ala Ala Ala Ala Gly Ala Ala Gly Ala
             80                  85                  90

Ala Gly Ala Gly Thr Cys Gly Ala Ala Thr Gly Ala Ala Cys Thr
                 95                 100                 105

Gly Thr Gly Thr Gly Cys Gly Cys Ala Gly Gly Thr Ala Gly Ala
                110                 115                 120

Ala Gly Cys Thr Thr Gly Gly Ala Gly Ala Thr Thr Ala Thr
                125                 130                 135

Cys Gly Thr Cys Ala Cys Thr Gly Cys Ala Ala Thr Gly Cys Thr
                140                 145                 150

Thr Cys Gly Cys Ala Ala Thr Ala Thr Gly Gly Cys Gly Cys Ala
                155                 160                 165

Ala Ala Ala Thr Gly Ala Cys Cys Ala Ala Cys Ala Gly Cys Gly
                170                 175                 180

Gly Thr Thr Gly Ala Thr Thr Gly Ala Thr Cys Ala Gly Gly Thr
                185                 190                 195

Ala Gly Ala Gly Gly Gly Gly Cys Gly Cys Thr Gly Thr Ala
                200                 205                 210

Cys Gly Ala Gly Gly Thr Ala Ala Ala Gly Cys Cys Cys Gly Ala
                215                 220                 225

Thr Gly Cys Cys Ala Gly Cys Ala Thr Thr Cys Cys Thr Gly Ala
                230                 235                 240

Cys Gly Ala Cys Gly Ala Thr Ala Cys Gly Gly Ala Gly Cys Thr
                245                 250                 255

Gly Cys Thr Gly Cys Gly Cys Gly Ala Thr Thr Ala Cys Gly Thr
                260                 265                 270

Ala Ala Ala Gly Ala Ala Gly Thr Thr Ala Thr Thr Gly Ala Ala
                275                 280                 285

Gly Cys Ala Thr Cys Cys Thr Cys Gly Thr Cys Ala Gly Thr Ala
                290                 295                 300

Ala Ala Ala Ala Gly Thr Ala Ala Thr Cys Thr Thr Thr Thr
                305                 310                 315

Cys Ala Ala Cys Ala Gly Cys Thr Gly Thr Cys Ala Thr Ala Ala
                320                 325                 330

Ala Gly Thr Thr Gly Thr Cys Ala Cys Gly Cys Cys Gly Ala
                335                 340                 345

Gly Ala Cys Thr Thr Ala Thr Ala Gly Thr Cys Gly Cys Thr Thr
                350                 355                 360

Thr Gly Thr Thr Thr Thr Thr Ala Thr Thr Thr Thr Thr Ala
                365                 370                 375

Ala Thr Gly Thr Ala Thr Thr Gly Thr Ala Ala Cys Thr Ala
                380                 385                 390

Gly Thr Ala Cys Gly Cys Ala Ala Gly Thr Thr Cys Ala Cys Gly
                395                 400                 405

Thr Ala Ala Ala Ala Ala Gly Gly Gly Thr Ala Thr Cys Thr Ala
```

```
                410              415              420
Gly Ala Ala Thr Thr Ala Thr Gly Ala Ala Gly Ala Gly Ala
                425              430              435
Ala Thr Ala Thr Cys Gly Cys Ala Thr Thr Cys Thr Thr Cys
                440              445              450
Thr Thr Gly Cys Ala Thr Cys Thr Ala Thr Gly Thr Thr Cys Gly
                455              460              465
Thr Thr Thr Thr Thr Thr Cys Thr Ala Thr Thr Gly Cys Thr Ala
                470              475              480
Cys Ala Ala Ala Thr Gly Cys Ala Thr Ala Cys Gly Cys Thr Gly
                485              490              495
Ala Thr Ala Thr Cys Ala Thr Gly Ala Thr Gly Ala Cys Thr Cys
                500              505              510
Ala Gly Thr Cys Thr Cys Cys Thr Thr Cys Thr Thr Cys Cys Ala
                515              520              525
Thr Gly Thr Ala Thr Gly Cys Ala Thr Cys Thr Cys Thr Ala Gly
                530              535              540
Gly Ala Gly Ala Gly Ala Gly Ala Gly Thr Cys Ala Cys Thr Ala
                545              550              555
Thr Cys Ala Cys Thr Thr Gly Thr Ala Ala Gly Gly Cys Gly Ala
                560              565              570
Gly Thr Cys Ala Gly Gly Ala Cys Ala Thr Thr Ala Ala Thr Ala
                575              580              585
Gly Cys Thr Ala Thr Thr Thr Ala Ala Ala Gly Cys Thr Gly Thr
                590              595              600
Thr Cys Cys Ala Gly Cys Ala Gly Ala Ala Cys Cys Ala Gly
                605              610              615
Gly Gly Ala Ala Ala Thr Cys Thr Cys Cys Thr Ala Ala Gly Ala
                620              625              630
Cys Cys Cys Thr Gly Ala Thr Cys Thr Cys Thr Cys Gly Thr Gly
                635              640              645
Cys Ala Ala Ala Cys Ala Gly Ala Thr Thr Gly Gly Thr Ala Gly
                650              655              660
Ala Thr Gly Gly Thr Gly Thr Cys Cys Ala Thr Cys Ala Ala
                665              670              675
Gly Ala Thr Thr Cys Ala Gly Thr Gly Gly Cys Ala Gly Thr Gly
                680              685              690
Gly Ala Thr Cys Thr Gly Gly Gly Cys Ala Ala Gly Ala Thr Thr
                695              700              705
Ala Thr Thr Cys Thr Cys Thr Cys Ala Cys Cys Ala Thr Cys Ala
                710              715              720
Gly Cys Ala Gly Cys Cys Thr Gly Ala Gly Thr Ala Thr Gly
                725              730              735
Ala Ala Gly Ala Thr Ala Thr Gly Gly Ala Ala Thr Thr Thr
                740              745              750
Ala Thr Thr Ala Thr Thr Gly Thr Cys Thr Ala Cys Ala Gly Thr
                755              760              765
Ala Thr Gly Ala Thr Gly Ala Cys Thr Thr Cys Cys Gly Thr
                770              775              780
Thr Cys Ala Cys Gly Thr Thr Cys Gly Gly Ala Gly Gly Gly
                785              790              795
Gly Gly Ala Cys Cys Ala Ala Gly Cys Thr Gly Gly Ala Ala Ala
                800              805              810
```

```
Thr Ala Ala Ala Ala Cys Gly Gly Ala Cys Cys Gly Thr Gly Gly
            815                 820                 825

Cys Thr Gly Cys Ala Cys Cys Ala Thr Cys Thr Gly Thr Cys Thr
            830                 835                 840

Thr Cys Ala Thr Cys Thr Thr Cys Cys Gly Cys Cys Ala Thr
            845                 850                 855

Cys Thr Gly Ala Thr Gly Ala Gly Cys Ala Gly Thr Thr Gly Ala
            860                 865                 870

Ala Ala Thr Cys Thr Gly Gly Ala Ala Cys Thr Gly Cys Cys Thr
            875                 880                 885

Cys Thr Gly Thr Thr Gly Thr Gly Thr Gly Cys Cys Thr Gly Cys
            890                 895                 900

Thr Gly Ala Ala Thr Ala Ala Cys Thr Thr Cys Thr Ala Thr Cys
            905                 910                 915

Cys Cys Ala Gly Ala Gly Ala Gly Gly Cys Cys Ala Ala Ala Gly
            920                 925                 930

Thr Ala Cys Ala Gly Thr Gly Gly Ala Ala Gly Gly Thr Gly Gly
            935                 940                 945

Ala Thr Ala Ala Cys Gly Cys Cys Cys Thr Cys Cys Ala Ala Thr
            950                 955                 960

Cys Gly Gly Gly Thr Ala Ala Cys Thr Cys Cys Cys Ala Gly Gly
            965                 970                 975

Ala Gly Ala Gly Thr Gly Thr Cys Ala Cys Ala Gly Ala Gly Cys
            980                 985                 990

Ala Gly Gly Ala Cys Ala Gly Cys Ala Ala Gly Gly Ala Cys Ala
            995                 1000                1005

Gly Cys Ala Cys Cys Thr Ala Cys Ala Gly Cys Cys Thr Cys Ala
            1010                1015                1020

Gly Cys Ala Gly Cys Ala Cys Cys Thr Gly Ala Cys Gly Cys
            1025                1030                1035

Thr Gly Ala Gly Cys Ala Ala Gly Cys Ala Gly Ala Cys Thr
            1040                1045                1050

Ala Cys Gly Ala Gly Ala Ala Ala Cys Ala Cys Ala Ala Ala Gly
            1055                1060                1065

Thr Cys Thr Ala Cys Gly Cys Cys Thr Gly Cys Gly Ala Ala Gly
            1070                1075                1080

Thr Cys Ala Cys Cys Cys Ala Thr Cys Ala Gly Gly Gly Cys Cys
            1085                1090                1095

Thr Gly Ala Gly Cys Thr Cys Gly Cys Cys Cys Gly Thr Cys Ala
            1100                1105                1110

Cys Ala Ala Ala Gly Ala Gly Cys Thr Thr Cys Ala Ala Cys Ala
            1115                1120                1125

Gly Gly Gly Gly Ala Gly Ala Gly Thr Gly Thr Thr Ala Ala Thr
            1130                1135                1140

Thr

<210> SEQ ID NO 37
<211> LENGTH: 370
<212> TYPE: PRT
<213> ORGANISM: Artificial sequence
<220> FEATURE:
<223> OTHER INFORMATION: sequence is synthesized

<400> SEQUENCE: 37
```

-continued

```
Ala Cys Gly Cys Gly Thr Ala Cys Gly Cys Thr Gly Ala Ala Gly
  1               5                  10                  15

Thr Gly Ala Ala Gly Cys Thr Gly Gly Ala Gly Gly Ala Gly Thr
                 20                  25                  30

Cys Thr Gly Gly Ala Gly Gly Ala Gly Gly Cys Thr Thr Gly Gly
                 35                  40                  45

Thr Gly Cys Ala Ala Cys Cys Thr Gly Gly Ala Gly Gly Ala Thr
                 50                  55                  60

Cys Cys Ala Thr Gly Ala Ala Ala Cys Thr Cys Thr Cys Thr Thr
                 65                  70                  75

Gly Thr Gly Thr Thr Gly Cys Cys Thr Cys Thr Gly Gly Ala Thr
                 80                  85                  90

Thr Cys Ala Cys Thr Thr Thr Thr Ala Gly Thr Gly Ala Cys Gly
                 95                 100                 105

Cys Cys Thr Gly Gly Ala Thr Gly Gly Ala Cys Thr Gly Gly Gly
                110                 115                 120

Thr Cys Cys Gly Cys Cys Ala Gly Thr Cys Thr Cys Cys Ala Gly
                125                 130                 135

Ala Gly Ala Gly Gly Gly Gly Gly Cys Thr Thr Gly Ala Gly Thr
                140                 145                 150

Gly Gly Gly Thr Thr Gly Cys Thr Gly Ala Ala Ala Thr Thr Ala
                155                 160                 165

Gly Ala Ala Gly Cys Ala Ala Ala Cys Cys Thr Ala Ala Thr Ala
                170                 175                 180

Ala Thr Cys Ala Thr Gly Cys Ala Ala Cys Ala Thr Ala Cys Thr
                185                 190                 195

Ala Thr Gly Cys Thr Gly Ala Gly Thr Cys Thr Gly Thr Gly Ala
                200                 205                 210

Ala Ala Gly Gly Gly Ala Gly Gly Thr Thr Cys Ala Cys Cys Ala
                215                 220                 225

Thr Cys Thr Cys Ala Ala Gly Ala Gly Ala Thr Gly Ala Thr Thr
                230                 235                 240

Cys Cys Ala Ala Ala Ala Gly Thr Ala Gly Thr Gly Thr Cys Thr
                245                 250                 255

Ala Cys Cys Thr Gly Cys Ala Ala Ala Thr Gly Ala Cys Cys Ala
                260                 265                 270

Gly Cys Thr Thr Ala Ala Gly Ala Cys Cys Thr Gly Ala Ala Gly
                275                 280                 285

Ala Cys Ala Cys Thr Gly Gly Cys Ala Thr Thr Thr Ala Thr Thr
                290                 295                 300

Ala Cys Thr Gly Thr Ala Cys Cys Cys Ala Cys Thr Thr Thr Gly
                305                 310                 315

Ala Cys Thr Ala Cys Thr Gly Gly Gly Gly Cys Cys Ala Ala Gly
                320                 325                 330

Gly Cys Ala Cys Cys Ala Cys Thr Cys Thr Cys Ala Cys Ala Gly
                335                 340                 345

Thr Cys Thr Cys Cys Thr Cys Ala Gly Cys Cys Ala Ala Ala Ala
                350                 355                 360

Cys Gly Ala Cys Gly Gly Gly Cys Cys Cys
                365                 370
```

<210> SEQ ID NO 38
<211> LENGTH: 382
<212> TYPE: PRT

-continued

<213> ORGANISM: Artificial sequence
<220> FEATURE:
<223> OTHER INFORMATION: sequence is synthesized

<400> SEQUENCE: 38

Ala Cys Gly Cys Gly Thr Ala Cys Gly Cys Thr Gly Ala Ala Gly
1 5 10 15

Thr Gly Ala Ala Gly Cys Thr Gly Gly Thr Gly Gly Ala Gly Thr
20 25 30

Cys Thr Gly Gly Gly Gly Gly Ala Gly Gly Cys Thr Thr Ala Gly
35 40 45

Thr Gly Ala Ala Gly Cys Cys Thr Gly Gly Ala Gly Gly Gly Thr
50 55 60

Cys Cys Cys Thr Gly Ala Ala Ala Cys Thr Cys Thr Cys Cys Thr
65 70 75

Gly Thr Gly Cys Ala Gly Cys Cys Thr Cys Thr Gly Gly Ala Thr
80 85 90

Thr Cys Ala Cys Thr Thr Thr Cys Ala Gly Thr Ala Gly Cys Thr
95 100 105

Ala Thr Gly Gly Cys Ala Thr Gly Thr Cys Thr Thr Gly Gly Gly
110 115 120

Thr Thr Cys Gly Cys Cys Ala Gly Ala Cys Thr Cys Cys Gly Gly
125 130 135

Ala Gly Ala Ala Gly Ala Gly Gly Cys Thr Gly Gly Ala Gly Thr
140 145 150

Gly Gly Gly Thr Cys Gly Cys Ala Ala Cys Cys Ala Thr Thr Ala
155 160 165

Gly Thr Gly Gly Thr Gly Gly Thr Ala Ala Thr Ala Ala Thr Thr
170 175 180

Ala Cys Ala Cys Cys Thr Thr Cys Thr Ala Thr Cys Cys Ala Gly
185 190 195

Ala Cys Ala Ala Thr Thr Thr Gly Ala Ala Gly Gly Gly Gly Cys
200 205 210

Gly Cys Thr Thr Cys Ala Cys Cys Ala Thr Cys Thr Cys Cys Ala
215 220 225

Gly Ala Gly Ala Cys Ala Ala Thr Gly Cys Cys Ala Ala Gly Ala
230 235 240

Ala Cys Ala Thr Cys Cys Thr Gly Thr Ala Cys Cys Thr Gly Cys
245 250 255

Ala Ala Ala Thr Cys Ala Gly Cys Ala Gly Thr Cys Thr Gly Ala
260 265 270

Gly Gly Thr Cys Thr Gly Thr Cys Gly Ala Cys Ala Cys Gly Gly
275 280 285

Cys Cys Thr Thr Gly Thr Ala Thr Thr Ala Cys Thr Gly Thr Gly
290 295 300

Cys Ala Ala Gly Cys Cys Thr Gly Thr Gly Gly Thr Ala Cys Cys
305 310 315

Gly Cys Gly Cys Cys Thr Cys Gly Thr Thr Thr Gly Cys Thr Thr
320 325 330

Ala Cys Thr Gly Gly Gly Gly Cys Cys Ala Ala Gly Gly Gly Ala
335 340 345

Cys Thr Cys Thr Gly Gly Thr Cys Ala Cys Cys Gly Thr Cys Thr
350 355 360

Cys Cys Thr Cys Ala Gly Cys Ala Ala Ala Ala Ala Cys Gly Ala

-continued

```
                    365                 370                 375
Cys Gly Gly Gly Cys Cys Cys
                    380

<210> SEQ ID NO 39
<211> LENGTH: 7
<212> TYPE: PRT
<213> ORGANISM: Artificial sequence
<220> FEATURE:
<223> OTHER INFORMATION: sequence is synthesized

<400> SEQUENCE: 39

Phe Ser Arg Leu Asp Pro Thr
                    5

<210> SEQ ID NO 40
<211> LENGTH: 7
<212> TYPE: PRT
<213> ORGANISM: Artificial sequence
<220> FEATURE:
<223> OTHER INFORMATION: sequence is synthesized

<400> SEQUENCE: 40

Phe Ser His Leu Asp Pro Thr
                    5
```